United States Patent
Kuehnert et al.

(10) Patent No.: US 7,420,056 B2
(45) Date of Patent: Sep. 2, 2008

(54) SUBSTITUTED BICYCLIC IMIDAZO-3-YLAMINE COMPOUNDS

(75) Inventors: Sven Kuehnert, Dueren (DE); Stefan Oberboersch, Aachen (DE); Corinna Sundermann, Aachen (DE); Michael Haurand, Aachen (DE); Ruth Jostock, Stolberg (DE); Klaus Schiene, Duesseldorf (DE); Thomas Tzschentke, Aachen (DE); Thomas Christoph, Aachen (DE); Dagmar Kaulartz, Stolberg (DE); Saskia Zemolka, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/685,953

(22) Filed: Mar. 14, 2007

(65) Prior Publication Data

US 2007/0155965 A1    Jul. 5, 2007

Related U.S. Application Data

(63) Continuation of application No. PCT/EP2005/054436, filed on Sep. 8, 2005.

(30) Foreign Application Priority Data

Sep. 14, 2004  (DE) .................. 10 2004 044 884

(51) Int. Cl.
*C07D 487/00*  (2006.01)
*A01N 43/90*  (2006.01)
*A61K 31/519*  (2006.01)

(52) U.S. Cl. .............. 544/281; 544/242; 544/245; 544/253; 544/282; 544/346; 544/350; 544/356; 544/368; 514/259.1; 514/259.41; 514/263.23

(58) Field of Classification Search .............. 544/281, 544/282, 350, 368; 514/259.1, 259.41, 263.23
See application file for complete search history.

(56) References Cited

U.S. PATENT DOCUMENTS

2003/0225070 A1    12/2003  Mutel et al.

FOREIGN PATENT DOCUMENTS

| DE | 199 48 438 A1 | 6/2001 |
|---|---|---|
| WO | WO 01/27110 A2 | 4/2001 |
| WO | WO 01/27119 A2 | 4/2001 |
| WO | WO 02/30428 A1 | 4/2002 |
| WO | WO 02/46166 A1 | 6/2002 |
| WO | WO 02/080911 A2 | 10/2002 |
| WO | WO 03/051315 A2 | 6/2003 |

OTHER PUBLICATIONS

International Search Report dated Jan. 18, 2006 with English translation of relevant portion ( Five (5) Pages).
German Search Report dated Jul. 4, 2005 with English translation (Eight (8) Pages).
PCT/IB/373 and PCT/ISA/237 including English translation (Nine (9) pages).

*Primary Examiner*—Cecilia Tsang
*Assistant Examiner*—Samantha Shterengarts
(74) *Attorney, Agent, or Firm*—Crowell & Moring LLP

(57) ABSTRACT

Substituted bicyclic imidazo-3-yl-amine compounds are provided, as well as processes for the production thereof and pharmaceutical formulations containing these compounds. The use of these compounds for the production of pharmaceutical formulations and related methods of treatment are also provided.

57 Claims, No Drawings

US 7,420,056 B2

SUBSTITUTED BICYCLIC IMIDAZO-3-YLAMINE COMPOUNDS

CROSS-REFERENCE TO RELATED APPLICATIONS

This application is a continuation of International patent application Serial No. PCT/EP2005/054436 filed Sep. 8, 2007 which claims benefit to German patent application Serial No. 10 2004 044 884.1 filed Sep. 14, 2004, the entire disclosures of which are hereby incorporated in their entirety.

FIELD OF THE INVENTION

The present invention relates to substituted bicyclic imidazo-3-yl-amine compounds, to processes for the production thereof, to pharmaceutical formulations containing these compounds, the use of these compounds for the production of pharmaceutical formulations and related methods of treatment.

BACKGROUND OF THE INVENTION

Pain is one of the basic clinical symptoms. There is a worldwide need for effective pain treatments. The urgency of the requirement for therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

Conventional opioids, such as for example morphine, are effective in the treatment of severe to very severe pain, but they often lead to unwanted accompanying symptoms, such as for example respiratory depression, vomiting, sedation, constipation or the development of tolerance. Moreover, they are frequently insufficiently effective in the case of neuropathic pain, suffered in particular by tumour patients.

SUMMARY OF THE INVENTION

One object of the present invention was accordingly to provide novel compounds which are suitable in particular as pharmaceutical active ingredients in pharmaceutical formulations, preferably in pharmaceutical formulations for the treatment of pain.

It has now surprisingly been found that the substituted bicyclic imidazo-3-yl-amine compounds of the general formula I stated hereinafter are suitable for mGluR5 receptor regulation (mGluR5=metabotropic glutamate receptor 5) and may therefore be used in particular as pharmaceutical active ingredients in pharmaceutical formulations for the prevention and/or treatment of disorders or diseases associated with these receptors or processes.

The present invention accordingly provides substituted imidazo-3-yl-amine compounds of the general formula I,

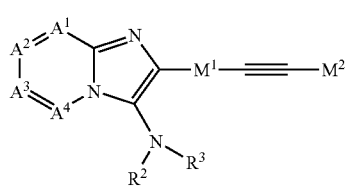

I in which
A1 represents a nitrogen atom or a C—R1a group,
A2 represents a nitrogen atom or a C—R1b group,
A3 represents a nitrogen atom or a C—R1c group,
A4 represents a nitrogen atom or a C—R1d group,
R1a, R1b, R1c, R1d, mutually independently, in each case represent a hydrogen; a halogen; —NO2; —CN; —NH2; —NHR4; —NR5R6; —NH—C(=O)—R7; —C(=O)—R8, —C(=O)—NH2; —C(=O)—NHR9; —C(=O)—NR10R11; —C(=O)—OR12; —(CH2)m-C(=O)—OR13 with m=1, 2, 3, 4 or 5; —O—C(=O)—R14; —(CH2)n-O—C(=O)—R15 with n=1, 2, 3, 4 or 5; —OR16; —(CH2)o-O—R17 with o=1, 2, 3; 4 or 5; —SR18; —(CH2)p-S(=O)t-R19 with p=1, 2, 3, 4 or 5 and t=0, 1 or 2; —NH—S(=O)2-R26R27; —S(=O)2-NR28R29, —SF5; a linear or branched, saturated or unsaturated, unsubstituted or at least monosubstituted aliphatic group; a saturated or unsaturated, unsubstituted or at least monosubstituted cycloaliphatic group optionally comprising at least one heteroatom as a ring member, which cycloaliphatic group may be attached via a linear or branched alkylene group and/or may be fused with an unsubstituted or at least monosubstituted mono- or polycyclic ring system; or represent an unsubstituted or at least monosubstituted aryl or heteroaryl group, which may be attached via a linear or branched alkylene group and/or may be fused with an unsubstituted or at least monosubstituted mono- or polycyclic ring system, or optionally R1a and R1b form an unsubstituted or at least monosubstituted anellated phenyl group with the C—C bridge joining them together, or optionally R1b and R1c form an unsubstituted or at least monosubstituted anellated phenyl group with the C—C bridge joining them together, or optionally R1c and R1d form an unsubstituted or at least monosubstituted anellated phenyl group with the C—C bridge joining them together, R2 and R3, mutually independently, in each case represent a hydrogen; —C(=O)—R20; —(CH2)q-C(=O)—R21 with q=1, 2, 3, 4 or 5; —C(=O)—O—R22; —(CH2)r-C(=O)—O—R23 with r=1, 2, 3, 4 or 5; —C(=O)—NHR24; —(CH2)s-C(=O)—NHR25 with s=1, 2, 3, 4 or 5; a linear or branched, saturated or unsaturated, unsubstituted or at least monosubstituted aliphatic group; a saturated or unsaturated, unsubstituted or at least monosubstituted cycloaliphatic group optionally comprising at least one heteroatom as a ring member, which cycloaliphatic group may be attached via a linear or branched alkylene group and/or may be fused with an unsubstituted or at least monosubstituted mono- or polycyclic ring system; or represent an unsubstituted or at least monosubstituted aryl or heteroaryl group, which may be attached via a linear or branched alkylene group and/or may be fused with an unsubstituted or at least monosubstituted mono- or polycyclic ring system, or R2 and R3, together with the nitrogen atom joining them together as a ring member, form a saturated or unsaturated heterocycloaliphatic group optionally comprising at least one further heteroatom as a ring member, which heterocycloaliphatic group may be fused with an unsubstituted or at least monosubstituted mono- or polycyclic ring system, R4, R5, R6, R7, R9, R10, R11, R14 and R15, in each case mutually independently, represent a linear or branched, saturated or unsaturated aliphatic group or an unsubstituted or at least monosubstituted aryl or heteroaryl group, which may be attached via a linear or branched alkylene group and/or may be fused with an unsubstituted or at least monosubstituted mono- or polycyclic ring system, R8, R12, R13, R16, R17, R18, R19, R20, R21, R22, R23, R24, R25, R26, R27, R28 and R29, in each case mutually independently, represent a hydrogen; a linear or branched, saturated or unsaturated aliphatic group or an unsubstituted or at least monosubstituted aryl or heteroaryl group, which may be attached via a linear or branched alkylene group and/or may be fused with an unsubstituted or at least monosubstituted mono- or polycyclic ring system, M1 represents an aryl or heteroaryl group, which may be substituted with at least one further substituent and/or fused with an unsubstituted or at least monosubstituted mono- or polycyclic ring system, M2 represents an aryl or heteroaryl group, which is unsubstituted or at least monosubstituted and optionally fused with an unsubstituted or at least monosubstituted mono- or polycyclic ring system, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

If one or more of the substituents R1a, R1b, R1c, R1d and R2 to R29 represent a saturated or unsaturated aliphatic group, i.e. an alkyl-, alkenyl- or alkynyl group, which is mono- or polysubstituted, this may preferably be substituted with 1, 2, 3, 4 or 5 substituents mutually independently selected from the group consisting of F, Cl, Br, —NO2, —CN, —OH, —SH and —NH2. Alkenyl groups comprise at least one, preferably 1, 2, 3 or 4 C—C double bonds and alkynyl groups comprise at least one, preferably 1, 2, 3 or 4 C—C triple bonds.

Examples of suitable alkyl, alkenyl and alkynyl groups, which may be mono- or polysubstituted, are methyl, ethyl, n-propyl, iso-propyl, n-butyl, iso-butyl, sec-butyl, tert-butyl, n-pentyl, 2-pentyl, 3-pentyl, iso-pentyl, neopentyl, n-hexyl, 2-hexyl, 3-hexyl, n-heptyl, n-octyl, n-nonyl, n-decyl, —C(H)(n-C3H7)2, —CH2-CH2-C(H)(CH3)-(CH2)3-CH3, (1,1,3,3-tetramethyl)-butyl, (1,1)-dimethyl-pentyl, (1,1)-dimethyl-butyl, vinyl, ethynyl, 1-propenyl, 2-propenyl, 1-propynyl, 2-propynyl, 1-butenyl, 2-butenyl, 3-butenyl, 1-butynyl, 2-butynyl, 3-butynyl, 1-pentenyl, 2-pentenyl, 3-pentenyl, 4-pentenyl, 1-pentynyl, 2-pentynyl, 3-pentynyl, 4-pentynyl, hexenyl, hexynyl, —CH═CH—CH═CH—CH3 and —CH2-CH2-CH═CH2.

Examples of suitable substituted alkyl and alkenyl groups are trifluoromethyl, difluoromethyl, monofluoromethyl, —(CH2)-OH, —(CH2)-NH2, —(CH2)-CN, —(CH2)-(CF3), —(CH2)-(CHF2), —(CH2)-(CH2F), —(CH2)-(CH2)-OH, —(CH2)-(CH2)-NH2, —(CH2)-(CH2)-CN, —(CF2)-(CF3), —(CH2)-(CH2)-(CF3), —CH═CH—(CH2)-OH, —CH═CH—(CH2)-NH2, —CH═CH—CN and —(CH2)-(CH2)-(CH2)-OH.

If one or more of the substituents R1a, R1b, R1c, R1d, R2 and R3 represent a cycloaliphatic group or comprise a cycloaliphatic group, which is mono- or polysubstituted, this may preferably optionally be substituted with 1, 2, 3, 4 or 5 substituents mutually independently selected from the group consisting of F, Cl, Br, I, —CN, —CF3, —SF5, —OH, —NH2, —O—CF3, —SH, —O—C1-5-alkyl, —(CH2)-O—C1-5-alkyl, —S—C1-5-alkyl, —C1-5 alkyl, —C2-5 alkenyl, —C2-5 alkynyl, —C(═O)—O—C1-5-alkyl, —C(═O)—CF3, —S(═O)2-C1-5-alkyl, —S(═O)—C1-5-alkyl, —S(═O)2-phenyl, oxo (═O), thioxo (═S), —N(C1-5-alkyl)2, —N(H)(C1-5-alkyl), —NO2, —S—CF3, —C(═O)—OH, —NH—S(═O)2-C1-5-alkyl, —NH—C(═O)-C1-5-alkyl, —C(═O)—H; —C(═O)—C1-5-alkyl, —C(═O)—NH2, —C(═O)—N(C1-5-alkyl)2, —C(═O)—N(H)(C1-5-alkyl) and phenyl, wherein the above-stated C1-5 alkyl groups may in each case be linear or branched and the phenyl groups may in each case be unsubstituted or substituted with 1, 2, 3 or 4 substituents mutually independently selected from the group consisting of F, Cl, Br, I, methyl, ethyl, methoxy and ethoxy.

Particularly preferably, the substituents may be selected, in each case mutually independently, from the group consisting of F, Cl, Br, I, —CN, methyl, ethyl, n-propyl, iso-propyl, n-butyl, sec-butyl, iso-butyl, tert-butyl, ethenyl, propenyl, ethynyl, propynyl, —OH, oxo, thioxo, —O—CH3, —O—C2H5, —O—C3H7, —(CH2)-O—CH3, —(CH2)-O—C2H5, —NH2, —N(CH3)2, —N(C2H5)2, —NH—CH3, —NH—C2H5, —NO2, —CF3, —SF5, —O—CF3, —S—CF3, —SH, —S—CH3, —S—C2H5, —S(═O)—CH3, —S(═O)—C2H5, —S(═O)2-CH3, —S(═O)2-C2H5, —NH—S(═O)2-CH3, —C(═O)—OH, —C(═O)—H, —C(═O)—CH3, —C(═O)—C2H5, —C(═O)—N(CH3)2, —C(═O)—NH—CH3, —C(═O)—NH2, —NH—C(═O)—CH3, —NH—C(═O)—C2H5, —C(═O)—O—CH3, —C(═O)—O—C2H5, —C(═O)—O—C(CH3)3 and phenyl, wherein the phenyl group may be substituted with 1, 2 or 3 substituents mutually independently selected from the group consisting of F, Cl, Br, methyl and methoxy.

If the cycloaliphatic groups comprise one or more heteroatoms as ring members, these may preferably optionally comprise 1, 2, 3, 4 or 5, particularly preferably 1, 2 or 3, heteroatoms as ring member(s), which may be selected in each case mutually independently from the group consisting of nitrogen, oxygen and sulfur.

Examples of cycloaliphatic groups which may be mono- or polysubstituted are cyclopropyl, cyclobutyl, cyclopentyl, cyclohexyl, cycloheptyl, cyclooctyl, cyclononyl, cyclodecyl, cycloundecyl, cyclododecyl, cycloheptyl, cyclopentenyl, cyclohexenyl, cycloheptenyl, cyclooctenyl, oxiranyl, aziridinyl, tetrahydrofuranyl, tetrahydrothienyl, pyrrolidinyl, isoxazolidinyl, isothioazolidinyl, pyrazolidinyl, oxazolidinyl, thiazolidinyl, imidazolidinyl, (1,2,4)-oxadiazolidinyl, (1,2,4)-thiadiazolidinyl, (1,2,4)-triazolidin-3-yl, (1,3,4)-thiadiazolidinyl, (1,3,4)-triazolidin-1-yl, (1,3,4)-triazolidin-2-yl, (2,3)-dihydrofuryl, (2,5)-dihydrofuryl, (2,3)-dihydrothienyl, (2,5)-dihydrothienyl, (2,3)-dihydropyrrolyl, (2,5)-dihydropyrrolyl, (2,3)-dihydroisoxazolyl, (4,5)-dihydroisoxazolyl, (2,5)-dihydroisothiazolyl, (2,3)-dihydropyrazolyl, (4,5)-dihydropyrazolyl, (2,5)-dihydropyrazolyl, (2,3)-dihydrooxazolyl, (4,5)-dihydrooxazolyl, (2,5)-dihydrooxazolyl, (2,3)-dihydrothiazolyl, (4,5)-dihydrothiazolyl, (2,5)-dihydrothiazolyl, (2,3)-dihydroimidazolyl, (4,5)-dihydroimidazolyl, (2,5)-dihydroimidazolyl, morpholinyl, piperidinyl, piperazinyl, azocanyl, tetrahydropyridazinyl, tetrahydropyrimidinyl, tetrahydropyrazinyl, (1,3,5)-tetrahydrotriazinyl, (1,2,4)-tetrahydrotriazin-1-yl, (1,2,4)-tetrahydrotriazin-3-yl, (1,3)-dihydrooxazinyl, (1,3)-dithian-2-yl, tetrahydropyranyl, (1,3)-dioxolan-2-yl, (3,4,5,6)-tetrahydropyridin-2-yl, (1,2,5,6)-tetrahydropyridin-1-yl, (1,2,3,4)-tetrahydropyridin-1-yl, (1,2)-dihydropyridin-1-yl, (1,4)-dihydropyridin-1-yl, 4H-1,3-thiazinyl, (1,3)-dihydrooxazin-2-yl, azepanyl, (1,4)-diazepanyl, thiomorpholinyl and dithiolanyl.

Particularly preferred examples of cycloaliphatic groups, which may be mono- or polysubstituted, are cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl(tetrahydrofuryl), piperidinyl, piperazinyl, morpholinyl, pyrrolidinyl, tetrahydrothiophenyl, tetrahydropyranyl, thiomorpholinyl, dioxolanyl, azepanyl, diazepanyl, azocanyl and dithiolanyl.

If the cycloaliphatic group is fused with an unsubstituted or at least monosubstituted mono- or polycyclic ring system, suitable unsubstituted or at least monosubstituted groups may be selected from the group consisting of 2,3-dihydro-benzo[1,4]dioxinyl; 3,4-dihydro-2H-benzo[1,4]oxazinyl; benzo[1,3]dioxolyl; (1,2,3,4)-tetrahydroquinazolinyl; indanyl; (1,2,3,4)-tetrahydronaphthyl; 1H-indenyl; (1,2,3,4)-tetrahydroquinolinyl; (1,2,3,4)-tetrahydroisochinolinyl; (2,3)-dihydro-1H-indolyl, (2,3)-dihydro-1H-isoindolyl and decahydroisoquinolinyl.

If the substituents R2 and R3, together with the nitrogen atom joining them together as a ring member, form a saturated or unsaturated heterocycloaliphatic group, which is mono- or polysubstituted, this may preferably optionally be substituted with 1, 2, 3, 4, or 5 substituents mutually independently selected from the group consisting of F, Cl, Br, I, —CN, —CF3, —SF5, —OH, —NH2, —O—CF3, —SH, —O—C1-5-alkyl, —(CH2)-O—C1-5-alkyl, —S—C1-5-alkyl, —C1-5 alkyl, —C2-5 alkenyl, —C2-5 alkynyl, —C(=O)—O—C1-5-alkyl, —C(=O)—CF3, —S(=O)2-C1-5-alkyl, —S(=O)—C1-5-alkyl, —S(=O)2-phenyl, oxo (=O), thioxo (=S), —N(C1-5-alkyl)2, —N(H)(C1-5-alkyl), —NO2, —S—CF3, —C(=O)—OH, —NH—S(=O)2-C1-5-alkyl, —NH—C(=O)—C1-5-alkyl, —C(=O)—H; —C(=O)—C1-5-alkyl, —C(=O)—NH2, —C(=O)—N(C1-5-alkyl)2, —C(=O)—N(H)(C1-5-alkyl) and phenyl, wherein the above-stated C1-5 alkyl groups may in each case be linear or branched and the phenyl groups may in each case be unsubstituted or substituted with 1, 2, 3 or 4 substituents mutually independently selected from the group consisting of F, Cl, Br, I, methyl, ethyl, methoxy and ethoxy.

Particularly preferably, the substituents may be selected, in each case mutually independently, from the group consisting of F, Cl, Br, I, —CN, methyl, ethyl, n-propyl, iso-propyl, n-butyl, sec-butyl, iso-butyl, tert-butyl, ethenyl, propenyl, ethynyl, propynyl, —OH, oxo, thioxo, —O—CH3, —O—C2H5, —O—C3H7, —(CH2)-O—CH3, —(CH2)-O—C2H5, —NH2, —N(CH3)2, —N(C2H5)2, —NH—CH3, —NH—C2H5, —NO2, —CF3, —SF5, —O—CF3, —S—CF3, —SH, —S—CH3, —S—C2H5, —S(=O)—CH3, —S(=O)—C2H5, —S(=O)2-CH3, —S(=O)2-C2H5, —NH—S(=O)2-CH3, —C(=O)—OH, —C(=O)—H, —C(=O)—CH3, —C(=O)—C2H5, —C(=O)—N(CH3)2, —C(=O)—NH—CH3, —C(=O)—NH2, —NH—C(=O)—CH3, —NH—C(=O)—C2H5, —C(=O)—O—CH3, —C(=O)—O—C2H5, —C(=O)—O—C(CH3)3 and phenyl, wherein the phenyl group may be substituted with 1, 2 or 3 substituents mutually independently selected from the group consisting of F, Cl, Br, methyl and methoxy.

If the heterocycloaliphatic groups comprise one or more heteroatoms as ring members, these may preferably optionally comprise 1, 2, 3, 4 or 5, particularly preferably 1, 2 or 3, heteroatoms as ring member(s), which may, in each case mutually independently, be selected from the group consisting of nitrogen, oxygen and sulfur.

Examples of suitable heterocycloaliphatic groups, which may be mono- or polysubstituted, are imidazolidinyl, piperidinyl, piperazinyl, morpholinyl, pyrrolidinyl, thiomorpholinyl, azepanyl, diazepanyl and azocanyl.

If the cycloaliphatic group is fused with an unsubstituted or at least monosubstituted mono- or polycyclic ring system, suitable unsubstituted or at least monosubstituted groups may be selected from the group consisting of (3,4)-dihydro-2H-benzo[1,4]oxazinyl; (1,2,3,4)-tetrahydroquinazolinyl; (1,2,3,4)-tetrahydroquinolinyl; (1,2,3,4)-tetrahydroisoquinolinyl; (2,3)-dihydro-1H-indolyl, (2,3)-dihydro-1H-isoindolyl and decahydroisoquinolinyl.

If one or more of the substituents R1a, R1b, R1c, R1d, R2 to R29 and M1 and M2 represent an aryl or heteroaryl group or comprise an aryl or heteroaryl group, which is mono- or polysubstituted, this may preferably optionally be substituted with 1, 2, 3, 4 or 5 substituents mutually independently selected from the group consisting of halogen, —CN, —CH2-CN, —NO2, —OH, —SH, —NH2, —CH2-NH2, —C(=O)—OH, C1-5-alkyl, —(CH2)-OH, —(CH2)-O—C1-5-alkyl, —C2-5-alkenyl, —C2-5alkynyl, —S—C1-5-alkyl, —O—C1-5alkyl, —CF3, —SF5, —CHF2, —CH2F, —O—CF3, —O—CHF2, —O—CH2F, —C(=O)—CF3, —S—CF3, —S—CHF2, —S—CH2F, —S(=O)2-phenyl, —S(=O)2-C1-5-alkyl, —S(=O)—C1-5alkyl, —NH—C1-5alkyl, —N—(C1-5-alkyl)2, —CH2-NH—C1-5-alkyl, —CH2-N—(C1-5-alkyl)2, —C(=O)—O—C1-5-alkyl, —C(=O)—H, —C(=O)—C1-5-alkyl, —CH2-O—C(=O)-phenyl, —O—C(=O)-phenyl, —NH—S(=O)2-C1-5-alkyl, —NH—C(=O)—C1-5-alkyl, —S(=O)2-NH2, —S(=O)2-NH—C1-5-alkyl, —S(=O)2-N(C1-5-alkyl)2, —NH—C(=NH)—NH2, —NH—S(=O)2-OH, —C(=O)—NH—C1-5-alkyl, —C(=O)—NH2, —C(=O)—N(C1-5-alkyl)2, —Si(phenyl)2[C1-5-alkyl], pyrazolyl, pyrrolyl, (1,3)-dioxolanyl, phenyl, furyl (furanyl), thiazolyl, thiadiazolyl, thiophenyl (thienyl), phenoxy, benzyl and phenethyl, wherein the cyclic substituents may themselves in each case optionally be substituted with 1, 2, 3 or 4 substituents mutually independently selected from the group consisting of F, Cl, Br, I), —CF3, methyl, ethyl, methoxy and ethoxy.

Particularly preferably, the substituents may be selected, in each case mutually independently, from the group consisting of F, Cl, Br, I, —CN, —CH2-CN, —NO2, —OH, —SH, methyl, ethyl, n-propyl, iso-propyl, n-butyl, iso-butyl, sec-butyl, tert-butyl, n-pentyl, neo-pentyl, ethenyl, propenyl, ethynyl, propynyl, —CH2-OH, —CH2-O—CH3, —CH2-O—C2H5, —OH, —SH, —NH2, —CH2-NH2, —C(=O)—OH, —S—CH3, —S—C2H5, —S(=O)—CH3, —S(=O)—C2H5, —S(=O)2-CH3, —S(=O)2-C2H5, —O—CH3, —O—C2H5, —O—C3H7, —O—C(CH3)3, —CF3, —SF5, —CHF2, —CH2F, —O—CF3, —O—CHF2, —O—CH2F, C(=O)—CF3, —S—CF3, —S—CHF2, —S—CH2F, —S(=O)2-phenyl, pyrazolyl, pyrrolyl, —N(CH3)2, —N(C2H5)2, —NH—CH3, —NH—C2H5, —CH2-O—C(=O)-phenyl, —S(=O)2-NH2, —S(=O)2-NH—CH3, —S(=O)2-N(CH3)2, —NH—C(=NH)—NH2, —NH—S(=O)2-OH, —NH—S(=O)2-CH3, —C(=O)—O—CH3, —C(=O)—O—C2H5, —C(=O)—O—C(CH3)3, —C(=O)—H, —C(=O)—CH3, —C(=O)—C2H5, —C(=O)—C(CH3)3, —NH—C(=O)—CH3, —NH—C(=O)—C2H5, —O—C(=O)-phenyl, —C(=O)—NH2, —C(=O)—NH—CH3, —C(=O)—N(CH3)2, —Si(phenyl)2[C(CH3)3], phenyl, (1,3)-dioxolanyl, furyl (furanyl), thiadiazolyl, thiophenyl (thienyl), phenoxy and benzyl, wherein the cyclic substituents may themselves in each case optionally be substituted with 1, 2, 3 or 4 substituents mutually independently selected from the group consisting of F, Cl, Br, I, —CF3, methyl and methoxy.

Examples of suitable aryl groups which may be mentioned are phenyl, 1-naphthyl, 2-naphthyl and anthracenyl.

If one or more of the substituents R1a, R1b, R1c, R1d, R2 to R29 and M1 and M2 represent a heteroaryl group or comprise a heteroaryl group, the heteroatom(s) thereof may preferably be selected, mutually independently, from the group consisting of oxygen, sulfur and nitrogen. Preferably, a heteroaryl group may optionally comprise 1, 2, 3, 4 or 5, particularly preferably 1, 2 or 3 heteroatoms.

Examples of suitable heteroaryl groups are for example furyl (furanyl), thienyl (thiophenyl), pyrazolyl, imidazolyl, thiazolyl, thiadiazolyl, triazolyl, pyrrolyl, oxazolyl, oxadiazolyl, isoxazolyl, pyridinyl, pyridazinyl, pyrimidinyl, pyrazinyl, pyranyl, diazinyl, triazinyl, tetrazinyl, tetrazolyl, purinyl, dithiazolyl and pentazolyl.

If the heteroaryl group is fused with an unsubstituted or at least monosubstituted mono- or polycyclic ring system, suitable unsubstituted or at least monosubstituted heteroaryl groups may be selected from the group consisting of indolyl, isoindolyl, benzo[b]furanyl, isobenzo[b]furanyl, indazolyl, indolizinyl, quinolinyl, isoquinolinyl, quinazolinyl, benzo[b]thiophenyl and isobenzo[b]thiophenyl.

If the substituents R1a and R1b or R1b and R1c or R1c and R1d, together with the C—C bridge joining them together, form an anellated phenyl group, which is mono- or polysubstituted, this may preferably be substituted with 1, 2, 3 or 4 substituents mutually independently selected from the group consisting of halogen, —CN, —CH2-CN, —NO2, —OH, —SH, —NH2, —CH2-NH2, —C(=O)—OH, C1-5 alkyl, —(CH2)-O—C1-5-alkyl, —C2-5 alkenyl, —C2-5 alkynyl, —S—C1-5-alkyl, —O—C1-5-alkyl, —CF3, —SF5, —CHF2, —CH2F, —O—CF3, —O—CHF2, —O—CH2F, —C(=O)—CF3, —S—CF3, —S—CHF2, —S—CH2F, —S(=O)2-phenyl, —S(=O)2-C1-5-alkyl, —S(=O)—C1-5-alkyl, —NH—C1-5-alkyl, —N—(C1-5-alkyl)2, —CH2-NH—C1-5-alkyl, —CH2-N—(C1-5-alkyl)2, —C(=O)—O—C1-5-alkyl, —C(=O)—H, —C(=O)—C1-5-alkyl, —CH2-O—C(=O)-phenyl, —O—C(=O)-phenyl, —NH—S(=O)2-C1-5-alkyl, —NH—C(=O)—C1-5-alkyl, —C(=O)—NH—C1-5-alkyl, —C(=O)—NH2, —C(=O)—N(C1-5-alkyl)2, —Si(phenyl)2[C1-5-alkyl], pyrazolyl, pyrrolyl, (1,3)-dioxolanyl, phenyl, furyl(furanyl), thiazolyl, thiadiazolyl, thiophenyl(thienyl), phenoxy, benzyl and phenethyl, wherein the cyclic substituents themselves may in each case optionally be substituted with 1, 2, 3 or 4 substituents mutually independently selected from the group consisting of F, Cl, Br, I), —CF3, methyl, ethyl, methoxy and ethoxy.

Particularly preferably, the substituents may be selected, in each case mutually independently, from the group consisting of F, Cl, Br, I, —CN, —CH2-CN, —NO2, —OH, —SH, methyl, ethyl, n-propyl, iso-propyl, n-butyl, iso-butyl, sec-butyl, tert-butyl, n-pentyl, neo-pentyl, ethenyl, propenyl, ethynyl, propynyl, —CH2-O—CH3, —CH2-O—C2H5, —OH, —SH, —NH2, —CH2-NH2, —C(=O)—OH, —S—CH3, —S—C2H5, —S(=O)—CH3, —S(=O)—C2H5, —S(=O)2-CH3, —S(=O)2-C2H5, —O—CH3, —O—C2H5, —O—C3H7, —O—C(CH3)3, —CF3, —SF5, —CHF2, —CH2F, —O—CF3, —O—CHF2, —O—CH2F, C(=O)—CF3, —S—CF3, —S—CHF2, —S—CH2F, —S(=O)2-phenyl, pyrazolyl, pyrrolyl, —N(CH3)2, —N(C2H5)2, —NH—CH3, —NH—C2H5, —CH2-O—C(=O)-phenyl, —NH—S(=O)2-CH3, —C(=O)—O—CH3, —C(=O)—O—C2H5, —C(=O)—O—C(CH3)3, —C(=O)—H, —C(=O)—CH3, —C(=O)—C2H5, —C(=O)—C(CH3)3, —NH—C(=O)—CH3, —NH—C(=O)—C2H5, —O—C(=O)-phenyl, —C(=O)—NH2, —C(=O)—NH—CH3, —C(=O)—N(CH3)2, —Si(phenyl)2[C(CH3)3], phenyl, (1,3)-dioxolanyl, furyl(furanyl), thiadiazolyl, thiophenyl(thienyl), phenoxy and benzyl, wherein the cyclic substituents may themselves in each case optionally be substituted with 1, 2, 3 or 4 substituents mutually independently selected from the group consisting of F, Cl, Br, I, —CF3, methyl and methoxy.

For the purposes of the present invention, a mono- or polycyclic ring system should be understood to mean mono- or polycyclic hydrocarbon groups which may be saturated, unsaturated or aromatic and optionally comprise one or more heteroatoms as ring members. Such a mono- or polycyclic ring system may, for example, be fused (anellated) with a cycloaliphatic group, an aryl group or a heteroaryl group.

If a polycyclic ring system, such as for example a bicyclic ring system, is present, the various rings may in each case mutually independently be of a different degree of saturation, i.e. be saturated, unsaturated or aromatic. The heteroatoms of each ring may, in each case mutually independently, preferably be selected from the group consisting of oxygen, nitrogen and sulfur. Preferably a ring contains 0, 1, 2 or 3 heteroatoms. Preferably, the respective rings of the mono- or polycyclic ring system are 5-, 6- or 7-membered, particularly preferably 5- or 6-membered.

If one or more of the substituents R1a, R1b, R1c, R1d, R2 to R29 and M1 and M2 comprise a monocyclic or polycyclic ring system, which is mono- or polysubstituted, this may preferably optionally be substituted with 1, 2, 3, 4 or 5 substituents, which may mutually independently be selected from the group consisting of halogen, —CN, —NO2, —OH, —SH, —NH2, oxo (=O), thioxo (=S), —C(=O)—OH, —C1-5 alkyl, —C2-5 alkenyl, —C2-5 alkynyl, —(CH2)-O—C1-5-alkyl, —S—C1-5-alkyl, —O—C1-5-alkyl, —CF3, —SF5, —CHF2, —CH2F, —O—CF3, —O—CHF2, —O—CH2F, —C(=O)—CF3, —S—CF3, —S—CHF2, —S—CH2F, —S(=O)2-phenyl, —S(=O)2-C1-5-alkyl, —S(=O)—C1-5-alkyl, —NH—C1-5-alkyl, —N(C1-5-alkyl)(C1-5-alkyl), —C(=O)—O—C1-5-alkyl, —C(=O)—H, —C(=O)—C1-5-alkyl, —CH2-O—C(=O)-phenyl, —O—C(=O)-phenyl, —NH—S(=O)2-C1-5-alkyl, —NH—C(=O)—C1-5-alkyl, —C(=O)—NH2, —C(=O)—NH—C1-5-alkyl, —C(=O)—N(C1-5-alkyl)2, pyrazolyl, phenyl, furyl (furanyl), thiadiazolyl, thiophenyl (thienyl), phenoxy and benzyl, wherein the cyclic substituents may themselves in each case optionally be substituted with 1, 2, 3 or 4 substituents mutually independently selected from the group consisting of F, Cl, Br, I, methyl, ethyl, methoxy and ethoxy.

Particularly preferably, the substituents may be selected, in each case mutually independently, from the group consisting of F, Cl, Br, I, —CN, —NO2, —OH, —SH, methyl, ethyl, n-propyl, iso-propyl, n-butyl, iso-butyl, sec-butyl, tert-butyl, n-pentyl, neo-pentyl, ethenyl, propenyl, ethynyl, propynyl, —CH2-O—CH3, —CH2-O—C2H5, —OH, —SH, —NH2, oxo, thioxo, —C(=O)—OH, —S—CH3, —S—C2H5, —S(=O)—CH3, —S(=O)2-CH3, —S(=O)—C2H5, —S(=O)2-C2H5, —O—CH3, —O—C2H5, —O—C3H7, —O—C(CH3)3, —CF3, —SF5, —CHF2, —CH2F, —O—CF3, —O—CHF2, —O—CH2F, —C(=O)—CF3, —S—CF3, —S—CHF2, —S—CH2F, —S(=O)2-phenyl, pyrazolyl, —N(CH3)2, —N(C2H5)2, —NH—CH3, —NH—C2H5, —CH2-O—C(=O)-phenyl, —NH—S(=O)2-CH3, —C(=O)—O—CH3, —C(=O)—O—C2H5, —C(=O)—H, —C(=O)—CH3, —C(=O)—C2H5, —NH—C(=O)—CH3, —NH—C(=O)—C2H5, —O—C(=O)-phenyl, —C(=O)—NH2, —C(=O)—NH—CH3, —C(=O)—N(CH3)2, phenyl, furyl(furanyl), thiadiazolyl, thiophenyl(thienyl), phenoxy and benzyl, wherein the cyclic substituents may themselves in each case optionally be substituted with 1, 2, 3 or 4 substituents mutually independently selected from the group consisting of F, Cl, Br, I, methyl and methoxy.

If one of the above-stated substituents R1a, R1b, R1c, R1d and R2 to R29 comprises a linear or branched alkylene group, the alkylene group may preferably be selected from the group consisting of —(CH2)-, —(CH2)2-, —C(H)(CH3)-, —(CH2)3-, —(CH2)4-, —(CH2)5- and —C(C2H5)(H)—.

The person skilled in the art will understand that some of the substituted imidazo-3-yl-amine compounds of the general formula I according to the invention may be present in the form of tautomers, which the present invention also provides and which may in each case also be present as active ingredients in the pharmaceutical formulations described below.

Preference is given to substituted imidazo-3-yl-amine compounds of the general formula I, in which A1 represents a nitrogen atom or a C—R1a group,
A2 represents a nitrogen atom or a C—R1b group,
A3 represents a nitrogen atom or a C—R1c group,
A4 represents a nitrogen atom or a C—R1d group,
R1a, R1b, R1c, R1d, mutually independently, in each case represent a hydrogen; a halogen; —NO2; —CN; —NH2; —NHR4; —NR5R6; —NH—C(=O)—R7; —C(=O)—R8, —C(=O)—NH2; —C(=O)—NHR9; —C(=O)—NR10R11; —C(=O)—OR12; —(CH2)m-C(=O)—OR13 with m=1, 2, 3, 4 or 5; —O—C(=O)—R14; —(CH2)n-O—C(=O)—R15 with n=1, 2, 3, 4 or 5; —OR16; —(CH2)o-O—R17 with o=1, 2, 3, 4 or 5; —SR18; —(CH2)p-S(=O)t-R19 with p=1, 2, 3, 4 or 5 and t=0, 1, or 2; —NH—S(=O)2-R26R27; —S(=O)2-NR28R29, —SF5; a linear or branched, saturated or unsaturated, unsubstituted or at least monosubstituted aliphatic C1-10 group; a saturated or unsaturated, unsubstituted or at least monosubstituted, cycloaliphatic C3-8 group, optionally comprising at least one heteroatom as a ring member, which cycloaliphatic C3-8 group may be attached via a linear or branched C1-5 alkylene group; or represent an unsubstituted or at least monosubstituted 5- to 14-membered aryl or heteroaryl group, which may be attached via a linear or branched C1-5 alkylene group, or optionally R1a and R1b form an unsubstituted or at least monosubstituted anellated phenyl group with the C—C bridge joining them together or optionally R1b and R1c form an unsubstituted or at least monosubstituted anellated phenyl group with the C—C bridge joining them together, or optionally R1c and R1d form an unsubstituted or at least monosubstituted anellated phenyl group with the C—C bridge joining them together, R2 and R3, mutually independently, in each case represent a hydrogen; —C(=O)—R20; —(CH2)q-C(=O)—R21 with q=1, 2, 3, 4 or 5; —C(=O)—O—R22; —(CH2)r-C(=O)—O—R23 with r=1, 2, 3, 4 or 5; —C(=O)—NHR24; —(CH2)s-C(=O)—NHR25 with s=1, 2, 3, 4 or 5 represent a linear or branched, saturated or unsaturated, unsubstituted or at least monosubstituted aliphatic C1-16 group; a saturated or unsaturated, unsubstituted or at least monosubstituted cycloaliphatic C4-8 group optionally comprising at least one heteroatom as a ring member, which cycloaliphatic C4-8 group may be attached via a linear or branched C1-5 alkylene group; or represent an unsubstituted or at least monosubstituted 5- to 14-membered aryl or heteroaryl group, which may be attached via a linear or branched C1-5 alkylene group, or R2 and R3, together with the nitrogen atom joining them together as a ring member, form a saturated or unsaturated heterocycloaliphatic C4-10 group optionally comprising at least one further heteroatom as a ring member, which heterocycloaliphatic C4-10 group is optionally fused with an unsubstituted or at least monosubstituted mono- or polycyclic ring system, wherein the rings of the ring system are in each case 5-, 6- or 7-membered;

R4, R5, R6, R7, R9, R10, R11, R14 and R15, in each case mutually independently, represent a linear or branched, saturated or unsaturated aliphatic C1-4 group or represent an unsubstituted or at least monosubstituted 5- to 14-membered aryl or heteroaryl group, which may be attached via a linear or branched C1-5 alkylene group, R8, R12, R13, R16, R17, R18, R19, R20, R21, R22, R23, R24, R25, R26, R27, R28 and R29, in each case mutually independently, represent a hydrogen; a linear or branched, saturated or unsaturated aliphatic C1-4 group or an unsubstituted or at least monosubstituted 5- to 14-membered aryl or heteroaryl group, which may be attached via a linear or branched C1-5 alkylene group, M1 represents a 5- or 6-membered aryl or heteroaryl group, which may be substituted with at least one further substituent and is optionally fused with an unsubstituted or at least monosubstituted mono- or bicyclic ring system, wherein the rings of the ring system are in each case 5-, 6- or 7-membered, and M2 represents a 5- or 6-membered aryl or heteroaryl group, which may be unsubstituted or at least monosubstituted and may be fused with an unsubstituted or at least monosubstituted mono- or bicyclic ring system, wherein the rings of the ring system are in each case 5-, 6- or 7-membered, wherein the above-stated cycloaliphatic groups may optionally comprise 1, 2, 3, 4 or 5 heteroatom(s) as ring member(s), which may be selected, in each case mutually independently, from the group consisting of nitrogen, oxygen and sulfur, the above-stated heterocycloaliphatic groups may optionally comprise a further 1, 2, 3, 4 or 5 heteroatom(s) as ring member(s), which may be selected, in each case mutually independently, from the group consisting of nitrogen, oxygen and sulfur, the rings of the mono- or polycyclic ring system in each case optionally comprise 0, 1, 2 or 3 heteroatom(s) as ring member(s), which are selected mutually independently from the group consisting of oxygen, nitrogen and sulfur; and the above-stated heteroaryl groups may optionally comprise 1, 2, 3, 4 or 5 heteroatom(s) as ring member(s), which may be selected, in each case mutually independently, from the group consisting of nitrogen, oxygen and sulfur; in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted imidazo-3-yl-amine compounds of the above-stated general formula I, in which A1 represents a C—R1a group, A2 represents a C—R1b group, A3 represents a C—R1c group and A4 represents a C—R1d group, or A1 represents a nitrogen atom, A2 represents a C—R1b group, A3 represents a C—R1c group and A4 represents a C—R1d group, or A1 represents a C—R1a group, A2 represents a nitrogen atom, A3 represents a C—R1c group and A4 represents a C—R1d group, or A1 represents a C—R1a group, A2 represents a C—R1b group, A3 represents a nitrogen atom and A4 represents a C—R1d group, or A1 represents a C—R1a group, A2 represents a C—R1b group, A3 represents a C—R1c group and A4 represents a nitrogen atom, or A1 and A3 in each case represent a nitrogen atom, A2 represents a C—R1b group, and A4 represents a C—R1d group, and the respective remaining groups R1a, R1b, R1c, R1d, R2 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted imidazo-3-yl-amine compounds of the above-stated general formula I, in which A1 represents a C—R1a group, A2 represents a C—R1b group, A3 represents a C—R1c group and A4 represents a C—R1d group, or A1 represents a nitrogen atom, A2 represents a C—R1b group, A3 represents a C—R1c group and A4 represents a C—R1d group, or A1 represents a C—R1a group, A2 represents a nitrogen atom, A3 represents a C—R1c group and A4 represents a C—R1d group, or A1 represents a C—R1a group, A2 represents a C—R1b group, A3 represents a C—R1c group and A4 represents a nitrogen atom, and the respective remaining groups R1a, R1b, R1c, R1d, R2 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted imidazo-3-yl-amine compounds of the above-stated general formula I, in which A1 represents a C—R1a group, A2 represents a C—R1b group, A3 represents a C—R1c group and A4 represents a C—R1d group, or A1 represents a C—R1a group, A2 represents a nitrogen atom, A3 represents a C—R1c group and A4 represents a C—R1d group, or A1 represents a nitrogen atom, A2 represents a C—R1b group, A3 represents a C—R1c group and A4 represents a C—R1d group, and the respective remaining groups R1a, R1b, R1c, R1d, R2 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted imidazo-3-yl-amine compounds of the above-stated general formula I, in which R1a, R1b, R1c, R1d, mutually independently, in each case represent —H; —F; —Cl, —Br; —I; —NO2; —CN; —CF3; —SF5; —NH2; —S(=O)2-NH2; —NHR4; —NR5R6; —C(=O)—OR12; —(CH2)m-C(=O)—OR13 with m=1, 2 or 3; —O—C(=O)—R14; —OR16; —(CH2)o-O—R17 with o=1, 2 or 3; a linear or branched C1-10 alkyl group; or represent an unsubstituted or at least monosubstituted 5- or 6-membered aryl or heteroaryl group, which may be attached via a linear or branched C1-4 alkylene group, preferably R1a, R1b, R1c, R1d, mutually independently, in each case represent —H; —F; —Cl, —Br; —I; —NO2; —CN; —CF3; —SF5; —NH2; —S(=O)2-NH2; —NHR4; —NR5R6; —C(=O)—OR12; —(CH2)m-C(=O)—OR13 with m=1, 2 or 3; —O—C(=O)—R14; —OR16; —(CH2)o-O—R17 with o=1, 2 or 3; a linear or branched alkyl group selected from the group consisting of methyl, ethyl, n-propyl, iso-propyl, n-butyl, iso-butyl, sec-butyl and tert-butyl, or an aryl or heteroaryl group selected from the group consisting of phenyl, furanyl, thiophenyl and pyridinyl, which is in each case unsubstituted or substituted with 1, 2, 3, 4 or 5 substituents mutually independently selected from the group consisting of F, Cl, Br, —CN, methyl, ethyl, n-propyl, iso-propyl, n-butyl, sec-butyl, iso-butyl, tert-butyl, —OH, —O—CH3, —O—C2H5 and is optionally attached via a —(CH2), —(CH2)2 or —(CH2)3 group, particularly preferably R1a, R1b, R1c, R1d, mutually independently, in each case represent —H; —F; —Cl, —Br; —CF3; —CN; —SF5; —C(=O)—OR12; —S(=O)2-NH2; —(CH2)m-C(=O)—OR13 with m=1 or 2; —OR16; —(CH2)o-O—R17 with o=1 or 2; a linear or branched alkyl group selected from the group consisting of methyl, ethyl, n-propyl, iso-propyl, n-butyl, iso-butyl, sec-butyl and tert-butyl, or a phenyl group, which is unsubstituted or substituted with 1, 2 or 3 substituents mutually independently selected from the group consisting of F, Cl, Br, methyl, ethyl, n-propyl, iso-propyl, n-butyl, sec-butyl, iso-butyl, tert-butyl, —O—CH3, —O—C2H5 and optionally attached via a —(CH2), —(CH2)2 or —(CH2)3 group, very particularly preferably R1a, R1b, R1c, R1d, mutually independently, in each case represent —H; —F; —Cl, —Br; —CF3; —CN; —SF5; —S(=O)2-NH2; —C(=O)—OR12; —(CH2)m-C(=O)—OR13 with m=1; —OR16; —(CH2)o-O—R17 with o=1; a linear or branched alkyl group selected from the group consisting of methyl, ethyl, n-propyl, iso-propyl, n-butyl, iso-butyl, sec-butyl and tert-butyl; or represent an unsubstituted phenyl group, which is optionally attached via a —(CH2), —(CH2)2 or —(CH2)3 group, and the respective remaining groups A1, A2, A3, A4, R2 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted imidazo-3-yl-amine compounds of the above-stated general formula I, in which R1a and R1b or R1b and R1c or R1c and R1d, together with the C—C bridge joining them together, form an anellated phenyl group, which may be substituted with 1, 2, 3 or 4 substituents mutually independently selected from the group consisting of F, Cl, Br, —CN, methyl, ethyl, n-propyl, iso-propyl, n-butyl, sec-butyl, iso-butyl, tert-butyl, —OH, —O—CH3, —O—C2H5;

and the respective remaining groups A1, A2, A3, A4, R2 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

The person skilled in the art will understand that, where R1a and R1b, together with the C—C bridge joining them together, form an anellated phenyl group, the following general formula Ia is obtained:

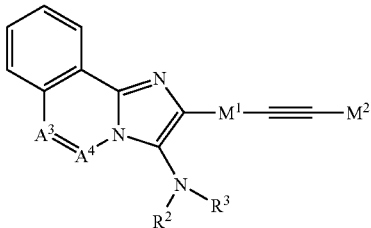

Ia

The person skilled in the art will understand that, where R1b and R1c, together with the C—C bridge joining them together, form an anellated phenyl group, the following general formula Ib is obtained:

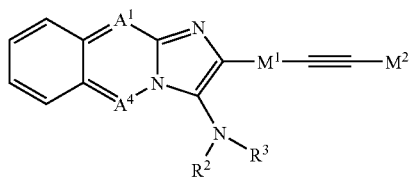

Ib

The person skilled in the art will understand that, where R1c and R1d, together with the C—C bridge joining them together, form an anellated phenyl group, the following general formula Ic is obtained:

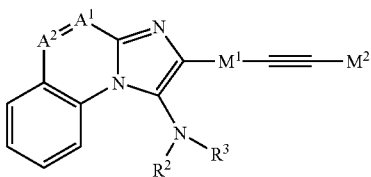

Ic

Also preferred are substituted imidazo-3-yl-amine compounds of the above-stated general formula I, in which R2 and R3, mutually independently, in each case represent a hydrogen; —C(=O)—R20; —(CH2)q-C(=O)—R21 with q=1, 2, 3, 4 or 5; —(CH2)r-C(=O)—O—R23 with r=1, 2, 3, 4 or 5; —C(=O)—NHR24; a linear or branched C1-16 alkyl group; an unsubstituted or at least monosubstituted C4-8 cycloalkyl group, which may be attached via a linear or branched C1-3 alkylene group; or represent an unsubstituted or at least monosubstituted, 5- or 6-membered aryl or heteroaryl group, which may be attached via a linear or branched C1-3 alkylene group, preferably R2 and R3, mutually independently, in each case represent a hydrogen; —C(=O)—R20; —(CH2)q-C(=O)—R21 with q=1, 2 or 3; —(CH2)r-C(=O)—O—R23 with r=1, 2 or 3; a linear or branched C1-10 alkyl group; a C4-8 cycloalkyl group, which is in each case unsubstituted or substituted with 1, 2, 3, 4 or 5 substituents mutually independently selected from the group consisting of F, Cl, Br, —CN, —CF3, —SF5, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group; or represent an aryl or heteroaryl group selected from the group consisting of phenyl, thiophenyl, furanyl and pyridinyl, which is in each case unsubstituted or substituted with 1, 2, 3, 4 or 5 substituents mutually independently selected from the group consisting of F, Cl, Br, —CN, —CF3, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group, particularly preferably R2 and R3, mutually independently, in each case represent a hydrogen; —C(=O)—R20; —(CH2)q-C(=O)—R21 with q=1 or 2; —(CH2)r-C(=O)—O—R23 with r=1 or 2; an alkyl group selected from the group consisting of methyl; ethyl; propyl; iso-propyl; n-butyl; tert-butyl; sec-butyl; iso-butyl; n-pentyl; n-hexyl; n-heptyl; n-octyl; (1,1,3,3)-tetramethyl-butyl; an unsubstituted cyclopentyl or cyclohexyl group, which may in each case be attached via a —(CH2)-, —(CH2)2 or —(CH2)3 group; or represent a phenyl or pyridinyl group, which is in each case unsubstituted or substituted with 1, 2 or 3 substituents mutually independently selected from the group consisting of F, Cl, Br, —CN, —CF3, methyl, ethyl, n-propyl, iso-propyl, tert-butyl, —O—CH3 and —O—C2H5 and is optionally attached via a —(CH2), —(CH2)2, —C(H)(CH3) or —(CH2)3 group, and the respective remaining groups A1, A2, A3, A4, R1a, R1b, R1c, R1d, R4 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted imidazo-3-yl-amine compounds of the above-stated general formula I, in which one the groups R2 and R3 represents a hydrogen; or represents a linear or branched C1-16 alkyl group and the other one of these two groups represents a hydrogen; —C(=O)—R20; —(CH2)q-C(=O)—R21 with q=1, 2, 3, 4 or 5; —(CH2)r-C(=O)—O—R23 with r=1, 2, 3, 4 or 5; —C(=O)—NHR24; a linear or branched C1-16 alkyl group; an unsubstituted or at least monosubstituted C4-8 cycloalkyl group, which may be attached via a linear or branched C1-3 alkylene group; or represents an unsubstituted or at least monosubstituted, 5- or 6-membered aryl or heteroaryl group, which may be attached via a linear or branched C1-3 alkylene group, preferably one of the two groups R2 and R3 represents a hydrogen; or represents a linear or branched C1-10 alkyl group and the other one of these two groups represents a hydrogen; —C(=O)—R20; —(CH2)q-C(=O)—R21 with q=1, 2 or 3; —(CH2)r-C(=O)—O—R23 with r=1, 2 or 3; a linear or branched C1-10 alkyl group; a C4-8 cycloalkyl group, which is in each case unsubstituted or substituted with 1, 2, 3, 4 or 5 substituents mutually independently selected from the group consisting of F, Cl, Br, —CN, —CF3, —SF5, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group; or represents an aryl or heteroaryl group selected from the group consisting of phenyl, thiophenyl, furanyl and pyridinyl, which is in each case unsubstituted or optionally substituted with 1, 2, 3, 4 or 5 substituents mutually independently selected from the group consisting of F, Cl, Br, —CN, —CF3, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group, particularly preferably one of the two groups R2 and R3 represents a hydrogen or an alkyl group selected from the group consisting of methyl; ethyl; propyl; iso-propyl; n-butyl; tert-butyl; sec-butyl; iso-butyl; n-pentyl; n-hexyl; n-heptyl; n-octyl; (1,1,3,3)-tetramethyl-butyl and the other one of these two groups represents a hydrogen; —C(=O)—R20; —(CH2)q-C(=O)—R21 with q=1 or 2; —(CH2)r-C(=O)—O—R23 with r=1 or 2; an alkyl group selected from the group consisting of methyl; ethyl; propyl; iso-propyl; n-butyl; tert-butyl; sec-butyl; iso-butyl; n-pentyl; n-hexyl; n-heptyl; n-octyl; (1,1,3,3)-tetramethyl-butyl, (1,1)-dimethyl-pentyl and (1,1)-dimethyl-butyl; an unsubstituted cyclopentyl or cyclohexyl group, which may in each case be attached via a —(CH2), —(CH2)2 or —(CH2)3 group; or represents a phenyl, 2-pyridinyl, 3-pyridinyl, 4-pyridinyl, 2-furanyl, 3-furanyl, 2-thiophenyl or 3-thiophenyl group, which is in each case unsubstituted or optionally substituted with 1, 2, 3, 4 or 5 substituents mutually independently selected from the group consisting of F, Cl, Br, —CN, —CF3, methyl, ethyl, n-propyl, iso-propyl, tert-butyl, —O—CH3 and —O—C2H5 and is optionally attached via a —(CH2), —(CH2)2, —C(H)(CH3) or —(CH2)3 group, and the respective remaining groups A1, A2, A3, A4, R1a, R1b, R1c, R1d, R4 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Likewise preferred are substituted imidazo-3-yl-amine compounds of the above-stated general formula I, in which R2 and R3, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl, which is in each case unsubstituted or optionally substituted with 1, 2, 3, 4 or 5 substituents mutually independently selected from the group consisting of F, Cl, Br, I, —CN, methyl, ethyl, n-propyl, iso-propyl, n-butyl, sec-butyl, iso-butyl, tert-butyl, —OH, oxo, thioxo, —O—CH3, —O—C2H5, —O—C3H7, —NH2, —N(CH3)2, —N(C2H5)2, —NH—CH3, —NH—C2H5, —O—CF3, —S—CF3, —S(=O)—CH3, —S(=O)—C2H5, —S(=O)2-CH3, —S(=O)2-C2H5, —C(=O)—OH, —C(=O)—H, —C(=O)—CH3, —C(=O)—C2H5, —C(=O)—N(CH3)2, —C(=O)—NH—CH3, —C(=O)—NH2, —C(=O)—O—CH3, —C(=O)—O—C2H5 and —C(=O)—O—C(CH3)3, preferably R2 and R3, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl;

and the respective remaining groups A1, A2, A3, A4, R1a, R1b, R1c, R1d, R4 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted imidazo-3-yl-amine compounds of the above-stated general formula I preferably, in which R4, R5, R6, R7, R9, R10, R11, R14 and R15, in each case mutually independently, represent a linear or branched C1-4 alkyl group or an unsubstituted or at least monosubstituted 5- to 14-membered aryl or heteroaryl group, which may be attached via a linear or branched C1-5 alkylene group, preferably R4, R5, R6, R7, R9, R10, R11, R14 and R15, in each case mutually independently, represent an alkyl group selected from the group consisting of methyl, ethyl, n-propyl, iso-propyl, n-butyl, iso-butyl, sec-butyl and tert-butyl, or represent an unsubstituted or at least monosubstituted 5- or 6-membered aryl or heteroaryl group, which may be attached via a linear or branched C1-3 alkylene group, particularly preferably R4, R5, R6, R7, R9, R10, R11, R14 and R15, in each case mutually independently, represent an alkyl group selected from the group consisting of methyl, ethyl, n-propyl and iso-propyl, or represent a phenyl group, which is in each case unsubstituted or substituted with 1, 2 or 3 substituents mutually independently selected from the group consisting of F, Cl, Br, —CN, —CF3, —SF5, methyl, ethyl, n-propyl, iso-propyl, tert-butyl, —O—CH3 and —O—C2H5 and is optionally attached via a —(CH2), —(CH2)2 or —(CH2)3 group, and in each case the remaining groups A1, A2, A3, A4, R1a, R1b, R1c, R1d, R2, R3, R8, R12, R13 and R16 to R29, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Also preferred are substituted imidazo-3-yl-amine compounds of the above-stated general formula I, in which R8, R12, R13, R16, R17, R18, R19, R20, R21, R22, R23, R24, R25, R26, R27, R28 and R29, in each case mutually independently, represent a hydrogen; a linear or branched C1-8 alkyl group, or an unsubstituted or at least monosubstituted 5- to 14-membered aryl or heteroaryl group, which may be attached via a linear or branched C1-5 alkylene group, preferably R8, R12, R13, R16, R17, R18, R19, R20, R21, R22, R23, R24, R25, R26, R27, R28 and R29, in each case mutually independently, represent a hydrogen; a linear or branched, saturated or unsaturated aliphatic C1-4 group or an unsubstituted or at least monosubstituted 5- to 6-membered aryl or heteroaryl group, which may be attached via a linear or branched C1-3 alkylene group, particularly preferably R8, R12, R13, R16, R17, R18, R19, R20, R21, R22, R23, R24, R25, R26, R27, R28 and R29, in each case mutually independently, represent a hydrogen; an alkyl group selected from the group consisting of methyl, ethyl, n-propyl and iso-propyl and tert-butyl, or represent a phenyl group, which is in each case unsubstituted or substituted with 1, 2 or 3 substituents mutually independently selected from the group consisting of F, Cl, Br, —CN, —CF3, —SF5, methyl, ethyl, n-propyl, iso-propyl, tert-butyl, —O—CH3 and —O—C2H5 and is optionally attached via a —(CH2), —(CH2)2 or —(CH2)3 group, and in each case the remaining groups A1, A2, A3, A4, R1a, R1b, R1c, R1d, R2 to R7, R9 to R11, R14 and R15, M1 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Likewise preferred are substituted imidazo-3-yl-amine compounds of the above-stated general formula I, in which M1 represents a 5- or 6-membered aryl or heteroaryl group, which may be substituted with at least one further substituent, wherein the heteroaryl group optionally comprises 1, 2, 3, 4 or 5 heteroatom(s) as ring member(s), which are mutually independently selected from the group consisting of nitrogen, oxygen and sulfur, preferably M1 represents an aryl or heteroaryl group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, imidazolyl, oxadiazolyl, triazolyl, diazinyl, triazinyl, tetrazinyl and tetrazolyl, which may be substituted with at least one further substituent, particularly preferably represents a group selected from the group consisting of groups 1 to 38,

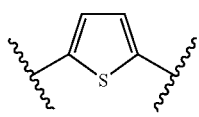

1

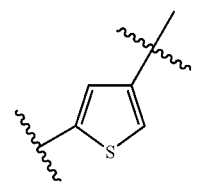

2

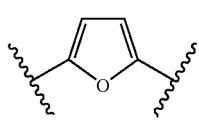

3

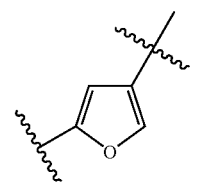

4

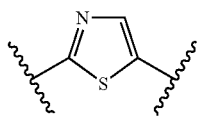

5

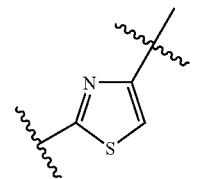

6

-continued

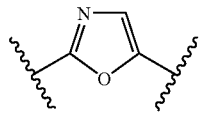

7

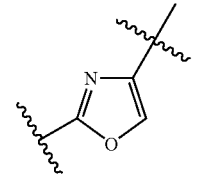

8

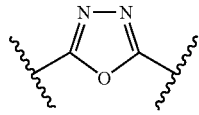

9

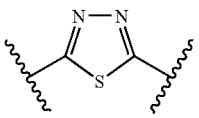

10

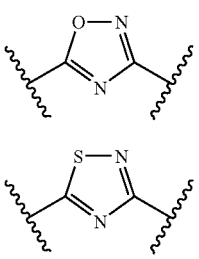

11

12

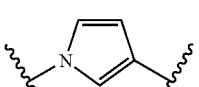

13

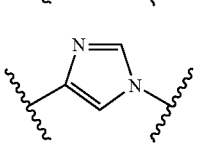

14

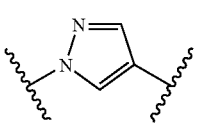

15

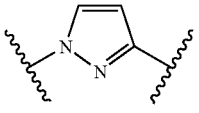

16

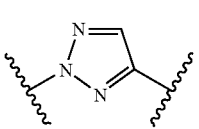

17

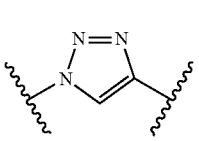

18

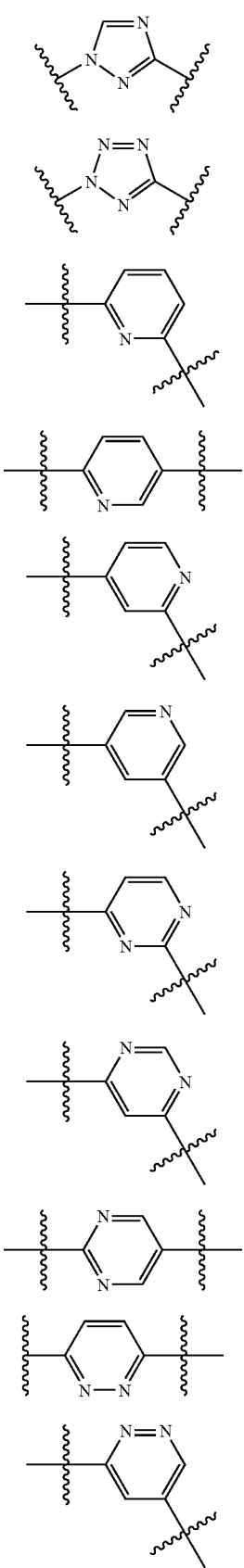
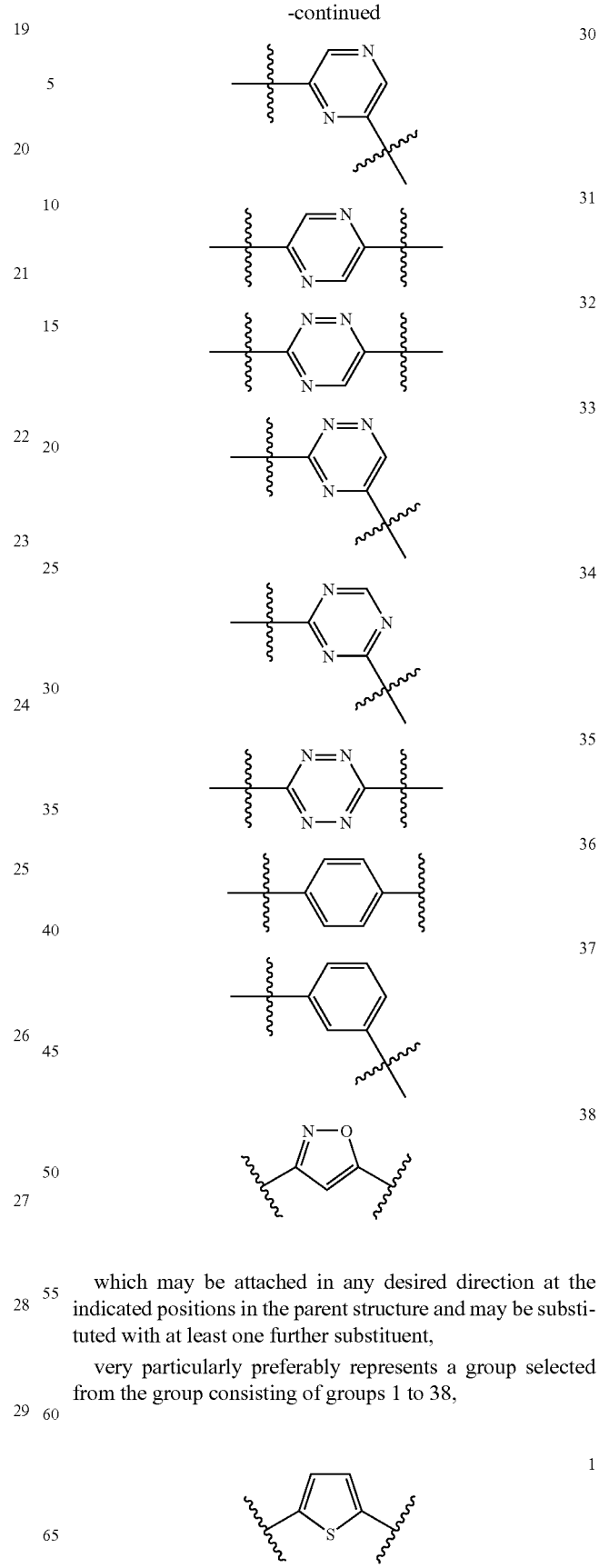
which may be attached in any desired direction at the indicated positions in the parent structure and may be substituted with at least one further substituent,
very particularly preferably represents a group selected from the group consisting of groups 1 to 38,
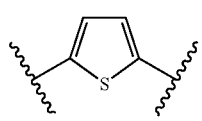

-continued
| | |
|---|---|
| 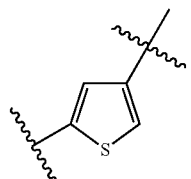 | 2 |
| 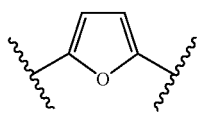 | 3 |
| 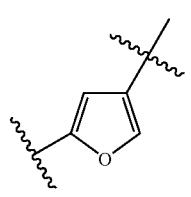 | 4 |
| 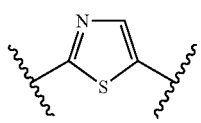 | 5 |
| 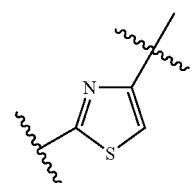 | 6 |
| 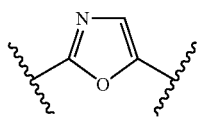 | 7 |
| 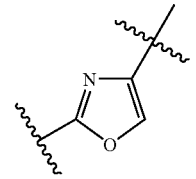 | 8 |
| 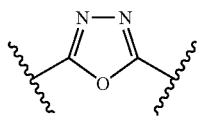 | 9 |
| 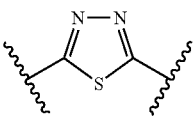 | 10 |
-continued
| | |
|---|---|
| 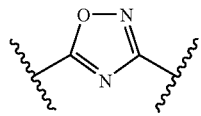 | 11 |
| 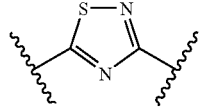 | 12 |
| 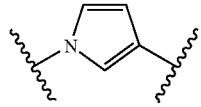 | 13 |
| 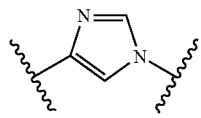 | 14 |
| 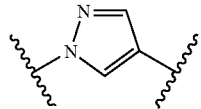 | 15 |
| 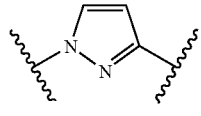 | 16 |
| 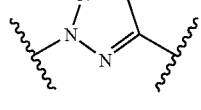 | 17 |
| 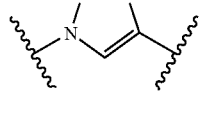 | 18 |
| 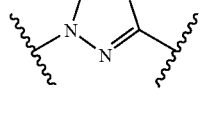 | 19 |
| 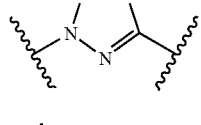 | 20 |
| 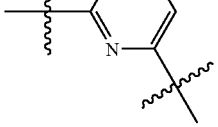 | 21 |
| | 22 |

-continued

23 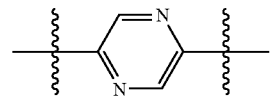

24 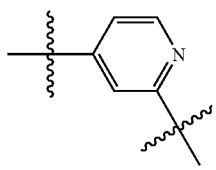

31 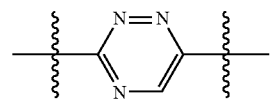

32 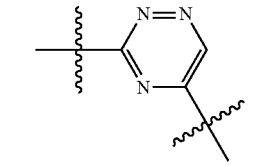

25 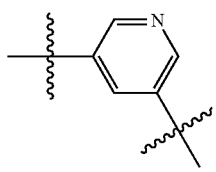

33 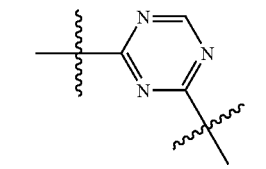

34 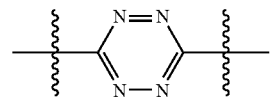

25 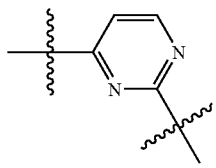

35 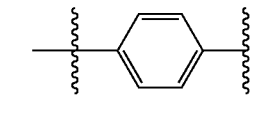

26 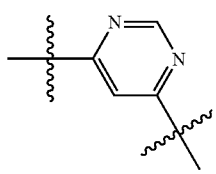

36 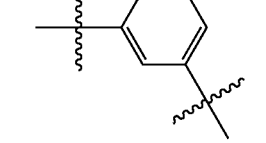

37 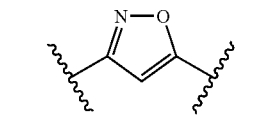

27 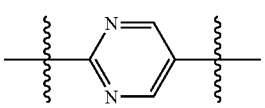

38

28 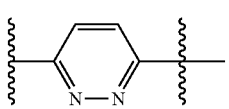

which may be attached in any desired direction at the indicated positions in the parent structure and is optionally substituted with 1, 2, 3 or 4 further substituents, which may mutually independently be selected from the group consisting of F, Cl, Br, —CN, —CH2-CN, —CF3, —SF5, methyl, ethyl, n-propyl, iso-propyl, n-butyl, sec-butyl, iso-butyl, tert-butyl, —OH, —O—CH3, —O—C2H5, —O—C3H7, —NH2, —N(CH3)2, —N(C2H5)2, —NO2, —O—CF3, —S—CF3, —SH, —C(=O)—CH3 and —C(=O)—C2H5, still more preferably represents a group selected from the group consisting of groups 1 to 9, 11, 21, 22 and 36 to 38, 29 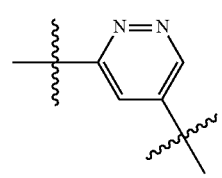

30 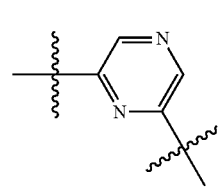

1 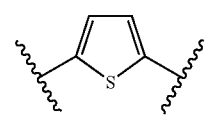

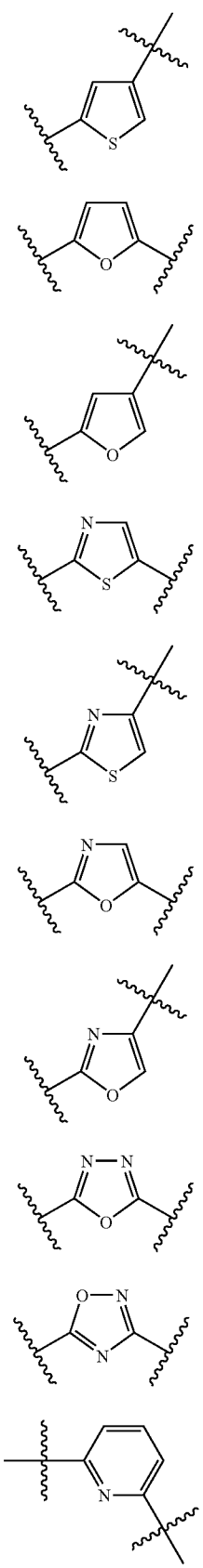

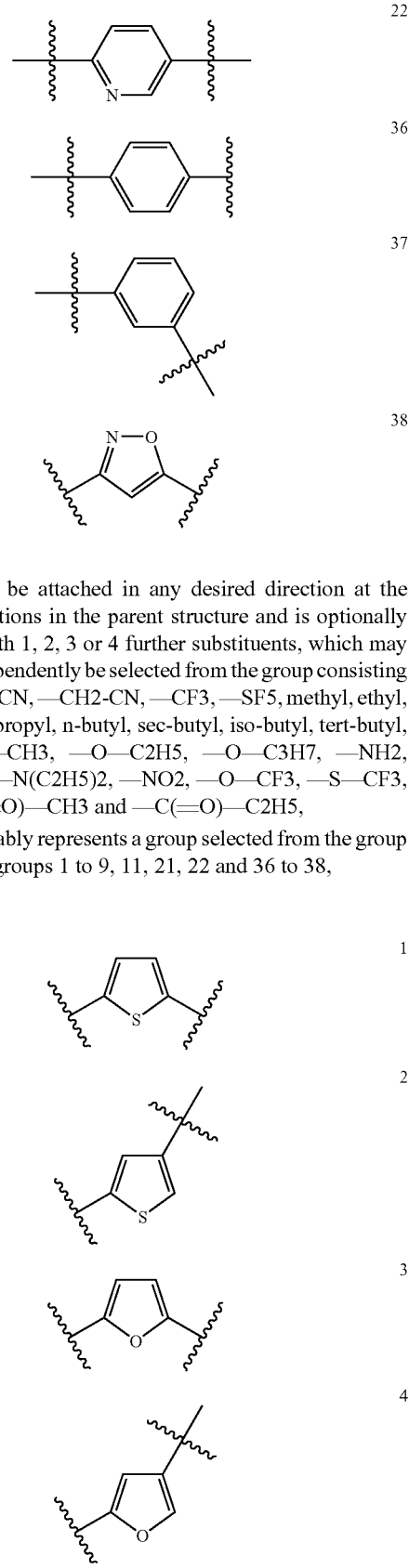

which may be attached in any desired direction at the indicated positions in the parent structure and is optionally substituted with 1, 2, 3 or 4 further substituents, which may mutually independently be selected from the group consisting of F, Cl, Br, —CN, —CH2-CN, —CF3, —SF5, methyl, ethyl, n-propyl, iso-propyl, n-butyl, sec-butyl, iso-butyl, tert-butyl, —OH, —O—CH3, —O—C2H5, —O—C3H7, —NH2, —N(CH3)2, —N(C2H5)2, —NO2, —O—CF3, —S—CF3, —SH, —C(=O)—CH3 and —C(=O)—C2H5, most preferably represents a group selected from the group consisting of groups 1 to 9, 11, 21, 22 and 36 to 38, -continued

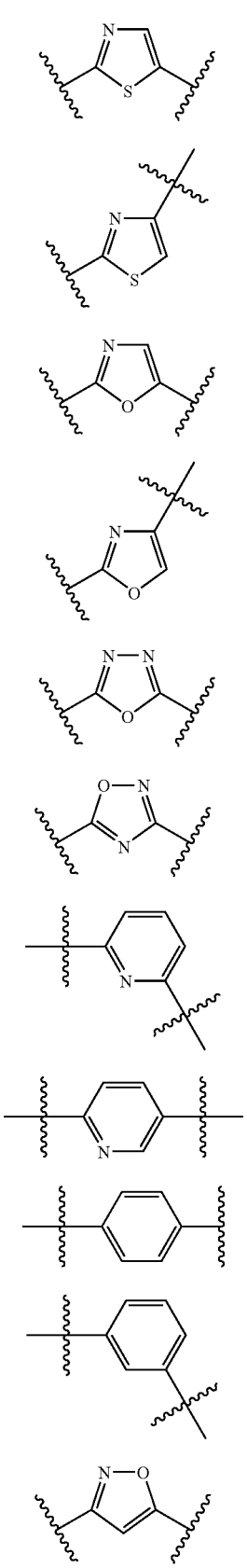

which may be attached in any desired direction at the indicated positions in the parent structure and is optionally substituted with 1 or 2 further substituents, which may mutually independently be selected from the group consisting of F, Cl, Br, —CN, —CH2-CN, —CF3, —SF5, methyl, ethyl, n-propyl, iso-propyl, tert-butyl, —O—CH3 and —O—CF3, and the respective remaining groups A1, A2, A3, A4, R1a, R1b, R1c, R1d, R2 to R29 and M2 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Also preferred are substituted imidazo-3-yl-amine compounds of the above-stated general formula I, in which M2 represent an unsubstituted or at least monosubstituted 5- or 6-membered aryl or heteroaryl group, wherein the heteroaryl group comprises 1, 2, 3, 4 or 5 heteroatom(s) as ring member(s), which are mutually independently selected from the group consisting of nitrogen, oxygen and sulfur, and wherein the aryl or heteroaryl group may be fused with an unsubstituted or at least monosubstituted mono- or bicyclic ring system, wherein the rings of the ring system are in each case 5- or 6-membered and may in each case comprise 1, 2, 3 or 4 heteroatom(s) as ring member(s), which are mutually independently selected from the group consisting of nitrogen, oxygen and sulfur, preferably M2 represents a group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, wherein the group may in each case be unsubstituted or at least monosubstituted, particularly preferably M2 represents a group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, wherein the respective group may be unsubstituted or optionally substituted with 1, 2, 3, 4 or 5 substituents, which are mutually independently selected from the group consisting of F, Cl, Br, —CN, —CF3, —SF5, —S—CH3, —S—C2H5, methyl, ethyl, n-propyl, iso-propyl, n-butyl, sec-butyl, iso-butyl, tert-butyl, ethenyl, propenyl, —OH, —O—CH3, —O—C2H5, —O—C3H7, —NH2, —N(CH3)2, —NH—CH3, —CH2-NH2, —N(C2H5)2, —NO2, —O—CF3, —C(=O)—H, —S—CF3, —SH, —C(=O)—O—CH3, —C(=O)—O—C2H5, phenyl, pyrrolyl, (1,3)-dioxolanyl, —Si(phenyl)2[C(CH3)3], —C(=O)—CH3, —C(=O)—C2H5, NH—S(=O)2-CH3, —NH—S(=O)2-C2H5, —S(=O)2-NH2, —S(=O)2-NH—CH3, —CH2-OH, —C(=O)—OH, —CH2- O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

very particularly preferably M2 represents a group selected from the group consisting of groups 1 to 36, -continued
| # | | # | |
|---|---|---|---|
| 1 | 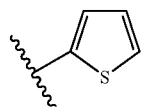 | 11 | 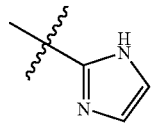 |
| 2 | 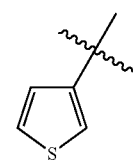 | 12 | 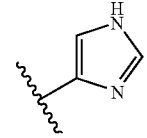 |
| 3 | 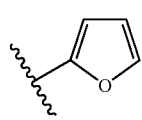 | 13 | 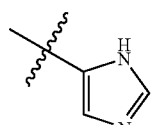 |
| 4 | 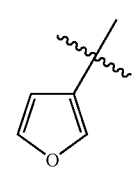 | 14 | 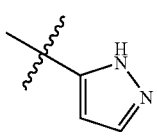 |
| 5 | 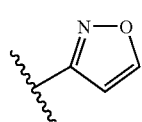 | 15 | 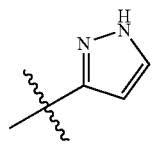 |
| 6 | 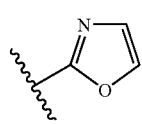 | 16 | 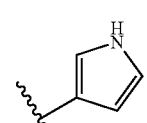 |
| 7 | 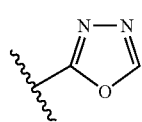 | 17 | 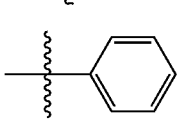 |
| 8 | 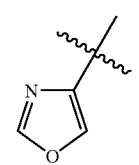 | 18 | 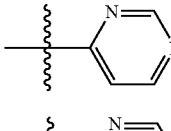 |
| 9 | 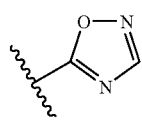 | 19 | 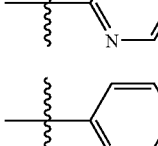 |
| 10 | 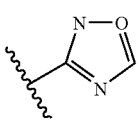 | 20 | 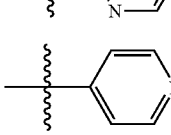 |
| | | 21 | 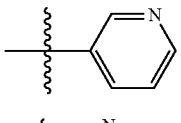 |
| | | 22 | 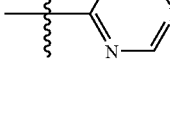 |

-continued

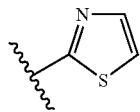
24

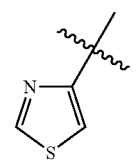
25

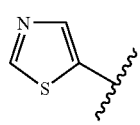
26

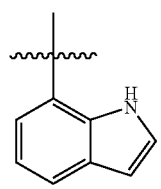
27

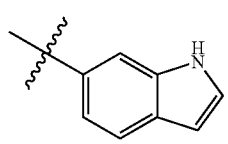
28

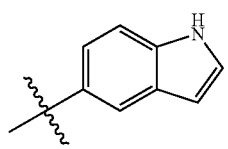
29

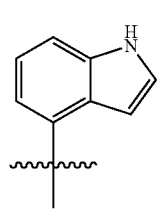
30

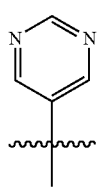
31

-continued

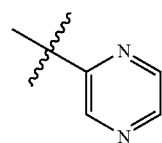
32

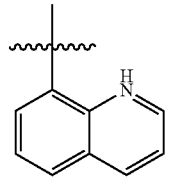
33

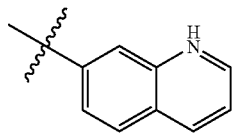
34

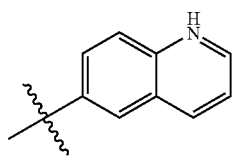
35

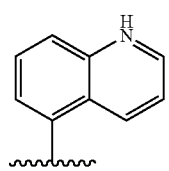
36 which is attached at the indicated point in the parent structure, wherein the respective group may be unsubstituted or optionally substituted with 1, 2, 3, 4, or 5 substituents, which are mutually independently selected from the gropu consisting of F, Cl, Br, —CN, —CF3, —SF5, —S—CH3, —S—C2H5, methyl, ethyl, n-propyl, iso-propyl, n-butyl, sec-butyl, iso-butyl, tert-butyl, ethenyl, propenyl, —OH, —O—CH3, —O—C2H5, —O—C3H7, —NH2, —N(CH3)2, —NH—CH3, —CH2-NH2, —N(C2H5)2, —NO2, —O—CF3, —S—CF3, —SH, —C(=O)—H, —C(=O)—O—CH3, —C(=O)—O—C2H5, phenyl, pyrrolyl, (1,3)-dioxolanyl, Si(phenyl)2[C(CH3)3], —C(=O)—CH3, —C(=O)—C2H5, NH—S(=O)2-CH3, —NH—S(=O)2-C2H5, —S(=O)2-NH2, —S(=O)2-NH—CH3, —CH2-OH, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

most preferably M2 represents a group selected from the group consisting of groups 1 to 36,

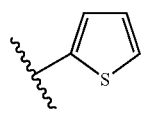
1

-continued
| | |
|---|---|
| 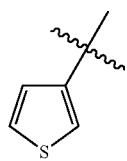 | 2 |
| 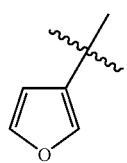 | 3 |
| 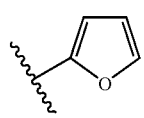 | 4 |
| 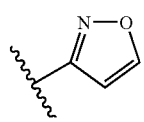 | 5 |
| 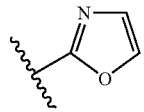 | 6 |
| 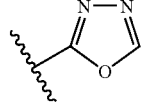 | 7 |
| 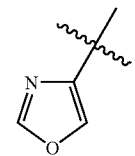 | 8 |
| 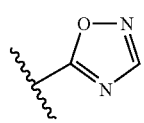 | 9 |
| 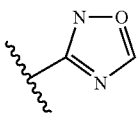 | 10 |
| 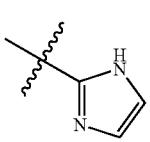 | 11 |
-continued
| | |
|---|---|
| 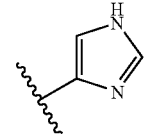 | 12 |
| 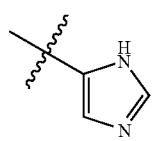 | 13 |
| 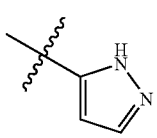 | 14 |
| 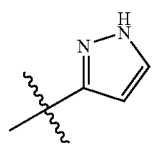 | 15 |
| 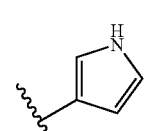 | 16 |
| 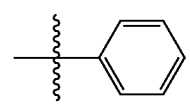 | 17 |
| 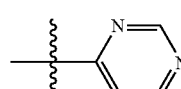 | 18 |
| 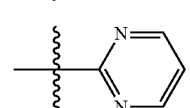 | 19 |
| 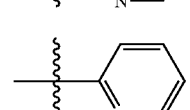 | 20 |
| 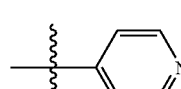 | 21 |
| 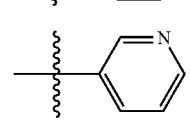 | 22 |
| 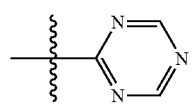 | 23 |
| 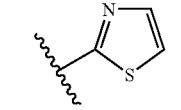 | 24 |

-continued

25
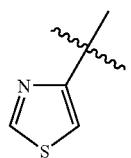

26
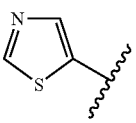

27
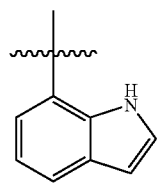

28
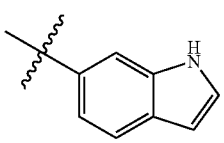

29
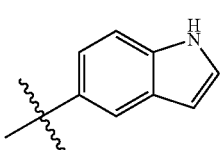

30
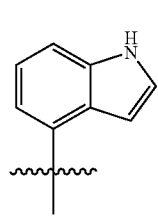

31
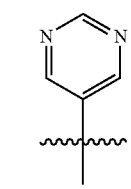

32
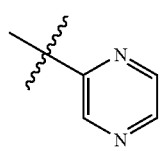

33
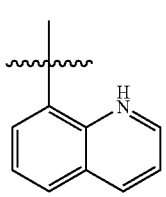

-continued

34
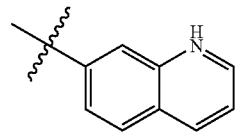

35
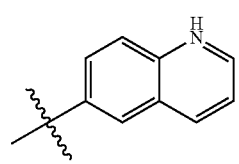

36
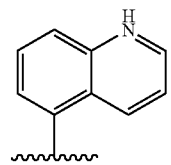

which is attached at the indicated point in the parent structure, wherein the respective group may be unsubstituted or substituted with 1, 2 or 3 substituents, which are mutually independently selected from the group consisting of F, Cl, Br, —CN, —CF3, —SF5, —S—CH3, —S—C2H5, methyl, ethyl, iso-propyl, tert-butyl, ethenyl, propenyl, —O—CH3, —O—C2H5, —NH2, —N(CH3)2, —NH—CH3, —CH2-NH2, —O—CF3, —C(=O)—H, —C(=O)—O—CH3, —C(=O)—O—C2H5, phenyl, pyrrolyl, (1,3)-dioxolanyl, —Si(phenyl)2[C(CH3)3)], —NO2, NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

and the respective remaining groups A1, A2, A3, A4, R1a, R1b, R1c, R1d, R2 to R29 and M1 have the above-stated meaning, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts, or in each case in the form of corresponding solvates.

Particular preference is given to substituted imidazo-3-yl-amine compounds of the general formula I, A1 represents a C—R1a group, A2 represents a C—R1b group, A3 represents a C—R1c group and A4 represents a C—R1d group; or A1 represents a nitrogen atom, A2 represents a C—R1b group, A3 represents a C—R1c group and A4 represents a C—R1d group; or A1 represents a C—R1a group, A2 represents a nitrogen atom, A3 represents a C—R1c group and A4 represents a C—R1d group;

R1a, R1b, R1c, R1d, mutually independently, in each case represent —H; —F; —Cl, —Br; —I; —NO2; —CN; —CF3; —SF5; —NH2; —S(=O)—NH2, —NHR4; —NR5R6; —C(=O)—OR12; —(CH2)m-C(=O)—OR13 with m=1, 2 or 3; —O—C(=O)—R14; —OR16; —(CH2)o-O—R17 with o=1, 2 or 3; a linear or branched alkyl group selected from the group consisting of methyl, ethyl, n-propyl, iso-propyl, n-butyl, iso-butyl, sec-butyl and tert-butyl, or an aryl or heteroaryl group selected from the group consisting of phenyl, furanyl, thiophenyl and pyridinyl, which is in each case unsubstituted or substituted with 1, 2, 3, 4 or 5 substituents mutually independently selected from the group consisting of F, Cl, Br, —CN, methyl, ethyl, n-propyl, iso-propyl, n-butyl, sec-butyl, iso-butyl, tert-butyl, —OH, —O—CH3, —O—C2H5 and optionally attached via a —(CH2)-, —(CH2)2- or —(CH2)3 group;

or optionally R1a and R1b or optionally R1b and R1c or optionally R1c and R1d, together with the C—C bridge joining them together, form an anellated phenyl group, which may be substituted with 1, 2, 3 or 4 substituents mutually independently selected from the group consisting of F, Cl, Br, —CN, methyl, ethyl, n-propyl, iso-propyl, n-butyl, sec-butyl, iso-butyl, tert-butyl, —OH, —O—CH3, —O—C2H5;

R2 and R3, mutually independently, in each case represent a hydrogen; —C(=O)—R20; —(CH2)q-C(=O)—R21 with q=1, 2 or 3; —(CH2)r-C(=O)—O—R23 with r=1, 2 or 3; a linear or branched C1-10 alkyl group; a C4-8 cycloalkyl group, which is in each case unsubstituted or substituted with 1, 2, 3, 4 or 5 substituents mutually independently selected from the group consisting of F, Cl, Br, —CN, —CF3, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group; or represent an aryl or heteroaryl group selected from the group consisting of phenyl, thiophenyl, furanyl and pyridinyl, which is in each case unsubstituted or substituted with 1, 2, 3, 4 or 5 substituents mutually independently selected from the group consisting of F, Cl, Br, —CN, —CF3, methyl, ethyl, n-propyl, iso-propyl, n-butyl, sec-butyl, iso-butyl, tert-butyl, —OH, —O—CH3 and —O—C2H5 and is optionally attached via a linear or branched C1-3 alkylene group;

or R2 and R3, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl, which may be in each case unsubstituted or optionally substituted with 1, 2, 3, 4 or 5 substituents mutually independently selected from the group consisting of F, Cl, Br, I, —CN, methyl, ethyl, n-propyl, iso-propyl, n-butyl, sec-butyl, iso-butyl, tert-butyl, —OH, oxo, thioxo, —O—CH3, —O—C2H5, —O—C3H7, —NH2, —N(CH3)2, —N(C2H5)2, —NH—CH3, —NH—C2H5, —O—CF3, —S—CF3, —S(=O)—CH3, —S(=O)—C2H5, —S(=O)2-CH3, —S(=O)2-C2H5, —C(=O)—OH, —C(=O)—H, —C(=O)—CH3, —C(=O)—C2H5, —C(=O)—N(CH3)2, —C(=O)—NH—CH3, —C(=O)—NH2, —C(=O)—O—CH3, —C(=O)—O—C2H5 and —C(=O)—O—C(CH3)3;

R4, R5, R6 and R14, in each case mutually independently, represent an alkyl group selected from the group consisting of methyl, ethyl, n-propyl and iso-propyl, or represent a phenyl group, which is in each case unsubstituted or substituted with 1, 2 or 3 substituents mutually independently selected from the group consisting of F, Cl, Br, —CN, —CF3, —SF5, methyl, ethyl, n-propyl, iso-propyl, tert-butyl, —O—CH3 and —O—C2H5 and is optionally attached via a —(CH2), —(CH2)2 or —(CH2)3 group;

R12, R13, R16, R17, R20, R21 and R23, in each case mutually independently, represent a hydrogen; an alkyl group selected from the group consisting of methyl, ethyl, n-propyl, iso-propyl and tert-butyl, or a phenyl group, which is in each case unsubstituted or substituted with 1, 2 or 3 substituents mutually independently selected from the group consisting of F, Cl, Br, —CN, —CF3, —SF5, methyl, ethyl, n-propyl, iso-propyl, tert-butyl, —O—CH3 and —O—C2H5 and is optionally attached via a —(CH2), —(CH2)2 or —(CH2)3 group;

M1 represents a group selected from the group consisting of groups 1, 9, 11, 21, 22 and 36 to 38,

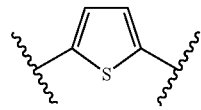

1

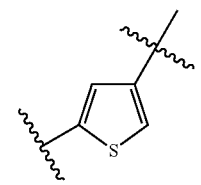

2

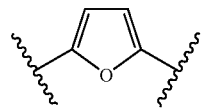

3

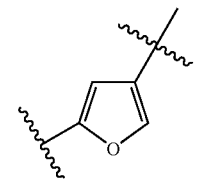

4

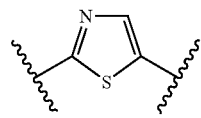

5

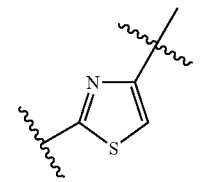

6

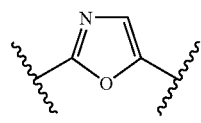

7

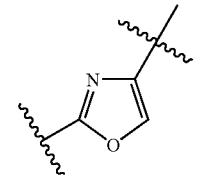

8

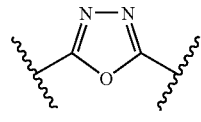

9

-continued

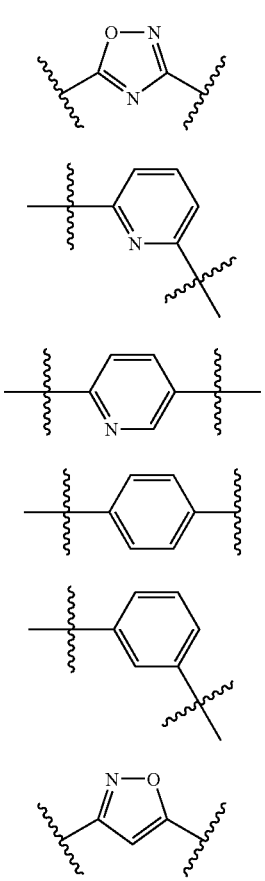

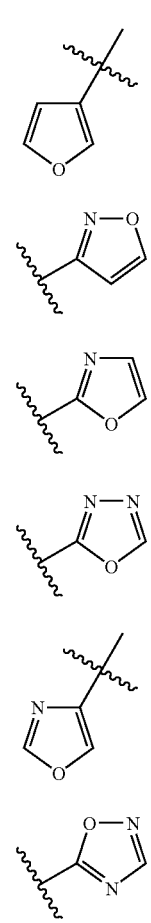

which may in each case be linked in any desired direction via the positions indicated with a wavy line to the bicyclic ring system and to the carbon atom of the triple bond and is optionally substituted with 1 or 2 further substituents, which are mutually independently selected from the group consisting of F, Cl, Br, —CN, —CH2-CH, —CF3, —SF5, methyl, ethyl, n-propyl, iso-propyl, n-butyl, iso-butyl, sec-butyl, tert-butyl, —O—CH3 and —O—CF3; and M2 represents a group selected from the group consisting of groups 1 to 36,

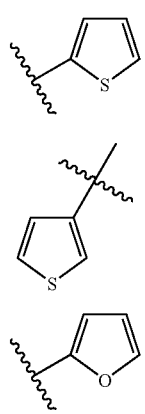

-continued
15
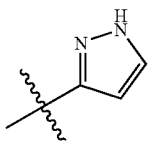
16
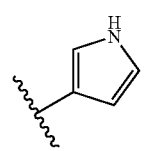
17
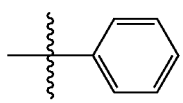
18
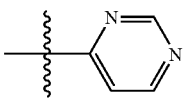
19
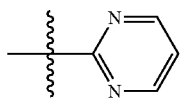
20
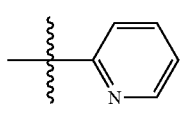
21
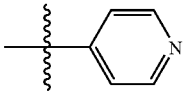
22
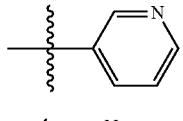
23
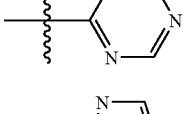
24
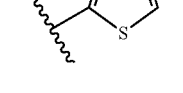
25
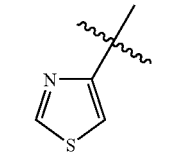
-continued
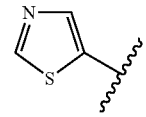
26
27
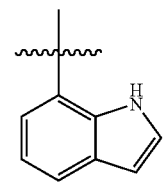
28
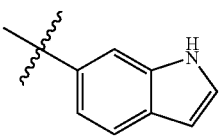
29
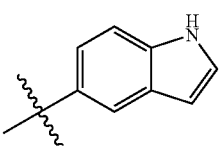
30
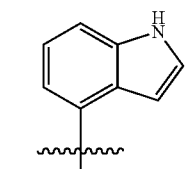
31
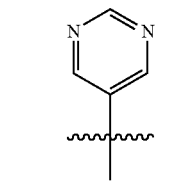
32
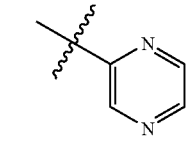
33
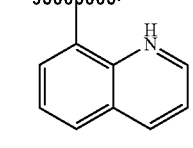
34
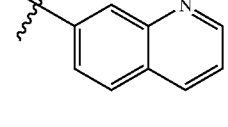

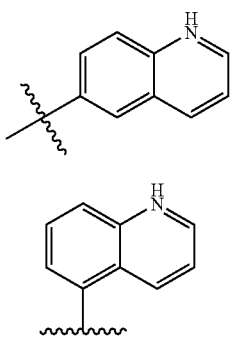

which is in each case linked via the position indicated with a wavy line to the carbon atom of the triple bond and is unsubstituted or optionally substituted with 1, 2 or 3 substituents, which are mutually independently selected from the group consisting of F, Cl, Br, —CN, —CF3, —SF5, —S—CH3, —S—C2H5, methyl, ethyl, n-propyl, iso-propyl, n-butyl, tert-butyl, ethenyl, propenyl, —O—CH3, —O—C2H5, —NH2, —N(CH3)2, —NH—CH3, —CH2-NH2, —O—CF3, —C(=O)—H, —C(=O)—O—CH3, —C(=O)—O—C2H5, phenyl, pyrrolyl, (1,3)-dioxolanyl, —Si(phenyl)2[C(CH3)3], —NO2, NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2- O—CH3, —C(=O)—NH2, —C(=O)—NH—CH3, —NH—C(=O)—CH3, —S(=O)2-N(CH3)2, —NH—S(=O)2-OH and —NH—C(=NH)—NH2;

in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particular preference is given to substituted imidazo-3-yl-amine compounds of the general formula I,

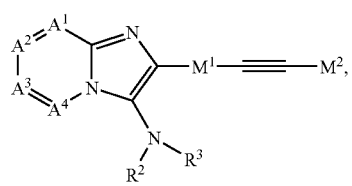

in which

A1 represents a C—R1a group, A2 represents a C—R1b group, A3 represents a C—R1c group and A4 represents a C—R1d group, or A1 represents a nitrogen atom, A2 represents a C—R1b group, A3 represents a C—R1c group and A4 represents a C—R1d group, or A1 represents a C—R1a group, A2 represents a nitrogen atom, A3 represents a C—R1c group and A4 represents a C—R1d group, R1a, R1b, R1c, R1d, in each case mutually independently, represent a hydrogen; —OR16; —F; —Cl; —Br; —CF3, —CN; —S(=O)2-NH2; —C(=O)—OR12, an alkyl group selected from the group consisting of methyl, ethyl, n-propyl, iso-propyl, n-butyl, sec-butyl, iso-butyl and tert-butyl; a phenyl group; a benzyl group; a phenethyl group or a (3-phenyl)-prop-1-yl group, or optionally R1a and R1b, together with the C—C bridge joining them together, form an unsubstituted anellated phenyl group;

or optionally R1c and R1d, together with the C—C bridge joining them together, form an unsubstituted anellated phenyl group;

R2 and R3, mutually independently, in each case represent a hydrogen; —C(=O)—R20; —(CH2)q-C(=O)—R21 with q=1; —(CH2)r-C(=O)—O—R23 with r=1; an alkyl group selected from the group consisting of methyl; ethyl; propyl; iso-propyl; n-butyl; tert-butyl; sec-butyl; iso-butyl; n-pentyl; n-hexyl; n-heptyl; n-octyl; (1,1,3,3)-tetramethyl-butyl; (1,1)-dimethyl-pentyl and (1,2)-dimethylbutyl; an unsubstituted cyclopentyl or cyclohexyl group, which may in each case be attached via a —(CH2), —(CH2)2 or —(CH2)3 group; or a phenyl, pyridinyl, thiophenyl or furanyl group, which is in each case unsubstituted or optionally substituted with 1, 2, 3, 4 or 5 substituents mutually independently selected from the group consisting of F, Cl, Br, —CN, —CF3, methyl, ethyl, n-propyl, iso-propyl, n-butyl, sec-butyl, iso-butyl, tert-butyl, —O—CH3 and —O—C2H5 and is optionally attached via a —(CH2), —(CH2)2, —(CH(CH3) or —(CH2)3 group, or R2 and R3, together with the nitrogen atom joining them together as a ring member, form a heterocycloaliphatic group selected from the group consisting of pyrrolidinyl, piperidinyl, piperazinyl and morpholinyl, R12 represents a hydrogen or an alkyl group selected from the group consisting of methyl, ethyl, n-propyl, iso-propyl and tert-butyl;

R16, R20, R21 and R23, in each case mutually independently represent an alkyl group selected from the group consisting of methyl, ethyl, n-propyl, iso-propyl and tert-butyl, or a phenyl group, which is in each case unsubstituted or substituted with 1 or 2 substituents mutually independently selected from the group consisting of F, Cl, Br, methyl, ethyl, —O—CH3 and —O—C2H5 and is optionally attached via a —(CH2) group, M1 represents a group selected from the group consisting of groups 1 to 6, 21, 22, 36 and 37,

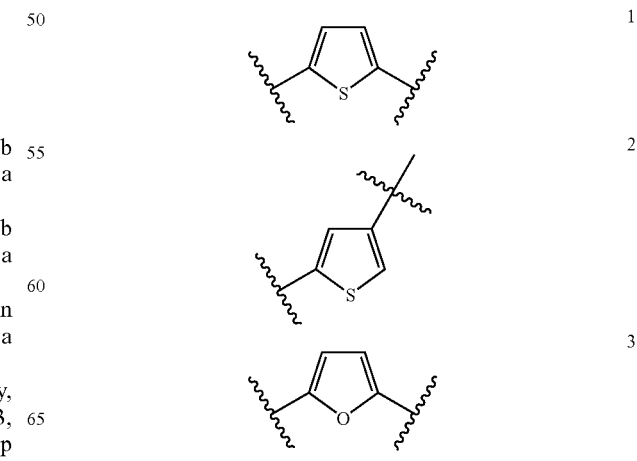

-continued

4
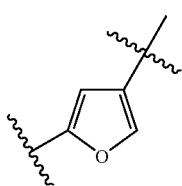

5
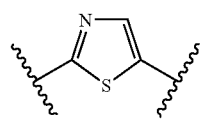

6
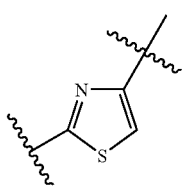

21
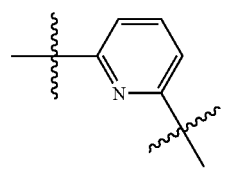

22
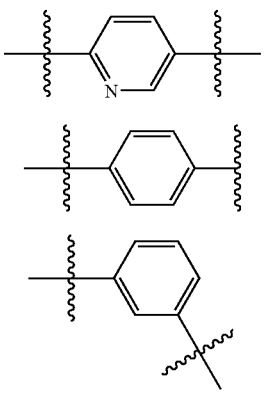

which may be attached in any desired direction at the indicated positions in the parent structure and is optionally substituted with 1 or 2 further substituents, which may mutually independently be selected from the group consisting of F, Cl, Br, —CN, —CH2-CN, —CF3, —SF5, methyl, ethyl, n-propyl, iso-propyl, tert-butyl, —O—CH3 and —O—CF3, and M2 represents a group selected from the group consisting of phenyl, 2-pyridinyl, 3-pyridinyl, 4-pyridinyl, 2-thiazolyl, 4-thiazolyl, 5-thiazolyl, 4-indolyl, 5-indolyl, 6-indolyl, 7-indolyl, 2-thiophenyl, 3-thiophenyl, 2-imidazolyl, 4-imidazolyl, 5-imidazolyl, 2-pyrimidinyl, 4-pyrimidinyl, 5-pyrimidinyl, 2-pyrazinyl, 5-quinolinyl, 6-quinolinyl, 7-quinolinyl and 8-quinolinyl, wherein the respective group is unsubstituted or optionally substituted with 1, 2, 3, 4 or 5 substituents, which are mutually independently selected from the group consisting of F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, NH—S(=O)2-CH3, —NH—S(=O)2-C2H5, —S(=O)2-NH2, —S(=O)2-NH—CH3, - CH2-OH, —C(=O)—CH3, —C(=O)—OH, —CH213 O—CH3, —C(=O)—NH2, —C(=O)—NH—CH3, —NH—C(=O)—CH3, —NH—C(=NH)—NH2, —NH—S(=O)2-OH; —S(=O)2-N(CH3)2 and —Si(phenyl)2[C(CH3)3], in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of corresponding salts or in each case in the form of corresponding solvates.

Very particularly preferred compounds are those of the general formula Id,

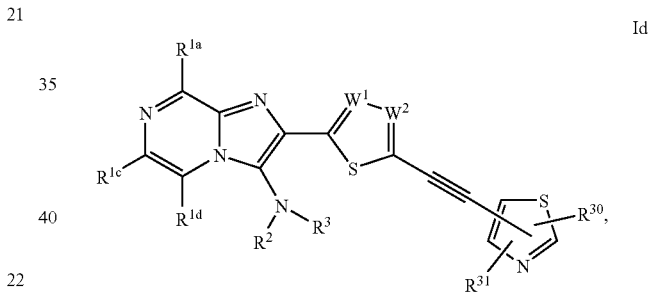

Id in which R1a, R1c, R1d, R2 and R3 in each case have the above-stated meaning;

W1 represents C and W2 represents C
or W1 represents C and W2 represents N
or W1 represents N and W2 represents C; and R30 and R31, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2- O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula Ie,

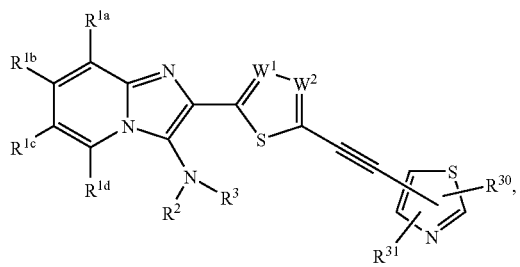

in which R1a, R1b, R1c, R1d, R2 and R3 in each case have the above-stated meaning;
W1 represents C and W2 represents C
or W1 represents C and W2 represents N
or W1 represents N and W2 represents C; and
R30 and R31, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)-OCH3, —C(=O)—O—C2H5, phenyl, pyrrolyl, (1,3)-dioxolanyl, —Si(phenyl)2 [C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2- O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula If,

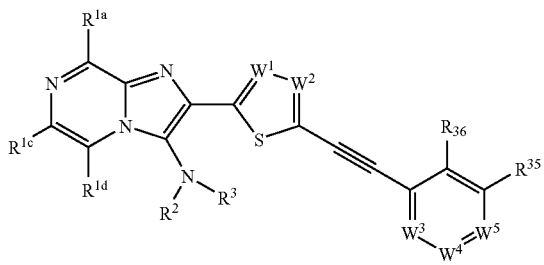

in which
R1a, R1c, R1d, R2 and R3 in each case have the above-stated meaning;
W1 represents C and W2 represents C
or W1 represents C and W2 represents N
or W1 represents N and W2 represents C;
W3 represents C—R32; W4 represents C—R33 and W5 represents C—R34;
or one of the groups W3, W4 and W5 represent N and the other two groups selected from the group consisting of W3, W4 and W5 represent C—R32 or C—R33;
and R32, R33, R34, R35 and R36, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula Ig,

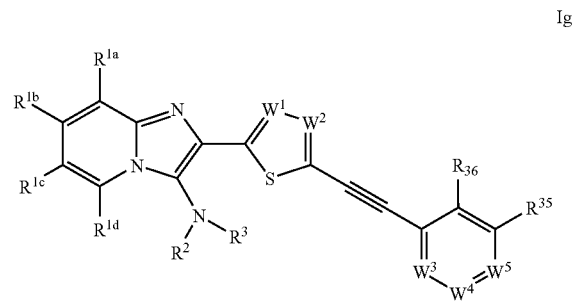

in which
R1a, R1b, R1c, R1d, R2 and R3 in each case have the above-stated meaning;
W1 represents C and W2 represents C
or W1 represents C and W2 represents N
or W1 represents N and W2 represents C;
W3 represents C—R32; W4 represents C—R33 and W5 represents C—R34;
or one of the groups W3, W4 and W5 represent N and the other two groups selected from the group consisting of W3, W4 and W5 represent C—R32 or C—R33;
and R32, R33, R34, R35 and R36, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula Ih,

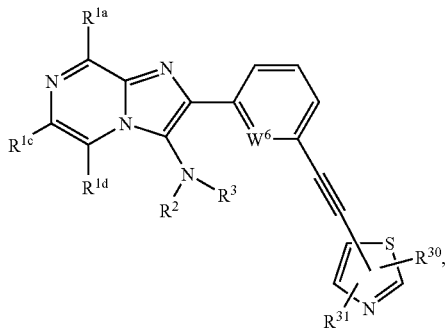

in which
R1a, R1c, R1d, R2 and R3 in each case have the above-stated meaning;

W6 represents C or N; and

R30 and R31, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula Ik,

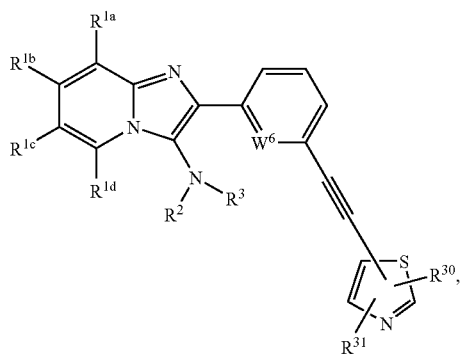

in which
R1a, R1b, R1c, R1d, R2 and R3 in each case have the above-stated meaning;

W6 represents C or N; and

R30 and R31, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula Im,

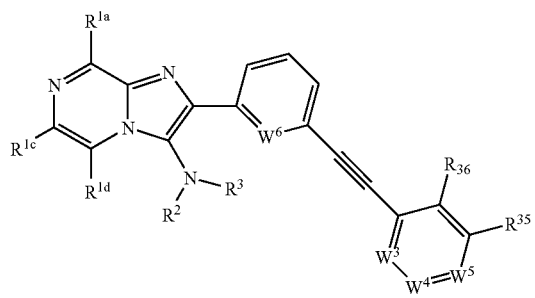

in which
R1a, R1c, R1d, R2 and R3 in each case have the meaning according to claim 14;

W6 represents C or N;

W3 represents C—R32; W4 represents C—R33 and W5 represents C—R34;

or one of the groups W3, W4 and W5 represents N and the other two groups selected from the group consisting of W3, W4 and W5 represent C—R32 or C—R33;

and R32, R33, R34, R35 and R36, mutually independently, in each case represent a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, —S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;

in each case optionally in the form of corresponding salts, or in each case optionally in the form of corresponding solvates.

Very particularly preferred compounds are those of the general formula In,

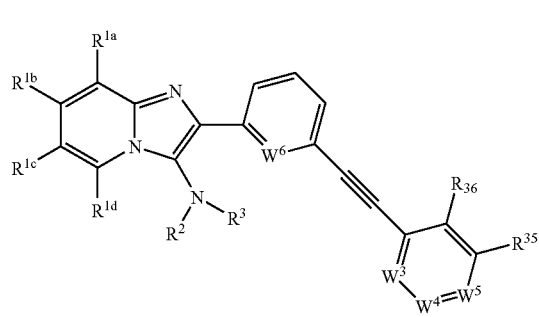

in which
R1a, R1b, R1c, R1d, R2 and R3 in each case have the above-stated meaning;
W6 represents C or N;
W3 represents C—R32; W4 represents C—R33 and W5 represents C—R34;
or one of the groups W3, W4 and W5 represent N and the other two groups selected from the group consisting of W3, W4 and W5 represent C—R32 or C—R33;
and R32, R33, R34, R35 and R36, mutually independently, in each case represents a group selected from the group consisting of H, F, Cl, Br, —CN, —CF3, —SF5, —S—CH3, —S—C2H5, methyl, ethyl, iso-propyl, tert-butyl, ethenyl, propenyl, —OH, —O—CH3, —O—C2H5, —NH2, —N(CH3)2, —NH—CH3, —CH2-NH2, —NO2, —O—CF3, —C(=O)—H; —C(=O)—OCH3, —C(=O)—O—C2H5, phenyl, pyrrolyl, (1,3)-dioxolanyl, —Si(phenyl)2[C(CH3)3], NH—S(=O)2-CH3, —NH—S(=O)2-C2H5, —S(=O)2-NH2, S(=O)2-NH—CH3, —CH2-OH, —C(=O)—CH3, —C(=O)—OH, —CH2-O—CH3, —C(=O)—NH2, —C(=O)—NH—CH3, —NH—C(=O)—CH3, —NH—C(=NH)—NH2, —NH—S(=O)2-OH and —S(=O)2-N(CH3)2;
in each case optionally in the form of corresponding salts, or in each case optionally in the form of corresponding solvates.

Still more preferred substituted imidazo-3-yl-amine compounds of the above general formula I are those selected from the group consisting of

[1] cyclopentyl-[2-(5-phenylethynyl-thiophen-2-yl)-imidazo[1,2-a]pyrazin-3-yl]-amine,
[2] cyclohexylmethyl-[5-methyl-2-(5-phenylethynyl-thiophen-2-yl)-imidazo[1,2-a]pyridin-3-yl]-amine,
[3] cyclohexylmethyl-[6-methyl-2-(5-phenylethynyl-thiophen-2-yl)-imidazo[1,2-a]pyridin-3-yl]-amine,
[4] cyclohexylmethyl-[7-methyl-2-(5-phenylethynyl-thiophen-2-yl)-imidazo[1,2-a]pyridin-3-yl]-amine,
[5] cyclohexylmethyl-[8-methyl-2-(5-phenylethynyl-thiophen-2-yl)-imidazo[1,2-a]pyridin-3-yl]-amine,
[6] cyclohexylmethyl-[5,7-dimethyl-2-(5-phenylethynyl-thiophen-2-yl)-imidazo[1,2-a]pyridin-3-yl]-amine,
[7] [8-benzyloxy-2-(5-phenylethynyl-thiophen-2-yl)-imidazo[1,2-a]pyridin-3-yl]-cyclohexylmethyl-amine,
[8] cyclohexylmethyl-[2-(5-phenylethynyl-thiophen-2-yl)-imidazo[1,2-a]pyrazin-3-yl]-amine,
[9] cyclohexylmethyl-[2-(5-phenylethynyl-thiophen-2-yl)-imidazo[1,2-a]pyrimidin-3-yl]-amine,
[10] (4-methoxy-benzyl)-[5-methyl-2-(5-phenylethynyl-thiophen-2-yl)-imidazo[1,2-a]pyridin-3-yl]-amine,
[11] (4-methoxy-benzyl)-[6-methyl-2-(5-phenylethynyl-thiophen-2-yl)-imidazo[1,2-a]pyridin-3-yl]-amine,
[12] (4-methoxy-benzyl)-[7-methyl-2-(5-phenylethynyl-thiophen-2-yl)-imidazo[1,2-a]pyridin-3-yl]-amine,
[13] (4-methoxy-benzyl)-[8-methyl-2-(5-phenylethynyl-thiophen-2-yl)-imidazo[1,2-a]pyridin-3-yl]-amine,
[14] [5,7-dimethyl-2-(5-phenylethynyl-thiophen-2-yl)-imidazo[1,2-a]pyridin-3-yl]-(4-methoxy-benzyl)-amine,
[15] [8-benzyloxy-2-(5-phenylethynyl-thiophen-2-yl)-imidazo[1,2-a]pyridin-3-yl]-(4-methoxy-benzyl)-amine,
[16] (4-methoxy-benzyl)-[2-(5-phenylethynyl-thiophen-2-yl)-imidazo[1,2-a]pyridin-3-yl]-amine,
[17] (4-methoxy-benzyl)-[2-(5-phenylethynyl-thiophen-2-yl)-imidazo[1,2-a]pyrazin-3-yl]-amine,
[18] tert-butyl-[2-(5-phenylethynyl-thiophen-2-yl)-imidazo[1,2-a]pyrazin-3-yl]-amine,
[19] tert-butyl-[6-methyl-2-(5-phenylethynyl-thiophen-2-yl)-imidazo[1,2-a]pyridin-3-yl]-amine,
[20] [8-benzyloxy-2-(5-phenylethynyl-thiophen-2-yl)-imidazo[1,2-a]pyridin-3-yl]-(3-methoxy-phenyl)-amine,
[21] (3-methoxy-benzyl)-[5-methyl-2-(5-phenylethynyl-thiophen-2-yl)-imidazo[1,2-a]pyridin-3-yl]-amine,
[22] (3-methoxy-benzyl)-[8-methyl-2-(5-phenylethynyl-thiophen-2-yl)-imidazo[1,2-a]pyridin-3-yl]-amine,
[23] [5,7-dimethyl-2-(5-phenylethynyl-thiophen-2-yl)-imidazo[1,2-a]pyridin-3-yl]-(3-methoxy-benzyl)-amine,
[24] [8-benzyloxy-2-(5-phenylethynyl-thiophen-2-yl)-imidazo[1,2-a]pyridin-3-yl]-(3-methoxy-benzyl)-amine,
[25] (3-methoxy-benzyl)-[2-(5-phenylethynyl-thiophen-2-yl)-imidazo[1,2-a]pyridin-3-yl]-amine,
[26] (3-methoxy-benzyl)-[2-(5-phenylethynyl-thiophen-2-yl)-imidazo[1,2-a]pyrazin-3-yl]-amine,
[27] [6-methyl-2-(5-phenylethynyl-thiophen-2-yl)-imidazo[1,2-a]pyridin-3-yl]-(1-phenyl-ethyl)-amine,
[28] [7-methyl-2-(5-phenylethynyl-thiophen-2-yl)-imidazo[1,2-a]pyridin-3-yl]-(1-phenyl-ethyl)-amine,
[29] [5,7-dimethyl-2-(5-phenylethynyl-thiophen-2-yl)-imidazo[1,2-a]pyridin-3-yl]-(1-phenyl-ethyl)-amine,
[30] [8-benzyloxy-2-(5-phenylethynyl-thiophen-2-yl)-imidazo[1,2-a]pyridin-3-yl]-(1-phenyl-ethyl)-amine,
[31] (1-phenyl-ethyl)-[2-(5-phenylethynyl-thiophen-2-yl)-imidazo[1,2-a]pyrazin-3-yl]-amine,
[32] (2-chloro-benzyl)-[5,7-dimethyl-2-(5-phenylethynyl-thiophen-2-yl)-imidazo[1,2-a]pyridin-3-yl]-amine,
[33] (3-chloro-4-fluoro-phenyl)-[7-phenyl-2-(5-phenylethynyl-thiophen-2-yl)-imidazo[1,2-a]pyridin-3-yl]-amine,
[34] (4-methoxy-benzyl)-[7-methyl-2-(5-phenylethynyl-thiophen-2-yl)-imidazo[1,2-a]pyrimidin-3-yl]-amine,
[35] [8-methyl-2-(5-phenylethynyl-thiophen-2-yl)-imidazo[1,2-a]pyridin-3-yl]-(1-phenyl-ethyl)-amine,
[36] [7-methyl-2-(5-phenylethynyl-thiophen-2-yl)-imidazo[1,2-a]pyrimidin-3-yl]-(1-phenyl-ethyl)-amine,
[37] (2-methoxy-benzyl)-[7-methyl-2-(5-phenylethynyl-thiophen-2-yl)-imidazo[1,2-a]pyridin-3-yl]-amine,
[38] (2-methoxy-benzyl)-[2-(5-phenylethynyl-thiophen-2-yl)-imidazo[1,2-a]pyridin-3-yl]-amine,
[39] (2-chloro-benzyl)-[2-(5-phenylethynyl-thiophen-2-yl)-imidazo[1,2-a]pyridin-3-yl]-amine,
[40] (2-methoxy-benzyl)-[7-methyl-2-(5-phenylethynyl-thiophen-2-yl)-imidazo[1,2-a]pyrimidin-3-yl]-amine,
[41] (3-methoxy-phenyl)-[6-methyl-2-(5-phenylethynyl-thiophen-2-yl)-imidazo[1,2-a]pyridin-3-yl]-amine,
[42] [5,7-dimethyl-2-(5-phenylethynyl-thiophen-2-yl)-imidazo[1,2-a]pyridin-3-yl]-(3-methoxy-phenyl)-amine,

[43] (3-methoxy-phenyl)-[2-(5-phenylethynyl-thiophen-2-yl)-imidazo[1,2-a]pyrazin-3-yl]-amine,
[44] [7-ethyl-2-(5-phenylethynyl-thiophen-2-yl)-imidazo[1,2-a]pyridin-3-yl]-(2-methoxy-benzyl)-amine,
[45] (2-chloro-benzyl)-[7-ethyl-2-(5-phenylethynyl-thiophen-2-yl)-imidazo[1,2-a]pyridin-3-yl]-amine,
[46] [7-tert-butyl-2-(5-phenylethynyl-thiophen-2-yl)-imidazo[1,2-a]pyridin-3-yl]-(3-chloro-4-fluoro-phenyl)-amine,
[47] (3-methoxy-benzyl)-[7-methyl-2-(5-phenylethynyl-thiophen-2-yl)-imidazo[1,2-a]pyrimidin-3-yl]-amine,
[48] [7-ethyl-2-(5-phenylethynyl-thiophen-2-yl)-imidazo[1,2-a]pyridin-3-yl]-(2-fluoro-phenyl)-amine,
[49] [7-tert-butyl-2-(5-phenylethynyl-thiophen-2-yl)-imidazo[1,2-a]pyridin-3-yl]-(2-fluoro-phenyl)-amine,
[50] (2,4-difluoro-phenyl)-[2-(5-phenylethynyl-thiophen-2-yl)-7-(3-phenyl-propyl)-imidazo[1,2-a]pyridin-3-yl]-amine,
[51] (4-fluoro-benzyl)-[7-methyl-2-(5-phenylethynyl-thiophen-2-yl)-imidazo[1,2-a]pyridin-3-yl]-amine,
[52] [5,7-dimethyl-2-(5-phenylethynyl-thiophen-2-yl)-imidazo[1,2-a]pyridin-3-yl]-(4-fluoro-benzyl)-amine,
[53] [7-ethyl-2-(5-phenylethynyl-thiophen-2-yl)-imidazo[1,2-a]pyridin-3-yl]-(3-trifluoromethyl-benzyl)-amine,
[54] [7-isopropyl-2-(5-phenylethynyl-thiophen-2-yl)-imidazo[1,2-a]pyridin-3-yl]-(3-trifluoromethyl-benzyl)-amine,
[55] tert-butyl-[2-(4-phenylethynyl-thiophen-2-yl)-imidazo[1,2-a]pyrazin-3-yl]-amine,
[56] [2-(5-phenylethynyl-thiophen-2-yl)-imidazo[1,2-a]pyrazin-3-yl]-(1,1,3,3-tetramethyl-butyl)-amine,
[57] butyl-[2-(4-phenylethynyl-thiophen-2-yl)-imidazo[1,2-a]pyrazin-3-yl]-amine,
[59] [2-(5-phenylethynyl-thiophen-2-yl)-imidazo[1,2-a]pyridin-3-yl]-(1,1,3,3-tetramethyl-butyl)-amine,
[60] [2-(5-pyridinyl-thiophen-2-yl)-imidazo[1,2-a]pyrazin-3-yl]-(1,1,3,3-tetramethyl-butyl)-amine,
[61] [2-(5-pyridin-4-ylethynyl-thiophen-2-yl)-imidazo[1,2-a]pyrazin-3-yl]-(1,1,3,3-tetramethyl-butyl)-amine,
[62] [6-chloro-2-(5-phenylethynyl-thiophen-2-yl)-imidazo[1,2-a]pyridin-3-yl]-(1,1,3,3-tetramethyl-butyl)-amine,
[63] [6,8-dichloro-2-(5-phenylethynyl-thiophen-2-yl)-imidazo[1,2-a]pyridin-3-yl]-(1,1,3,3-tetramethyl-butyl)-amine,
[64] [2-(5-pyridin-2-ylethynyl-thiophen-2-yl)-imidazo[1,2-a]pyrazin-3-yl]-(1,1,3,3-tetramethyl-butyl)-amine,
[65] dimethyl-[2-(5-phenylethynyl-thiophen-2-yl)-imidazo[1,2-a]pyrazin-3-yl]-amine,
[66] methyl-[2-(5-phenylethynyl-thiophen-2-yl)-imidazo[1,2-a]pyrazin-3-yl]-amine,
[67] N-[2-(5-phenylethynyl-thiophen-2-yl)-imidazo[1,2-a]pyrazin-3-yl]-acetamide,
[68] ethyl-[2-(5-phenylethynyl-thiophen-2-yl)-imidazo[1,2-a]pyrazin-3-yl]-amine,
[69] propyl-[2-(5-phenylethynyl-thiophen-2-yl)-imidazo[1,2-a]pyrazin-3-yl]-amine,
[70] butyl-[2-(5-phenylethynyl-thiophen-2-yl)-imidazo[1,2-a]pyrazin-3-yl]-amine,
[71] (2-methylpropyl)-[2-(5-phenylethynyl-thiophen-2-yl)-imidazo[1,2-a]pyrazin-3-yl]-amine,
[72] pentyl-[2-(5-phenylethynyl-thiophen-2-yl)-imidazo[1,2-a]pyrazin-3-yl]-amine,
[73] {(methoxycarbonylmethyl)-[2-(5-phenylethynyl-thiophen-2-yl)-imidazo[1,2-a]pyrazin-3-yl]-amino}-acetic acid methyl ester,
[74] benzyl-[2-(5-phenylethynyl-thiophen-2-yl)-imidazo[1,2-a]pyrazin-3-yl]-amine,
[75] [2-(5-phenylethynyl-thiophen-2-yl)-imidazo[1,2-a]pyrazin-3-ylamino]-acetic acid methyl ester,
[76] tert-butyl-[2-(5-pyridin-4-ylethynyl-thiophen-2-yl)-imidazo[1,2-a]pyrazin-3-yl]-amine,
[77] tert-butyl-[2-(5-pyridin-2-ylethynyl-thiophen-2-yl)-imidazo[1,2-a]pyrazin-3-yl]-amine,
[78] N-[2-(5-phenylethynyl-thiophen-2-yl)-imidazo[1,2-a]pyrazin-3-yl]-benzamide,
[79] [2-(5-phenylethynyl-thiophen-2-yl)-imidazo[1,2-a]pyrazin-3-yl]-bis-pyridin-3-ylmethyl-amine,
[80] 2,2-dimethyl-N-[2-(5-phenylethynyl-thiophen-2-yl)-imidazo[1,2-a]pyrazin-3-yl]-propionamide,
[81] 3-methoxy-N-[2-(5-phenylethynyl-thiophen-2-yl)-imidazo[1,2-a]pyrazin-3-yl]-benzamide,
[82] tert-butyl-[2-(5-pyridin-3-ylethynyl-thiophen-2-yl)-imidazo[1,2-a]pyrazin-3-yl]-amine
[83] 2-(5-phenylethynyl-thiophen-2-yl)-imidazo[1,2-a]pyrazin-3-ylamine
[84] methyl-2-(5-(phenylethynyl)thiophen-2-yl)-3-(2,4,4-trimethylpentan-2-ylamino)imidazo[1,2-a]pyrazine-8-carboxylate
[85] 2-(5-(phenylethynyl)thiophen-2-yl)-N-(2,4,4-trimethylpentan-2-yl)imidazo[1,2-a]pyrimidin-3-amine
[86] 2-(5-((6-methylpyridin-2-yl)ethynyl)thiophen-2-yl)-N-(2,4,4-trimethylpentan-2-yl)imidazo[1,2-a]pyrazin-3-amine
[87] N-cyclohexyl-2-(5-(phenylethynyl)thiophen-2-yl)imidazo[1,2-a]pyrazin-3-amine
[88] 2-(5-(phenylethynyl)thiophen-2-yl)-3-(piperidin-1-yl)imidazo[1,2-a]pyrazine
[89] N-tert-butyl-N-methyl-2-(5-(phenylethynyl)thiophen-2-yl)imidazo[1,2-a]pyrazin-3-amine
[90] methyl-2-(5-(phenylethynyl)thiophen-2-yl)-3-(2,4,4-trimethylpentan-2-ylamino)imidazo[1,2-a]pyridine-6-carboxylate
[91] N-tert-butyl-2-(5-(pyridin-2-ylethynyl)thiophen-2-yl)imidazo[1,2-a]pyrazin-3-amine hydrochloride
[92] 8-bromo-N-cyclopentyl-6-methyl-2-(5-(pyridin-2-ylethynyl)thiophen-2-yl)imidazo[1,2-a]pyridin-3-amine
[93] N,N-diethyl-2-(5-(phenylethynyl)thiophen-2-yl)imidazo[1,2-a]pyrazin-3-amine
[94] N-tert-butyl-2-(5-(pyridin-2-ylethynyl)thiophen-2-yl)imidazo[1,2-a]pyridin-3-amine
[95] N-tert-butyl-2-(5-(phenylethynyl)furan-2-yl)imidazo[1,2-a]pyrazin-3-amine
[96] 8-bromo-N-tert-butyl-6-methyl-2-(3-(pyridin-2-ylethynyl)phenyl)imidazo[1,2-a]pyridin-3-amine
[97] N-tert-butyl-8-methyl-2-(5-(phenylethynyl)thiophen-2-yl)imidazo[1,2-a]pyridin-3-amine
[98] N-methyl-2-(5-(phenylethynyl)thiophen-2-yl)-N-(2,4,4-trimethylpentan-2-yl)imidazo[1,2-a]pyrazin-3-amine hydrochloride
[99] 2-(5-(phenylethynyl)thiophen-2-yl)-3-(pyrrolidin-1-yl)imidazo[1,2-a]pyrazine hydrochloride
[100] N-tert-butyl-2-(5-((4-fluorophenyl)ethynyl)thiophen-2-yl)imidazo[1,2-a]pyrazin-3-amine hydrochloride
[101] N-tert-butyl-7-methyl-2-(5-(phenylethynyl)thiophen-2-yl)imidazo[1,2-a]pyridin-3-amine
[102] N-tert-butyl-5-methyl-2-(5-(phenylethynyl)thiophen-2-yl)imidazo[1,2-a]pyridin-3-amine
[103] 8-chloro-2-(3-(pyridin-2-ylethynyl)phenyl)-6-(trifluoromethyl)-N-(2,4,4-trimethylpentan-2-yl)imidazo[1,2-a]pyridin-3-amine
[104] N-tert-butyl-2-(5-((3-fluorophenyl)ethynyl)thiophen-2-yl)imidazo[1,2-a]pyrazin-3-amine hydrochloride
[105] N-tert-butyl-2-(5-((2-fluorophenyl)ethynyl)thiophen-2-yl)imidazo[1,2-a]pyrazin-3-amine hydrochloride

[106] methyl-3-(tert-butylamino)-2-(5-(phenylethynyl)thiophen-2-yl)imidazo[1,2-a]pyrazine-8-carboxylate
[107] N-tert-butyl-2-(5-(pyrazin-2-ylethynyl)thiophen-2-yl)imidazo[1,2-a]pyrazin-3-amine
[108] 2-(5-((4-aminophenyl)ethynyl)thiophen-2-yl)-N-tert-butylimidazo[1,2-a]pyrazin-3-amine
[109] N-isopropyl-2-(5-(phenylethynyl)thiophen-2-yl)imidazo[1,2-a]pyrazin-3-amine
[110] N-tert-butyl-2-(5-(thiophen-2-ylethynyl)thiophen-2-yl)imidazo[1,2-a]pyrazin-3-amine hydrochloride
[111] N-tert-butyl-2-(3-(pyridin-2-ylethynyl)phenyl)imidazo[1,2-a]pyrazin-3-amine
[112] N-tert-butyl-2-(5-((2-methoxyphenyl)ethynyl)thiophen-2-yl)imidazo[1,2-a]pyrazin-3-amine hydrochloride
[113] N-tert-butyl-2-(5-((3-methoxyphenyl)ethynyl)thiophen-2-yl)imidazo[1,2-a]pyrazin-3-amine hydrochloride
[114] N-tert-butyl-2-(5-((4-methoxyphenyl)ethynyl)thiophen-2-yl)imidazo[1,2-a]pyrazin-3-amine hydrochloride
[115] N-tert-butyl-2-(5-(phenylethynyl)thiophen-2-yl)imidazo[1,2-a]quinolin-1-amine
[116] N-tert-butyl-2-(4-(pyridin-2-ylethynyl)phenyl)imidazo[1,2-a]pyrazin-3-amine
[117] N-tert-butyl-2-(3-((6-methylpyridin-2-yl)ethynyl)phenyl)imidazo[1,2-a]pyrazin-3-amine
[118] N-tert-butyl-2-(2-methyl-6-(phenylethynyl)pyridin-3-yl)imidazo[1,2-a]pyrazin-3-amine
[119] N-tert-butyl-2-(5-(pyridin-2-ylethynyl)furan-2-yl)imidazo[1,2-a]pyrazin-3-amine
[120] 3-(tert-butylamino)-2-(5-(phenylethynyl)thiophen-2-yl)imidazo[1,2-a]pyrazine-8-carboxylic acid
[121] 4-((5-(3-(tert-butylamino)imidazo[1,2-a]pyrazin-2-yl)thiophen-2-yl)ethynyl)phenol hydrochloride
[122] 3-((5-(3-(tert-butylamino)imidazo[1,2-a]pyrazin-2-yl)thiophen-2-yl)ethynyl)phenol
[123] 2-(5-((3-aminophenyl)ethynyl)thiophen-2-yl)-N-tert-butylimidazo[1,2-a]pyrazin-3-amine hydrochloride
[124] 2-(5-((2-aminophenyl)ethynyl)thiophen-2-yl)-N-tert-butylimidazo[1,2-a]pyrazin-3-amine hydrochloride
[125] N-tert-butyl-2-(5-(phenylethynyl)thiophen-2-yl)imidazo[2,1-a]isoquinolin-3-amine
[126] N-tert-butyl-2-(6-(phenylethynyl)pyridin-3-yl)imidazo[1,2-a]pyrazin-3-amine
[127] N-tert-butyl-2-(5-(pyridin-4-ylethynyl)thiophen-2-yl)imidazo[1,2-a]pyrazin-3-amine hydrochloride
[128] 2-(5-((6-aminopyridin-3-yl)ethynyl)thiophen-2-yl)-N-tert-butylimidazo[1,2-a]pyrazin-3-amine hydrochloride
[129] N-tert-butyl-2-(5-(pyrimidin-2-ylethynyl)thiophen-2-yl)imidazo[1,2-a]pyrazin-3-amine hydrochloride
[130] N-tert-butyl-2-(5-((4-methylpyridin-2-yl)ethynyl)thiophen-2-yl)imidazo[1,2-a]pyrazin-3-amine hydrochloride
[131] N-tert-butyl-2-(5-((5-methylpyridin-2-yl)ethynyl)thiophen-2-yl)imidazo[1,2-a]pyrazin-3-amine hydrochloride
[132] N-tert-butyl-2-(5-(pyridin-4-ylethynyl)thiophen-2-yl)imidazo[1,2-a]pyridin-3-amine hydrochloride
[133] N-tert-butyl-2-(5-(thiazol-2-ylethynyl)thiophen-2-yl)imidazo[1,2-a]pyrazin-3-amine
[134] 2-(5-(pyridin-2-ylethynyl)thiophen-2-yl)imidazo[1,2-a]pyrazin-3-amine hydrochloride
[135] N-tert-butyl-2-(5-((5-methylthiophen-2-yl)ethynyl)thiophen-2-yl)imidazo[1,2-a]pyrazin-3-amine hydrochloride
[136] 2-(5-((6-aminopyridin-2-yl)ethynyl)thiophen-2-yl)-N-tert-butylimidazo[1,2-a]pyrazin-3-amine hydrochloride
[137] N-tert-butyl-2-(5-((3-methylthiophen-2-yl)ethynyl)thiophen-2-yl)imidazo[1,2-a]pyrazin-3-amine
[138] N-tert-butyl-2-(4-(phenylethynyl)thiazol-2-yl)imidazo[1,2-a]pyrazin-3-amine
[139] N-tert-butyl-2-(5-(m-tolylethynyl)thiophen-2-yl)imidazo[1,2-a]pyrazin-3-amine
[140] 3-((5-(3-(tert-butylamino)imidazo[1,2-a]pyrazin-2-yl)thiophen-2-yl)ethynyl)benzonitrile hydrochloride
[141] N-tert-butyl-2-(5-(pyridin-2-ylethynyl)thiophen-2-yl)imidazo[1,2-a]pyrimidin-3-amine
[142] N-tert-butyl-2-(6-(phenylethynyl)pyridin-2-yl)imidazo[1,2-a]pyrazin-3-amine hydrochloride
[143] N-tert-butyl-N-methyl-2-(5-(pyridin-2-ylethynyl)thiophen-2-yl)imidazo[1,2-a]pyrazin-3-amine
[144] 4-((5-(3-(tert-butylamino)imidazo[1,2-a]pyrazin-2-yl)thiophen-2-yl)ethynyl)benzonitrile hydrochloride
[145] 2-(5-((1H-indol-6-yl)ethynyl)thiophen-2-yl)-N-tert-butylimidazo[1,2-a]pyrazin-3-amine hydrochloride
[146] N-tert-butyl-2-(2-(phenylethynyl)thiazol-5-yl)imidazo[1,2-a]pyrazin-3-amine
[147] N-tert-butyl-2-(5-(quinolin-6-ylethynyl)thiophen-2-yl)imidazo[1,2-a]pyrazin-3-amine hydrochloride
[148] 2-(5-((3-(1H-pyrrol-1-yl)phenyl)ethynyl)thiophen-2-yl)-N-tert-butylimidazo[1,2-a]pyrazin-3-amine hydrochloride
[149] 2-(5-((1H-indol-4-yl)ethynyl)thiophen-2-yl)-N-tert-butylimidazo[1,2-a]pyrazin-3-amine hydrochloride
[150] N-tert-butyl-2-(5-((3-nitrophenyl)ethynyl)thiophen-2-yl)imidazo[1,2-a]pyrazin-3-amine hydrochloride
[151] N-tert-butyl-2-(5-((4-nitrophenyl)ethynyl)thiophen-2-yl)imidazo[1,2-a]pyrazin-3-amine hydrochloride
[152] N-tert-butyl-2-(5-(thiazol-4-ylethynyl)thiophen-2-yl)imidazo[1,2-a]pyrazin-3-amine hydrochloride
[153] 2-((5-(3-(tert-butylamino)imidazo[1,2-a]pyrazin-2-yl)thiophen-2-yl)ethynyl)phenol
[154] 2-(5-((3-(aminomethyl)phenyl)ethynyl)thiophen-2-yl)-N-tert-butylimidazo[1,2-a]pyrazin-3-amine
[155] 2-(5-(biphenyl-3-ylethynyl)thiophen-2-yl)-N-tert-butylimidazo[1,2-a]pyrazin-3-amine hydrochloride
[156] N-tert-butyl-2-(5-(thiophen-3-ylethynyl)thiophen-2-yl)imidazo[1,2-a]pyrazin-3-amine hydrochloride
[157] N-tert-butyl-2-(5-((3-(dimethylamino)phenyl)ethynyl)thiophen-2-yl)imidazo[1,2-a]pyrazin-3-amine hydrochloride
[158] N-tert-butyl-2-(5-((6-methylpyridin-2-yl)ethynyl)thiophen-2-yl)imidazo[1,2-a]pyrazin-3-amine hydrochloride
[159] N-tert-butyl-2-(5-((3-fluoropyridin-2-yl)ethynyl)thiophen-2-yl)imidazo[1,2-a]pyrazin-3-amine hydrochloride
[160] N-tert-butyl-2-(5-((3-(methylamino)phenyl)ethynyl)thiophen-2-yl)imidazo[1,2-a]pyrazin-3-amine hydrochloride
[161] N-tert-butyl-2-(5-(p-tolylethynyl)thiophen-2-yl)imidazo[1,2-a]pyrazin-3-amine
[162] N-tert-butyl-2-(5-(o-tolylethynyl)thiophen-2-yl)imidazo[1,2-a]pyrazin-3-amine hydrochloride
[163] N-tert-butyl-2-(4-methyl-5-(phenylethynyl)thiophen-2-yl)imidazo[1,2-a]pyrazin-3-amine hydrochloride
[164] N-tert-butyl-2-(4-methyl-5-(pyridin-2-ylethynyl)thiophen-2-yl)imidazo[1,2-a]pyrazin-3-amine hydrochloride
[165] N-tert-butyl-2-(5-((6-fluoropyridin-2-yl)ethynyl)thiophen-2-yl)imidazo[1,2-a]pyrazin-3-amine

[166] N-tert-butyl-2-(5-((2-nitrophenyl)ethynyl)thiophen-2-yl)imidazo[1,2-a]pyrazin-3-amine
[167] N-tert-butyl-8-chloro-2-(5-(pyridin-2-ylethynyl)thiophen-2-yl)imidazo[1,2-a]pyrazin-3-amine
[168] N-tert-butyl-2-(5-((6-methoxypyridin-2-yl)ethynyl)thiophen-2-yl)imidazo[1,2-a]pyrazin-3-amine
[169] N-tert-butyl-2-(5-((5-fluoropyridin-2-yl)ethynyl)thiophen-2-yl)imidazo[1,2-a]pyrazin-3-amine hydrochloride
[170] 2-(4-(3-(tert-butylamino)imidazo[1,2-a]pyrazin-2-yl)-2-(phenylethynyl)phenyl)acetonitrile
[171] N-tert-butyl-2-(5-((5-methoxypyridin-3-yl)ethynyl)thiophen-2-yl)imidazo[1,2-a]pyrazin-3-amine hydrochloride
[172] 5-((5-(3-(tert-butylamino)imidazo[1,2-a]pyrazin-2-yl)thiophen-2-yl)ethynyl)nicotinonitrile hydrochloride
[173] N-tert-butyl-2-(5-((3-(methylthio)phenyl)ethynyl)thiophen-2-yl)imidazo[1,2-a]pyrazin-3-amine
[174] methyl-3-((5-(3-(tert-butylamino)imidazo[1,2-a]pyrazin-2-yl)thiophen-2-yl)ethynyl)benzoate
[175] N-tert-butyl-2-(5-((3,5-difluoropyridin-2-yl)ethynyl)thiophen-2-yl)imidazo[1,2-a]pyrazin-3-amine
[176] N-tert-butyl-2-(5-(phenylethynyl)thiazol-2-yl)imidazo[1,2-a]pyrazin-3-amine
[177] N-tert-butyl-2-(2-(pyridin-4-ylethynyl)thiazol-5-yl)imidazo[1,2-a]pyrazin-3-amine
[178] 3-((5-(3-(tert-butylamino)imidazo[1,2-a]pyrazin-2-yl)thiophen-2-yl)ethynyl)benzaldehyde
[179] 3-((5-(3-(tert-butylamino)imidazo[1,2-a]pyrazin-2-yl)thiophen-2-yl)ethynyl)-4-fluorobenzonitrile
[180] N-tert-butyl-2-(5-((3-(trifluoromethyl)phenyl)ethynyl)thiophen-2-yl)imidazo[1,2-a]pyrazin-3-amine hydrochloride
[181] N-tert-butyl-2-(2-(pyridin-2-ylethynyl)thiazol-5-yl)imidazo[1,2-a]pyrazin-3-amine
[182] N-tert-butyl-2-(3-methyl-5-(phenylethynyl)thiophen-2-yl)imidazo[1,2-a]pyrazin-3-amine hydrochloride
[183] N-tert-butyl-2-(3-methyl-5-(pyridin-2-ylethynyl)thiophen-2-yl)imidazo[1,2-a]pyrazin-3-amine hydrochloride
[184] N-tert-butyl-2-(5-((3-vinylphenyl)ethynyl)thiophen-2-yl)imidazo[1,2-a]pyrazin-3-amine
[185] 2-(5-((1H-imidazol-4-yl)ethynyl)thiophen-2-yl)-N-tert-butylimidazo[1,2-a]pyrazin-3-amine hydrochloride
[186] N-tert-butyl-2-(5-((3-methylpyridin-2-yl)ethynyl)thiophen-2-yl)imidazo[1,2-a]pyrazin-3-amine
[187] N,N-dimethyl-2-(5-(pyridin-2-ylethynyl)thiophen-2-yl)imidazo[1,2-a]pyrazin-3-amine
[188] N-tert-butyl-2-(5-((2-(tert-butyldiphenylsilyl)thiazol-5-yl)ethynyl)thiophen-2-yl)imidazo[1,2-a]pyridin-3-amine
[189] 3-((5-(3-(tert-butylamino)imidazo[1,2-a]pyridin-2-yl)thiophen-2-yl)ethynyl)benzonitrile
[190] N-tert-butyl-2-(5-(phenylethynyl)thiazol-2-yl)imidazo[1,2-a]pyridin-3-amine
[191] N-tert-butyl-2-(5-(thiazol-5-ylethynyl)thiophen-2-yl)imidazo[1,2-a]pyridin-3-amine
[192] N-tert-butyl-2-(5-(pyridin-2-ylethynyl)thiophen-2-yl)imidazo[1,2-a]pyridin-3-amine hydrochloride
[321] 6-chloro-N-cyclohexyl-2-(3-((6-methylpyridin-2-yl)ethynyl)phenyl)imidazo[1,2-a]pyridin-3-amine
[194] 5,7-dimethyl-N-phenethyl-2-(5-(phenylethynyl)thiophen-2-yl)imidazo[1,2-a]pyrimidin-3-amine
[195] N-(3-methoxyphenethyl)-5,7-dimethyl-2-(5-(phenylethynyl)thiophen-2-yl)imidazo[1,2-a]pyrimidin-3-amine
[196] N-(3-methoxyphenethyl)-5,7-dimethyl-2-(4-(phenylethynyl)thiophen-2-yl)imidazo[1,2-a]pyrimidin-3-amine
[197] N-(3-methoxyphenethyl)-5,7-dimethyl-2-(5-(phenylethynyl)furan-2-yl)imidazo[1,2-a]pyrimidin-3-amine
[198] N-(4-chlorobenzyl)-8-methyl-2-(5-(phenylethynyl)thiophen-2-yl)imidazo[1,2-a]pyridin-3-amine
[199] N-(3-methoxyphenethyl)-5-methyl-2-(4-(phenylethynyl)thiophen-2-yl)imidazo[1,2-a]pyridin-3-amine
[200] N-(2-methylhexan-2-yl)-2-(4-(phenylethynyl)thiophen-2-yl)imidazo[1,2-a]pyrazin-3-amine
[201] N-phenethyl-2-(4-(phenylethynyl)thiophen-2-yl)imidazo[1,2-a]pyrazin-3-amine
[202] N-(3-methoxyphenethyl)-2-(4-(phenylethynyl)thiophen-2-yl)imidazo[1,2-a]pyrazin-3-amine
[203] 2-(4-(phenylethynyl)thiophen-2-yl)-N-(2-(thiophen-2-yl)ethyl)imidazo[1,2-a]pyrazin-3-amine
[204] N-(4-chlorobenzyl)-2-(5-(phenylethynyl)thiophen-2-yl)imidazo[1,2-a]pyridin-3-amine
[205] N-(2-methylpentan-2-yl)-2-(5-(phenylethynyl)thiophen-2-yl)imidazo[1,2-a]pyridin-3-amine
[206] N-(cyclohexylmethyl)-2-(4-(phenylethynyl)thiophen-2-yl)imidazo[1,2-a]pyrazin-3-amine
[207] N-(2-methoxybenzyl)-2-(5-(phenylethynyl)furan-2-yl)imidazo[1,2-a]pyrazin-3-amine
[208] N-(cyclohexylmethyl)-2-(4-(phenylethynyl)thiophen-2-yl)imidazo[1,2-a]pyridin-3-amine
[209] N-(2-methylpentan-2-yl)-2-(4-(phenylethynyl)thiophen-2-yl)imidazo[1,2-a]pyridin-3-amine
[210] 8-bromo-6-methyl-2-(3-((6-methylpyridin-2-yl)ethynyl)phenyl)-N-(2,4,4-trimethylpentan-2-yl)imidazo[1,2-a]pyridin-3-amine
[211] 8-bromo-N-cyclopentyl-6-methyl-2-(3-(pyridin-2-ylethynyl)phenyl)imidazo[1,2-a]pyridin-3-amine
[212] N-cyclopentyl-2-(4-(phenylethynyl)thiophen-2-yl)imidazo[1,2-a]pyrazin-3-amine
[213] N-(1-phenylethyl)-2-(4-(phenylethynyl)thiophen-2-yl)imidazo[1,2-a]pyridin-3-amine
[214] N-(2-methylpentan-2-yl)-2-(4-(phenylethynyl)thiophen-2-yl)imidazo[1,2-a]pyrazin-3-amine
[215] 8-bromo-N-cyclohexyl-6-methyl-2-(5-(pyridin-2-ylethynyl)furan-2-yl)imidazo[1,2-a]pyridin-3-amine
[216] N-cyclopentyl-2-(5-(phenylethynyl)furan-2-yl)imidazo[1,2-a]pyrazin-3-amine
[217] N-(3-methoxyphenethyl)-7-methyl-2-(4-(phenylethynyl)thiophen-2-yl)imidazo[1,2-a]pyrimidin-3-amine
[218] 8-(benzyloxy)-2-(5-(phenylethynyl)thiophen-2-yl)-N-(2,4,4-trimethylpentan-2-yl)imidazo[1,2-a]pyridin-3-amine
[219] 8-(benzyloxy)-N-cyclopentyl-2-(4-(phenylethynyl)thiophen-2-yl)imidazo[1,2-a]pyridin-3-amine
[220] 8-(benzyloxy)-N-(2-methylpentan-2-yl)-2-(4-(phenylethynyl)thiophen-2-yl)imidazo[1,2-a]pyridin-3-amine
[221] 6-chloro-N-(4-fluorobenzyl)-2-(5-(phenylethynyl)furan-2-yl)imidazo[1,2-a]pyridin-3-amine
[222] 6-bromo-N-butyl-5-methyl-2-(4-(phenylethynyl)thiophen-2-yl)imidazo[1,2-a]pyridin-3-amine
[223] N-(furan-2-yl)-8-methyl-2-(5-(phenylethynyl)furan-2-yl)imidazo[1,2-a]pyridin-3-amine
[224] N-(furan-2-yl)-2-(5-(phenylethynyl)furan-2-yl)imidazo[1,2-a]pyridin-3-amine
[225] N-(furan-2-yl)-2-(5-(phenylethynyl)furan-2-yl)-7-propylimidazo[1,2-a]pyridin-3-amine
[226] 5,7-dimethyl-2-(4-(phenylethynyl)thiophen-2-yl)-N-(3-(trifluoromethyl)phenyl)imidazo[1,2-a]pyrimidin-3-amine
[227] 6-bromo-N-(4-chlorophenethyl)-8-methyl-2-(4-(phenylethynyl)thiophen-2-yl)imidazo[1,2-a]pyridin-3-amine
[228] N-(4-chlorophenethyl)-7-phenyl-2-(4-(phenylethynyl)thiophen-2-yl)imidazo[1,2-a]pyridin-3-amine

[229] N-phenethyl-7-phenyl-2-(4-(phenylethynyl)thiophen-2-yl)imidazo[1,2-a]pyridin-3-amine
[230] N-(4-chlorobenzyl)-5,7-dimethyl-2-(4-(phenylethynyl)thiophen-2-yl)imidazo[1,2-a]pyridin-3-amine
[231] 6-bromo-N-(4-chlorobenzyl)-5-methyl-2-(4-(phenylethynyl)thiophen-2-yl)imidazo[1,2-a]pyridin-3-amine
[232] 8-bromo-N-(4-chlorobenzyl)-6-methyl-2-(4-(phenylethynyl)thiophen-2-yl)imidazo[1,2-a]pyridin-3-amine
[233] N-(3-methoxyphenethyl)-2-(4-(phenylethynyl)thiophen-2-yl)-5-propylimidazo[1,2-a]pyridin-3-amine
[234] 6-bromo-8-methyl-2-(4-(phenylethynyl)thiophen-2-yl)-N-(2-(thiophen-2-yl)ethyl)imidazo[1,2-a]pyridin-3-amine
[235] 7-phenyl-2-(4-(phenylethynyl)thiophen-2-yl)-N-(2-(thiophen-2-yl)ethyl)imidazo[1,2-a]pyridin-3-amine
[236] 6,8-dibromo-N-(2-methylpentan-2-yl)-2-(5-(phenylethynyl)thiophen-2-yl)imidazo[1,2-a]pyridin-3-amine
[237] 6-bromo-N-(2,6-dimethylphenyl)-8-methyl-2-(4-(phenylethynyl)thiophen-2-yl)imidazo[1,2-a]pyridin-3-amine
[238] N-cyclohexyl-2-(3-(pyridin-2-ylethynyl)phenyl)imidazo[1,2-a]pyrazin-3-amine
[239] 2-(3-(pyridin-2-ylethynyl)phenyl)-N-(2,4,4-trimethylpentan-2-yl)imidazo[1,2-a]pyrazin-3-amine
[240] N-cyclopentyl-2-(4-(pyridin-2-ylethynyl)phenyl)imidazo[1,2-a]pyrazin-3-amine
[241] 8-chloro-2-(4-(pyridin-2-ylethynyl)phenyl)-6-(trifluoromethyl)-N-(2,4,4-trimethylpentan-2-yl)imidazo[1,2-a]pyridin-3-amine
[242] N-(4-fluorophenyl)-2-(4-(pyridin-2-ylethynyl)phenyl)imidazo[1,2-a]pyrazin-3-amine
[243] N-cyclopentyl-2-(2-methyl-6-(phenylethynyl)pyridin-3-yl)imidazo[1,2-a]pyrazin-3-amine
[244] N-cyclohexyl-2-(2-methyl-6-(phenylethynyl)pyridin-3-yl)imidazo[1,2-a]pyrazin-3-amine
[245] N-cyclopentyl-2-(5-(pyridin-2-ylethynyl)furan-2-yl)imidazo[1,2-a]pyrazin-3-amine
[246] 8-bromo-N-cyclopentyl-6-methyl-2-(5-(pyridin-2-ylethynyl)furan-2-yl)imidazo[1,2-a]pyridin-3-amine
[247] N-cyclohexyl-2-(5-(pyridin-2-ylethynyl)furan-2-yl)imidazo[1,2-a]pyrazin-3-amine
[248] 2-(5-(pyridin-2-ylethynyl)furan-2-yl)-N-(2,4,4-trimethylpentan-2-yl)imidazo[1,2-a]pyrazin-3-amine
[249] N-cyclopentyl-2-(3-((6-methylpyridin-2-yl)ethynyl)phenyl)imidazo[1,2-a]pyrazin-3-amine
[250] 8-bromo-N-cyclopentyl-6-methyl-2-(4-(pyridin-2-ylethynyl)phenyl)imidazo[1,2-a]pyridin-3-amine
[251] N-cyclohexyl-2-(3-((6-methylpyridin-2-yl)ethynyl)phenyl)imidazo[1,2-a]pyrazin-3-amine
[252] N-(4-fluorophenyl)-2-(3-((6-methylpyridin-2-yl)ethynyl)phenyl)imidazo[1,2-a]pyrazin-3-amine
[253] 2-(5-(pyridin-2-ylethynyl)thiophen-2-yl)-N-(2,4,4-trimethylpentan-2-yl)imidazo[1,2-a]pyrimidin-3-amine
[254] N-cyclohexyl-2-(3-(pyridin-2-ylethynyl)phenyl)imidazo[1,2-a]pyrimidin-3-amine
[255] 2-(3-(pyridin-2-ylethynyl)phenyl)-N-(2,4,4-trimethylpentan-2-yl)imidazo[1,2-a]pyrimidin-3-amine
[256] 2-(6-(phenylethynyl)pyridin-3-yl)-N-(2,4,4-trimethylpentan-2-yl)imidazo[1,2-a]pyrimidin-3-amine
[257] N-cyclopentyl-2-(5-(pyridin-2-ylethynyl)furan-2-yl)imidazo[1,2-a]pyrimidin-3-amine
[258] N-tert-butyl-2-(5-(pyridin-2-ylethynyl)furan-2-yl)imidazo[1,2-a]pyrimidin-3-amine
[259] N-cyclopentyl-2-(3-((6-methylpyridin-2-yl)ethynyl)phenyl)imidazo[1,2-a]pyrimidin-3-amine
[260] N-cyclopentyl-2-(3-(pyridin-2-ylethynyl)phenyl)imidazo[1,2-a]pyridin-3-amine
[261] N-tert-butyl-2-(3-(pyridin-2-ylethynyl)phenyl)imidazo[1,2-a]pyridin-3-amine
[262] 2-(3-(pyridin-2-ylethynyl)phenyl)-N-(2,4,4-trimethylpentan-2-yl)imidazo[1,2-a]pyridin-3-amine
[263] N-(4-fluorophenyl)-2-(3-(pyridin-2-ylethynyl)phenyl)imidazo[1,2-a]pyridin-3-amine
[264] N-tert-butyl-2-(4-(pyridin-2-ylethynyl)phenyl)imidazo[1,2-a]pyridin-3-amine
[265] N-cyclopentyl-2-(2-methyl-6-(phenylethynyl)pyridin-3-yl)imidazo[1,2-a]pyridin-3-amine
[266] N-(4-fluorophenyl)-2-(2-methyl-6-(phenylethynyl)pyridin-3-yl)imidazo[1,2-a]pyridin-3-amine
[267] N-cyclopentyl-6-methyl-2-(5-(pyridin-2-ylethynyl)thiophen-2-yl)imidazo[1,2-a]pyridin-3-amine
[268] N-tert-butyl-6-methyl-2-(5-(pyridin-2-ylethynyl)thiophen-2-yl)imidazo[1,2-a]pyridin-3-amine
[269] N-cyclohexyl-6-methyl-2-(5-(pyridin-2-ylethynyl)thiophen-2-yl)imidazo[1,2-a]pyridin-3-amine
[270] 6-methyl-2-(5-(pyridin-2-ylethynyl)thiophen-2-yl)-N-(2,4,4-trimethylpentan-2-yl)imidazo[1,2-a]pyridin-3-amine
[271] 6-methyl-2-(2-methyl-6-(phenylethynyl)pyridin-3-yl)-N-(2,4,4-trimethylpentan-2-yl)imidazo[1,2-a]pyridin-3-amine
[272] N-cyclopentyl-6-methyl-2-(5-(pyridin-2-ylethynyl)furan-2-yl)imidazo[1,2-a]pyridin-3-amine
[273] N-cyclohexyl-6-methyl-2-(3-((6-methylpyridin-2-yl)ethynyl)phenyl)imidazo[1,2-a]pyridin-3-amine
[274] N-cyclohexyl-7-methyl-2-(5-(pyridin-2-ylethynyl)thiophen-2-yl)imidazo[1,2-a]pyridin-3-amine
[275] 7-methyl-2-(5-(pyridin-2-ylethynyl)thiophen-2-yl)-N-(2,4,4-trimethylpentan-2-yl)imidazo[1,2-a]pyridin-3-amine
[276] N-tert-butyl-7-methyl-2-(3-(pyridin-2-ylethynyl)phenyl)imidazo[1,2-a]pyridin-3-amine
[277] N-(4-fluorophenyl)-7-methyl-2-(3-(pyridin-2-ylethynyl)phenyl)imidazo[1,2-a]pyridin-3-amine
[278] N-tert-butyl-7-methyl-2-(4-(pyridin-2-ylethynyl)phenyl)imidazo[1,2-a]pyridin-3-amine
[279] N-(4-fluorophenyl)-7-methyl-2-(5-(pyridin-2-ylethynyl)furan-2-yl)imidazo[1,2-a]pyridin-3-amine
[280] N-cyclohexyl-8-methyl-2-(6-(phenylethynyl)pyridin-3-yl)imidazo[1,2-a]pyridin-3-amine
[281] N-cyclopentyl-2-(6-(phenylethynyl)pyridin-3-yl)imidazo[1,2-a]pyridin-3-amine
[282] N-tert-butyl-2-(6-(phenylethynyl)pyridin-3-yl)imidazo[1,2-a]pyridin-3-amine
[283] N-cyclohexyl-2-(6-(phenylethynyl)pyridin-3-yl)imidazo[1,2-a]pyridin-3-amine
[284] 2-(6-(phenylethynyl)pyridin-3-yl)-N-(2,4,4-trimethylpentan-2-yl)imidazo[1,2-a]pyridin-3-amine
[285] N-tert-butyl-2-(5-(pyridin-2-ylethynyl)furan-2-yl)imidazo[1,2-a]pyridin-3-amine
[286] N-cyclohexyl-2-(5-(pyridin-2-ylethynyl)furan-2-yl)imidazo[1,2-a]pyridin-3-amine
[287] N-(4-fluorophenyl)-2-(5-(pyridin-2-ylethynyl)furan-2-yl)imidazo[1,2-a]pyridin-3-amine
[288] N-cyclohexyl-2-(3-((6-methylpyridin-2-yl)ethynyl)phenyl)imidazo[1,2-a]pyridin-3-amine
[289] 2-(3-((6-methylpyridin-2-yl)ethynyl)phenyl)-N-(2,4,4-trimethylpentan-2-yl)imidazo[1,2-a]pyridin-3-amine
[290] N-tert-butyl-5-methyl-2-(3-((6-methylpyridin-2-yl)ethynyl)phenyl)imidazo[1,2-a]pyridin-3-amine
[291] 5-methyl-2-(3-((6-methylpyridin-2-yl)ethynyl)phenyl)-N-(2,4,4-trimethylpentan-2-yl)imidazo[1,2-a]pyridin-3-amine

[292] N-cyclohexyl-5,7-dimethyl-2-(3-(pyridin-2-ylethynyl)phenyl)imidazo[1,2-a]pyrimidin-3-amine
[293] N-cyclohexyl-5,7-dimethyl-2-(2-methyl-6-(phenylethynyl)pyridin-3-yl)imidazo[1,2-a]pyrimidin-3-amine
[294] N-cyclopentyl-5,7-dimethyl-2-(5-(pyridin-2-ylethynyl)furan-2-yl)imidazo[1,2-a]pyrimidin-3-amine
[295] N-tert-butyl-5,7-dimethyl-2-(5-(pyridin-2-ylethynyl)furan-2-yl)imidazo[1,2-a]pyrimidin-3-amine
[296] N-(4-fluorophenyl)-8-methyl-2-(3-(pyridin-2-ylethynyl)phenyl)imidazo[1,2-a]pyridin-3-amine
[297] N-cyclohexyl-8-methyl-2-(4-(pyridin-2-ylethynyl)phenyl)imidazo[1,2-a]pyridin-3-amine
[298] N-cyclohexyl-7-ethyl-2-(5-(pyridin-2-ylethynyl)thiophen-2-yl)imidazo[1,2-a]pyridin-3-amine
[299] 7-ethyl-2-(5-(pyridin-2-ylethynyl)thiophen-2-yl)-N-(2,4,4-trimethylpentan-2-yl)imidazo[1,2-a]pyridin-3-amine
[300] N-cyclohexyl-7-ethyl-2-(3-(pyridin-2-ylethynyl)phenyl)imidazo[1,2-a]pyridin-3-amine
[301] N-cyclopentyl-7-ethyl-2-(4-(pyridin-2-ylethynyl)phenyl)imidazo[1,2-a]pyridin-3-amine
[302] N-cyclopentyl-7-ethyl-2-(6-(phenylethynyl)pyridin-3-yl)imidazo[1,2-a]pyridin-3-amine
[303] N-tert-butyl-7-ethyl-2-(6-(phenylethynyl)pyridin-3-yl)imidazo[1,2-a]pyridin-3-amine
[304] N-tert-butyl-7-ethyl-2-(5-(pyridin-2-ylethynyl)furan-2-yl)imidazo[1,2-a]pyridin-3-amine
[305] 7-isopropyl-2-(5-(pyridin-2-ylethynyl)thiophen-2-yl)-N-(2,4,4-trimethylpentan-2-yl)imidazo[1,2-a]pyridin-3-amine
[306] N-tert-butyl-7-isopropyl-2-(3-(pyridin-2-ylethynyl)phenyl)imidazo[1,2-a]pyridin-3-amine
[307] N-tert-butyl-7-isopropyl-2-(4-(pyridin-2-ylethynyl)phenyl)imidazo[1,2-a]pyridin-3-amine
[308] N-cyclohexyl-7-isopropyl-2-(5-(pyridin-2-ylethynyl)furan-2-yl)imidazo[1,2-a]pyridin-3-amine
[309] N-tert-butyl-7-isopropyl-2-(3-((6-methylpyridin-2-yl)ethynyl)phenyl)imidazo[1,2-a]pyridin-3-amine
[310] 6-chloro-N-cyclopentyl-2-(5-(pyridin-2-ylethynyl)thiophen-2-yl)imidazo[1,2-a]pyridin-3-amine
[311] N-tert-butyl-6-chloro-2-(5-(pyridin-2-ylethynyl)thiophen-2-yl)imidazo[1,2-a]pyridin-3-amine
[312] 6-chloro-N-cyclohexyl-2-(3-(pyridin-2-ylethynyl)phenyl)imidazo[1,2-a]pyridin-3-amine
[313] 6-chloro-2-(3-(pyridin-2-ylethynyl)phenyl)-N-(2,4,4-trimethylpentan-2-yl)imidazo[1,2-a]pyridin-3-amine
[314] N-tert-butyl-6-chloro-2-(4-(pyridin-2-ylethynyl)phenyl)imidazo[1,2-a]pyridin-3-amine
[315] 6-chloro-N-cyclohexyl-2-(4-(pyridin-2-ylethynyl)phenyl)imidazo[1,2-a]pyridin-3-amine
[316] N-tert-butyl-6-chloro-2-(5-(pyridin-2-ylethynyl)furan-2-yl)imidazo[1,2-a]pyridin-3-amine
[317] 6-chloro-N-cyclohexyl-2-(5-(pyridin-2-ylethynyl)furan-2-yl)imidazo[1,2-a]pyridin-3-amine
[318] 6-chloro-2-(5-(pyridin-2-ylethynyl)furan-2-yl)-N-(2,4,4-trimethylpentan-2-yl)imidazo[1,2-a]pyridin-3-amine
[319] 6-chloro-N-cyclopentyl-2-(3-((6-methylpyridin-2-yl)ethynyl)phenyl)imidazo[1,2-a]pyridin-3-amine
[320] N-tert-butyl-6-chloro-2-(3-((6-methylpyridin-2-yl)ethynyl)phenyl)imidazo[1,2-a]pyridin-3-amine
[321] N-tert-butyl-2-(5-(pyridin-2-ylethynyl)thiophen-2-yl)imidazo[1,2-a]pyridin-3-amine bis-hydrochloride
[322] N-methyl-2-(5-(pyridin-2-ylethynyl)thiophen-2-yl)imidazo[1,2-a]pyrazin-3-amine
[323] N-tert-butyl-2-(5-(pyridin-2-ylethynyl)thiophen-2-yl)imidazo[1,2-a]pyridin-3-amine bis-hydrochloride
[324] [2-(5-pyridin-2-ylethynyl-thiophen-2-yl)-imidazo[1,2-a]pyridin-3-yl]-(1,1,3,3-tetramethyl-butyl)-amine
[325] tert-butyl-[2-(5-pyrimidin-2-ylethynyl-thiophen-2-yl)-imidazo[1,2-a]pyridin-3-yl]-amine hydrochloride
[326] {2-[5-(3-amino-pyridin-2-ylethynyl)-thiophen-2-yl]-imidazo[1,2-a]pyridin-3-yl}-tert-butyl-amine
[327] tert-butyl-[2-(5-pyridin-2-ylethynyl-thiazol-2-yl)-imidazo[1,2-a]pyridin-3-yl]-amine
[328] tert-butyl-[2-(2-pyridin-2-ylethynyl-thiazol-5-yl)-imidazo[1,2-a]pyridin-3-yl]-amine
[329] tert-butyl-{2-[5-(6-fluoro-pyridin-2-ylethynyl)-thiophen-2-yl]-imidazo[1,2-a]pyridin-3-yl}-amine hydrochloride
[330] tert-butyl-{2-[5-(3-chloro-5-fluoro-phenylethynyl)-thiophen-2-yl]-imidazo[1,2-a]pyridin-3-yl}-amine hydrochloride
[331] tert-butyl-[2-(5-pyridin-2-ylethynyl-thiophen-2-yl)-imidazo[1,2-b]pyridazin-3-yl]-amine hydrochloride
[332] tert-butyl-[2-(5-thiazol-2-ylethynyl-thiophen-2-yl)-imidazo[1,2-a]pyridin-3-yl]-amine hydrochloride
[333] tert-butyl-{2-[5-(3-trifluoromethoxy-phenylethynyl)-thiophen-2-yl]-imidazo[1,2-a]pyrazin-3-yl}-amine
[334] tert-butyl-{2-[5-(3-[1,3]dioxolan-2-yl-phenylethynyl)-thiophen-2-yl]-imidazo[1,2-a]pyridin-3-yl}-amine
[335] tert-butyl-{2-[5-(3,5-dimethyl-phenylethynyl)-thiophen-2-yl]-imidazo[1,2-a]pyridin-3-yl}-amine hydrochloride
[336] tert-butyl-{2-[5-(3-fluoro-pyridin-2-ylethynyl)-thiophen-2-yl]-imidazo[1,2-a]pyridin-3-yl}-amine hydrochloride
[337] tert-butyl-{2-[5-(3-methyl-3H-imidazol-4-ylethynyl)-thiophen-2-yl]-imidazo[1,2-a]pyridin-3-yl}-amine hydrochloride
[338] tert-butyl-{2-[5-(5-chloro-thiophen-2-ylethynyl)-thiophen-2-yl]-imidazo[1,2-a]pyridin-3-yl}-amine hydrochloride
[339] tert-butyl-{2-[5-(5-methyl-pyridin-2-ylethynyl)-thiophen-2-yl]-imidazo[1,2-a]pyridin-3-yl}-amine hydrochloride
[340] 1-{3-[5-(3-tert-butylamino-imidazo[1,2-a]pyridin-2-yl)-thiophen-2-ylethynyl]-phenyl}-ethanone hydrochloride
[341] {3-[5-(3-tert-butylamino-imidazo[1,2-a]pyridin-2-yl)-thiophen-2-ylethynyl]-phenyl}-methanol hydrochloride
[342] N-tert-butyl-2-(5-((3-methoxypyridin-2-yl)ethynyl)thiophen-2-yl)imidazo[1,2-a]pyridin-3-amine
[343] N-tert-butyl-2-(5-(thiophen-2-ylethynyl)thiophen-2-yl)imidazo[1,2-a]pyridin-3-amine hydrochloride
[344] 5-((5-(3-(tert-butylamino)imidazo[1,2-a]pyridin-2-yl)thiophen-2-yl)ethynyl)-2-fluorobenzonitrile hydrochloride
[345] N-tert-butyl-2-(5-((3,4-difluorophenyl)ethynyl)thiophen-2-yl)imidazo[1,2-a]pyridin-3-amine
[346] N-tert-butyl-2-(5-((3-(methoxymethyl)phenyl)ethynyl)thiophen-2-yl)imidazo[1,2-a]pyridin-3-amine
[347] 2-(5-((3-aminophenyl)ethynyl)thiophen-2-yl)-N-tert-butylimidazo[1,2-a]pyridin-3-amine hydrochloride
[348] N-tert-butyl-2-(5-((4-fluoro-3-methylphenyl)ethynyl)thiophen-2-yl)imidazo[1,2-a]pyridin-3-amine hydrochloride
[349] N-tert-butyl-2-(5-((3,5-difluorophenyl)ethynyl)thiophen-2-yl)imidazo[1,2-a]pyridin-3-amine
[350] N-tert-butyl-2-(5-(thiophen-3-ylethynyl)thiophen-2-yl)imidazo[1,2-a]pyridin-3-amine hydrochloride
[351] N-tert-butyl-2-(5-((3-methylpyridin-2-yl)ethynyl)thiophen-2-yl)imidazo[1,2-a]pyridin-3-amine hydrochloride

[352] 3-((5-(3-(tert-butylamino)imidazo[1,2-a]pyridin-2-yl)thiophen-2-yl)ethynyl)benzenesulfonamide hydrochloride
[353] 3-((5-(3-(tert-butylamino)imidazo[1,2-a]pyridin-2-yl)hiophen-2-yl)ethynyl)benzoic acid
[354] 3-((5-(3-(tert-butylamino)imidazo[1,2-a]pyridin-2-yl)thiophen-2-yl)ethynyl)benzamide hydrochloride
[355] N-(3-((5-(3-(tert-butylamino)imidazo[1,2-a]pyridin-2-yl)thiophen-2-yl)ethynyl)phenyl)acetamide
[356] N-tert-butyl-N-methyl-2-(5-(pyridin-2-ylethynyl)thiophen-2-yl)imidazo[1,2-a]pyridin-3-amine
[357] N,N-dimethyl-2-(5-(pyridin-2-ylethynyl)thiophen-2-yl)imidazo[1,2-a]pyridin-3-amine
[358] N-tert-butyl-N-methyl-2-(5-(pyridin-2-ylethynyl)thiazol-2-yl)imidazo[1,2-a]pyridin-3-amine
[359] (6-((5-(3-(tert-butylamino)imidazo[1,2-a]pyridin-2-yl)thiophen-2-yl)ethynyl)pyridin-2-yl)methanol
[360] N-(3-((5-(3-(tert-butylamino)imidazo[1,2-a]pyridin-2-yl)thiophen-2-yl)ethynyl)phenyl)methanesulfonamide
[361] N-tert-butyl-8-methyl-2-(5-(pyridin-2-ylethynyl)thiophen-2-yl)imidazo[1,2-a]pyrazin-3-amine hydrochloride
[362] 2-(5-(pyridin-2-ylethynyl)thiophen-2-yl)imidazo[1,2-a]pyridin-3-amine
[363] N-tert-butyl-2-(5-((3-chlorophenyl)ethynyl)thiophen-2-yl)imidazo[1,2-a]pyridin-3-amine
[364] N-tert-butyl-2-(5-((2,3-difluorophenyl)ethynyl)thiophen-2-yl)imidazo[1,2-a]pyridin-3-amine and
[365] N-tert-butyl-7-chloro-2-(5-(pyridin-2-ylethynyl)thiophen-2-yl)imidazo[1,2-a]pyridin-3-amine and in each case the corresponding salts thereof, in particular the hydrochlorides thereof, and in each case the corresponding solvates thereof.

The present invention also provides a process for the production of compounds of the above-stated general formula I, in accordance with which at least one compound of the general formula II,

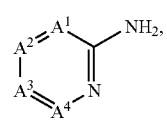

in which A1, A2, A3 and A4 have the above-stated meaning, is reacted in a reaction medium, optionally in the presence of at least one organic or inorganic acid or at least one transition metal salt, with at least one isocyanide of the general formula III,

in which R2 has the above-stated meaning, and with at least one aldehyde of the general formula IV,

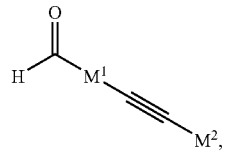

in which M1 and M2 have the above-stated meaning, and the resultant compound of the general formula V,

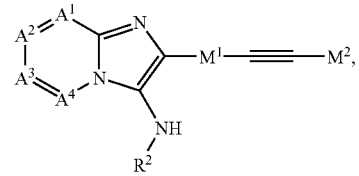

in which A1, A2, A3, A4, R2, M1 and M2 have the above-stated meaning, is optionally purified and/or isolated, and optionally converted into a corresponding salt and this is optionally purified and/or isolated, or at least one compound of the general formula II,

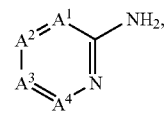

in which A1, A2, A3 and A4 have the above-stated meaning, is reacted in a reaction medium, optionally in the presence of at least one organic or inorganic acid or at least one transition metal salt, with at least one isocyanide of the general formula III,

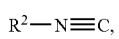

in which R2 has the above-stated meaning, and with at least one aldehyde of the general formula IV,

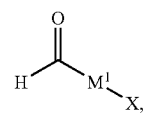

in which M1 has the above-stated meaning and X represents a leaving group, preferably a halogen or a sulfonic acid ester, particularly preferably chlorine, bromine or trifluoromethanesulfonate, and the resultant compound of the general formula VII,

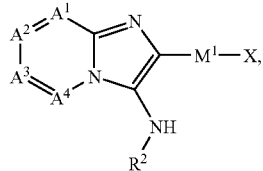

VII in which A1, A2, A3, A4, R2, M1 and X have the above-stated meaning, is optionally purified and/or isolated, and optionally converted into a corresponding salt and this is optionally purified and/or isolated, and
by reaction with at least one acetylene of the general formula XI,

XI in which R, mutually independently, in each case represents a linear or branched alkyl group or represents an unsubstituted phenyl group, is converted in a reaction medium, optionally in the presence of at least one suitable catalyst, optionally in the presence of at least one copper(I) salt, preferably in the presence of copper(I) iodide, and optionally in the presence of at least one inorganic and/or organic base, into a correspondingly substituted compound of the general formula

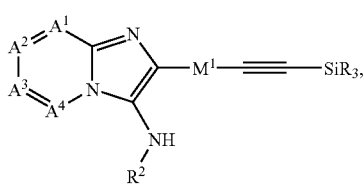

XII in which A1, A2, A3, A4, R2 and M1 have the above-stated meaning and R, mutually independently, in each case represents a linear or branched alkyl group or represents an unsubstituted phenyl group, and is optionally purified and/or isolated, and optionally converted into a corresponding salt and this is optionally purified and/or isolated,
and at least one compound of the general formula XII is converted in a reaction medium, optionally in the presence of at least one inorganic and/or organic base, optionally in the presence of at least one inorganic salt, and optionally in the presence of at least one ammonium salt, into a correspondingly substituted compound of the general formula XIII,

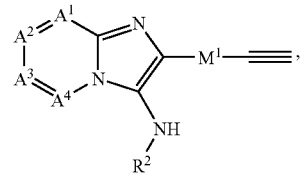

XIII in which A1, A2, A3, A4, R2 and M1 have the above-stated meaning, and is optionally purified and/or isolated, and optionally converted into a corresponding salt and this is optionally purified and/or isolated,
and at least one compound of the general formula XIII and/or at least one compound of the general formula XII, is converted by reaction with at least one compound of the general formula M2-X, in which M2 has the above-stated meaning and X represents a leaving group, preferably a halogen or a sulfonic acid ester, particularly preferably chlorine, bromine or trifluoromethanesulfonate, in a reaction medium, optionally in the presence of at least one suitable catalyst, optionally in the presence of at least one inorganic and/or organic base, optionally in the presence of at least one inorganic salt and optionally in the presence of at least one ammonium salt, into a correspondingly substituted compound of the general formula V,

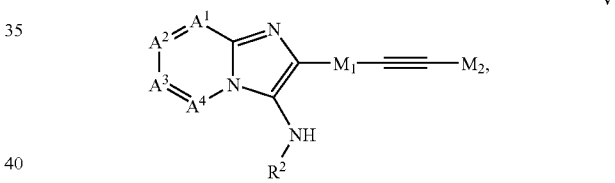

V in which A1, A2, A3, A4, R2, M1 and M2 have the above-stated meaning, and is optionally purified and/or isolated, and optionally converted into a corresponding salt and this is optionally purified and/or isolated,
or a compound of the general formula VII is converted by reaction with at least one acetylene of the general formula VIII,

VIII in which $M^2$ has the above-stated meaning, in a reaction medium, optionally in the presence of at least one suitable catalyst, optionally in the presence of at least one copper(I) salt, preferably in the presence of copper(I) iodide and optionally in the presence of at least one inorganic and/or organic base, into a correspondingly substituted compound of the general formula V,

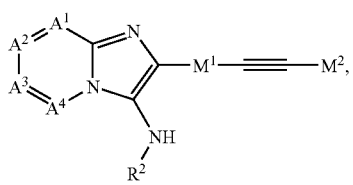

V in which A1, A2, A3, A4, R2, M1 and M2 have the above-stated meaning, and is optionally purified and/or isolated, and optionally converted into a corresponding salt and this is optionally purified and/or isolated, and optionally the compound of the general formula V is converted by reaction with at least one compound of the general formula R3-X, in which R3 has the above-stated meaning and X represents a leaving group, preferably a halogen or a sulfonic acid ester, particularly preferably chlorine, in a reaction medium, in the presence of at least one organic or inorganic base, preferably in the presence of at least one metal hydride salt, or by reaction with at least one compound of the general formula R20-C(=O)—OH, in which R20 has the above-stated meaning, in a reaction medium, optionally in the presence of at least one organic or inorganic base and/or in the presence of at least one coupling agent, or by reaction with at least one compound of the general formula R20-C(=O)—X, in which R20 has the above-stated meaning and X represents a leaving group, preferably a halogen or a sulfonic acid ester, particularly preferably chlorine, bromine or trifluoromethanesulfonate, in a reaction medium, optionally in the presence of at least one organic or inorganic base, or by reaction with at least one compound of the general formula R20-C(=O)—H, in which R20 has the above-stated meaning, in a reaction medium, optionally in the presence of at least one reducing agent, into a compound of the general formula I, optionally in the form of a corresponding salt,

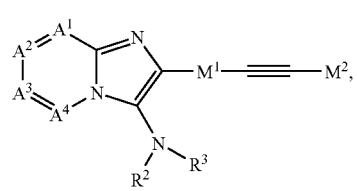

I in which A1, A2, A3, A4, R2, R3, M1 and M2 have the above-stated meaning, and this is optionally purified and/or isolated.

The present invention also provides a process for the production of compounds of the above-stated general formula I, in accordance with which at least one compound of the general formula V,

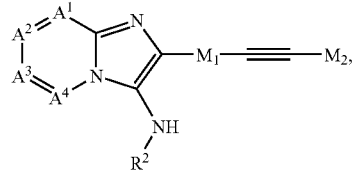

V in which A1, A2, A3, A4, R2, M1 and M2 have the above-stated meaning, is converted optionally in a reaction medium in the presence of at least one organic or inorganic acid, and the resultant compound of the general formula IX,

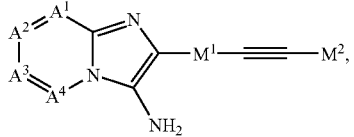

IX in which A1, A2, A3, A4, M1 and M2 have the above-stated meaning, is optionally purified and/or isolated, and optionally converted into a corresponding salt and this is optionally purified and/or isolated and converted in a reaction medium, in the presence of at least one inorganic or organic base, preferably in the presence of at least one metal hydride salt, with at least one compound of the general formula R3-X, in which R3 has the above-stated meaning and X represents a leaving group, preferably a halogen or a sulfonic acid ester, particularly preferably chlorine, or in a reaction medium, optionally in the presence of at least one organic or inorganic base and/or optionally in the presence of at least one coupling agent with at least one compound of the general formula R20-C(=O)—OH, in which R20 has the above-stated meaning, or in a reaction medium, optionally in the presence of at least one organic or inorganic base with at least one compound of the general formula R20-C(=O)—X, in which R20 has the above-stated meaning and X represents a leaving group, preferably a halogen or a sulfonic acid ester, particularly preferably chlorine, bromine or trifluoromethanesulfonate, or in a reaction medium, optionally in the presence of at least one reducing agent with at least one compound of the general formula R20-C(=O)—H, in which R20 has the above-stated meaning, into a corresponding compound of the general formula X, optionally in the form of a corresponding salt,

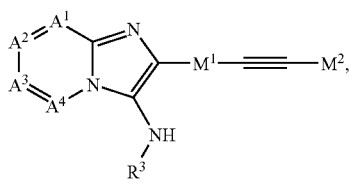

in which A1, A2, A3, A4, R3, M1 and M2 have the above-stated meaning, and this is optionally purified and/or isolated, and optionally the compound of the general formula X is converted, by reaction with at least one compound of the general formula R2-X, in which R2 has the above-stated meaning and X represents a leaving group, preferably a halogen or a sulfonic acid ester, particularly preferably chlorine, in a reaction medium, in the presence of at least one organic or inorganic base, preferably in the presence of at least one metal hydride salt, or by reaction with at least one compound of the general formula R20-C(=O)—OH, in which R20 has the above-stated meaning, in a reaction medium, optionally in the presence of at least one organic or inorganic base and/or in the presence of at least one coupling agent, or by reaction with at least one compound of the general formula R20-C(=O)—X, in which R20 has the above-stated meaning and X represents a leaving group, preferably a halogen or a sulfonic acid ester, particularly preferably chlorine, bromine or trifluoromethanesulfonate, in a reaction medium, optionally in the presence of at least one organic or inorganic base, or by reaction with at least one compound of the general formula R20-C(=O)—H, in which R20 has the above-stated meaning, in a reaction medium, optionally in the presence of at least one reducing agent, into a compound of the above-stated general formula I, optionally in the form of a corresponding salt,

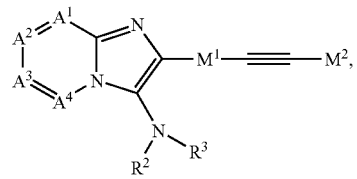

in which A1, A2, A3, A4, R2, R3, M1 and M2 have the above-stated meaning, and this is optionally purified and/or isolated.

The processes according to the invention for the production of substituted imidazo-3-yl-amine compounds of the above-stated general formula I are also indicated in the following schemes 1 to 4.

Scheme 1.

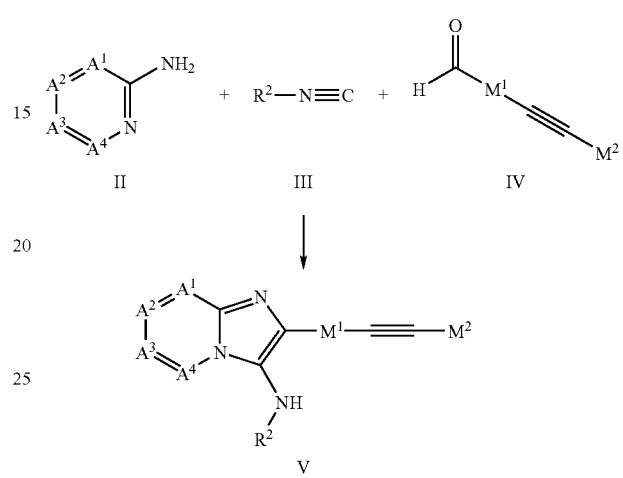

In a three-component coupling reaction, amines of the general formula II are reacted with isocyanides of the general formula III and aldehydes of the general formula IV in a reaction medium, preferably selected from the group consisting of chloroform, dichloromethane, acetonitrile, methanol and ethanol, with the addition of at least one organic or inorganic acid, preferably trifluoroacetic acid or perchloric acid, or with the addition of at least one transition metal salt, preferably with the addition of at least one transition metal triflate (transition metal trifluoromethanesulfonate), particularly preferably with the addition of at least one transition metal triflate selected from the group consisting of scandium (III) trifluoromethanesulfonate, ytterbium trifluoromethanesulfonate and indium(III) trifluoromethanesulfonate, preferably at temperatures of 0° C. to 150° C. to yield compounds of the general formula V.

A further process for the production of substituted imidazo-3-yl-amine compounds of the above-stated general formula I is indicated in scheme 2.

Scheme 2.

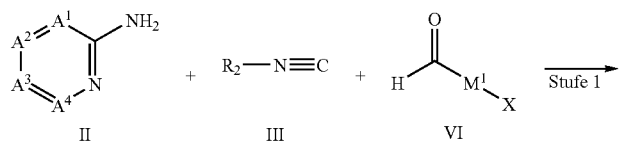

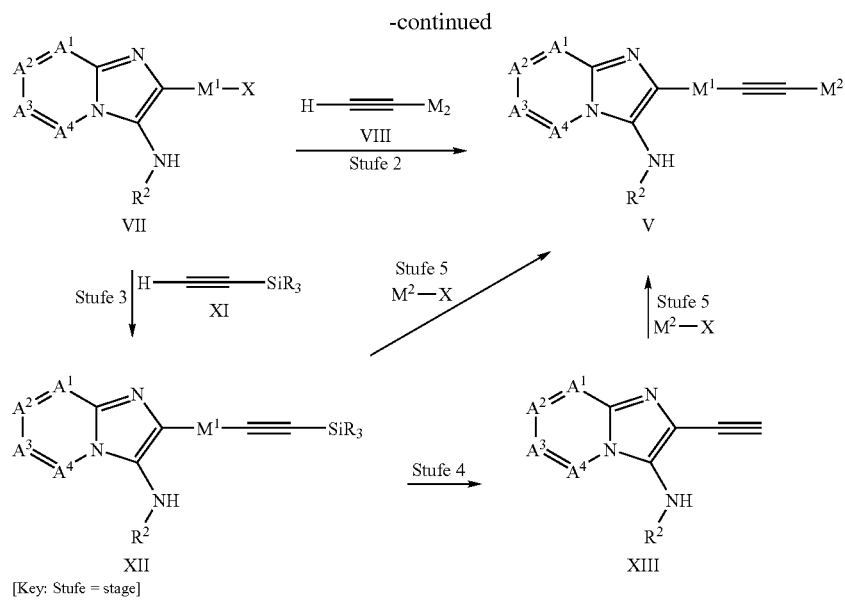

[Key: Stufe = stage]

In stage 1, in a three-component coupling reaction, amines of the general formula II are reacted with isocyanides of the general formula III and aldehydes of the general formula VI, in which X represents a leaving group, preferably a halogen or a sulfonic acid ester, particularly preferably chlorine, bromine or trifluoromethanesulfonate, in a reaction medium, preferably selected from the group consisting of chloroform, dichloromethane, acetonitrile, methanol and ethanol, with the addition of at least one organic or inorganic acid, preferably selected from the group consisting of trifluoroacetic acid or perchloric acid, or with the addition of at least one transition metal salt, preferably with the addition of at least one transition metal triflate(transition metal trifluoromethanesulfonate), particularly preferably with the addition of at least one transition metal trifluoromethanesulfonate selected from the group consisting of scandium(III) trifluoromethanesulfonate, ytterbium trifluoromethanesulfonate and indium (III) trifluoromethanesulfonate, preferably at temperatures of 0° C. to 150° C. to yield compounds of the general formula VII, in which X represents a leaving group, preferably a halogen or a sulfonic acid ester, particularly preferably chlorine, bromine or trifluoromethanesulfonate.

In stage 2, compounds of the above-stated general formula VII, in which X represents a halogen or a sulfonic acid ester, particularly preferably chlorine, bromine or trifluoromethanesulfonate, are reacted with acetylenes of the general formula VIII in a reaction medium, preferably selected from the group consisting of methanol, ethyl acetate, ethanol, isopropanol, n-butanol, dioxane, chloroform, dichloromethane, pyridine, dimethyl sulfoxide, toluene, tetrahydrofuran, dimethylformamide, acetonitrile, diethyl ether, water and corresponding mixtures, particularly preferably selected from the group consisting of dimethylformamide, ethyl acetate, tetrahydrofuran, water and corresponding mixtures, preferably with the addition of at least one palladium catalyst, preferably selected from the group consisting of palladium (II) dichloride [PdCl2], bis(triphenylphosphine)palladium (II) acetate [Pd(PPh3)2(OAc)2], bis(triphenylphosphine)palladium(II) chloride [PdCl2(PPh3)2], palladium(II) acetate [Pd(OAc)2; Ac=acetate], bis(acetonitrile)palladium(II) chloride [(CH3CN)2)PdCl2], bis(benzonitrile)palladium(II) chloride [(PhCN)2PdCl2]and tetrakis(triphenylphosphine) palladium [(PPh3)4Pd], particularly preferably selected from the group consisting of Pd(PPh3)2(OAc)2, (PPh3)4Pd and PdCl2(PPh3)2, optionally in the presence of at least one copper(I) salt, preferably in the presence of copper(I) iodide, optionally in the presence of at least one phosphine, preferably a phosphine selected from the group consisting of triphenylphosphine, tri(tert-butyl)phosphine, triphenylarsine and tri(ortho-toluyl)phosphine, particularly preferably in the presence of triphenylphosphine, optionally with the addition of at least one inorganic salt, preferably with the addition of lithium and/or zinc chloride, optionally with the addition of at least one organic base, preferably an organic base selected from the group consisting of triethylamine, diisopropylamine, diisopropylethylamine and [1,4]-diazabicyclo-[2.2.2]octane and/or the addition of at least one inorganic base, preferably selected from the group consisting of potassium carbonate, sodium hydrogencarbonate and caesium carbonate, wherein in particular the organic base may also be the reaction medium, at temperatures of preferably −70° C. to 300° C., particularly preferably −70° C. to 150° C., to yield compounds of the general formula V.

In stage 3, compounds of the above-stated general formula VII are reacted with compounds of the above-stated general formula XI under the conditions stated in scheme 2, stage 2, to yield compounds of the general formula XII.

In stage 4, compounds of the above-stated general formula XII are reacted in a reaction medium, preferably selected from the group consisting of methanol, ethyl acetate, ethanol, isopropanol, n-butanol, dioxane, chloroform, dichloromethane, pyridine, dimethyl sulfoxide, toluene, tetrahydrofuran, dimethylformamide, acetonitrile, diethyl ether, water and corresponding mixtures, particularly preferably selected from the group consisting of dimethylformamide, ethyl acetate, tetrahydrofuran, water and corresponding mixtures, optionally in the presence of at least one inorganic base, preferably in the presence of at least one inorganic base selected from the group consisting of potassium carbonate, sodium hydroxide, potassium hydrogencarbonate, sodium hydrogencarbonate, potassium hydroxide and lithium hydroxide, optionally in the presence of at least one inorganic base, preferably at least one inorganic base selected from the group consisting of triethylamine and pyridine, optionally in the presence of at least one inorganic salt, preferably in the presence of at least one ammonium salt or in the presence of potassium fluoride and/or sodium fluoride, particularly preferably in the presence of at least one ammonium salt selected from the group consisting of tetra-n-butylammonium fluoride, tetra-n-butyl-ammonium iodide and tetrabutylammonium bromide, at temperatures of preferably −70° C. to 300° C., particularly preferably of −70° C. to 150° C., to yield compounds of the general formula XIII.

In stage 5, compounds of the above-stated general formulae XII and XIII are reacted with compounds of the general formula M2-X, in which X represents a halogen or a sulfonic acid ester, particularly preferably chlorine, bromine or trifluoromethanesulfonate, in a reaction medium, preferably selected from the group consisting of methanol, ethyl acetate, ethanol, isopropanol, n-butanol, dioxane, chloroform, dichloromethane, pyridine, dimethyl sulfoxide, toluene, tetrahydrofuran, dimethylformamide, acetonitrile, diethyl ether, water and corresponding mixtures, particularly preferably selected from the group consisting of dimethylformamide, ethyl acetate, tetrahydrofuran, water and corresponding mixtures, preferably with the addition of at least one palladium catalyst, preferably selected from the group consisting of palladium (II) dichloride [PdCl2], bis(triphenylphosphine)palladium (II) acetate [Pd(PPh3)2(OAc)2], bis(triphenylphosphine)palladium(II) chloride [PdCl2(PPh3)2], palladium(II) acetate [Pd(OAc)2; Ac=acetate], bis(acetonitrile)palladium(II) chloride [(CH3CN)2PdCl2], bis(benzonitrile)-palladium(II) chloride [(PhCN)2PdCl2] and tetrakis(triphenylphosphine) palladium [(PPh3)4Pd], particularly preferably selected from the group consisting of Pd(PPh3)2(OAc)2, (PPh3)4Pd and PdCl2(PPh3)2, optionally in the presence of at least one copper(I) salt, preferably in the presence of copper(I) iodide, optionally in the presence of at least one phosphine, preferably a phosphine selected from the group consisting of triphenylphosphine, tri(tert-butyl)phosphine, triphenylarsine and tri(ortho-toluyl)phosphine, particularly preferably in the presence of triphenylphosphine, optionally with the addition of at least one inorganic salt, preferably with the addition of lithium and/or zinc chloride, optionally in the presence of at least one ammonium salt or in the presence of potassium fluoride and/or sodium fluoride, preferably in the presence of at least one ammonium salt selected from the group consisting of tetra-n-butyl-ammonium fluoride, tetra-n-butyl-ammonium iodide and tetrabutyl-ammonium bromide, optionally with the addition at least one organic base, preferably an organic base selected from the group consisting of triethylamine, diisopropylamine, diisopropylethylamine and [1,4]-diazabicyclo-[2.2.2]octane and/or the addition of at least one inorganic base, preferably selected from the group consisting of potassium carbonate, sodium hydrogencarbonate and caesium carbonate, wherein in particular the organic base may also be the reaction medium, at temperatures of preferably −70° C. to 300° C., particularly preferably of −70° C. to 150° C., to yield compounds of the general formula V.

The reaction of compounds of the general formula XII with compounds of the general formula M2-X preferably proceeds in the presence of at least one ammonium salt or in the presence of potassium fluoride and/or sodium fluoride.

The compounds of the general formula V may be reacted as described in scheme 3 to yield compounds of the formula X.

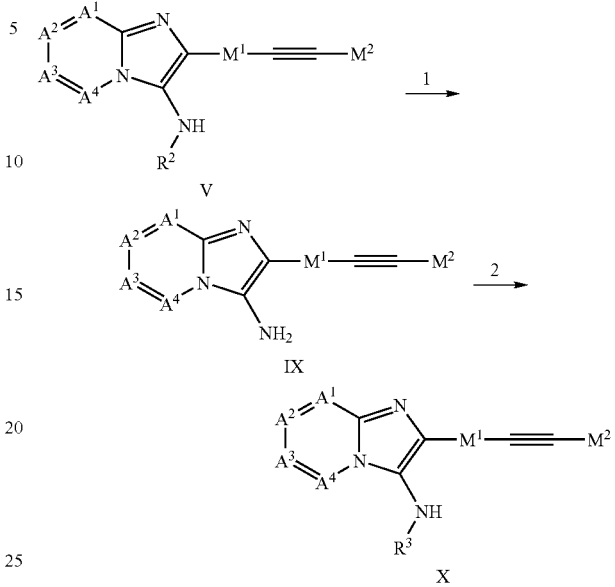

Scheme 3.

In stage 1, compounds of the above-stated general formula V are reacted in a reaction medium, preferably selected from the group consisting of ethanol, methanol and acetone, with the addition of at least one organic acid, preferably acetic acid or trifluoroacetic acid and/or with the addition of at least one inorganic acid, preferably hydrochloric acid or sulfuric acid, at temperatures of preferably 0° C. to 80° C. to yield compounds of the general formula IX.

In stage 2, compounds of the above-stated general formula IX are reacted with carboxylic acids of the general formula R20-(C=O)—OH, in which R20 has the above-stated meaning, in a reaction medium, preferably selected from the group consisting of diethyl ether, tetrahydrofuran, acetonitrile, methanol, ethanol, dimethylformamide and dichloromethane, optionally in the presence of at least one coupling reagent, preferably selected from the group consisting of 1-benzotriazolyloxy-tris-(dimethylamino)-phosphonium hexafluorophosphate (BOP), dicyclohexylcarbodiimide (DCC), N'-(3-dimethylaminopropyl)-N-ethylcarbodiimide (EDCI), N-[(dimethylamino)-1H-1,2,3-triazolo[4,5-b]pyridino-1-ylmethylene]-N-methylmethanaminium hexafluorophosphate N-oxide (HATU), O-(benzotriazol-1-yl)-N,N N', N'-tetramethyluronium hexafluorophosphate (HBTU) and 1-hydroxy-7-azabenzotriazole (HOAt), optionally in the presence of at least one inorganic base, preferably selected from the group consisting of potassium carbonate and caesium carbonate, or an organic base, preferably selected from the group consisting of triethylamine, pyridine, dimethylaminopyridine and diisopropylethylamine preferably at temperatures of −70° C. to 100° C. to yield compounds of the general formula X.

Alternatively, compounds of the general formula IX are reacted with carboxylic acid derivatives or carbonic acid derivatives of the general formula R20-(C=O)—X, wherein X represents a halogen, preferably chlorine or bromine, in a reaction medium, preferably selected from the group consisting of diethyl ether, tetrahydrofuran, acetonitrile, methanol, ethanol, dimethylformamide and dichloromethane, with or without the addition of at least one organic or inorganic base, for example triethylamine, dimethylaminopyridine, pyridine or diisopropylamine, optionally in the presence of at least one organic base, preferably selected from the group consisting of triethylamine, dimethylaminopyridine, pyridine and diisopropylamine, or an inorganic base at temperatures of preferably −70° C. to 100° C. to yield compounds of the general formula X.

As a further alternative, compounds of the general formula IX are reacted with aldehydes of the general formula R20-C(=O)—H in a reaction medium, preferably selected from the group consisting of diethyl ether, tetrahydrofuran, methanol, ethanol, dichloromethane and toluene, with the addition of at least one reducing agent, preferably selected from the group consisting of sodium borohydride, sodium acetoxyborohydride or sodium cyanoborohydride, at temperatures of preferably −70° C. to 100° C. to yield compounds of the general formula X.

Likewise, compounds of the general formula IX may be reacted with compounds of the general formula R3-X, in which X represents a halogen, preferably chlorine, in a reaction medium, preferably selected from the group consisting of toluene, tetrahydrofuran and diethyl ether, with the addition of at least one metal hydride salt, preferably with the addition of at least one metal hydride salt selected from the group consisting of sodium hydride, potassium hydride and lithium hydroxide, at temperatures of preferably 0° C. to 40° C. to yield compounds of the general formula X.

Compounds of the general formulae X and V may, as indicated in scheme 4, be further reacted to yield the compounds of the general formula I, wherein the same methods as described under scheme 3, stage 2 may be used.

Scheme 4.

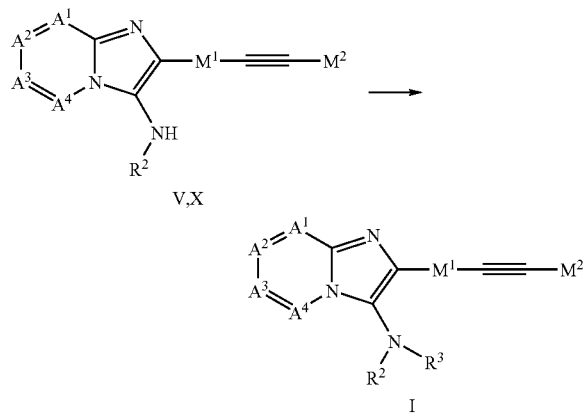

The compounds of the above-stated formulae II, III, IV, VI and VIII, and the above-stated general formulae R2-X, R3-X, R20-C(=O)—OH, R20-C(=O)—X and R20-C(=O)—H are in each case commercially available and/or may be produced using conventional processes known to the person skilled in the art.

The above-described reactions may in each case be performed under conventional conditions familiar to the person skilled in the art, for example with regard to pressure or the sequence of addition of the components. Optimum control of the process under the respective conditions may optionally be established by the person skilled in the art by simple preliminary testing.

The intermediate and final products obtained by the above-described reactions may in each case, if desired and/or necessary, be purified and/or isolated by conventional methods known to the person skilled in the art. Suitable purification methods are, for example, extraction methods and chromatographic methods such as column chromatography or preparative chromatography.

All the above-described process steps and in each case also the purification and/or isolation of intermediate or final products may be performed in part or entirely under an inert gas atmosphere, preferably under a nitrogen atmosphere.

The substituted imidazo-3-yl-amine compounds according to the invention of the above-stated general formulae I, Ia, Ib, Ic, Id, Ie, If, Ig, Ih, Ik, Im and In, hereinafter designated only as compounds of the general formula I, and corresponding stereoisomers may be isolated both in the form of the free bases thereof, the free acids thereof and in the form of corresponding salts, in particular physiologically acceptable salts.

The free bases of the particular substituted imidazo-3-yl-amine compounds according to the invention of the above-stated general formula I and corresponding stereoisomers may, for example, be converted into the corresponding salts, preferably physiologically acceptable salts by reaction with an inorganic or organic acid, preferably with hydrochloric acid, hydrobromic acid, sulfuric acid, phosphoric acid, methanesulfonic acid, p-toluenesulfonic acid, carbonic acid, formic acid, acetic acid, oxalic acid, succinic acid, tartaric acid, mandelic acid, fumaric acid, lactic acid, citric acid, glutamic acid or aspartic acid.

The free bases of the respective substituted imidazo-3-yl-amine compounds of the above-stated general formula I and corresponding stereoisomers may likewise be converted into the corresponding physiologically acceptable salts with the free acid or a salt of a sugar substitute, such as for example saccharin, cyclamate or acesulfame.

The free acids of the substituted imidazo-3-yl-amine compounds of the above-stated general formula I and corresponding stereoisomers may correspondingly be converted into the corresponding physiologically acceptable salts by reaction with a suitable base. Alkali metal salts, alkaline earth metal salts or ammonium salts [NHxR4-x]+, in which x=0, 1, 2, 3 or 4 and R represents a linear or branched C1-4 alkyl group may be mentioned by way of example.

The substituted imidazo-3-yl-amine compounds according to the invention of the above-stated general formula I and corresponding stereoisomers may optionally, like the corresponding acids, the corresponding bases or salts of these compounds, also be obtained in the form of the solvates thereof, preferably in the form of the hydrates thereof, by conventional methods known to the person skilled in the art.

If the substituted imidazo-3-yl-amine compounds according to the invention of the above-stated general formula I are obtained after the production thereof in the form of the stereoisomers thereof, preferably in the form of the racemates thereof or other mixtures of their various enantiomers and/or diastereomers, these may be separated and optionally isolated by conventional methods known to the person skilled in the art. Examples which may be mentioned are chromatographic separation methods, in particular liquid chromatography methods at standard pressure or at elevated pressure, preferably MPLC and HPLC methods, and fractional crystallisation methods. Individual enantiomers, e.g. diastereomeric salts formed by means of HPLC on a chiral stationary phase or by means of crystallisation with chiral acids, such as (+)-tartaric acid, (−)-tartaric acid or (+)-10-camphorsulfonic acid, may here in particular be separated from one another.

The substituted imidazo-3-yl-amine compounds according to the invention of the above-stated general formula I and corresponding stereoisomers as well as in each case the corresponding acids, bases, salts and solvates are toxicologically safe and are therefore suitable as pharmaceutical active ingredients in pharmaceutical formulations.

The present invention accordingly also provides a pharmaceutical formulation containing at least one imidazo-3-yl-amine compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically acceptable auxiliary substances.

The pharmaceutical formulation according to the invention is suitable for mGluR5 receptor regulation, in particular for inhibiting the mGluR5 receptor and thus also for the prevention and/or treatment of disorders and/or diseases, which are mediated at least in part by mGluR5 receptors.

The pharmaceutical formulation according to the invention is therefore preferably suitable for the treatment and/or prevention of pain, preferably of pain selected from the group consisting of acute pain, chronic pain, neuropathic pain and visceral pain; of migraine; depression; neurodegenerative diseases, preferably selected from the group consisting of Parkinson's disease, Alzheimer's disease, Huntington's chorea and multiple sclerosis; cognitive disorders, preferably cognitive deficiency states, particularly preferably of attention deficit syndrome (ADS); panic attacks; anxiety disorder; epilepsy; coughing; urinary incontinence; diarrhoea; pruritus; schizophrenia; cerebral ischaemia; muscle spasms; cramps; irritable bowel syndrome; disorders of food intake, preferably selected from the group consisting of bulimia, cachexia, anorexia and obesity; abuse of alcohol and/or drugs (in particular nicotine and/or cocaine) and/or medicines, dependency on alcohol and/or drugs (in particular nicotine and/or cocaine) and/or dependency on medicines, preferably for the prevention and/or reduction of withdrawal symptoms associated with dependency on alcohol and/or drugs (in particular nicotine and/or cocaine) and/or dependency on medicines; the development of tolerance phenomena with regard to drugs and/or medicines, in particular with regard to opioids; of gastro-oesophageal reflux syndrome; of gastro-oesophageal reflux; for diuresis; for antinatriuresis; for influencing the cardiovascular system; for anxiolysis; for increasing vigilance; for increasing libido; for modulating locomotor activity, and for local anaesthesia.

Particularly preferably, the pharmaceutical formulation according to the invention is suitable for the treatment and/or prevention of pain preferably selected from the group consisting of acute pain, chronic pain, neuropathic pain and visceral pain; depression; epilepsy; neurodegenerative diseases, preferably selected from the group consisting of Parkinson's disease, Alzheimer's disease, Huntington's chorea and multiple sclerosis; abuse of alcohol and/or drugs (in particular nicotine and/or cocaine) and/or abuse of medicines, dependency on alcohol and/or drugs (in particular nicotine and/or cocaine) and/or dependency on medicines, preferably for the prevention and/or reduction of withdrawal symptoms associated with dependency on alcohol and/or drugs (in particular nicotine and/or cocaine) and/or dependency on medicines; the development of tolerance phenomena with regard to drugs and/or medicines, in particular with regard to opioids; or for anxiolysis.

The pharmaceutical formulation according to the invention is very particularly preferably suitable for the treatment and/or prevention of pain, preferably of pain selected from the group consisting of acute pain, chronic pain, neuropathic pain and visceral pain.

The present invention also provides the use of at least one imidazo-3-yl-amine compound according to the invention of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical formulation for mGluR5 receptor regulation, preferably for inhibiting the mGluR5-receptor.

It is preferred to use at least one substituted imidazo-3-yl-amine compound of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical formulation for the prevention and/or treatment of disorders and/or diseases which are mediated at least in part by mGluR5 receptors.

It is particularly preferred to use at least one substituted imidazo-3-yl-amine compound the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical formulation for the treatment and/or prevention of pain preferably selected from the group consisting of acute pain, chronic pain, neuropathic pain and visceral pain; of migraine; depression; neurodegenerative diseases, preferably selected from the group consisting of Parkinson's disease, Alzheimer's disease, Huntington's chorea and multiple sclerosis; cognitive disorders, preferably cognitive deficiency states, particularly preferably of attention deficit syndrome (ADS); panic attacks; anxiety disorder; epilepsy; coughing; urinary incontinence; diarrhoea; pruritus; schizophrenia; cerebral ischaemia; muscle spasms; cramps; irritable bowel syndrome; disorders of food intake, preferably selected from the group consisting of bulimia, cachexia, anorexia and obesity; abuse of alcohol and/or drugs (in particular nicotine and/or cocaine) and/or abuse of medicines, dependency on alcohol and/or drugs (in particular nicotine and/or cocaine) and/or dependency on medicines, preferably for the prevention and/or reduction of withdrawal symptoms associated with dependency on alcohol and/or drugs (in particular nicotine and/or cocaine) and/or dependency on medicines; the development of tolerance phenomena with regard to drugs and/or medicines, in particular with regard to opioids; of gastro-oesophageal reflux syndrome; of gastro-oesophageal reflux; for diuresis; for antinatriuresis; for influencing the cardiovascular system; for anxiolysis; for increasing vigilance; for increasing libido; for modulating locomotor activity, and for local anaesthesia.

It is very particularly preferred to use at least one substituted imidazo-3-yl-amine compound of the above-stated general formula I, in each case optionally in the form of one of the pure stereoisomers thereof, in particular enantiomers or diastereomers, the racemates thereof or in the form of a mixture of stereoisomers, in particular the enantiomers and/or diastereomers, in any desired mixing ratio, or in each case in the form of a corresponding salt, or in each case in the form of a corresponding solvate, and optionally one or more pharmaceutically compatible auxiliary substances for the production of a pharmaceutical formulation for the treatment and/or prevention of pain preferably selected from the group consisting of acute pain, chronic pain, neuropathic pain and visceral pain.

The pharmaceutical formulation according to the invention is suitable for administration to adults and children including small children and babies.

The pharmaceutical formulation according to the invention may be formulated as a liquid, semisolid or solid dosage form, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally pressed into tablets, packaged in capsules or suspended in a liquid, and may also be administered as such.

In addition to at least one substituted imidazo-3-yl-amine compound of the above-stated general formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or optionally in the form of a corresponding salt or in each case in the form of a corresponding solvate, the pharmaceutical formulation according to the invention conventionally contains further physiologically acceptable pharmaceutical auxiliary substances, which may preferably be selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical formulation is to be administered orally, subcutaneously, parenterally, intravenously, intraperitoneally, intradermally, intramuscularly, intranasally, buccally, rectally or topically, for example onto infections of the skin, mucous membranes and eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration.

The substituted imidazo-3-yl-amine compounds according to the invention used in the pharmaceutical formulation according to the invention in a depot in dissolved form or in a dressing, optionally with the addition of skin penetration promoters, are suitable percutaneous administration preparations.

Orally or percutaneously administrable formulations may also release the particular substituted imidazo-3-yl-amine compound according to the invention in delayed manner.

Production of the pharmaceutical formulations according to the invention proceeds with the assistance of conventional means, devices, methods and processes known from the prior art, as are described for example in "Remington's Pharmaceutical Sciences", ed. A. R. Gennaro, 17th ed., Mack Publishing Company, Easton, Pa. (1985), in particular in part 8, chapters 76 to 93. The corresponding description is hereby introduced as a reference and is deemed to be part of the disclosure.

The quantity of the particular substituted imidazo-3-yl-amine compounds according to the invention of the above-stated general formula I to be administered to the patient may vary and is for example dependent on the weight or age of the patient and on the mode of administration, the indication and the severity of the complaint. Conventionally, 0.005 to 2000 mg/kg, preferably 0.05 to 500 mg/kg, particularly preferably 0.05 to 100 mg/kg of patient body weight of at least one such compound according to the invention are administered per day.

Pharmacological Methods:

1. Method for Determining Affinity for the mGluR5 Receptor

Pig brain homogenate is produced by homogenisation (Polytron Pt 3000, Kinematica AG, 10,000 revolutions per minute for 90 seconds) of pig brain hemispheres without medulla, cerebellum and pons in a buffer of pH 8.0 (30 mM Hepes, Sigma, order number H3375+1 tablet Complete Roche Diagnostics, order number 1836145 made up to 100 ml) in a ratio of 1:20 (brain weight/volume) and differential centrifugation at 900×g and 40,000×g. 450 µg of protein from brain homogenate is incubated in each case in 250 µl incubation batches in 96-well microtitre plates with 5 nM 3[H]-MPEP (Tocris, order number R1212) (MPEP=2-methyl-6-(3-methoxyphenyl)-ethynylpyridine) and the compounds to be investigated (10 µM in the test) in the buffer (as above) at room temperature for 60 minutes.

The batches are then filtered with the assistance of a Brandel Cell Harvester (Brandel, Grade Robotic 9600) on Unifilter plates with glass filter mats (Perkin Elmer, order number 6005177) and then washed 3 times with buffer (as above) using 250 µl per sample. The filter plates are then dried for 60 minutes at 55° C. Then 30 µl of Ultima Gold™ scintillating material (Packard BioScience, order number 6013159) is added per well and after 3 hours the samples are measured using the β counter (Microbeta, Perkin Elmer). Nonspecific binding is determined by the addition of 10 µM MPEP (Tocris, order number 1212).

2. Neuropathic Pain in Rats

Efficacy against neuropathic pain was investigated in the Bennett model (chronic constriction injury; Bennett and Xie, 1988, Pain 33: 87-107). The corresponding parts of the literature are hereby deemed to be part of the present disclosure.

Sprague-Dawley rats weighing 140-160 g are provided under Nembutal anaesthesia with four loose ligatures of the right ischial nerve. On the paw innervated by the damaged nerve, the animals develop hypersensitivity which, after one week's convalescence, is quantified over a period of approx. four weeks by means of a cold metal plate at 4° C. (cold allodynia). The animals are observed on this plate for a period of 2 min. and the number of withdrawal responses by the damaged paw is measured. Relative to the preliminary value prior to administration of the substance, the action of the substance is determined on four occasions over a period of one hour (15, 30, 45, 60 min. after administration) and the resultant area under the curve (AUC) and the inhibition of cold allodynia at the individual measuring points is stated as a percentage action relative to the vehicle control (AUC) or to the initial value (individual measurement points). The size of the group is n=10. The significance of an antiallodynic action is determined with reference to the AUC values by means of a paired T-test ($*0.05 \geq p > 0.01$; $**0.01 \geq p > 0.001$;

\*\*\*p≦0.001; Armitage and Berry, 1987, Stat. Methods in Medical Research, London: Blackwell Scientific Publications).

3. "Elevated Plus Maze" Model

Compounds are tested for a possible anxiolytic effect in the "elevated plus maze" (EPM) model. The tests are carried out on male Sprague-Dawley rats (200-250 g) using 2 "elevated plus mazes" (Med Associates) with electronically controlled infrared photobeams for determining the location of the animals in the maze. Each maze has 2 open and 2 closed arms and a central platform. The edges of the open arms are delimited by narrow strips. The entire maze is mounted on a metal stand.

At the beginning of a 5 minute test, each animal is individually placed on the central platform with its head in the direction of a closed arm.

The following parameters are determined or calculated and evaluated:

the number and percentage of entries into the open and closed arms, and the percentage of time spent in the open and closed arms and on the central platform.

The data are analysed by means of single factor ANOVA (comparison of treatment groups vs. vehicle group). The significance level is set at $p<0.05$. All groups have a size of N=10.

The test is also described in Hogg, S. (1996) A review of the validity and variability of the elevated plus-maze as an animal model of anxiety. Pharmacol. Biochem. Behav. 54, 21-30 and Rodgers, R. J., Cole, J. C. (1994) The elevated plus-maze: pharmacology, methodology and ethology, in: Cooper, S. J., Hendrie, C. A. (eds.) Ethology and Psychopharmacology, Wiley & Sons; pp. 9-44. The corresponding passages of the literature are hereby deemed to be part of the disclosure.

4. Formaldehyde Test a. Formaldehyde Test (Rat)

The formaldehyde test as described in Dubuisson, D. and Dennis, S. G., 1977, Pain, 4, 161-174 is a model of acute and chronic pain. The corresponding passages from the literature are hereby deemed to be part of the disclosure. A biphasic nociceptive response is induced in freely mobile test animals by a single formaldehyde injection into the dorsal side of a hind paw, said response being detected by the observation of three clearly distinguishable behaviour patterns. The response is in two phases: phase 1= immediate response (duration up to 10 min; paw shaking, licking), phase 2=late response (after a resting phase; likewise paw shaking, licking; duration up to 60 min). The 1st phase reflects direct stimulation of the peripheral nocisensors with an elevated spinal nociceptive input or glutamate release (acute pain phase); the 2nd phase reflects spinal and peripheral hypersensitisation (chronic pain phase). In the investigations presented here, it was the chronic pain component (phase 2) which was evaluated.

Formaldehyde is administered subcutaneously in a volume of 50 μl and a concentration of 5% into the dorsal side of the right hind paw of each animal. The substances to be tested are administered intraperitoneally (i.p.) 15 min before the formaldehyde injection, or intravenously (i.v.) 5 min before the formaldehyde injection. The specific behavioural changes, such as raising and shaking the paw, changes in weight bearing of the animal and biting and licking responses are observed and recorded over the observation period of 21 to 27 min after the formaldehyde injection. The various behaviours are summarised as a "pain rate" (PR), which is the calculated nociceptive response averaged over 3 min sub-intervals. The PR is calculated on the basis of a numerical weighting (=in each case a factor of 1, 2, 3) of the observed behaviours (corresponding behaviour score 1, 2, 3) and is calculated using the following formula: $PR=[(T0\times 0)+(T1\times 1)+(T2\times 2)+(T3\times 3)]/180$ wherein T0, T1, T2, and T3 correspond to the time in seconds for which the animal exhibited behaviour 0, 1, 2 or 3 respectively. Group size is 10 animals (n=10).

b. Formaldehyde Test in Mice

Formaldehyde is administered subcutaneously in a volume of 20 μl and a concentration of 1% into the dorsal side of the right hind paw of each animal. The substances to be tested are administered intraperitoneally (i.p.) 15 min before the formaldehyde injection. The specific behavioural changes, such as raising and shaking the paw (score 3, Dubuisson & Dennis, 1977) are observed and recorded over the observation period of 21 to 24 min after the formaldehyde injection. Group size is 10 animals (n=10).

The invention is explained below with reference to Examples. These explanations are given merely by way of example and do not restrict the general concept of the invention.

EXAMPLES

Certain embodiments of the present invention may be further understood by reference to the following specific examples. These examples and the terminology used herein are for the purpose of describing particular embodiments only and are not intended to be limiting.

The yields of the compounds produced are not optimised.

All temperatures are uncorrected.

Abbreviations:

| | |
|---|---|
| equivalent | molar equivalent |
| aq. | aqueous |
| d | days |
| DCC | dicyclohexylcarbodiimide |
| DCM | dichloromethane |
| DMAP | 4-dimethylaminopyridine |
| DMF | N,N-dimethylformamide |
| DIPE | diisopropyl ether |
| EA | ethyl acetate |
| EDCI | N'-(3-dimethylaminopropyl)-N-ethylcarbodiimide |
| ether | diethyl ether |
| EtOH | ethanol |
| sat. | saturated |
| H2O | water |
| HATU | N-[(dimethyamino)-1H-1,2,3-triazolo[4,5-b]pyridino-1-ylmethylene]-N-methylmethanaminium hexafluorophosphate N-oxide |
| HBTU | O-(benzotriazol-1-yl)-N,N,N',N'-tetramethyluronium hexafluorophosphate |
| MeCN | acetonitrile |
| MeOH | methanol |
| NEt3 | triethylamine |
| RT | room temperature |
| CC | column chromatography |
| THF | tetrahydrofuran |

The chemicals and solvents used were purchased from conventional suppliers (Acros, Avocado, Aldrich, Bachem, Fluka, Lancaster, Maybridge, Merck, Sigma, TCI, etc.) or synthesised by conventional methods known to the person skilled in the art.

Silica gel 60 (0.040-0.063 mm) from E. Merck, Darmstadt, was used as the stationary phase for the column chromatography.

Thin-layer chromatography was performed with pre-coated silica gel 60 F 254 HPTLC plates from E. Merck, Darmstadt.

The mixture ratios of solvents, mobile solvents or for chromatographic investigations are always stated by volume/volume.

Analysis was carried out by mass spectroscopy and NMR.

General Methods for the Production of Substituted Bicyclic imidazo-3-yl-amines According to the Examples General synthesis scheme 1:

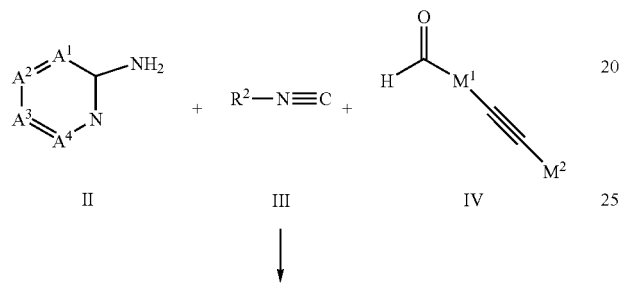

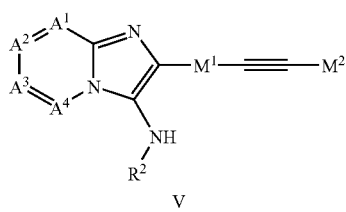

Amines (1 equivalent) of the general formula II (1 equivalent) were reacted at temperatures of 0° C. to 150° C. with isocyanides of the general formula III and aldehydes (1 equivalent) of the general formula IV to yield compounds of the general formula V in organic solvents or solvent mixtures, for example of chloroform, DCM, MeCN, MeOH or EtOH, with addition of an organic or inorganic acid, for example trifluoroacetic acid or perchloric acid, or with addition of a transition metal triflate, for example scandium(III) triflate, ytterbium triflate or indium(III) triflate.

General synthesis scheme 2:

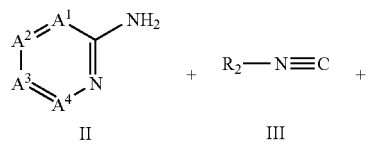

-continued

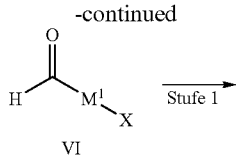

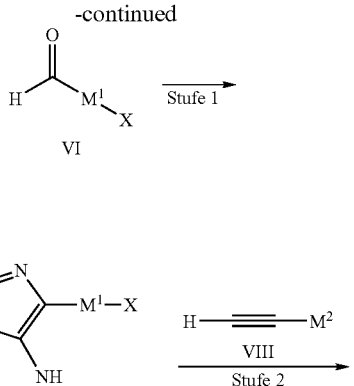

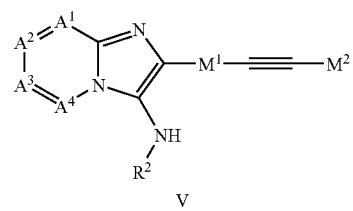

[Key: Stufe = stage]

In stage 1, amines (1 equivalent) of the general formula II were reacted at temperatures of 0° C. to 150° C. with isocyanides (1 equivalent) of the general formula III and aldehydes (1 equivalent) of the general formula VI, in which X represents a halogen, to yield compounds of the general formula VII in organic solvents or solvent mixtures, for example of chloroform, DCM, MeCN, MeOH or EtOH, with addition of an organic or inorganic acid, for example trifluoroacetic acid or perchloric acid, or with addition of a transition metal triflate, for example scandium(III) triflate, ytterbium triflate or indium(III) triflate.

In stage 2, compounds of the general formula VII (1 equivalent), in which X represents a halogen, were reacted at temperatures of −70° C. to 150° C. with acetylenes (2.5 equivalents) of the general formula VIII to yield compounds of the general formula V in a solvent or solvent mixture, for example of toluene, THF, DMF, MeCN, ether, NEt3 or diisopropylamine, with addition of a palladium catalyst, for example bis(triphenylphosphine)palladium(II) chloride, of copper(I) iodide and an organic base, for example NEt3 or diisopropylamine, and/or inorganic base, for example potassium carbonate or caesium carbonate.

General synthesis scheme 3:

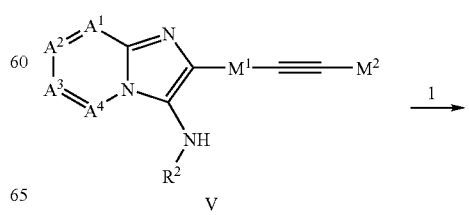

General synthesis scheme 4:

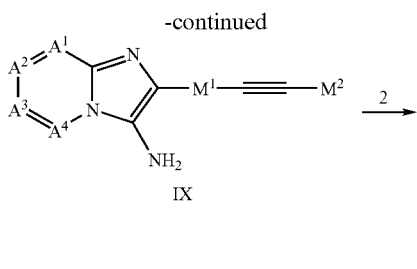

IX

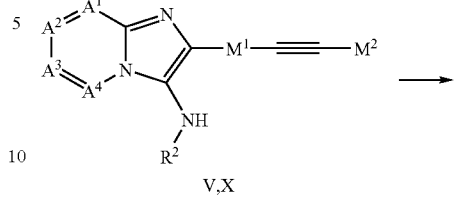

V,X

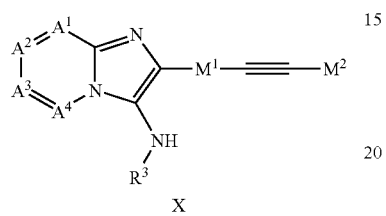

X

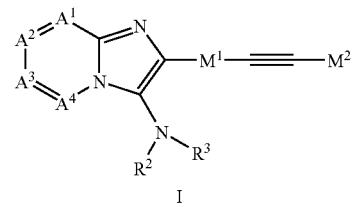

I

In stage 1, compounds of the general formula V were reacted at temperatures of 0° C. to 80° C. to yield amines of the general formula IX in a solvent or solvent mixture, for example of EtOH, MeOH or acetone, with addition of an organic or inorganic acid, for example acetic acid, trifluoroacetic acid, hydrochloric acid or sulfuric acid.

In stage 2, compounds of the general formula IX (1 equivalent) were reacted at temperatures of −70° C. to 100° C. with carboxylic acids (1 equivalent) of the general formula R20-(C=O)—OH in a solvent or solvent mixture, for example of ether, THF, MeCN, MeOH, EtOH, DMF or DCM, with or without addition of a coupling reagent (1 equivalent), for example DCC, BOP, HATU or EDCI and optionally in the presence of at least one inorganic or organic base, for example NEt3 or diisopropylethylamine, to yield compounds of the general formula X.

Alternatively, compounds of the general formula IX (1 equivalent) were reacted at temperatures of −70° C. to 100° C. with carboxylic acid halides (1 equivalent) or carbonic acid derivatives of the general formula R20-(C=O)—X, wherein X represents a halogen, in a solvent or solvent mixture, for example of ether, THF, MeCN, MeOH, EtOH, DMF or DCM, with or without addition of an organic or inorganic base, for example NEt3, DMAP, pyridine or diisopropylamine, to yield compounds of the general formula X.

As a further alternative, compounds of the general formula IX (1 equivalent) were reacted at temperatures of −70° C. to 100° C. with aldehydes (1 equivalent) of the general formula R20-C(=O)—H in a solvent or solvent mixture, for example of ether, THF, MeOH, EtOH, DCM or toluene, and subsequent addition of a reducing agent, for example sodium borohydride, sodium acetoxyborohydride or sodium cyanoborohydride, to yield compounds of the general formula X.

Compounds of the general formula IX (1 equivalent) were likewise reacted at temperatures of 0° C. to 40° C. with compounds of the general formula R3-X (1.1 equivalents), in which X represents a halogen, preferably chlorine, in a solvent or solvent mixture, for example of toluene, THF or ether, with addition of a metal hydride salt (1.1 equivalents), preferably with addition of sodium hydride, to yield compounds of the general formula X.

The compounds of the general formula V or X may be reacted using the same methods as described in general synthesis scheme 3, stage 2 to yield compounds of the general formula I.

The above-described methods for the production of substituted bicyclic imidazo-3-yl-amines are described in greater detail below with reference to some example compounds:

Example 1

Synthesis of cyclopentyl-[2-(5-phenylethynyl-thiophen-2-yl)-imidazo[1,2-a]pyrazin-3-yl]-amine 10 μl (0.022 mmol) of 20% aq. perchloric acid, a solution of 31.8 mg (0.15 mmol) of 5-phenylethynyl-thiophene-2-carbaldehyde in a mixture of MeOH and DCM (0.5 ml, 1:1 vol/vol) and a solution of 11.1 mg (0.115 mmol) of cyclopentyl isocyanide in MeOH (0.5 ml) were added in succession to a solution of 9.5 mg (0.1 mmol) of 2-aminopyrazine in MeOH (1 ml). The reaction solution was stirred at RT for 36 h and then combined with sat. aq. NaCl solution (3 ml) and stirred at RT for a further 45 min. The phases were separated and the aq. phase was extracted with DCM (2×3 ml). The collected organic phases were dried over MgSO4, filtered and evaporated under a vacuum. The group was purified by means of preparative HPLC, wherein 18 mg (0.047 mmol, 47%) of cyclopentyl-[2-(5-phenylethynyl-thiophen-2-yl)-imidazo[1,2-a]pyrazin-3-yl]-amine were obtained.

Example 18 tert-Butyl-[2-(5-phenylethynyl-thiophen-2-yl)-imidazo[1,2-a]pyrazin-3-yl]-amine a) Synthesis of [2-(5-bromothiophen-2-yl)-imidazo[1,2-a]pyrazin-3-yl]-tert-butyl-amine 237 mg (2.50 mmol) of 2-aminopyrazine were dissolved together with 208 mg (2.50 mmol) of tert-butylisonitrile and 0.27 ml (2.50 mmol) of 5-bromothiophene-2-carbaldehyde in DCM (5 ml). After addition of perchloric acid (0.25 ml), the mixture was stirred at RT for 5 d. Washing was then performed with a sat. aq. sodium carbonate solution and a sat. aq. common salt solution. The organic phase was dried over magnesium sulfate, filtered and evaporated under a vacuum. After carrying out column chromatography (EA/DIPE/DCM 2:2:1) with the group, 471 mg (1.3 mmol, 54% of theoretical) of [2-(5-bromothiophen-2-yl)-imidazo[1,2-a]pyrazin-3-yl]-tert-butyl-amine were obtained.

b) Synthesis of tert-butyl-[2-(5-phenylethynyl-thiophen-2-yl)-imidazo[1,2-a]pyrazin-3-yl]-amine 420 mg (1.2 mmol) of [2-(5-bromothiophen-2-yl)-imidazo[1,2-a]pyrazin-3-yl]-tert-butyl-amine were dissolved together with 0.33 ml (3.0 mmol) of phenylacetylene, 42 mg (0.06 mmol) of bis(triphenylphosphine)-palladium(II) chloride and 22 mg (0.12 mmol) of copper(I) iodide in DMF (9 ml). After addition of 1.6 ml (12.0 mmol) of triethylamine, the mixture was stirred at 50° C. for 16 h. The reaction solution was then diluted with EA and combined with a sat. aq. sodium carbonate solution. The phases were separated and the aqueous phase extracted with EA. The combined organic phases were washed 2× with a sat. aq. sodium carbonate solution and 2× with a sat. aq. common salt solution and dried over magnesium sulfate. After filtration and removal of the solvents under a vacuum, column chromatography (EA/DCM 1:4) was carried out with the group, after which 326 mg (0.88 mmol, 73% of theoretical) of tert-butyl-[2-(5-phenylethynyl-thiophen-2-yl)-imidazo[1,2-a]pyrazin-3-yl]-amine were obtained.

Example 31

(1-Phenyl-ethyl)-[2-(5-phenylethynyl-thiophen-2-yl)-imidazo[1,2-a]pyrazin-3-yl]-amine a) Synthesis of [2-(5-bromothiophen-2-yl)-imidazo[1,2-a]pyrazin-3-yl]-(1-phenyl-ethyl)-amine 951 mg (10.0 mmol) of 2-aminopyrazine were dissolved together with 1.31 g (10.0 mmol) of 1-phenylethylisonitrile and 1.08 ml (10.0 mmol) of 5-bromothiophene-2-carbaldehyde in chloroform (24 ml). After addition of perchloric acid (1.00 ml), the mixture was stirred at RT for 5 d. The mixture was then combined with a sat. aq. sodium carbonate solution and the phases were separated. The aqueous phase was extracted with DCM. The combined organic phases were washed with a sat. aq. sodium carbonate solution and dried over magnesium sulfate, filtered and evaporated under a vacuum. After carrying out column chromatography (EA/DCM 1:1) with the group, 831 mg (2.1 mmol, 21% of theoretical) of [2-(5-bromothiophen-2-yl)-imidazo[1,2-a]pyrazin-3-yl]-(1-phenyl-ethyl)-amine were obtained.

b) Synthesis of (1-phenyl-ethyl)-[2-(5-phenylethynyl-thiophen-2-yl)-imidazo[1,2-a]pyrazin-3-yl]-amine 497 mg (1.25 mmol) of [2-(5-bromothiophen-2-yl)-imidazo[1,2-a]pyrazin-3-yl]-(1-phenyl-ethyl)-amine were dissolved together with 0.34 ml (3.13 mmol) of phenylacetylene, 43 mg (0.06 mmol) of bis(triphenylphosphine)-palladium(II) chloride and 24 mg (0.13 mmol) of copper(I) iodide in DMF (10 ml) After addition of 1.7 ml (12.5 mmol) of triethylamine, the mixture was stirred at 50° C. for 16 h. The reaction solution was then diluted with EA and combined with a sat. aq. sodium carbonate solution. The phases were separated and the aqueous phase extracted with EA. The combined organic phases were washed 2× with a sat. aq. sodium carbonate solution and 2× with a sat. aq. common salt solution and dried over magnesium sulfate. After filtration and removal of the solvents under a vacuum, column chromatography (EA/DCM 1:3) was carried out with the group, after which 158 mg (0.38 mmol, 30% of theoretical) of (1-phenyl-ethyl)-[2-(5-phenylethynyl-thiophen-2-yl)-imidazo[1,2-a]pyrazin-3-yl]-amine were obtained.

Example 56

[2-(5-Phenylethynyl-thiophen-2-yl)-imidazo[1,2-a]pyrazin-3-yl]-(1,1,3,3-tetramethyl-butyl)-amine a) Synthesis of [2-(5-bromothiophen-2-yl)-imidazo[1,2-a]pyrazin-3-yl]-(1,1,3,3-tetramethyl-butyl)-amine 4.76 g (50.0 mmol) of 2-aminopyrazine were dissolved together with 8.76 ml (50.0 mmol) of 1,1,3,3-tetramethyl-butylisonitrile and 5.42 ml (50.0 mmol) of 5-bromothiophene-2-carbaldehyde in chloroform (40 ml) After addition of perchloric acid (5 ml), the mixture was stirred at 50° C. for 16 h. After cooling to RT, washing was performed 2× with a sat. aq. sodium carbonate solution. The organic phase was dried over magnesium sulfate, filtered and evaporated under a vacuum. After carrying out column chromatography (EA/DCM 1:3) with the group, 11.39 g (28.0 mmol, 56% of theoretical) of [2-(5-bromothiophen-2-yl)-imidazo[1,2-a]pyrazin-3-yl]-(1,1,3,3-tetramethyl-butyl)-amine were obtained.

b) Synthesis of [2-(5-phenylethynyl-thiophen-2-yl)-imidazo[1,2-a]pyrazin-3-yl]-(1,1,3,3-tetramethyl-butyl)-amine 3.65 g (9.0 mmol) of [2-(5-bromothiophen-2-yl)-imidazo[1,2-a]pyrazin-3-yl]-(1,1,3,3-tetra-methyl-butyl)-amine were dissolved together with 1.18 ml (10.8 mmol) of phenylacetylene, 0.16 g (0.23 mmol) of bis(triphenylphosphine)-palladium(II) chloride and 0.08 g (0.45 mmol) of copper(I) iodide in DMF (30 ml). After addition of 2.50 ml (18.00 mmol) of triethylamine, the mixture was stirred at 50° C. for 16 h. The reaction solution was then diluted with EA and combined with a sat. aq. sodium carbonate solution. The phases were separated and the aqueous phase extracted with EA. The combined organic phases were washed 2× with a sat. aq. sodium carbonate solution and dried over magnesium sulfate. After filtration and removal of the solvents under a vacuum, column chromatography (EA/DIPE/DCM 3:3:4) was carried out with the group, after which 3.38 g (7.9 mmol, 88% of theoretical) of [2-(5-phenylethynyl-thiophen-2-yl)-imidazo[1,2-a]pyrazin-3-yl]-(1,1,3,3-tetramethyl-butyl)-amine were obtained.

Example 59

[2-(5-Phenylethynyl-thiophen-2-yl)-imidazo[1,2-a]pyridin-3-yl]-(1,1,3,3-tetramethyl-butyl)-amine a) Synthesis of [2-(5-bromothiophen-2-yl)-imidazo[1,2-a]pyridin-3-yl]-(1,1,3,3-tetramethyl-butyl)-amine 235 mg (2.5 mmol) of 2-aminopyridine were dissolved together with 0.42 ml (2.5 mmol) of 1,1,3,3-tetramethyl-butylisonitrile and 0.27 ml (2.5 mmol) of 5-bromothiophene-2-carbaldehyde in DCM (5 ml). After addition of perchloric acid (0.25 ml), the mixture was stirred at RT for 5 d. Washing was then performed with a sat. aq. sodium carbonate solution and a sat. aq. common salt solution. The organic phase was dried over magnesium sulfate, filtered and evaporated under a vacuum. After carrying out column chromatography (EA/DIPE/DCM 2:2:1) with the group, 724 mg (1.7 mmol, 71% of theoretical) of [2-(5-bromothiophen-2-yl)-imidazo[1,2-a]pyridin-3-yl]-(1,1,3,3-tetramethyl-butyl)-amine were obtained.

b) Synthesis of [2-(5-phenylethynyl-thiophen-2-yl)-imidazo[1,2-a]pyridin-3-yl]-(1,1,3,3-tetramethyl-butyl)-amine 324 mg (0.80 mmol) of [2-(5-bromothiophen-2-yl)-imidazo[1,2-a]pyridin-3-yl]-(1,1,3,3-tetramethyl-butyl)-amine were dissolved together with 0.11 ml (0.96 mmol) of phenylacetylene, 14 mg (0.02 mmol) of bis(triphenylphosphine)-palladium(II) chloride and 7 mg (0.04 mmol) of copper(I) iodide in DMF (6 ml) After addition of 1.1 ml (8.0 mmol) of triethylamine, the mixture was stirred at 50° C. for 2 d. The reaction solution was then diluted with EA and combined with a sat. aq. sodium carbonate solution. The phases were separated and the aqueous phase extracted with EA. The combined organic phases were washed 2× with a sat. aq. sodium carbonate solution and 2× with a sat. aq. common salt solution and dried over magnesium sulfate. After filtration and removal of the solvents under a vacuum, column chromatography (EA/DIPE/DCM 3:3:4) was carried out with the group, after which 54 mg (0.13 mmol, 16% of theoretical) of [2-(5-phenylethynyl-thiophen-2-yl)-imidazo[1,2-a]pyridin-3-yl]-(1,1,3,3-tetramethyl-butyl)-amine were obtained.

Example 60

[2-(5-Pyridin-3-ylethynyl-thiophen-2-yl)-imidazo[1,2-a]pyrazin-3-yl]-(1,1,3,3-tetramethyl-butyl)-amine Synthesis of [2-(5-pyridin-3-ylethynyl-thiophen-2-yl)-imidazo[1,2-a]pyrazin-3-yl]-(1,1,3,3-tetramethyl-butyl)-amine 600 mg (1.48 mmol) of [2-(5-bromothiophen-2-yl)-imidazo[1,2-a]pyrazin-3-yl]-(1,1,3,3-tetra-methyl-butyl)-amine were dissolved together with 183 mg (1.77 mmol) of 3-ethynylpyridine, 104 mg (0.15 mmol) of bis(triphenylphosphine)-palladium(II) chloride and 28 mg (0.15 mmol) of copper(I)-iodide in DMF (10 ml). After addition of 2.00 ml (14.78 mmol) of triethylamine, the mixture was stirred at 50° C. for 3 d. The reaction solution was then diluted with EA and combined with a sat. aq. sodium carbonate solution. The phases were separated and the aqueous phase extracted with EA. The combined organic phases were washed 2× with a sat. aq. sodium carbonate solution and dried over sodium sulfate. After filtration and removal of the solvents under a vacuum, column chromatography (EA) was carried out with the group. After crystallisation of the resultant crude product, 310 mg (0.72 mmol, 49% of theoretical) of [2-(5-pyridin-3-ylethynyl-thiophen-2-yl)-imidazo[1,2-a]pyrazin-3-yl]-(1,1,3,3-tetramethyl-butyl)-amine were obtained.

Example 83

2-(5-Phenylethynyl-thiophen-2-yl)-imidazo[1,2-a]pyrazin-3-ylamine hydrochloride 2.32 g (5.44 mmol) of [2-(5-phenylethynyl-thiophen-2-yl)-imidazo[1,2-a]pyrazin-3-yl]-(1,1,3,3-tetramethylbutyl)-amine (Example 60) were dissolved in methanol (90 ml) and combined with 5.3 ml (54.4 mmol) of a 32% HCl solution. The reaction solution was stirred at RT for 16 h. The resultant precipitate was filtered out and rewashed with methanol, 1.39 g (3.95 mmol, 73% of theoretical) of 2-(5-phenylethynyl-thiophen-2-yl)-imidazo[1,2-a]pyrazin-3-ylamine hydrochloride being obtained as a solid.

Example 65

Dimethyl-[2-(5-phenylethynyl-thiophen-2-yl)-imidazo[1,2-a]pyrazin-3-yl]-amine 790 mg (2.5 mmol) of 2-(5-phenylethynyl-thiophen-2-yl)-imidazo[1,2-a]pyrazin-3-ylamine hydrochloride (Example 83) were dissolved in DMF (8 ml). After addition of 300 mg (7.5 mmol) of sodium hydride (60% dispersion in mineral oil) in portions, the mixture was stirred at RT for 30 min. 0.3 ml (5.0 mmol) of methyl iodide dissolved in DMF (2 ml) was then added dropwise. The reaction solution was stirred at RT for a further 4 h and then quenched with water (20 ml) and extracted with EA (2×50 ml). The combined organic phases were dried over MgSO4, filtered and evaporated under a vacuum. 351 mg (1.0 mmol, 40% of theoretical) of dimethyl-[2-(5-phenylethynyl-thiophen-2-yl)-imidazo[1,2-a]pyrazin-3-yl]-amine were obtained from the group by crystallisation (EA).

Example 68

Ethyl-[2-(5-phenylethynyl-thiophen-2-yl)-imidazo[1,2-a]pyrazin-3-yl]-amine 395 mg (1.25 mmol) of 2-(5-phenylethynyl-thiophen-2-yl)-imidazo[1,2-a]pyrazin-3-ylamine hydrochloride (Example 83) were dissolved in DMF (8 ml). After addition of 100 mg (2.5 mmol) of sodium hydride (60% dispersion in mineral oil), the mixture was stirred at RT for 1 h. A solution of 74 µl (0.8 mmol) of ethyl bromide in DMF (2 ml) was then added dropwise. The reaction solution was stirred at RT for 16 h, quenched with water (10 ml) and extracted with EA (2×50 ml). The combined organic phases were dried over MgSO4, filtered and evaporated under a vacuum. 253 mg (0.74 mmol, 58% of theoretical) of ethyl-[2-(5-phenylethynyl-thiophen-2-yl)-imidazo[1,2-a]pyrazin-3-yl]-amine were obtained by means of column chromatography (silica gel, EA/DCM 4:1).

Example 94

Synthesis of N-tert-butyl-2-(5-(pyridin-2-ylethynyl)thiophen-2-yl)imidazo[1,2-a]pyridin-3-amine 1.32 g (14.1 mmol) of 2-aminopyrazine were dissolved together with 3.00 g (14.1 mmol) of 5-pyridin-2-ylethynyl-thiophene-2-carbaldehyde, 1.59 ml (14.1 mmol) of tert.-butyl-isonitrile and 2.07 g (4.2 mmol) of scandium(III) trifluoromethanesulfonate in chloroform (40 ml). The reaction solution was heated to 80° C. for 60 min in the microwave (800 watt, MLS-Ethos1600) and then diluted with DCM. Washing was then performed with a 1M Na2CO3 solution and a sat. aq. NaCl solution. The mixture was then dried over Na2SO4, filtered and evaporated under a vacuum. 3.43 g (9.2 mmol, 65%) of N-tert-butyl-2-(5-(pyridin-2-ylethynyl)thiophen-2-yl)imidazo[1,2-a]pyridin-3-amine were obtained by crystallisation of the group from EA.

Example 116

Synthesis of N-tert-butyl-2-(4-(pyridin-2-ylethynyl)phenyl)-imidazo[1,2-a]pyrazin-3-amine 500 mg (2.4 mmol) of 4-pyridin-2-ylethynyl-benzaldehyde, 200 mg (2.4 mmol) of tert.-butyl-isonitrile and 215 µl (0.48 mmol) of 20% aq. perchloric acid were added in succession to a solution of 229 mg (2.4 mmol) of 2-aminopyrazine in chloroform (20 ml). The reaction solution was stirred at 45° C. for 16 h and then diluted with DCM. Washing was then performed with a 1M Na2CO3 solution and a sat. aq. NaCl solution. The mixture was then dried over MgSO4, filtered and evaporated under a vacuum. CC (EA) was carried out with the group, 565 mg (1.5 mmol, 64%) of N-tert-butyl-2-(4-(pyridin-2-ylethynyl)phenyl)-imidazo[1,2-a]pyrazin-3-amine being obtained.

Example 120

Synthesis of 3-(tert-butylamino)-2-(5-(phenylethynyl)thiophen-2-yl)imidazo[1,2-a]pyrazine-8-carboxylic acid A solution of 200 mg (0.47 mmol) of 3-(tert-butylamino)-2-(5-(phenylethynyl)-thiophen-2-yl)imidazo[1,2-a]pyrazine-8-carboxylic acid methyl ester (Example 106) in a mixture of MeOH (5 ml) and MeCN (5.5 ml) was combined with 5 ml (0.51 mmol) of a 0.1M aq. NaOH solution and stirred at RT for 1 h. The reaction mixture was then combined with 26 µl of a 5 N aq. acetic acid solution. The solvents were then largely removed by distillation under a vacuum. The residual aq. phase was repeatedly extracted with EA. The combined organic phases were dried over MgSO4, filtered and evaporated under a vacuum. 87 mg (0.21 mmol, 44%) of 3-(tert-butylamino)-2-(5-(phenylethynyl)thiophen-2-yl)imidazo[1,2-a]pyrazine-8-carboxylic acid were obtained by crystallisation of the group from DCM/hexane (1:2).

Example 141

Synthesis of N-tert-butyl-2-(5-(pyridin-2-ylethynyl)thiophen-2-yl)imidazo[1,2-a]pyrimidin-3-amine A solution of 222 mg (2.34 mmol) of 2-aminopyrimidine, 499 mg (2.34 mmol) of 5-pyridin-2-ylethynyl-thiophene-2-carbaldehyde, 195 mg (2.34 mmol) of tert.-butyl-isonitrile and 234 µl of a 20% aq. perchloric acid in chloroform (20 ml) was stirred at 47° C. for 3 d. The mixture was then diluted with DCM and combined with a 1M aq. Na2CO3 solution. The phases were separated and the organic phase was washed with a sat. NaCl solution and dried over MgSO4. After filtration and removal of the solvents under a vacuum, CC (EA) was carried out with the group, 80 mg (0.21 mmol, 9%) of N-tert-butyl-2-(5-(pyridin-2-ylethynyl)thiophen-2-yl)imidazo[1,2-a]pyrimidin-3-amine being obtained.

Example 143

Synthesis of N-tert-butyl-N-methyl-2-(5-(pyridin-2-ylethynyl)thiophen-2-yl)imidazo[1,2-a]pyrazin-3-amine 43 mg (1.08 mmol, 60% in mineral oil) of sodium hydride were added to a solution of 135 mg (0.36 mmol) of tert-butyl-[2-(5-pyridin-2-ylethynyl-thiophen-2-yl)-imidazo[1,2-a]pyrazin-3-yl]-amine (Example 77) in DMF (3 ml) and the mixture was stirred at RT for 1 h. A solution of 67 µl (1.08 mmol) of methyl iodide in DMF (500 µl) was then added dropwise thereto and the mixture stirred at RT for a further 16 h. A further 43 mg (1.08 mmol, 60% in mineral oil) of sodium hydride and a solution of 67 µl (1.08 mmol) of methyl iodide in DMF (500 µl) were then added and the mixture stirred at RT for a further 16 h. The reaction solution was combined in succession with water, a 1M aq. Na2CO3 solution and a mixture of EA/THF (3:1). The organic phase was separated off and the aq. phase was extracted with EA. The combined organic phases were dried over MgSO4, filtered and evaporated under a vacuum. 33 mg (0.09 mmol, 24%) of N-tert-butyl-N-methyl-2-(5-(pyridin-2-ylethynyl)thiophen-2-yl)imidazo[1,2-a]pyrazin-3-amine were obtained by CC (acetone/MeCN 1:1).

Example 156

Synthesis of N-tert-butyl-2-(5-(thiophen-3-ylethynyl)thiophen-2-yl)imidazo[1,2-a]pyrazin-3-amine hydrochloride 94 mg (0.5 mmol) of copper(I) iodide, 129 mg (0.5 mmol) of triphenylphosphine, 1.32 ml (9.5 mmol) of NEt3, 701 mg (1.9 mmol) of tetra-n-butyl-ammonium iodide and 173 mg (0.25 mmol) of bis(triphenylphosphine)-palladium(II) chloride were added to a solution of 699 mg (1.9 mmol) of tert-butyl-[2-(5-trimethylsilanylethynyl-thiophen-2-yl)-imidazo[1,2-a]pyrazin-3-yl]-amine (synthesis described in Example 158, part a) and 402 mg (2.5 mmol) of 3-bromo-thiophene in DMF (20 ml). 2.5 ml (2.5 mmol) of a 1M solution of tetra-n-butyl-ammonium fluoride in THF were added dropwise to the reaction solution over a period of 1 h. The mixture was then stirred at 70° C. for 18 h. After cooling to RT, the mixture was diluted with EA and combined with a 0.5M aq. Na2CO3 solution. The phases were separated and the aq. phase was extracted with EA. The combined organic phases were dried over MgSO4, filtered and evaporated under a vacuum. CC (acetonitrile/EA 1:3) was carried out with the group, 912 mg of slightly contaminated product being isolated. 304 mg (0.73 mmol, 38%) of N-tert-butyl-2-(5-(thiophen-3-ylethynyl)thiophen-2-yl)imidazo[1,2-a]pyrazin-3-amine hydrochloride were obtained by hydrochloride precipitation in accordance with the method described in Example 192.

Example 158

N-tert-butyl-2-(5-((6-methylpyridin-2-yl)ethynyl)thiophen-2-yl)imidazo[1,2-a]pyrazin-3-amine hydrochloride a) Synthesis of tert-butyl-[2-(5-trimethylsilanylethynyl-thiophen-2-yl)-imidazo[1,2-a]pyrazin-3-yl]-amine 21.4 ml (155 mmol) of trimethylsilylacetylene, 2.4 g (12.9 mmol) of copper(I) iodide and 4.5 g (6.5 mmol) of bis(triphenylphosphine)-palladium(II) chloride were added to a solution of 45.3 g (129 mmol) of [2-(5-bromo-thiophen-2-yl)-imidazo[1,2-a]pyrazin-3-yl]-tert-butyl-amine (synthesis described in Example 18, part a) in DMF (760 ml) and NEt3 (90 ml). The reaction solution was heated to 60° C. for 4 h and stirred at RT for 16 h. The mixture was then combined with a 1M aq. Na2CO3 solution and diluted with EA. The phases were separated and the aq. phase was extracted with EA. The combined organic phases were washed with water and dried over MgSO4. After filtration and removal of the solvents under a vacuum, the resultant group was redissolved with an EA/DCM (1:1) mixture and filtered through diatomaceous earth. The filtrate was evaporated under a vacuum. 30.8 g (84 mmol, 65%) of tert-butyl-[2-(5-trimethylsilanylethynyl-thiophen-2-yl)-imidazo[1,2-a]pyrazin-3-yl]-amine were obtained from the group were by crystallisation from tert.-butyl-methyl ether.

b) Synthesis of tert-butyl-[2-(5-ethynyl-thiophen-2-yl)-imidazo[1,2-a]pyrazin-3-yl]-amine A solution of 14.0 g (38.0 mmol) of tert-butyl-[2-(5-trimethylsilanylethynyl-thiophen-2-yl)-imidazo[1,2-a]pyrazin-3-yl]-amine in a mixture of MeOH (385 ml) and MeCN (440 ml) was combined with 417 ml (41.8 mmol) of a 0.1M aq. NaOH solution. The reaction solution was stirred at RT for 1 h. The solvents were then largely removed under a vacuum. The resultant aq. solution was repeatedly extracted with EA and the combined organic phases were dried over MgSO4, filtered and evaporated under a vacuum, 11.1 g (37.4 mmol, 99%) of tert-butyl-[2-(5-ethynyl-thiophen-2-yl)-imidazo[1,2-a]pyrazin-3-yl]-amine being obtained.

c) Synthesis of N-tert-butyl-2-(5-((6-methylpyridin-2-yl)ethynyl)thiophen-2-yl)imidazo[1,2-a]pyrazin-3-amine 300 mg (1.0 mmol) of tert-butyl-[2-(5-ethynyl-thiophen-2-yl)-imidazo[1,2-a]pyrazin-3-yl]-amine were dissolved together with 138 µl (1.2 mmol) of 2-bromo-6-methyl-pyridine in DMF (7 ml). 1.4 ml (10.0 mmol) of NEt3, 19 mg (0.1 mmol) of copper(I) iodide and 71 mg (0.1 mmol) bis(triphenylphosphine)-palladium(II) chloride were added to this solution. The reaction mixture was heated to 50° C. for 6 h. The mixture was then diluted with EA and combined with a 1M aq. Na2CO3 solution. The phases were separated and the aq. phase was extracted with EA. The combined organic phases were dried over MgSO4, filtered and evaporated under a vacuum. 166 mg (0.42 mmol, 42%) of N-tert-butyl-2-(5-((6-methylpyridin-2-yl)ethynyl)thiophen-2-yl)imidazo[1,2-a]pyrazin-3-amine were obtained by CC (acetone/MeCN 1:1) of the group.

d) Synthesis of N-tert-butyl-2-(5-((6-methylpyridin-2-yl)ethynyl)thiophen-2-yl)imidazo[1,2-a]pyrazin-3-amine hydrochloride 115 mg (0.27 mmol, 65%) of N-tert-butyl-2-(5-((6-methylpyridin-2-yl)ethynyl)thiophen-2-yl)imidazo[1,2-a]pyrazin-3-amine hydrochloride were obtained from 161 mg (0.42 mmol) of N-tert-butyl-2-(5-((6-methylpyridin-2-yl)ethynyl)thiophen-2-yl)imidazo[1,2-a]pyrazin-3-amine in accordance with the method described in Example 192.

Example 165

Synthesis of N-tert-butyl-2-(5-((6-fluoropyridin-2-yl)ethynyl)thiophen-2-yl)imidazo[1,2-a]pyrazin-3-amine 500 mg (1.69 mmol) of tert-butyl-[2-(5-ethynyl-thiophen-2-yl)-imidazo[1,2-a]pyrazin-3-yl]-amine (synthesis described in Example 158 part b) were dissolved together with 355 mg (2.02 mmol) of 2-bromo-6-fluoro-pyridine in DMF (20 ml). 2.4 ml (16.9 mmol) of NEt3, 32 mg (0.17 mmol) of copper(I) iodide and 119 mg (0.17 mmol) bis(triphenylphosphine)-palladium(II) chloride were added to this solution. The reaction mixture was heated to 50° C. for 6 h. The mixture was then diluted with EA and combined with a 1M aq. Na2CO3 solution. The phases were separated and the aq. phase was extracted with EA. The combined organic phases were washed with a 1M aq. Na2CO3 solution, dried over MgSO4, filtered and evaporated under a vacuum. 200 mg (0.51 mmol, 30%) of N-tert-butyl-2-(5-((6-fluoropyridin-2-yl)ethynyl)thiophen-2-yl)imidazo[1,2-a]pyrazin-3-amine were obtained by CC (EA) of the group.

Example 176

Synthesis of N-tert-butyl-2-(5-(phenylethynyl)thiazol-2-yl)imidazo[1,2-a]pyrazin-3-amine A solution of 290 mg (3.0 mmol) of 2-aminopyrazine, 650 mg (3.0 mmol) of 5-pyridin-2-ylethynyl-thiazole-2-carbaldehyde, 344 µl (3.0 mmol) of tert.-butyl-isonitrile and 305 µl of a 20% aq. perchloric acid in DCM (6 ml) was stirred at RT for 6 d. The mixture was then diluted with ether and the phases were separated. The organic phase was washed with water and dried over MgSO4. After filtration and removal of the solvents under a vacuum, CC (hexane/tert.-butyl-methyl ether 3:2) was carried out with the group, 170 mg (0.46 mmol, 15%) of N-tert-butyl-2-(5-(phenylethynyl)thiazol-2-yl)imidazo[1,2-a]pyrazin-3-amine being obtained.

Example 192

Synthesis of N-tert-butyl-2-(5-(pyridin-2-ylethynyl)thiophen-2-yl)imidazo[1,2-a]pyridin-3-amine hydrochloride A solution of 6.93 g (18.6 mmol) of N-tert-butyl-2-(5-(pyridin-2-ylethynyl)thiophen-2-yl)imidazo[1,2-a]pyridin-3-amine (Example 94) in DCM (180 ml) was combined with 335 µl (18.6 mmol) of water and 2.35 ml (18.6 mmol) of chlorotrimethylsilane and stirred at RT for 16 h. The resultant precipitate was filtered out and dried under a vacuum at 40° C., 6.09 g (14.8 mmol, 80%) of N-tert-butyl-2-(5-(pyridin-2-ylethynyl)thiophen-2-yl)imidazo[1,2-a]pyridin-3-amine hydrochloride being obtained.

Example 331 tert-Butyl-[2-(5-pyridin-2-ylethynyl-thiophen-2-yl)-imidazo[1,2-b]pyridazin-3-yl]-amine hydrochloride a) Synthesis of [2-(5-bromo-thiophen-2-yl)-imidazo[1,2-b]pyridazin-3-yl]-tert-butyl-amine 13.1 g (158 mmol) of tert.-butyl-isonitrile, 30.2 g (158 mmol) of 5-bromo-thiophene-2-carboxaldehyde and 5.2 g of a 20% aq. perchloric acid solution were added to a solution of 15.0 g (158 mmol) of 3-amino-pyridazine in DCM (150 ml). The reaction solution was stirred at 40° C. for 5 hours. The mixture was then combined with water (200 ml) and the phases were separated. The aq. phase was extracted with DCM. The combined organic phases were washed in succession with a sat. NaHCO3 solution and a sat. aq. NaCl solution, dried over Na2SO4, filtered and evaporated under a vacuum. CC (alumina, EA/hexane 2:98) was carried out with the group, 1.7 g (4.8 mmol, 3%) of [2-(5-bromo-thiophen-2-yl)-imidazo[1,2-b]pyridazin-3-yl]-tert-butyl-amine being obtained.

b) Synthesis of tert-butyl-[2-(5-pyridin-2-ylethynyl-thiophen-2-yl)-imidazo[1,2-b]pyridazin-3-yl]-amine hydrochloride 0.42 ml (7.4 mmol) of 2-ethynylpyridine, 7.9 ml (57.0 mmol) of NEt3, 280 mg (0.26 mmol) of copper(I) iodide and 519 mg (0.74 mmol) of bis(triphenylphosphine)-palladium(II) chloride were added to a solution of 2.0 g (5.7 mmol) of [2-(5-bromo-thiophen-2-yl)-imidazo[1,2-b]pyridazin-3-yl]-tert-butyl-amine in DMF (50 ml). The reaction solution was heated to 50° C. for 6 h. The mixture was then diluted with EA and combined with a 1M aq. Na2CO3 solution. The phases were separated and the aq. phase was extracted with EA. The combined organic phases were dried over MgSO4, filtered and evaporated under a vacuum. 546 mg of amine were obtained by CC (EA) with the group. Using the method described in Example 192, 440 mg (1.1 mmol, 19%) of tert-butyl-[2-(5-pyridin-2-ylethynyl-thiophen-2-yl)-imidazo[1,2-b]pyridazin-3-yl]-amine hydrochloride were produced therefrom.

Example 332 tert-Butyl-[2-(5-thiazol-2-ylethynyl-thiophen-2-yl)-imidazo[1,2-a]pyridin-3-yl]-amine hydrochloride a) Synthesis of [2-(5-bromo-thiophen-2-yl)-imidazo[1,2-a]pyridin-3-yl]-tert-butyl-amine A solution of 32.3 g (343.4 mmol) of 2-aminopyridine, 37.2 ml (343.4 mmol) of 5-pyridin-2-ylethynyl-thiophene-2-carbaldehyde, 28.6 g (343.4 mmol) of tert.-butyl-isonitrile and 34.3 ml of a 20% aq. perchloric acid in DCM (660 ml)

was stirred at RT for 10 d. The reaction solution was then diluted with DCM and washed in succession with a 1M aq. Na2CO3 solution and a sat. aq. NaCl solution. The organic phase was dried over MgSO4, filtered and evaporated under a vacuum. 56.3 g (160.7 mmol, 47%) of [2-(5-bromo-thiophen-2-yl)-imidazo[1,2-a]pyridin-3-yl]-tert-butyl-amine were obtained from the group by crystallisation from EA.

b) Synthesis of tert-butyl-[2-(5-trimethylsilanylethynyl-thiophen-2-yl)-imidazo[1,2-a]pyridin-3-yl]-amine 5.0 ml (36.0 mmol) of trimethylsilylacetylene, 0.57 g (3.0 mmol) of copper(I) iodide and 2.1 g (3.0 mmol) of bis(triphenylphosphine)-palladium(II) chloride were added to a solution of 10.5 g (30.0 mmol) of [2-(5-bromo-thiophen-2-yl)-imidazo[1,2-a]pyridin-3-yl]-tert-butyl-amine in DMF (180 ml) and NEt3 (21 ml). The reaction solution was stirred at 50° C. for 16 hours. The mixture was then combined with a 1M aq. Na2CO3 solution and diluted with EA. This mixture was filtered through diatomaceous earth. The phases were then separated and the aq. phase was extracted with EA. The combined organic phases were dried over MgSO4, filtered and evaporated under a vacuum. CC (EA/DCM 1:1) was carried out with the group, 8.0 g (21.8 mmol, 73%) of tert-butyl-[2-(5-trimethylsilanylethynyl-thiophen-2-yl)-imidazo[1,2-a]pyridin-3-yl]-amine being obtained.

c) Synthesis of tert-butyl-[2-(5-ethynyl-thiophen-2-yl)-imidazo[1,2-a]pyridin-3-yl]-amine 11.5 g (31.3 mmol) of tert-butyl-[2-(5-trimethylsilanyl-ethynyl-thiophen-2-yl)-imidazo[1,2-a]pyridin-3-yl]-amine were dissolved in a mixture of MeOH (230 ml) and DCM (50 ml) and combined with 431 mg (3.13 mmol) of potassium carbonate The reaction solution was stirred at RT for 30 min and then combined with water (200 ml). The mixture was then extracted with DCM and the organic phase was washed with water and dried over MgSO4. After filtration and evaporation under a vacuum, 9.0 g (30.5 mmol, 97%) of tert-butyl-[2-(5-ethynyl-thiophen-2-yl)-imidazo[1,2-a]pyridin-3-yl]-amine were obtained.

d) Synthesis of tert-butyl-[2-(5-thiazol-2-ylethynyl-thiophen-2-yl)-imidazo[1,2-a]pyridin-3-yl]-amine hydrochloride 383 µl (4.3 mmol) of 2-bromothiazole, 882 µl (6.36 mmol) of triethylamine, 43 mg (0.23 mmol) of copper(I) iodide and 87 mg (0.13 mmol) of bis(triphenylphosphine)-palladium(II) chloride were added to a solution of 1.0 g (3.4 mmol) of tert-butyl-[2-(5-ethynyl-thiophen-2-yl)-imidazo[1,2-a]pyridin-3-yl]-amine in EA (20 ml). This reaction solution was stirred at 50° C. for 16 hours. The mixture then filtered through diatomaceous earth and evaporated under a vacuum. CC (EA/DCM 3:7) was carried out with the group, 902 mg (2.4 mmol, (70%) of tert-butyl-[2-(5-thiazol-2-ylethynyl-thiophen-2-yl)-imidazo[1,2-a]pyridin-3-yl]-amine being obtained. Using the method described in Example 192, tert-butyl-[2-(5-thiazol-2-ylethynyl-thiophen-2-yl)-imidazo[1,2-a]pyridin-3-yl]-amine hydrochloride was produced therefrom.

The production, not described in detail above, of the other compounds according to the Examples stated below also proceeded in a similar manner to the above-stated production methods, the educts used in each case being known to the person skilled in the art on the basis of these methods.

| Example | Name |
|---|---|
| 1 | cyclopentyl-[2-(5-phenylethynyl-thiophen-2-yl)-imidazo[1,2-a]pyrazin-3-yl]-amine |
| 2 | cyclohexylmethyl-[5-methyl-2-(5-phenylethynyl-thiophen-2-yl)-imidazo[1,2-a]pyridin-3-yl]-amine |
| 3 | cyclohexylmethyl-[6-methyl-2-(5-phenylethynyl-thiophen-2-yl)-imidazo[1,2-a]pyridin-3-yl]-amine |
| 4 | cyclohexylmethyl-[7-methyl-2-(5-phenylethynyl-thiophen-2-yl)-imidazo[1,2-a]pyridin-3-yl]-amine |
| 5 | cyclohexylmethyl-[8-methyl-2-(5-phenylethynyl-thiophen-2-yl)-imidazo[1,2-a]pyridin-3-yl]-amine |
| 6 | cyclohexylmethyl-[5,7-dimethyl-2-(5-phenylethynyl-thiophen-2-yl)-imidazo[1,2-a]pyridin-3-yl]-amine |
| 7 | [8-benzyloxy-2-(5-phenylethynyl-thiophen-2-yl)-imidazo[1,2-a]pyridin-3-yl]-cyclohexylmethyl-amine |
| 8 | cyclohexylmethyl-[2-(5-phenylethynyl-thiophen-2-yl)-imidazo[1,2-a]pyrazin-3-yl]-amine |
| 9 | cyclohexylmethyl-[2-(5-phenylethynyl-thiophen-2-yl)-imidazo[1,2-a]pyrimidin-3-yl]-amine |
| 10 | (4-methoxy-benzyl)-[5-methyl-2-(5-phenylethynyl-thiophen-2-yl)-imidazo[1,2-a]pyridin-3-yl]-amine |
| 11 | (4-methoxy-benzyl)-[6-methyl-2-(5-phenylethynyl-thiophen-2-yl)-imidazo[1,2-a]pyridin-3-yl]-amine |
| 12 | (4-methoxy-benzyl)-[7-methyl-2-(5-phenylethynyl-thiophen-2-yl)-imidazo[1,2-a]pyridin-3-yl]-amine |
| 13 | (4-methoxy-benzyl)-[8-methyl-2-(5-phenylethynyl-thiophen-2-yl)-imidazo[1,2-a]pyridin-3-yl]-amine |
| 14 | [5,7-dimethyl-2-(5-phenylethynyl-thiophen-2-yl)-imidazo[1,2-a]pyridin-3-yl]-(4-methoxy-benzyl-amine |
| 15 | [8-benzyloxy-2-(5-phenylethynyl-thiophen-2-yl)-imidazo[1,2-a]pyridin-3-yl]-(4-methoxy-benzyl)-amine |
| 16 | (4-methoxy-benzyl)-[2-(5-phenylethynyl-thiophen-2-yl)-imidazo[1,2-a]pyridin-3-yl]-amine |
| 17 | (4-methoxy-benzyl)-[2-(5-phenylethynyl-thiophen-2-yl)-imidazo[1,2-a]pyrazin-3-yl]-amine |
| 18 | tert-Butyl-[2-(5-phenylethynyl-thiophen-2-yl)-imidazo[1,2-a]pyrazin-3-yl]-amine |
| 19 | tert-butyl-[6-methyl-2-(5-phenylethynyl-thiophen-2-yl)-imidazo[1,2-a]pyridin-3-yl]-amine |

-continued

| Example | Name |
|---|---|
| 20 | [8-benzyloxy-2-(5-phenylethynyl-thiophen-2-yl)-imidazo[1,2-a]pyridin-3-yl]-(3-methoxy-phenyl)-amine |
| 21 | (3-methoxy-benzyl)-[5-methyl-2-(5-phenylethynyl-thiophen-2-yl)-imidazo[1,2-a]pyridin-3-yl]-amine |
| 22 | (3-methoxy-benzyl)-[8-methyl-2-(5-phenylethynyl-thiophen-2-yl)-imidazo[1,2-a]pyridin-3-yl]-amine |
| 23 | [5,7-dimethyl-2-(5-phenylethynyl-thiophen-2-yl)-imidazo[1,2-a]pyridin-3-yl]-(3-methoxy-benzyl)-amine |
| 24 | [8-benzyloxy-2-(5-phenylethynyl-thiophen-2-yl)-imidazo[1,2-a]pyridin-3-yl]-(3-methoxy-benzyl)-amine |
| 25 | (3-methoxy-benzyl)-[2-(5-phenylethyyl-thiophen-2-yl)-imidazo[1,2-a]pyridin-3-yl]-amine |
| 26 | (3-methoxy-benzyl)-[2-(5-phenylethynyl-thiophen-2-yl)-imidazo[1,2-a]pyrazin-3-yl]-amine |
| 27 | [6-methyl-2-(5-phenylethynyl-thiophen-2-yl)-imidazo[1,2-a]pyridin-3-yl]-(1-phenyl-ethyl)-amine |
| 28 | [7-methyl-2-(5-phenylethynyl-thiophen-2-yl)-imidazo[1,2-a]pyridin-3-yl]-(1-phenyl-ethyl)-amine |
| 29 | [5,7-dimethyl-2-(5-phenylethynyl-thiophen-2-yl)-imidazo[1,2-a]pyridin-3-yl]-(1-phenyl-ethyl)-amine |
| 30 | [8-benzyloxy-2-(5-phenylethynyl-thiophen-2-yl)-imidazo[1,2-a]pyridin-3-yl]-(1-phenyl-ethyl)-amine |
| 31 | (1-phenyl-ethyl)-[2-(5-phenylethynyl-thiophen-2-yl)-imidazo[1,2-a]pyrazin-3-yl]-amine |
| 32 | (2-chloro-benzyl)-[5,7-dimethyl-2-(5-phenylethynyl-thiophen-2-yl)-imidazo[1,2-a]pyridin-3-yl]-amine |
| 33 | (3-chloro-4-fluoro-phenyl)-[7-phenyl-2-(5-phenylethynyl-thiophen-2-yl)-imidazo[1,2-a]pyridin-3-yl]-amine |
| 34 | (4-methoxy-benzyl)-[7-methyl-2-(5-phenylethynyl-thiophen-2-yl)-imidazo[1,2-a]pyrimidin-3-yl]-amine |
| 35 | [8-methyl-2-(5-phenylethynyl-thiophen-2-yl)-imidazo[1,2-a]pyridin-3-yl]-(1-phenyl-ethyl)-amine |
| 36 | [7-methyl-2-(5-phenylethynyl-thiophen-2-yl)-imidazo[1,2-a]pyrimidin-3-yl]-(1-phenyl-ethyl)-amine |
| 37 | (2-methoxy-benzyl)-[7-methyl-2-(5-phenylethynyl-thiophen-2-yl)-imidazo[1,2-a]pyridin-3-yl]-amine |
| 38 | (2-methoxy-benzyl)-[2-(5-phenylethynyl-thiophen-2-yl)-imidazo[1,2-a]pyridin-3-yl]-amine |
| 39 | (2-chloro-benzyl)-[2-(5-phenylethynyl-thiophen-2-yl)-imidazo[1,2-a]pyridin-3-yl]-amine |
| 40 | (2-methoxy-benzyl)-[7-methyl-2-(5-phenylethynyl-thiophen-2-yl)-imidazo[1,2-a]pyrimidin-3-yl]-amine |
| 41 | (3-methoxy-phenyl)-[6-methyl-2-(5-phenylethynyl-thiophen-2-yl)-imidazo[1,2-a]pyridin-3-yl]-amine |
| 42 | [5,7-dimethyl-2-(5-phenylethynyl-thiophen-2-yl)-imidazo[1,2-a]pyridin-3-yl]-(3-methoxy-phenyl)-amine |
| 43 | (3-methoxy-phenyl)-[2-(5-phenylethynyl-thiophen-2-yl)-imidazo[1,2-a]pyrazin-3-yl]-amine |
| 44 | [7-ethyl-2-(5-phenylethynyl-thiophen-2-yl)-imidazo[1,2-a]pyridin-3-yl]-(2-methoxy-benzyl)-amine |
| 45 | (2-chloro-benzyl)-[7-ethyl-2-(5-phenylethynyl-thiophen-2-yl)-imidazo[1,2-a]pyridin-3-yl]-amine |
| 46 | [7-tert-butyl-2-(5-phenylethynyl-thiophen-2-yl)-imidazo[1,2-a]pyridin-3-yl]-(3-chloro-4-fluoro-phenyl)-amine |
| 47 | (3-methoxy-benzyl)-[7-methyl-2-(5-phenylethynyl-thiophen-2-yl)-imidazo[1,2-a]pyrimidin-3-yl]-amine |
| 48 | [7-ethyl-2-(5-phenylethynyl-thiophen-2-yl)-imidazo[1,2-a]pyridin-3-yl]-(2-fluoro-phenyl)-amine |
| 49 | [7-tert-butyl-2-(5-phenylethynyl-thiophen-2-yl)-imidazo[1,2-a]pyridin-3-yl]-(2-fluoro-phenyl)-amine |
| 50 | (2,4-difluoro-phenyl)-[2-(5-phenylethynyl-thiophen-2-yl)-7-(3-phenyl-propyl)-imidazo[1,2-a]pyridin-3-yl]-amine |
| 51 | (4-fluoro-benzyl)-[7-methyl-2-(5-phenylethynyl-thiophen-2-yl)-imidazo[1,2-a]pyridin-3-yl]-amine |
| 52 | [5,7-dimethyl-2-(5-phenylethynyl-thiophen-2-yl)-imidazo[1,2-a]pyridin-3-yl]-(4-fluoro-benzyl)-amine |
| 53 | [7-ethyl-2-(5-phenylethynyl-thiophen-2-yl)-imidazo[1,2-a]pyridin-3-yl]-(3-trifluoromethyl-benzyl)-amine |
| 54 | [7-isopropyl-2-(5-phenylethynyl-thiophen-2-yl)-imidazo[1,2-a]pyridin-3-yl]-(3-trifluoromethyl-benzyl)-amine |
| 55 | tert-butyl-[2-(4-phenylethynyl-thiophen-2-yl)-imidazo[1,2-a]pyrazin-3-yl]-amine |
| 56 | [2-(5-phenylethynyl-thiophen-2-yl)-imidazo[1,2-a]pyrazin-3-yl]-(1,1,3,3-tetramethyl-butyl)-amine |
| 57 | butyl-[2-(4-phenylethynyl-thiophen-2-yl)-imidazo[1,2-a]pyrazin-3-yl]-amine |
| 59 | [2-(5-phenylethynyl-thiophen-2-yl)-imidazo[1,2-a]pyridin-3-yl]-(1,1,3,3-tetramethyl-butyl)-amine |

-continued

| Example | Name |
|---|---|
| 60 | [2-(5-pyridin-3-ylethynyl-thiophen-2-yl)-imidazo[1,2-a]pyrazin-3-yl]-(1,1,3,3-tetramethyl-butyl)-amine |
| 61 | [2-(5-pyridin-4-ylethynyl-thiophen-2-yl)-imidazo[1,2-a]pyrazin-3-yl]-(1,1,3,3-tetramethyl-butyl)-amine |
| 62 | [6-chloro-2-(5-phenylethynyl-thiophen-2-yl)-imidazo[1,2-a]pyridin-3-yl]-(1,1,3,3-tetramethyl-butyl)-amine |
| 63 | [6,8-dichloro-2-(5-phenylethynyl-thiophen-2-yl)-imidazo[1,2-a]pyridin-3-yl]-(1,1,3,3-tetramethyl-butyl)-amine |
| 64 | [2-(5-pyridin-2-ylethynyl-thiophen-2-yl)-imidazo[1,2-a]pyrazin-3-yl]-(1,1,3,3-tetramethyl-butyl)-amine |
| 65 | dimethyl-[2-(5-phenylethynyl-thiophen-2-yl)-imidazo[1,2-a]pyrazin-3-yl]-amine |
| 66 | methyl-[2-(5-phenylethynyl-thiophen-2-yl)-imidazo[1,2-a]pyrazin-3-yl]-amine |
| 67 | N-[2-(5-phenylethynyl-thiophen-2-yl)-imidazo[1,2-a]pyrazin-3-yl]-acetamide |
| 68 | ethyl-[2-(5-phenylethynyl-thiophen-2-yl)-imidazo[1,2-a]pyrazin-3-yl]-amine |
| 69 | propyl-[2-(5-phenylethynyl-thiophen-2-yl)-imidazo[1,2-a]pyrazin-3-yl]-amine |
| 70 | butyl-[2-(5-phenylethynyl-thiophen-2-yl)-imidazo[1,2-a]pyrazin-3-yl]-amine |
| 71 | (2-methylpropyl)-[2-(5-phenylethynyl-thiophen-2-yl)-imidazo[1,2-a]pyrazin-3-yl]-amine |
| 72 | pentyl-[2-(5-phenylethynyl-thiophen-2-yl)-imidazo[1,2-a]pyrazin-3-yl]-amine |
| 73 | {(methoxycarbonylmethyl)-[2-(5-phenylethynyl-thiophen-2-yl)-imidazo[1,2-a]pyrazin-3-yl]-amino}-acetic acid methyl ester |
| 74 | benzyl-[2-(5-phenylethynyl-thiophen-2-yl)-imidazo[1,2-a]pyrazin-3-yl]-amine |
| 75 | [2-(5-phenylethynyl-thiophen-2-yl)-imidazo[1,2-a]pyrazin-3-ylamino]-acetic acid methyl ester |
| 76 | tert-butyl-[2-(5-pyridin-4-ylethynyl-thiophen-2-yl)-imidazo[1,2-a]pyrazin-3-yl]-amine |
| 77 | tert-butyl-[2-(5-pyridin-2-ylethynyl-thiophen-2-yl)-imidazo[1,2-a]pyrazin-3-yl]-amine |
| 78 | N-[2-(5-phenylethynyl-thiophen-2-yl)-imidazo[1,2-a]pyrazin-3-yl]-benzamide |
| 79 | [2-(5-phenylethynyl-thiophen-2-yl)-imidazo[1,2-a]pyrazin-3-yl]-bis-pyridine-3-ylmethyl-amine |
| 80 | 2,2-dimethyl-N-[2-(5-phenylethynyl-thiophen-2-yl)-imidazo[1,2-a]pyrazin-3-yl]-propionamide |
| 81 | 3-methoxy-N-[2-(5-phenylethynyl-thiophen-2-yl)-imidazo[1,2-a]pyrazin-3-yl]-benzamide |
| 82 | tert-butyl-[2-(5-pyridin-3-ylethynyl-thiophen-2-yl)-imidazo[1,2-a]pyrazin-3-yl]-amine |
| 83 | 2-(5-phenylethynyl-thiophen-2-yl)-imidazo[1,2-a]pyrazin-3-ylamine |
| 84 | methyl-2-(5-(phenylethynyl)thiophen-2-yl)-3-(2,4,4-trimethylpentan-2-ylamino)imidazo[1,2-a]pyrazine-8-carboxylate |
| 85 | 2-(5-(phenylethynyl)thiophen-2-yl)-N-(2,4,4-trimethylpentan-2-yl)imidazo[1,2-a]pyrimidin-3-amine |
| 86 | 2-(5-((6-methylpyridin-2-yl)ethynyl)thiophen-2-yl)-N-(2,4,4-trimethylpentan-2-yl)imidazo[1,2-a]pyrazin-3-amine |
| 87 | N-cyclohexyl-2-(5-(phenylethynyl)thiophen-2-yl)imidazo[1,2-a]pyrazin-3-amine |
| 88 | 2-(5-(phenylethynyl)thiophen-2-yl)-3-(piperidin-1-yl)imidazo[1,2-a]pyrazine |
| 89 | N-tert-butyl-N-methyl-2-(5-(phenylethynyl)thiophen-2-yl)imidazo[1,2-a]pyrazin-3-amine |
| 90 | methyl-2-(5-(phenylethynyl)thiophen-2-yl)-3-(2,4,4-trimethylpentan-2-ylamino)imidazo[1,2-a]pyridine-6-carboxylate |
| 91 | N-tert-butyl-2-(5-(pyridin-2-ylethynyl)thiophen-2-yl)imidazo[1,2-a]pyrazin-3-amine hydrochloride |
| 92 | 8-bromo-N-cyclopentyl-6-methyl-2-(5-(pyridin-2-ylethynyl)thiophen-2-yl)imidazo[1,2-a]pyridin-3-amine |
| 93 | N,N-diethyl-2-(5-(phenylethynyl)thiophen-2-yl)imidazo[1,2-a]pyrazin-3-amine |
| 94 | N-tert-butyl-2-(5-(pyridin-2-ylethynyl)thiophen-2-yl)imidazo[1,2-a]pyridin-3-amine |
| 95 | N-tert-butyl-2-(5-(phenylethynyl)furan-2-yl)imidazo[1,2-a]pyrazin-3-amine |
| 96 | 8-bromo-N-tert-butyl-6-methyl-2-(3-(pyridin-2-ylethynyl)phenyl)imidazo-[1,2-a]pyridin-3-amine |
| 97 | N-tert-butyl-8-methyl-2-(5-(phenylethynyl)thiophen-2-yl)imidazo[1,2-a]pyridin-3- |
| 98 | N-methyl-2-(5-(phenylethynyl)thiophen-2-yl)-N-(2,4,4-trimethylpentan-2-yl)imidazo[1,2-a]pyrazin-3-amine hydrochloride |
| 99 | 2-(5-(phenylethynyl)thiophen-2-yl)-3-(pyrrolidin-1-yl)imidazo[1,2-a]pyrazine hydrochloride |
| 100 | N-tert-butyl-2-(5-((4-fluorophenyl)ethynyl)thiophen-2-yl)imidazo[1,2-a]pyrazin-3-amine hydrochloride |
| 101 | N-tert-butyl-7-methyl-2-(5-(phenylethynyl)thiophen-2-yl)imidazo[1,2-a]pyridin-3-amine |
| 102 | N-tert-butyl-5-methyl-2-(5-(phenylethynyl)thiophen-2-yl)imidazo[1,2-a]pyridin-3-amine |
| 103 | 8-chloro-2-(3-(pyridin-2-ylethynyl)phenyl)-6-(trifluoromethyl)-N-(2,4,4-trimethylpentan-2-yl)imidazo[1,2-a]pyridin-3-amine |
| 104 | N-tert-butyl-2-(5-((3-fluorophenyl)ethynyl)thiophen-2-yl)imidazo[1,2-a]pyrazin-3-amine hydrochloride |
| 105 | N-tert-butyl-2-(5-((2-fluorophenyl)ethynyl)thiophen-2-yl)imidazo[1,2-a]pyrazin-3-amine hydrochloride |
| 106 | methyl-3-(tert-butylamino)-2-(5-(phenylethynyl)thiophen-2-yl)imidazo-[1,2-a]pyrazine-8-carboxylate |
| 107 | N-tert-butyl-2-(5-(pyrazin-2-ylethynyl)thiophen-2-yl)imidazo[1,2-a]pyrazin-3-amine |

-continued

| Example | Name |
|---|---|
| 108 | 2-(5-((4-aminophenyl)ethynyl)thiophen-2-yl)-N-tert-butylimidazo[1,2-a]pyrazin-3-amine |
| 109 | N-isopropyl-2-(5-(phenylethynyl)thiophen-2-yl)imidazo[1,2-a]pyrazin-3-amine |
| 110 | N-tert-butyl-2-(5-(thiophen-2-ylethynyl)thiophen-2-yl)imidazo[1,2-a]pyrazin-3-amine hydrochloride |
| 111 | N-tert-butyl-2-(3-(pyridine-2-ylethynyl)phenyl)imidazo[1,2-a]pyrazin-3-amine |
| 112 | N-tert-butyl-2-(5-((2-methoxyphenyl)ethynyl)thiophen-2-yl)imidazo[1,2-a]pyrazin-3-amine hydrochloride |
| 113 | N-tert-butyl-2-(5-((3-methoxyphenyl)ethynyl)thiophen-2-yl)imidazo[1,2-a]pyrazin-3-amine hydrochloride |
| 114 | N-tert-butyl-2-(5-((4-methoxyphenyl)ethynyl)thiophen-2-yl)imidazo[1,2-a]pyrazin-3-amine hydrochloride |
| 115 | N-tert-butyl-2-(5-(phenylethynyl)thiophen-2-yl)imidazo[1,2-a]quinolin-1-amine |
| 116 | N-tert-butyl-2-(4-(pridin-2-ylethynyl)phenyl)imidazo[1,2-a]pyrazin-3-amine |
| 117 | N-tert-butyl-2-(3-((6-methylpyridin-2-yl)ethynyl)phenyl)imidazo[1,2-a]pyrazin-3-amine |
| 118 | N-tert-butyl-2-(2-methyl-6-(phenylethynyl)pyridin-3-yl)imidazo[1,2-a]pyrazin-3-amine |
| 119 | N-tert-butyl-2-(5-(pyridin-2-ylethynyl)furan-2-yl)imidazo[1,2-a]pyrazin-3-amine |
| 120 | 3-(tert-butylamino)-2-(5-(phenylethynyl)thiophen-2-yl)imidazo[1,2-a]pyrazine-8-carboxylic acid |
| 121 | 4-((5-(3-(tert-butylamino)imidazo[1,2-a]pyrazin-2-yl)thiophen-2-yl)ethynyl)phenol hydrochloride |
| 122 | 3-((5-(3-(tert-butylamino)imidazo[1,2-a]pyrazin-2-yl)thiophen-2-yl)ethynyl)phenol |
| 123 | 2-(5-((3-aminophenyl)ethynyl)thiophen-2-yl)-N-tert-butylimidazo[1,2-a]pyrazin-3-amine hydrochloride |
| 124 | 2-(5-((2-aminophenyl)ethynyl)thiophen-2-yl)-N-tert-butylimidazo[1,2-a]pyrazin-3-amine hydrochloride |
| 125 | N-tert-butyl-2-(5-(phenylethynyl)thiophen-2-yl)imidazo[2,1-a]isoquinolin-3-amine |
| 126 | N-tert-butyl-2-(6-(phenylethynyl)pyridin-3-yl)imidazo[1,2-a]pyrazin-3-amine |
| 127 | N-tert-butyl-2-(5-(pyridin-4-ylethynyl)thiophen-2-yl)imidazo[1,2-a]pyrazin-3-amine hydrochloride |
| 128 | 2-(5-((6-aminopyridin-3-yl)ethynyl)thiophen-2-yl)-N-tert-butylimidazo[1,2-a]pyrazin-3-amine hydrochloride |
| 129 | N-tert-butyl-2-(5-(pyrimidin-2-ylethynyl)thiophen-2-yl)imidazo[1,2-a]pyrazin-3-amine hydrochloride |
| 130 | N-tert-butyl-2-(5-((4-methylpyridin-2-yl)ethynyl)thiophen-2-yl)imidazo[1,2-a]pyrazin-3-amine hydrochloride |
| 131 | N-tert-butyl-2-(5-((5-methylpyridin-2-yl)ethynyl)thiophen-2-yl)imidazo-[1,2-a]pyrazin-3-amine hydrochloride |
| 132 | N-tert-butyl-2-(5-(pyridin-4-ylethynyl)thiophen-2-yl)imidazo[1,2-a]pyridin-3-amine hydrochloride |
| 133 | N-tert-butyl-2-(5-(thiazol-2-ylethynyl)thiophen-2-yl)imidazo[1,2-a]pyrazin-3-amine |
| 134 | 2-(5-(pyridin-2-ylethynyl)thiophen-2-yl)imidazo[1,2-a]pyrazin-3-amine hydrochloride |
| 135 | N-tert-butyl-2-(5-((5-methylthiophen-2-yl)ethylnyl)thiophen-2-yl)imidazo-[1,2-a]pyrazin-3-amine hydrochloride |
| 136 | 2-(5-((6-aminopyridin-2-yl)ethynyl)thiophen-2-yl)-N-tert-butylimidazo[1,2-a]pyrazin-3-amine hydrochloride |
| 137 | N-tert-butyl-2-(5-((3-methylthiophen-2-yl)ethynyl)thiophen-2-yl)-imidazo[1,2-a]pyrazin-3-amine |
| 138 | N-tert-butyl-2-(4-(phenylethynyl)thiazol-2-yl)imidazo[1,2-a]pyrazin-3-amine |
| 139 | N-tert-butyl-2-(5-(m-tolylethynyl)thiophen-2-yl)imidazo[1,2-a]pyrazin-3-amine |
| 140 | 3-((5-(3-(tert-butylamino)imidazo[1,2-a]pyrazin-2-yl)thiophen-2-yl)ethynyl)benzonitrile hydrochloride |
| 141 | N-tert-butyl-2-(5-(pyridin-2-ylethynyl)thiophen-2-yl)imidazo[1,2-a]pyrimidin-3-amine |
| 142 | N-tert-butyl-2-(6-(phenylethynyl)pyridin-2-yl)imidazo[1,2-a]pyrazin-3-amine hydrochloride |
| 143 | N-tert-butyl-N-methyl-2-(5-(pyridin-2-ylethynyl)thiophen-2-yl)imidazo-[1,2-a]pyrazin-3-amine |
| 144 | 4-((5-(3-(tert-butylamino)imidazo[1,2-a]pyrazin-2-yl)thiophen-2-yl)ethynyl)benzonitrile hydrochloride |
| 145 | 2-(5-((1H-indol-6-yl)ethynyl)thiophen-2-yl)-N-tert-butylimidazo[1,2-a]pyrazin-3-amine hydrochloride |
| 146 | N-tert-butyl-2-(2-(phenylethynyl)thiazol-5-yl)imidazo[1,2-a]pyrazin-3-amine |
| 147 | N-tert-butyl-2-(5-(quinolin-6-ylethynyl)thiophen-2-yl)imidazo[1,2-a]pyrazin-3-amine hydrochloride |
| 148 | 2-(5-((3-(1H-pyrrol-1-yl)phenyl)ethynyl)thiophen-2-yl)-N-tert-butylimidazo-[1,2-a]pyrazin-3-amine hydrochloride |
| 149 | 2-(5-((1H-indol-4-yl)ethynyl)thiophen-2-yl)-N-tert-butylimidazo[1,2-a]pyrazin-3-amine hydrochloride |
| 150 | N-tert-butyl-2-(5-((3-nitrophenyl)ethynyl)thiophen-2-yl)imidazo[1,2-a]pyrazin-3-amine hydrochloride |
| 151 | N-tert-butyl-2-(5-((4-nitrophenyl)ethynyl)thiophen-2-yl)imidazo[1,2-a]pyrazin-3-amine hydrochloride |

-continued

| Example | Name |
|---|---|
| 152 | N-tert-butyl-2-(5-(thiazol-4-ylethynyl)thiophen-2-yl)imidazo[1,2-a]pyrazin-3-amine hydrochloride |
| 153 | 2-((5-(3-(tert-butylamino)imidazo[1,2-a]pyrazin-2-yl)thiophen-2-yl)ethynyl)phenol |
| 154 | 2-(5-((3-(aminomethyl)phenyl)ethynyl)thiophen-2-yl)-N-tert-butylimidazo-[1,2-a]pyrazin-3-amine |
| 155 | 2-(5-(biphenyl-3-ylethynyl)thiophen-2-yl)-N-tert-butylimidazo[1,2-a]pyrazin-3-amine hydrochloride |
| 156 | N-tert-butyl-2-(5-(thiophen-3-ylethynyl)thiophen-2-yl)imidazo[1,2-a]pyrazin-3-amine hydrochloride |
| 157 | N-tert-butyl-2-(5-((3-(dimethylamino)phenyl)ethynyl)thiophen-2-yl)imidazo-[1,2-a]pyrazin-3-amine hydrochloride |
| 158 | N-tert-butyl-2-(5-((6-methylpyridin-2-yl)ethynyl)thiophen-2-yl)imidazo-[1,2-a]pyrazin-3-amine hydrochloride |
| 159 | N-tert-butyl-2-(5-((3-fluoropyridin-2-yl)ethynyl)thiophen-2-yl)imidazo[1,2-a]pyrazin-3-amine hydrochloride |
| 160 | N-tert-butyl-2-(5-((3-(methylamino)phenyl)ethynyl)thiophen-2-yl)imidazo-[1,2-a]pyrazin-3-amine hydrochloride |
| 161 | N-tert-butyl-2-(5-(p-tolylethynyl)thiophen-2-yl)imidazo[1,2-a]pyrazin-3-amine |
| 162 | N-tert-butyl-2-(5-(o-tolylethynyl)thiophen-2-yl)imidazo[1,2-a]pyrazin-3-amine hydrochloride |
| 163 | N-tert-butyl-2-(4-methyl-5-(phenylethynyl)thiophen-2-yl)imidazo[1,2-a]pyrazin-3-amine hydrochloride |
| 164 | N-tert-butyl-2-(4-methyl-5-(pyridin-2-ylethynyl)thiophen-2-yl)imidazo[1,2-a]pyrazin-3-amine hydrochloride |
| 165 | N-tert-butyl-2-(5-((6-fluoropyridin-2-yl)ethynyl)thiophen-2-yl)imidazo[1,2-a]pyrazin-3-amine |
| 166 | N-tert-butyl-2-(5-((2-nitrophenyl)ethynyl)thiophen-2-yl)imidazo[1,2-a]pyrazin-3-amine |
| 167 | N-tert-butyl-8-chloro-2-(5-(pyridin-2-ylethynyl)thiophen-2-yl)imidazo[1,2-a]pyrazin-3-amine |
| 168 | N-tert-butyl-2-(5-((6-methoxypyridin-2-yl)ethynyl)thiophen-2-yl)imidazo[1,2-a]-pyrazin-3-amine |
| 169 | N-tert-butyl-2-(5-((5-fluoropyridin-2-yl)ethynyl)thiophen-2-yl)imidazo[1,2-a]pyrazin-3-amine hydrochloride |
| 170 | 2-(4-(3-(tert-butylamino)imidazo[1,2-a]pyrazin-2-yl)-2-(phenylethynyl)-phenyl)acetonitrile |
| 171 | N-tert-butyl-2-(5-((5-methoxypyridin-3-yl)ethynyl)thiophen-2-yl)imidazo-[1,2-a]pyrazin-3-amine hydrochloride |
| 172 | 5-((5-(3-(tert-butylamino)imidazo[1,2-a]pyrazin-2-yl)thiophen-2-yl)ethynyl)-nicotinonitrile hydrochloride |
| 173 | N-tert-butyl-2-(5-((3-(methylthio)phenyl)ethynyl)thiophen-2-yl)imidazo-[1,2-a]pyrazin-3-amine |
| 174 | methyl-3-((5-(3-(tert-butylamino)imidazo[1,2-a]pyrazin-2-yl)thiophen-2-yl)ethynyl)benzoate |
| 175 | N-tert-butyl-2-(5-((3,5-difluoropyridin-2-yl)ethynyl)thiophen-2-yl)imidazo-[1,2-a]pyrazin-3-amine |
| 176 | N-tert-butyl-2-(5-(phenylethynyl)thiazol-2-yl)imidazo[1,2-a]pyrazin-3-amine |
| 177 | N-tert-butyl-2-(2-(pyridin-4-ylethynyl)thiazol-5-yl)imidazo[1,2-a]pyrazin-3-amine |
| 178 | 3-((5-(3-(tert-butylamino)imidazo[1,2-a]pyrazin-2-yl)thiophen-2-yl)ethynyl)-benzaldehyde |
| 179 | 3-((5-(3-(tert-butylamino)imidazo[1,2-a]pyrazin-2-yl)thiophen-2-yl)ethynyl)-4-fluorobenzonitrile |
| 180 | N-tert-butyl-2-(5-((3-(trifluoromethyl)phenyl)ethynyl)thiophen-2-yl)imidazo[1,2-a]pyrazin-3-amine hydrochloride |
| 181 | N-tert-butyl-2-(2-(pyridin-2-ylethynyl)thiazol-5-yl)imidazo[1,2-a]pyrazin-3-amine |
| 182 | N-tert-butyl-2-(3-methyl-5-(phenylethynyl)thiophen-2-yl)imidazo[1,2-a]pyrazin-3-amine hydrochloride |
| 183 | N-tert-butyl-2-(3-methyl-5-(pyridin-2-ylethynyl)thiophen-2-yl)imidazo[1,2-a]pyrazin-3-amine hydrochloride |
| 184 | N-tert-butyl-2-(5-((3-vinylphenyl)ethynyl)thiophen-2-yl)imidazo[1,2-a]pyrazin-3-amine |
| 185 | 2-(5-((1H-imidazol-4-yl)ethynyl)thiophen-2-yl)-N-tert-butylimidazo[1,2-a]pyrazin-3-amine hydrochloride |
| 186 | N-tert-butyl-2-(5-((3-methylpyridin-2-yl)ethynyl)thiophen-2-yl)imidazo[1,2-a]-pyrazin-3-amine |
| 187 | N,N-dimethyl-2-(5-(pyridin-2-ylethynyl)thiophen-2-yl)imidazo[1,2-a]pyrazin-3-amine |
| 188 | N-tert-butyl-2-(5-((2-(tert-butyldiphenylsilyl)thiazol-5-yl)ethynyl)thiophen-2-yl)imidazo[1,2-a]pyridin-3-amine |
| 189 | 3-((5-(3-(tert-butylamino)imidazo[1,2-a]pyridin-2-yl)thiophen-2-yl)ethynyl)-benzonitrile |
| 190 | N-tert-butyl-2-(5-(phenylethynyl)thiazol-2-yl)imidazo[1,2-a]pyrazin-3-amine |
| 191 | N-tert-butyl-2-(5-(thiazol-5-ylethynyl)thiophen-2-yl)imidazo[1,2-a]pyrazin-3-amine |
| 192 | N-tert-butyl-2-(5-(pyridin-2-ylethynyl)thiophen-2-yl)imidazo[1,2-a]pyridin-3-amine hydrochloride |
| 193 | 6-chloro-N-cyclohexyl-2-(3-((6-methylpyridin-2-yl)ethynyl)phenyl)-imidazo[1,2-a]pyridin-3-amine |

-continued

| Example | Name |
|---|---|
| 194 | 5,7-dimethyl-N-phenethyl-2-(5-(phenylethynyl)thiophen-2-yl)imidazo[1,2-a]-pyrimidin-3-amine |
| 195 | N-(3-methoxyphenethyl)-5,7-dimethyl-2-(5-(phenylethynyl)thiophen-2-yl)imidazo[1,2-a]pyrimidin-3-amine |
| 196 | N-(3-methoxyphenethyl)-5,7-dimethyl-2-(4-(phenylethynyl)thiophen-2-yl)imidazo[1,2-a]pyrimidin-3-amine |
| 197 | N-(3-methoxyphenethyl)-5,7-dimethyl-2-(5-(phenylethynyl)furan-2-yl)imidazo[1,2-a]pyrimidin-3-amine |
| 198 | N-(4-chlorobenzyl)-8-methyl-2-(5-(phenylethynyl)thiophen-2-yl)imidazo-[1,2-a]pyridin-3-amine |
| 199 | N-(3-methoxyphenethyl)-5-methyl-2-(4-(phenylethynyl)thiopen-2-yl)imidazo-[1,2-a]pyridin-3-amine |
| 200 | N-(2-methylhexan-2-yl)-2-(4-(phenylethynyl)thiophen-2-yl)imidazo[1,2-a]pyrazin-3-amine |
| 201 | N-phenethyl-2-(4-(phenylethynyl)thiophen-2-yl)imidazo[1,2-a]pyrazin-3-amine |
| 202 | N-(3-methoxyphenethyl)-2-(4-(phenylethynyl)thiophen-2-yl)imidazo[1,2-a]pyrazin-3-amine |
| 203 | 2-(4-(phenylethynyl)thiophen-2-yl)-N-(2-(thiophen-2-yl)ethyl)imidazo[1,2-a]pyrazin-3-amine |
| 204 | N-(4-chlorobenzyl)-2-(5-(phenylethynyl)thiophen-2-yl)imidazo[1,2-a]pyridin-3-amine |
| 205 | N-(2-methylpentan-2-yl)-2-(5-(phenylethynyl)thiophen-2-yl)imidazo[1,2-a]pyrazin-3-amine |
| 206 | N-(cyclohexylmethyl)-2-(4-(phenylethynyl)thiophen-2-yl)imidazo[1,2-a]pyrazin-3-amine |
| 207 | N-(2-methoxybenzyl)-2-(5-(phenylethynyl)furan-2-yl)imidazo[1,2-a]pyrazin-3-amine |
| 208 | N-(cyclohexylmethyl)-2-(4-(phenylethynyl)thiophen-2-yl)imidazo[1,2-a]pyridin-3-amine |
| 209 | N-(2-methylpentan-2-yl)-2-(4-(phenylethynyl)thiophen-2-yl)imidazo[1,2-a]pyrazin-3-amine |
| 210 | 8-bromo-6-methyl-2-(3-((6-methylpyridin-2-yl)ethynyl)phenyl)-N-(2,4,4-trimethylpentan-2-yl)imidazo[1,2-a]pyridin-3-amine |
| 211 | 8-bromo-N-cyclopentyl-6-methyl-2-(3-(pyridin-2-ylethynyl)phenyl)imidazo-[1,2-a]pyridin-3-amine |
| 212 | N-cyclopentyl-2-(4-(phenylethynyl)thiophen-2-yl)imidazo[1,2-a]pyrazin-3-amine |
| 213 | N-(1-phenylethyl)-2-(4-(phenylethynyl)thiophen-2-yl)imidazo[1,2-a]pyrazin-3-amine |
| 214 | N-(2-methylpentan-2-yl)-2-(4-(phenylethynyl)thiophen-2-yl)imidazo[1,2-a]pyrazin-3-amine |
| 215 | 8-bromo-N-cyclohexyl-6-methyl-2-(5-(pyridin-2-ylethynyl)furan-2-yl)imidazo-[1,2-a]pyridin-3-amine |
| 216 | N-cyclopentyl-2-(5-(phenylethynyl)furan-2-yl)imidazo[1,2-a]pyrazin-3-amine |
| 217 | N-(3-methoxyphenethyl)-7-methyl-2-(4-(phenylethynyl)thiophen-2-yl)imidazo[1,2-a]pyrimidin-3-amine |
| 218 | 8-(benzyloxy)-2-(5-(phenylethynyl)thiophen-2-yl)-N-(2,4,4-trimethylpentan-2-yl)imidazo[1,2-a]pyridin-3-amine |
| 219 | 8-(benzyloxy)-N-cyclopentyl-2-(4-(phenylethynyl)thiophen-2-yl)imidazo-[1,2-a]pyridin-3-amine |
| 220 | 8-(benzyloxy)-N-(2-methylpentan-2-yl)-2-(4-(phenylethynyl)thiophen-2-yl)-imidazo[1,2-a]pyridin-3-amine |
| 221 | 6-chloro-N-(4-fluorobenzyl)-2-(5-(phenylethynyl)furan-2-yl)imidazo[1,2-a]pyridin-3-amine |
| 222 | 6-bromo-N-butyl-5-methyl-2-(4-(phenylethynyl)thiophen-2-yl)imidazo-[1,2-a]pyridin-3-amine |
| 223 | N-(furan-2-yl)-8-methyl-2-(5-(phenylethynyl)furan-2-yl)imidazo[1,2-a]pyridin-3-amine |
| 224 | N-(furan-2-yl)-2-(5-(phenylethynyl)furan-2-yl)imidazo[1,2-a]pyridin-3-amine |
| 225 | N-(furan-2-yl)-2-(5-(phenylethynyl)furan-2-yl)-7-propylimidazo[1,2-a]pyridin-3-amine |
| 226 | 5,7-dimethyl-2-(4-(phenylethynyl)thiophen-2-yl)-N-(3-(trifluoromethyl)phenyl)imidazo[1,2-a]pyrimidin-3-amine |
| 227 | 6-bromo-N-(4-chlorophenethyl)-8-methyl-2-(4-(phenylethynyl)thiophen-2-yl)imidazo[1,2-a]pyridin-3-amine |
| 228 | N-(4-chlorophenethyl)-7-phenyl-2-(4-(phenylethynyl)thiophen-2-yl)imidazo-[1,2-a]pyridin-3-amine |
| 229 | N-phenethyl-7-phenyl-2-(4-(phenylethynyl)thiophen-2-yl)imidazo[1,2-a]pyridin-3-amine |
| 230 | N-(4-chlorobenzyl)-5,7-dimethyl-2-(4-(phenylethynyl)thiophen-2-yl)imidazo-[1,2-a]pyridin-3-amine |
| 231 | 6-bromo-N-(4-chlorobenzyl)-5-methyl-2-(4-(phenylethynyl)thiophen-2-yl)imidazo[1,2-a]pyridin-3-amine |
| 232 | 8-bromo-N-(4-chlorobenzyl)-6-methyl-2-(4-(phenylethynyl)thiophen-2-yl)imidazo-[1,2-a]pyridin-3-amine |
| 233 | N-(3-methoxyphenethyl)-2-(4-(phenylethynyl)thiophen-2-yl)-5-propylimidazo[1,2-a]pyridin-3-amine |

-continued

| Example | Name |
|---|---|
| 234 | 6-bromo-8-methyl-2-(4-(phenylethynyl)thiophen-2-yl)-N-(2-(thiophen-2-yl)ethyl)imidazo[1,2-a]pyridin-3-amine |
| 235 | 7-phenyl-2-(4-(phenylethynyl)thiophen-2-yl)-N-(2-(thiophen-2-yl)ethyl)imidazo-[1,2-a]pyridin-3-amine |
| 236 | 6,8-dibromo-N-(2-methylpentan-2-yl)-2-(5-(phenylethynyl)thiophen-2-yl)imidazo-[1,2-a]pyridin-3-amine |
| 237 | 6-bromo-N-(2,6-dimethylphenyl)-8-methyl-2-(4-(phenylethynyl)thiophen-2-yl)-imidazo[1,2-a]pyridin-3-amine |
| 238 | N-cyclohexyl-2-(3-(pyridin-2-ylethynyl)phenyl)imidazo[1,2-a]pyrazin-3-amine |
| 239 | 2-(3-(pyridin-2-ylethynyl)phenyl)-N-(2,4,4-trimethylpentan-2-yl)imidazo-[1,2-a]pyrazin-3-amine |
| 240 | N-cyclopentyl-2-(4-(pyridin-2-ylethynyl)phenyl)imidazo[1,2-a]pyrazin-3-amine |
| 241 | 8-chloro-2-(4-(pyridin-2-ylethynyl)phenyl)-6-(trifluoromethyl)-N-(2,4,4-trimethylpentan-2-yl)imidazo[1,2-a]pyridin-3-amine |
| 242 | N-(4-fluorophenyl)-2-(4-(pyridin-2-ylethynyl)phenyl)imidazo[1,2-a]pyrazin-3-amine |
| 243 | N-cyclopentyl-2-(2-methyl-6-(phenylethynyl)pyridin-3-yl)imidazo[1,2-a]pyrazin-3-amine |
| 244 | N-cyclohexyl-2-(2-methyl-6-(phenylethynyl)pyridin-3-yl)imidazo[1,2-a]pyrazin-3-amine |
| 245 | N-cyclopentyl-2-(5-(pyridin-2-ylethynyl)furan-2-yl)imidazo[1,2-a]pyrazin-3-amine |
| 246 | 8-bromo-N-cyclopentyl-6-methyl-2-(5-(pyridin-2-ylethynyl)furan-2-yl)imidazo-[1,2-a]pyridin-3-amine |
| 247 | N-cyclopentyl-2-(5-(pyridin-2-ylethynyl)furan-2-yl)imidazo[1,2-a]pyrazin-3-amine |
| 248 | 2-(5-(pyridin-2-ylethynyl)furan-2-yl)-N-(2,4,4-trimethylpentan-2-yl)imidazo-[1,2-a]pyrazin-3-amine |
| 249 | N-cyclopentyl-2-(3-((6-methylpyridin-2-yl)ethynyl)phenyl)imidazo[1,2-a]pyrazin-3-amine |
| 250 | 8-bromo-N-cyclopentyl-6-methyl-2-(4-(pyridin-2-ylethynyl)phenyl)imidazo[1,2-a]-pyridin-3-amine |
| 251 | N-cyclohexyl-2-(3-((6-methylpyridin-2-yl)ethynyl)phenyl)imidazo[1,2-a]pyrazin-3-amine |
| 252 | N-(4-fluorophenyl)-2-(3-((6-methylpyridin-2-yl)ethynyl)phenyl)imidazo[1,2-a]-pyrazin-3-amine |
| 253 | 2-(5-(pyridin-2-ylethynyl)thiophen-2-yl)-N-(2,4,4-trimethylpentan-2-yl)imidazo-[1,2-a]pyrimidin-3-amine |
| 254 | N-cyclohexyl-2-(3-(pyridin-2-ylethynyl)phenyl)imidazo[1,2-a]pyrimidin-3-amine |
| 255 | 2-(3-(pyridin-2-ylethynyl)phenyl)-N-(2,4,4-trimethylpentan-2-yl)imidazo-[1,2-a]pyrimidin-3-amine |
| 256 | 2-(6-(phenylethynyl)pyridin-3-yl)-N-(2,4,4-trimethylpentan-2-yl)imidazo-[1,2-a]pyrimidin-3-amine |
| 257 | N-cyclopentyl-2-(5-(pyridin-2-ylethynyl)furan-2-yl)imidazo[1,2-a]pyrimidin-3-amine |
| 258 | N-tert-butyl-2-(5-(pyridin-2-ylethynyl)furan-2-yl)imidazo[1,2-a]pyrimidin-3-amine |
| 259 | N-cyclopentyl-2-(3-((6-methylpyridin-2-yl)ethynyl)phenyl)imidazo[1,2-a]pyrimidin-3-amine |
| 260 | N-cyclopentyl-2-(3-(pyridin-2-ylethynyl)phenyl)imidazo[1,2-a]pyridin-3-amine |
| 261 | N-tert-butyl-2-(3-(pyridin-2-ylethynyl)phenyl)imidazo[1,2-a]pyridin-3-amine |
| 262 | 2-(3-(pyridin-2-ylethynyl)phenyl)-N-(2,4,4-trimethylpentan-2-yl)imidazo[1,2-a]-pyridin-3-amine |
| 263 | N-(4-fluorophenyl)-2-(3-(pyridin-2-ylethynyl)phenyl)imidazo[1,2-a]pyridin-3-amine |
| 264 | N-tert-butyl-2-(4-(pyridin-2-ylethynyl)phenyl)imidazo[1,2-a]pyridin-3-amine |
| 265 | N-cyclopentyl-2-(2-methyl-6-(phenylethynyl)pyridin-3-yl)imidazo[1,2-a]pyridin-3-amine |
| 266 | N-(4-fluorophenyl)-2-(2-methyl-6-(phenylethynyl)pyridin-3-yl)imidazo[1,2-a]pyridin-3-amine |
| 267 | N-cyclopentyl-6-methyl-2-(5-(pyridin-2-ylethynyl)thiophen-2-yl)imidazo[1,2-a]-pyridin-3-amine |
| 268 | N-tert-butyl-6-methyl-2-(5-(pyridin-2-ylethynyl)thiophen-2-yl)imidazo[1,2-a]pyridin-3-amine |
| 269 | N-cyclohexyl-6-methyl-2-(5-(pyridin-2-ylethynyl)thiophen-2-yl)imidazo[1,2-a]-pyridin-3-amine |
| 270 | 6-methyl-2-(5-(pyridin-2-ylethynyl)thiophen-2-yl)-N-(2,4,4-trimethylpentan-2-yl)imidazo[1,2-a]pyridin-3-amine |
| 271 | 6-methyl-2-(2-methyl-6-(phenylethynyl)pyridin-3-yl)-N-(2,4,4-trimethylpentan-2-yl)imidazo[1,2-a]pyridin-3-amine |
| 272 | N-cyclopentyl-6-methyl-2-(5-(pyridin-2-ylethynyl)furan-2-yl)imidazo[1,2-a]pyridin-3-amine |
| 273 | N-cyclohexyl-6-methyl-2-(3-((6-methylpyridin-2-yl)ethynyl)phenyl)imidazo[1,2-a]-pyridin-3-amine |
| 274 | N-cyclohexyl-7-methyl-2-(5-(pyridin-2-ylethynyl)thiophen-2-yl)imidazo[1,2-a]-pyridin-3-amine |
| 275 | 7-methyl-2-(5-(pyridin-2-ylethynyl)thiophen-2-yl)-N-(2,4,4-trimethylpentan-2-yl)imidazo[1,2-a]pyridin-3-amine |
| 276 | N-tert-butyl-7-methyl-2-(3-(pyridin-2-ylethynyl)phenyl)imidazo[1,2-a]pyridin-3-amine |
| 277 | N-(4-fluorophenyl)-7-methyl-2-(3-(pyridin-2-ylethynyl)phenyl)imidazo[1,2-a]pyridin-3-amine |

-continued

| Example | Name |
|---|---|
| 278 | N-tert-butyl-7-methyl-2-(4-(pyridin-2-ylethynyl)phenyl)imidazo[1,2-a]pyridin-3-amine |
| 279 | N-(4-fluorophenyl)-7-methyl-2-(5-(pyridin-2-ylethynyl)furan-2-yl)imidazo[1,2-a]pyridin-3-amine |
| 280 | N-cyclohexyl-8-methyl-2-(6-(phenylethynyl)pyridin-3-yl)imidazo[1,2-a]pyridin-3-amine |
| 281 | N-cyclopentyl-2-(6-(phenylethynyl)pyridin-3-yl)imidazo[1,2-a]pyridin-3-amine |
| 282 | N-tert-butyl-2-(6-(phenylethynyl)pyridin-3-yl)imidazo[1,2-a]pyridin-3-amine |
| 283 | N-cyclohexyl-2-(6-(phenylethynyl)pyridin-3-yl)imidazo[1,2-a]pyridin-3-amine |
| 284 | 2-(6-(phenylethynyl)pyridin-3-yl)-N-(2,4,4-trimethylpentan-2-yl)imidazo[1,2-a]pyridin-3-amine |
| 285 | N-tert-butyl-2-(5-(pyridin-2-ylethynyl)furan-2-yl)imidazo[1,2-a]pyridin-3-amine |
| 286 | N-cyclohexyl-2-(5-(pyridin-2-ylethynyl)furan-2-yl)imidazo[1,2-a]pyridin-3-amine |
| 287 | N-(4-fluorophenyl)-2-(5-(pyridin-2-ylethynyl)furan-2-yl)imidazo[1,2-a]pyridin-3-amine |
| 288 | N-cyclohexyl-2-(3-((6-methylpyridin-2-yl)ethynyl)phenyl)imidazo[1,2-a]pyridin-3-amine |
| 289 | 2-(3-((6-methylpyridin-2-yl)ethynyl)phenyl)-N-(2,4,4-trimethylpentan-2-yl)imidazo[1,2-a]pyridin-3-amine |
| 290 | N-tert-butyl-5-methyl-2-(3-((6-methylpyridin-2-yl)ethynyl)phenyl)imidazo-[1,2-a]pyridin-3-amine |
| 291 | 5-methyl-2-(3-((6-methylpyridin-2-yl)ethynyl)phenyl)-N-(2,4,4-trimethylpentan-2-yl)imidazo[1,2-a]pyridin-3-amine |
| 292 | N-cyclohexyl-5,7-dimethyl-2-(3-(pyridin-2-ylethynyl)phenyl)imidazo[1,2-a]-pyrimidin-3-amine |
| 293 | N-cyclohexyl-5,7-dimethyl-2-(2-methyl-6-(phenylethynyl)pyridin-3-yl)imidazo-[1,2-a]pyrimidin-3-amine |
| 294 | N-cyclopentyl-5,7-dimethyl-2-(5-(pyridin-2-ylethynyl)furan-2-yl)imidazo-[1,2-a]pyrimidin-3-amine |
| 295 | N-tert-butyl-5,7-dimethyl-2-(5-(pyridin-2-ylethynyl)furan-2-yl)imidazo-[1,2-a]pyrimidin-3-amine |
| 296 | N-(4-fluorophenyl)-8-methyl-2-(3-(pyridin-2-ylethynyl)phenyl)imidazo[1,2-a]pyridin-3-amine |
| 297 | N-cyclohexyl-8-methyl-2-(4-(pyridin-2-ylethynyl)phenyl)imidazo[1,2-a]pyridin-3-amine |
| 298 | N-cyclohexyl-7-ethyl-2-(5-(pyridin-2-ylethynyl)thiophen-2-yl)imidazol[1,2-a]pyridin-3-amine |
| 299 | 7-ethyl-2-(5-(pyridin-2-ylethynyl)thiophen-2-yl)-N-(2,4,4-trimethylpentan-2-yl)-imidazo[1,2-a]pyridin-3-amine |
| 300 | N-cyclohexyl-7-ethyl-2-(3-(pyridin-2-ylethynyl)phenyl)imidazo[1,2-a]pyridin-3-amine |
| 301 | N-cyclopentyl-7-ethyl-2-(4-(pyridin-2-ylethynyl)phenyl)imidazo[1,2-a]pyridin-3-amine |
| 302 | N-cyclopentyl-7-ethyl-2-(6-(phenylethynyl)pyridin-3-yl)imidazo[1,2-a]pyridin-3-amine |
| 303 | N-tert-butyl-7-ethyl-2-(6-(phenylethynyl)pyridin-3-yl)imidazo[1,2-a]pyridin-3-amine |
| 304 | N-tert-butyl-7-ethyl-2-(5-(pyridin-2-ylethynyl)furan-2-yl)imidazo[1,2-a]pyridin-3-amine |
| 305 | 7-isopropyl-2-(5-(pyridin-2-ylethynyl)thiophen-2-yl)-N-(2,4,4-trimethylpentan-2-yl)imidazo[1,2-a]pyridin-3-amine |
| 306 | N-tert-butyl-7-isopropyl-2-(3-(pyridin-2-ylethynyl)phenyl)imidazo[1,2-a]pyridin-3-amine |
| 307 | N-tert-butyl-7-isopropyl-2-(4-(pyridin-2-ylethynyl)phenyl)imidazo[1,2-a]pyridin-3-amine |
| 308 | N-cyclohexyl-7-isopropyl-2-(5-(pyridin-2-ylethynyl)furan-2-yl)imidazo[1,2-a]pyridin-3-amine |
| 309 | N-tert-butyl-7-isopropyl-2-(3-((6-methylpyridin-2-yl)ethynyl)phenyl)imidazo[1,2-a]-pyridin-3-amine |
| 310 | 6-chloro-N-cyclopentyl-2-(5-(pyridin-2-ylethynyl)thiophen-2-yl)imidazo[1,2-a]-pyridin-3-amine |
| 311 | N-tert-butyl-6-chloro-2-(5-(pyridin-2-ylethynyl)thiophen-2-yl)imidazo[1,2-a]pyridin-3-amine |
| 312 | 6-chloro-N-cyclohexyl-2-(3-(pyridin-2-ylethynyl)pheny)imidazo[1,2-a]pyridin-3-amine |
| 313 | 6-chloro-2-(3-(pyridin-2-ylethynyl)phenyl)-N-(2,4,4-trimethypentan-2-yl)-imidazo[1,2-a]pyridin-3-amine |
| 314 | N-tert-butyl-6-chloro-2-(4-(pyridin-2-ylethynyl)phenyl)imidazo[1,2-a]-pyridin-3-amine |
| 315 | 6-chloro-N-cyclohexyl-2-(4-(pyridin-2-ylethynyl)phenyl)imidazo[1,2-a]pyridin-3-amine |
| 316 | N-tert-butyl-6-chloro-2-(5-(pyridin-2-ylethynyl)furan-2-yl)imidazo[1,2-a]pyridin-3-amine |
| 317 | 6-chloro-N-cyclohexyl-2-(5-(pyridin-2-ylethynyl)furan-2-yl)imidazo[1,2-a]pyridin-3-amine |
| 318 | 6-chloro-2-(5-(pyrodin-2-ylethynyl)furan-2-yl)-N-(2,4,4-trimethylpentan-2-yl)imidazo[1,2-a]pyridin-3-amine |

-continued

| Example | Name |
|---|---|
| 319 | 6-chloro-N-cyclopentyl-2-(3-((6-methylpyridin-2-yl)ethynyl)phenyl)imidazo-[1,2-a]pyridin-3-amine |
| 320 | N-tert-butyl-6-chloro-2-(3-((6-methylpyridin-2-yl)ethynyl)phenyl)imidazo-[1,2-a]pyridin-3-amine |
| 321 | N-tert-butyl-2-(5-(pyridin-2-ylethynyl)thiophen-2-yl)imidazo[1,2-a]pyridin-3-amine bis-hydrochloride |
| 322 | N-methyl-2-(5-(pyridin-2-ylethynyl)thiophen-2-yl)imidazo[1,2-a]pyrazin-3-amine |
| 323 | N-tert-butyl-2-(5-(pyridin-2-ylethynyl)thiophen-2-yl)imidazo[1,2-a]pyridin-3-amine bis-hydrochloride |
| 324 | [2-(5-pyridin-2-ylethynyl-thiophen-2-yl)-imidazo[1,2-a]pyridin-3-yl]-(1,1,3,3-tetramethyl-butyl)-amine |
| 325 | tert-butyl-[2-(5-pyrimidin-2-ylethynyl-thiophen-2-yl)-imidazo[1,2-a]pyridin-3-yl]-amine hydrochloride |
| 326 | {2-[5-(3-amino-pyridin-2-ylethynyl)-thiophen-2-yl]-imidazo[1,2-a]pyridin-3-yl}-tert-butyl-amine |
| 327 | tert-butyl-[2-(5-pyridin-2-ylethynyl-thiazol-2-yl)-imidazo[1,2-a]pyridin-3-yl]-amine |
| 328 | tert-butyl-[2-(2-pyridin-2-ylethynyl-thiazol-5-yl)-imidazo[1,2-a]pyridin-3-yl]-amine |
| 329 | tert-butyl-{2-[5-(6-fluoro-pyridin-2-ylethynyl)-thiophen-2-yl]-imidazo[1,2-a]pyridin-3-yl}-amine hydrochloride |
| 330 | tert-butyl-{2-[5-(3-chloro-5-fluoro-phenylethynyl)-thiophen-2-yl]-imidazo[1,2-a]pyridin-3-yl}-amine hydrochloride |
| 331 | tert-butyl-[2-(5-pyridin-2-ylethynyl-thiophen-2-yl)-imidazo[1,2-b]pyridazin-3-yl]-amine hydrochloride |
| 332 | tert-butyl-[2-(5-thiazol-2-ylethynyl-thiophen-2-yl)-imidazo[1,2-b]pyridazin-3-yl]-amine hydrochloride |
| 333 | tert-butyl-{2-[5-(3-trifluoromethoxy-phenylethynyl)-thiophen-2-yl]-imidazo[1,2-a]pyrazin-3-yl}-amine |
| 334 | tert-butyl-{2-[5-(3-[1,3]dioxolan-2-yl-phenylethynyl)-thiophen-2-yl]-imidazo[1,2-a]pyridin-3-yl}-amine |
| 335 | tert-butyl-{2-[5-(3,5-dimethyl-phenylethynyl)-thiophen-2-yl]-imidazo[1,2-a]pyridin-3-yl}-amine hydrochloride |
| 336 | tert-butyl-{2-[5-(3-fluoro-pyridin-2-ylethynyl)-thiophen-2-yl]-imidazo[1,2-a]pyridin-3-yl}-amine hydrochloride |
| 337 | tert-butyl-{2-[5-(3-methyl-3H-imidazol-4-ylethynyl)-thiophen-2-yl]-imidazo[1,2-a]pyridin-3-yl}-amine hydrochloride |
| 338 | tert-butyl-{2-[5-(5-chloro-thiophen-2-ylethynyl)-thiophen-2-yl]-imidazo[1,2-a]pyridin-3-yl}-amine hydrochloride |
| 339 | tert-butyl-{2-[5-(5-methyl-pyridin-2-ylethynyl)-thiophen-2-yl]-imidazo[1,2-a]pyridin-3-yl}-amine hydrochloride |
| 340 | 1-{3-[5-(3-tert-butylamino-imidazo[1,2-a]pyridin-2-yl)-thiophen-2-ylethynyl]-phenyl}-ethanone hydrochloride |
| 341 | {3-[5-(3-tert-butylamino-imidazo[1,2-a]pyridin-2-yl)-thiophen-2-ylethynyl]-phenyl}-methanol hydrochloride |
| 342 | N-tert-butyl-2-(5-((3-methoxypyridin-2-yl)ethynyl)thiophen-2-yl)imidazo[1,2-a]pyridin-3-amine |
| 343 | N-tert-butyl-2-(5-(thiophen-2-ylethynyl)thiophen-2-yl)imidazo[1,2-a]pyridin-3-amine hydrochloride |
| 344 | 5-((5-(3-(tert-butylamino)imidazo[1,2-a]pyridin-2-yl)thiophen-2-yl)ethynyl)-2-fluorobenzonitrile hydrochloride |
| 345 | N-tert-butyl-2-(5-((3,4-difluorophenyl)ethynyl)thiophen-2-yl)imidazo[1,2-a]pyridin-3-amine |
| 346 | N-tert-butyl-2-(5-((3-(methoxymethyl)phenyl)ethynyl)thiophen-2-yl)imidazo-[1,2-a]pyridin-3-amine |
| 347 | 2-(5-((3-aminophenyl)ethynyl)thiophen-2-yl)-N-tert-butylimidazo[1,2-a]pyridin-3-amine hydrochloride |
| 348 | N-tert-butyl-2-(5-((4-fluoro-3-methylphenyl)ethynyl)thiophen-2-yl)imidazo-[1,2-a]pyridin-3-amine hydrochloride |
| 349 | N-tert-butyl-2-(5-((3,5-difluorophenyl)ethynyl)thiophen-2-yl)imidazo[1,2-a]pyridin-3-amine |
| 350 | N-tert-butyl-2-(5-(thiophen-3-ylethynyl)thiophen-2-yl)imidazo[1,2-a]pyridin-3-amine hydrochloride |
| 351 | N-tert-butyl-2-(5-((3-methylpyridin-2-yl)ethynyl)thiophen-2-yl)imidazo[1,2-a]pyridin-3-amine hydrochloride |
| 352 | 3-((5-(3-(tert-butylamino)imidazo[1,2-a]pyridin-2-yl)thiophen-2-yl)ethynyl)-benzenesulfonamide hydrochloride |
| 353 | 3-((5-(3-(tert-butylamino)imidazo[1,2-a]pyridin-2-yl)thiophen-2-yl)ethynyl)benzoic acid |
| 354 | 3-((5-(3-(tert-butylamino)imidazo[1,2-a]pyridin-2-yl)thiophen-2-yl)ethynyl)-benzamide hydrochloride |
| 355 | N-(3-((5-(3-(tert-butylamino)imidazo[1,2-a]pyridin-2-yl)thiophen-2-yl)ethynyl)-phenyl)acetamide |
| 356 | N-tert-butyl-N-methyl-2-(5-(pyridin-2-ylethynyl)thiophen-2-yl)imidazo[1,2-a]pyridin-3-amine |
| 357 | N,N-dimethyl-2-(5-(pyridin-2-ylethynyl)thiophen-2-yl)imidazo[1,2-a]pyridin-3-amine |
| 358 | N-tert-butyl-N-methyl-2-(5-(pyridin-2-ylethynyl)thiazol-2-yl)imidazo[1,2-a]pyridin-3-amine |

-continued

| Example | Name |
|---|---|
| 359 | (6-((5-(3-(tert-butylamino)imidazo[1,2-a]pyridin-2-yl)thiophen-2-yl)ethynyl)pyridin-2-yl)methanol |
| 360 | N-(3-((5-(3-(tert-butylamino)imidazo[1,2-a]pyridin-2-yl)thiophen-2-yl)ethynyl)-phenyl)methanesulfonamide |
| 361 | N-tert-butyl-8-methyl-2-(5-(pyridin-2-ylethynyl)thiophen-2-yl)imidazo[1,2-a]pyrazin-3-amine hydrochloride |
| 362 | 2-(5-(pyridin-2-ylethynyl)thiophen-2-yl)imidazo[1,2-a]pyridin-3-amine |
| 363 | N-tert-butyl-2-(5-((3-chlorophenyl)ethynyl)thiophen-2-yl)imidazo[1,2-a]pyridin-3-amine |
| 364 | N-tert-butyl-2-(5-((2,3-difluorophenyl)ethynyl)thiophen-2-yl)imidazo[1,2-a]pyridin-3-amine |
| 365 | N-tert-butyl-7-chloro-2-(5-(pyridin-2-ylethynyl)thiophen-2-yl)imidazo[1,2-a]pyridin-3-amine |

Pharmacological Data:

1. The affinity of the substituted imidazo-3-yl-amine compounds of the general formula I according to the invention for the mGluR5 receptor was determined as described above.

The substituted imidazo-3-yl-amine compounds according to the invention exhibit an excellent affinity for the mGluR5 receptor.

Table 1 below shows the pharmacological data for the substituted imidazo-3-yl-amine compounds according to the Examples 1 to 332:

TABLE 1

| Compound according to Example | mGluR5 receptor inhibition of $^3$[H]-MPEP binding [10 μM] in % at a concentration of the example compounds of 10 μM | $IC_{50}$ |
|---|---|---|
| 1 | 52 | |
| 2 | 95 | |
| 3 | 95 | |
| 4 | 91 | |
| 5 | 100 | |
| 6 | 92 | |
| 7 | 89 | |
| 8 | 100 | |
| 9 | 98 | |
| 10 | 95 | |
| 11 | 82 | |
| 12 | 96 | |
| 13 | 96 | |
| 14 | 100 | |
| 15 | 98 | |
| 16 | 93 | |
| 17 | 96 | |
| 18 | | 0.0640 |
| 19 | 78 | |
| 20 | 79 | |
| 21 | 91 | |
| 22 | 84 | |
| 23 | 86 | |
| 24 | 94 | |
| 25 | 81 | |
| 26 | 97 | |
| 27 | 82 | |
| 28 | 98 | |
| 29 | 87 | |
| 30 | 73 | |
| 31 | | 0.5300 |
| 32 | 98 | |
| 33 | 98 | |
| 34 | 98 | |
| 35 | 95 | |
| 36 | 100 | |
| 37 | 85 | |
| 38 | 87 | |
| 39 | 72 | |

TABLE 1-continued

| Compound according to Example | mGluR5 receptor inhibition of $^3$[H]-MPEP binding [10 μM] in % at a concentration of the example compounds of 10 μM | $IC_{50}$ |
|---|---|---|
| 40 | 87 | |
| 41 | 73 | |
| 42 | 93 | |
| 43 | 83 | |
| 44 | 75 | |
| 45 | 93 | |
| 46 | 76 | |
| 47 | 79 | |
| 48 | 82 | |
| 49 | 85 | |
| 50 | 90 | |
| 51 | 89 | |
| 52 | 75 | |
| 53 | 80 | |
| 54 | 69 | |
| 55 | 77 | |
| 56 | 100 | |
| 57 | 94 | |
| 59 | | 2.0700 |
| 60 | | 1.2000 |
| 61 | | 0.0425 |
| 62 | 26 | |
| 63 | 65 | |
| 64 | | 0.0330 |
| 65 | | 3.8400 |
| 66 | | 3.1750 |
| 67 | | 3.8400 |
| 68 | | 2.3200 |
| 69 | | 2.9300 |
| 70 | | 1.0600 |
| 71 | | 1.2700 |
| 72 | | 5.3400 |
| 73 | | 2.2100 |
| 74 | | 1.1000 |
| 75 | | 1.2900 |
| 76 | | 0.0037 |
| 77 | | 0.0057 |
| 79 | 35 | |
| 82 | | 0.2000 |
| 83 | 35 | |
| 84 | | 1.3200 |
| 85 | | 2.0100 |
| 86 | | 0.3200 |
| 87 | 35 | |
| 88 | | 1.4000 |
| 89 | | 0.0450 |
| 91 | | 0.0054 |
| 92 | 82 | |
| 93 | | 0.2500 |
| 94 | | 0.0033 |
| 95 | | 1.7400 |

TABLE 1-continued

| Compound according to Example | mGluR5 receptor inhibition of ³[H]-MPEP binding [10 μM] in % at a concentration of the example compounds of 10 μM | IC$_{50}$ |
|---|---|---|
| 96 | 79 | |
| 97 | | 0.5900 |
| 98 | | 0.2500 |
| 99 | | 0.5400 |
| 100 | | 0.3400 |
| 101 | | 2.4700 |
| 102 | | 8.8500 |
| 103 | 66 | |
| 104 | | 0.0920 |
| 105 | | 0.1500 |
| 106 | | 0.2100 |
| 107 | | 0.0520 |
| 108 | | 1.2400 |
| 109 | | 0.3000 |
| 110 | | 0.0490 |
| 111 | | 1.3700 |
| 112 | | 7.5200 |
| 113 | | 0.0750 |
| 114 | | 2.1100 |
| 115 | | 7.7400 |
| 116 | | 0.0760 |
| 117 | | 0.8800 |
| 118 | | 6.3800 |
| 119 | | 0.0360 |
| 120 | | 3.6300 |
| 121 | | 2.5400 |
| 122 | | 0.1300 |
| 123 | | 0.0140 |
| 124 | | 0.1700 |
| 125 | | 6.5200 |
| 126 | | 3.2500 |
| 127 | | 0.0084 |
| 128 | | 15.5500 |
| 129 | | 0.0120 |
| 130 | | 0.0370 |
| 131 | | 0.1400 |
| 132 | | 0.0160 |
| 133 | | 0.0150 |
| 134 | | 0.5700 |
| 135 | | 1.2000 |
| 136 | | 13.7700 |
| 137 | | 0.8600 |
| 138 | | 15.1100 |
| 139 | | 0.0710 |
| 140 | | 0.0260 |
| 141 | | 0.0028 |
| 143 | | 0.0032 |
| 144 | | 3.6800 |
| 146 | | 0.0350 |
| 148 | | 0.3300 |
| 150 | | 0.1100 |
| 152 | | 0.0230 |
| 153 | | 2.9900 |
| 154 | | 0.5900 |
| 156 | | 0.0270 |
| 157 | | 1.5500 |
| 158 | | 0.0330 |
| 159 | | 0.0100 |
| 160 | | 0.0940 |
| 161 | | 7.7400 |
| 162 | | 4.2400 |
| 164 | | 0.0540 |
| 165 | | 0.0180 |
| 166 | | 11.3300 |
| 167 | | 0.0120 |
| 168 | | 0.6400 |
| 169 | | 0.0110 |
| 171 | | 0.3600 |
| 172 | | 0.0360 |
| 173 | | 0.8000 |
| 174 | | 0.8400 |
| 175 | | 0.0510 |
| 176 | | 0.0190 |
| 177 | | 0.0160 |
| 178 | | 0.0240 |
| 179 | | 0.0260 |
| 180 | | 0.5800 |
| 181 | | 0.0180 |
| 182 | | 8.8500 |
| 183 | | 0.2300 |
| 184 | | 0.2700 |
| 185 | | 0.1900 |
| 192 | | 0.0053 |
| 193 | 79 | |
| 194 | 30 | |
| 195 | 53 | |
| 196 | 68 | |
| 197 | 31 | |
| 198 | 67 | |
| 199 | 57 | |
| 200 | 62 | |
| 201 | 55 | |
| 202 | 70 | |
| 203 | 60 | |
| 204 | 30 | |
| 205 | 92 | |
| 206 | 63 | |
| 207 | 35 | |
| 208 | 57 | |
| 209 | 55 | |
| 210 | 68 | |
| 211 | 82 | |
| 212 | 90 | |
| 213 | 84 | |
| 214 | 77 | |
| 215 | 51 | |
| 216 | 49 | |
| 217 | 62 | |
| 218 | 38 | |
| 219 | 33 | |
| 220 | 31 | |
| 221 | 40 | |
| 222 | 33 | |
| 223 | 80 | |
| 224 | 69 | |
| 225 | 43 | |
| 226 | 41 | |
| 227 | 61 | |
| 228 | 43 | |
| 229 | 30 | |
| 230 | 60 | |
| 231 | 62 | |
| 232 | 75 | |
| 233 | 75 | |
| 234 | 64 | |
| 235 | 32 | |
| 236 | 66 | |
| 237 | 36 | |
| 238 | 92 | |
| 239 | 60 | |
| 240 | 95 | |
| 241 | 65 | |
| 242 | 91 | |
| 243 | 80 | |
| 244 | 54 | |
| 245 | 92 | |
| 246 | 74 | |
| 247 | 83 | |
| 248 | 68 | |
| 249 | 80 | |
| 250 | 69 | |
| 251 | 80 | |
| 252 | 86 | |
| 253 | 73 | |
| 254 | 77 | |
| 255 | 81 | |

TABLE 1-continued

| Compound according to Example | mGluR5 receptor inhibition of $^3$[H]-MPEP binding [10 μM] in % at a concentration of the example compounds of 10 μM | IC$_{50}$ |
|---|---|---|
| 256 | 43 | |
| 257 | 77 | |
| 258 | 86 | |
| 259 | 82 | |
| 260 | 64 | |
| 261 | 79 | |
| 262 | 72 | |
| 263 | 85 | |
| 264 | 83 | |
| 265 | 68 | |
| 266 | 63 | |
| 267 | 85 | |
| 268 | 75 | |
| 269 | 94 | |
| 270 | 93 | |
| 271 | 31 | |
| 272 | 72 | |
| 273 | 84 | |
| 274 | 85 | |
| 275 | 85 | |
| 276 | 93 | |
| 277 | 95 | |
| 278 | 93 | |
| 279 | 67 | |
| 280 | 31 | |
| 281 | 83 | |
| 282 | 72 | |
| 283 | 82 | |
| 284 | 68 | |
| 285 | 88 | |
| 286 | 72 | |
| 287 | 30 | |
| 288 | 89 | |
| 289 | 51 | |
| 290 | 88 | |
| 291 | 92 | |
| 292 | 88 | |
| 293 | 70 | |
| 294 | 79 | |
| 295 | 84 | |
| 296 | 85 | |
| 297 | 80 | |
| 298 | 95 | |
| 299 | 86 | |
| 300 | 50 | |
| 301 | 78 | |
| 302 | 55 | |
| 303 | 67 | |
| 304 | 94 | |
| 305 | 75 | |
| 306 | 76 | |
| 307 | 88 | |
| 308 | 70 | |
| 309 | 82 | |
| 310 | 86 | |
| 311 | 86 | |
| 312 | 64 | |
| 313 | 33 | |
| 314 | 79 | |
| 315 | 75 | |
| 316 | 55 | |
| 317 | 58 | |
| 318 | 43 | |
| 319 | 81 | |
| 320 | 77 | |
| 321 | | 0.0093 |
| 322 | | 0.1200 |
| 323 | | 0.1100 |
| 324 | | 0.0590 |
| 325 | | 0.0130 |
| 326 | | 0.0390 |
| 332 | | 0.0140 |
| 333 | | 0.4200 |
| 334 | | 10.0400 |
| 335 | | |
| 336 | | 0.0061 |
| 337 | | 6.2600 |
| 338 | 52 | |
| 339 | | 0.3200 |
| 340 | | 0.6200 |
| 341 | | 0.2400 |
| 342 | | 1.3600 |
| 343 | | 0.0930 |
| 344 | | 0.1700 |
| 345 | | |
| 346 | | 0.6700 |
| 347 | | 0.9200 |
| 348 | 44 | |
| 349 | 39 | |
| 350 | | 0.5700 |
| 351 | | 0.2300 |

2. The investigated compound according to the invention of Example 192 exhibited a pronounced, long-lasting antiallodynic action. The results are summarised in Table 2 below.

TABLE 2

Testing of inhibition against neuropathic pain in rats, [% MPE, maximum possible effect] inhibition at the individual measuring points and over the entire measurement time (AUC, area under the curve)

| Dose (mg/kg) p.o. | | % MPE at time after administration of the compounds | | | | AUC (0-60 min) | t-test |
|---|---|---|---|---|---|---|---|
| | | 15 min | 30 min | 45 min | 60 min | | |
| 0 | Mean | 0.4 | 3.3 | 2.4 | 3.4 | n.a. | |
| | Standard error of the mean | 1.5 | 1.0 | 0.7 | 0.8 | n.a. | |
| 0.215 | Mean | 27.1 | 19.9 | 9.3 | 5.4 | 15.0 | ** |
| | Standard error of the mean | 5.4 | 4.6 | 3.1 | 2.2 | 3.5 | |

TABLE 2-continued

Testing of inhibition against neuropathic pain in rats, [% MPE, maximum possible effect] inhibition at the individual measuring points and over the entire measurement time (AUC, area under the curve)

| Dose (mg/kg) p.o. | | % MPE at time after administration of the compounds | | | | AUC (0-60 min) | t-test |
|---|---|---|---|---|---|---|---|
| | | 15 min | 30 min | 45 min | 60 min | | |
| 0.464 | Mean | 30.2 | 27.7 | 20.3 | 12.4 | 22.3 | *** |
| | Standard error of the mean | 4.8 | 4.2 | 4.2 | 4.5 | 3.0 | |
| 1 | Mean | 48.7 | 50.9 | 39.4 | 31.2 | 42.9 | *** |
| | Standard error of the mean | 5.9 | 3.6 | 5.8 | 5.7 | 4.2 | |
| 2.15 | Mean | 42.9 | 54.7 | 34.3 | 13.7 | 38.2 | *** |
| | Standard error of the mean | 7.8 | 7.0 | 6.3 | 4.7 | 3.9 | |
| 4.64 | Mean | 46.2 | 72.1 | 39.9 | 23.9 | 47.4 | *** |
| | Standard error of the mean | 6.5 | 5.8 | 7.5 | 8.0 | 5.3 | | n.a. not applicable

3. The compound according to the invention of Example 192 was tested 60 min after p.o. administration and produced a dose-dependent anxiolytic effect characterised by a significant increase of the time in the open arms. The lowest active dose was 2.15 mg/kg, and an ED50 value of 2.75 (95% confidence interval 0.65-5.58) mg/kg was determined.

4. The substituted imidazo-3-yl-amine compounds according to the invention likewise exhibit an excellent action in the formaldehyde test in mice or in rats as shown in Table 3 below.

TABLE 3

| | ED$_{50}$ value [mg/kg] or % inhibition | | | | |
|---|---|---|---|---|---|
| | Rat | | | Mouse | |
| Example | i.v. | p.o. | i.p. | p.o. | i.p. |
| 91 | — | 7.3 | 4.7 | 2.3 | 1.2 |
| 110 | — | 61% at 21.5 mg/kg | — | — | — |
| 116 | — | — | — | — | 15.2 |
| 127 | — | 5.9 | 2.2 | — | 7.7 |
| 192 | 0.8 | 7.6 | 41% at 4.64 mg/kg | — | — |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A bicyclic imidazo-3-yl-amine compound corresponding to formula I,

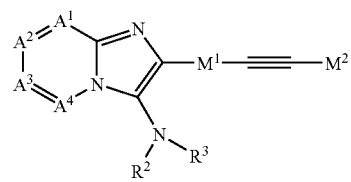

wherein
A$^1$ represents a nitrogen atom or a C—R$^{1a}$ group,
A$^2$ represents a nitrogen atom or a C—R$^{1b}$ group,
A$^3$ represents a nitrogen atom or a C—R$^{1c}$ group,
A$^4$ represents a nitrogen atom or a C—R$^{1d}$ group,
R$^{1a}$, R$^{1b}$, R$^{1c}$, R$^{1d}$, mutually independently, in each case represent a hydrogen; a halogen; —NO$_2$; —CN; —NH$_2$; —NHR$^4$; —NR$^5$R$^6$; —NH—C(=O)—R$^7$; —C(=O)—R$^8$, —C(=O)—NH$_2$; —C(=O)—NHR$^9$; —C(=O)—NR$^{10}$R$^{11}$; —C(=O)—OR$^{12}$; —(CH$_2$)$_m$—C(=O)—OR$^{13}$ with m=1, 2, 3, 4 or 5; —O—C(=O)—R$^{14}$; —(CH$_2$)$_n$—O—C(=O)—R$^{15}$ with n=1, 2, 3, 4 or 5; —OR$^{16}$; —(CH$_2$)$_o$—O—R$^{17}$ with o=1, 2, 3; 4 or 5; —SR$^{18}$; —(CH$_2$)$_p$—S(=O)$_t$—R$^{19}$ with p=1, 2, 3, 4 or 5 and t=0, 1 or 2; —NH—S(=O)$_2$—R$^{26}$R$^{27}$; —S(=O)$_2$—NR$^{28}$R$^{29}$, —SF$_5$; a linear or branched, saturated or unsaturated, unsubstituted or at least monosubstituted aliphatic group; a saturated or unsaturated, unsubstituted or at least monosubstituted cycloaliphatic group optionally comprising at least one heteroatom as a ring member, which cycloaliphatic group may be attached via a linear or branched alkylene group or may be fused with an unsubstituted or at least monosubstituted mono- or polycyclic ring system; or represent an unsubstituted or at least monosubstituted aryl or heteroaryl group, which may be attached via a linear or branched alkylene group or may be fused with an unsubstituted or at least monosubstituted mono- or polycyclic ring system,
or R$^{1a}$ and R$^{1b}$ form an unsubstituted or at least monosubstituted anellated phenyl group with the C—C bridge joining them together, or $R^{1b}$ and $R^{1c}$ form an unsubstituted or at least monosubstituted anellated phenyl group with the C—C bridge joining them together, or $R^{1c}$ and $R^{1d}$ form an unsubstituted or at least monosubstituted anellated phenyl group with the C—C bridge joining them together, $R^2$ and $R^3$, mutually independently, in each case represent hydrogen; —C(=O)—$R^{20}$; —(CH$_2$)$_q$—C(=O)—$R^{21}$ with q=1, 2, 3, 4 or 5; —C(=O)—O—$R^{22}$; —(CH$^2$)$_r$—C(=O)—O—$R^{23}$ with r=1, 2, 3, 4 or 5; —C(=O)—NHR$^{24}$; —(CH$_2$)$_s$—C(=O)—NHR$^{25}$ with s=1, 2, 3, 4 or 5; a linear or branched, saturated or unsaturated, unsubstituted or at least monosubstituted aliphatic group; a saturated or unsaturated, unsubstituted or at least monosubstituted cycloaliphatic group optionally comprising at least one heteroatom as a ring member, which cycloaliphatic group may be attached via a linear or branched alkylene group or may be fused with an unsubstituted or at least monosubstituted mono- or polycyclic ring system; or represent an unsubstituted or at least monosubstituted aryl or heteroaryl group, which may be attached via a linear or branched alkylene group or may be fused with an unsubstituted or at least monosubstituted mono- or polycyclic ring system, or $R^2$ and $R^3$, together with the nitrogen atom joining them together as a ring member, form a saturated or unsaturated heterocycloaliphatic group optionally comprising at least one further heteroatom as a ring member, which heterocycloaliphatic group may be fused with an unsubstituted or at least monosubstituted mono- or polycyclic ring system, $R^4$, $R^5$, $R^6$, $R^7$, $R^9$, $R^{10}$, $R^{11}$, $R^{14}$ and $R^{15}$, in each case mutually independently, represent a linear or branched, saturated or unsaturated aliphatic group or an unsubstituted or at least monosubstituted aryl or heteroaryl group, which may be attached via a linear or branched alkylene group and/or may be fused with an unsubstituted or at least monosubstituted mono- or polycyclic ring system, $R^8$, $R^{12}$, $R^{13}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$, in each case mutually independently, represent hydrogen; a linear or branched, saturated or unsaturated aliphatic group or an unsubstituted or at least monosubstituted aryl or heteroaryl group, which may be attached via a linear or branched alkylene group or may be fused with an unsubstituted or at least monosubstituted mono- or polycyclic ring system, $M^1$ represents an aryl or heteroaryl group, which may be substituted with at least one further substituent and optionally may be fused with an unsubstituted or at least monosubstituted mono- or polycyclic ring system, $M^2$ represents an aryl or heteroaryl group, which is unsubstituted or at least monosubstituted and optionally fused with an unsubstituted or at least monosubstituted mono- or polycyclic ring system, or a salt thereof.

2. The compound of claim 1, wherein said compound exists in an enantiomeric or diastereoisomeric form and is present in the form of a pure enantiomer or pure diastereoisomer.

3. The compound of claim 1, wherein said compound exists in the form of a mixture of stereoisomers and is present in the form of a mixture of stereoisomers.

4. The compound of claim 3, wherein said compound is present in the form of a racemic mixture.

5. A compound according to claim 1, wherein
$A^1$ represents a nitrogen atom or a C—$R^{1a}$ group,
$A^2$ represents a nitrogen atom or a C—$R^{1b}$ group,
$A^3$ represents a nitrogen atom or a C—$R^{1c}$ group,
$A^4$ represents a nitrogen atom or a C—$R^{1d}$ group,
$R^{1a}$, $R^{1b}$, $R^{1c}$, $R^{1d}$, mutually independently, in each case represent hydrogen; a halogen; —NO$_2$; —CN; —NH$_2$; —NHR$^4$; —NR$^5$R$^6$; —NH—C(=O)—R$^7$; —C(=O)—R$^8$, —C(=O)—NH$_2$; —C(=O)—NHR$^9$; —C(=O)—NR$^{10}$R$^{11}$; —C(=O)—OR$^{12}$; —(CH$^2$)$_m$—C(=O)—OR$^{13}$ with m=1, 2, 3, 4 or 5; —O—C(=O)—R$^{14}$; —(CH$_2$)$_N$—O—C(=O)—R$^{15}$ with N=1, 2, 3, 4 or 5; —OR$^{16}$; —(CH$_2$)$_o$—O—R$^{17}$ with o=1, 2, 3; 4 or 5; —SR$^{18}$; —(CH$_2$)$_p$—S(=O)$_t$—R$^{19}$ with p=1, 2, 3, 4 or 5 and t=0, 1 or 2; —NH—S(=O)$_2$—R$^{26}$R$^{27}$; —S(=O)$_2$—NR$^{28}$R$^{29}$, —SF$_5$; a linear or branched, saturated or unsaturated, unsubstituted or at least monosubstituted aliphatic C$_{1-10}$ group; a saturated or unsaturated, unsubstituted or at least monosubstituted cycloaliphatic C$_{3-8}$ group optionally comprising at least one heteroatom as a ring member, which cycloaliphatic C$_{3-8}$ group may be attached via a linear or branched C$_{1-5}$ alkylene group; or represent an unsubstituted or at least monosubstituted 5- to 14-membered aryl or heteroaryl group which may be attached via a linear or branched C$_{1-5}$ alkylene group, or $R^{1a}$ and $R^{1b}$ form an unsubstituted or at least monosubstituted anellated phenyl group with the C—C bridge joining them together, or $R^{1b}$ and $R^{1c}$ form an unsubstituted or at least monosubstituted anellated phenyl group with the C—C bridge joining them together, or $R^{1c}$ and $R^{1d}$ form an unsubstituted or at least monosubstituted anellated phenyl group with the C—C bridge joining them together, $R^2$ and $R^3$, mutually independently, in each case represent hydrogen; —C(=O)—$R^{20}$; —(CH$_2$)$_q$—C(=O)—$R^{21}$ with q=1, 2, 3, 4 or 5; —C(=O)—O—$R^{22}$; —(CH$^2$)$_r$—C(=O)—O—$R^{23}$ with r=1, 2, 3, 4 or 5; —C(=O)—NHR$^{24}$; —(CH$_2$)$_s$—C(=O)—NHR$^{25}$ with s=1, 2, 3, 4 or 5; a linear or branched, saturated or unsaturated, unsubstituted or at least monosubstituted aliphatic C$_{1-16}$ group; a saturated or unsaturated, unsubstituted or at least monosubstituted cycloaliphatic C$_{4-8}$ group, optionally comprising at least one heteroatom as a ring member, which cycloaliphatic C$_{4-8}$ group may be attached via a linear or branched C$_{1-5}$ alkylene group; or represent an unsubstituted or at least monosubstituted 5- to 14-membered aryl or heteroaryl group, which may be attached via a linear or branched C$_{1-5}$ alkylene group, or $R^2$ and $R^3$, together with the nitrogen atom joining them together as a ring member, form a saturated or unsaturated heterocycloaliphatic C$_{4-10}$ group optionally comprising at least one further heteroatom as a ring member, which heterocycloaliphatic C$_{4-10}$ group is optionally fused with an unsubstituted or at least monosubstituted mono- or polycyclic ring system, wherein the rings of the ring system are in each case 5-, 6- or 7-membered;

$R^4$, $R^5$, $R^6$, $R^7$, $R^9$, $R^{10}$, $R^{11}$, $R^{14}$ and $R^{15}$, in each case mutually independently, represent a linear or branched, saturated or unsaturated aliphatic C$_{1-4}$ group or represent an unsubstituted or at least monosubstituted 5- to 14-membered aryl or heteroaryl group, which may be attached via a linear or branched C$_{1-5}$ alkylene group, $R^8$, $R^{12}$, $R^{13}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$ and $R^{29}$, in each case mutually independently, represent a hydrogen group; a linear or branched, saturated or unsaturated aliphatic C$_{1-4}$ group or an unsubstituted or at least monosubstituted 5- to 14-membered aryl or heteroaryl group, which may be attached via a linear or branched $C_{1-5}$ alkylene group, $M^1$ represents a 5- or 6-membered aryl or heteroaryl group, which may be substituted with at least one further substituent and is optionally fused with an unsubstituted or at least monosubstituted mono- or bicyclic ring system, wherein the rings of the ring system are in each case 5-, 6- or 7-membered, and $M^2$ represents a 5- or 6-membered aryl or heteroaryl group, which may be unsubstituted or at least monosubstituted and may be fused with an unsubstituted or at least monosubstituted mono- or bicyclic ring system, wherein the rings of the ring system are in each case 5-, 6- or 7-membered;

wherein the above-stated cycloaliphatic groups may optionally comprise 1, 2, 3, 4 or 5 heteroatom(s) as ring member(s), which may be selected, in each case mutually independently, from the group consisting of nitrogen, oxygen and sulfur, the above-stated heterocycloaliphatic groups may optionally comprise a further 1, 2, 3, 4 or 5 heteroatom(s) as ring member(s), which may be selected, in each case mutually independently, from the group consisting of nitrogen, oxygen and sulfur, the rings of the mono- or polycyclic ring system in each case optionally comprise 0, 1, 2 or 3 heteroatom(s) as ring member(s), which are selected mutually independently from the group consisting of oxygen, nitrogen and sulfur;

and the above-stated heteroaryl groups may optionally comprise 1, 2, 3, 4 or 5 heteroatom(s) as ring member(s), which may be selected, in each case mutually independently, from the group consisting of nitrogen, oxygen and sulfur.

6. A compound according to claim 1, wherein
$A^1$ represents a C—$R^{1a}$ group,
$A^2$ represents a C—$R^{1b}$ group,
$A^3$ represents a C—$R^{1c}$ group and
$A^4$ represents a C—$R^{1d}$ group,
or
$A^1$ represents a nitrogen atom,
$A^2$ represents a C—$R^{1b}$ group,
$A^3$ represents a C—$R^{1c}$ group and
$A^4$ represents a C—$R^{1d}$ group,
or
$A^1$ represents a C—$R^{1a}$ group,
$A^2$ represents a nitrogen atom,
$A^3$ represents a C—$R^{1c}$ group and
$A^4$ represents a C—$R^{1d}$ group,
or
$A^1$ represents a C—$R^{1a}$ group,
$A^2$ represents a C—$R^{1b}$ group,
$A^3$ represents a nitrogen atom and
$A^4$ represents a C—$R^{1d}$ group,
or
$A^1$ represents a C—$R^{1a}$ group,
$A^2$ represents a C—$R^{1b}$ group,
$A^3$ represents a C—$R^{1c}$ group and
$A^4$ represents a nitrogen atom,
or
$A^1$ and $A^3$ in each case represent a nitrogen atom,
$A^2$ represents a C—$R^{1b}$ group, and
$A^4$ represents a C—$R^{1d}$ group.

7. A compound according to claim 6, wherein
$A^1$ represents a C—$R^{1a}$ group,
$A^2$ represents a C—$R^{1b}$ group,
$A^3$ represents a C—$R^{1c}$ group and
$A^4$ represents a C—$R^{1d}$ group,
or
$A^1$ represents a nitrogen atom,
$A^2$ represents a C—$R^{1b}$ group,
$A^3$ represents a C—$R^{1c}$ group and
$A^4$ represents a C—$R^{1d}$ group,
or
$A^1$ represents a C—$R^{1a}$ group,
$A^2$ represents a nitrogen atom,
$A^3$ represents a C—$R^{1c}$ group and
$A^4$ represents a C—$R^{1d}$ group,
or
$A^1$ represents a C—$R^{1a}$ group,
$A^2$ represents a C—$R^{1b}$ group,
$A^3$ represents a C—$R^{1c}$ group and
$A^4$ represents a nitrogen atom.

8. A compound according to claim 1, wherein $R^{1a}$, $R^{1b}$, $R^{1c}$, $R^{1d}$, mutually independently, in each case represent —H; —F; —Cl; —Br; —I; —$NO_2$; —CN; —$CF_3$; —$SF_5$; —$NH_2$; —S(=O)—$NH_2$, —$NHR^4$; —$NR^5R^6$; —C(=O)—$OR^{12}$; —$(CH^?)_m$—C(=O)—$OR^{13}$ with m=1, 2 or 3; —O—C(=O)—$R^{14}$; —$OR^{16}$; —$(CH^?)_o$—O—$R^{17}$ with o=1, 2 or 3; a linear or branched $C_{1-10}$ alkyl group; or represent an unsubstituted or at least monosubstituted 5- or 6-membered aryl or heteroaryl group, which may be attached via a linear or branched $C_{1-4}$ alkylene group.

9. A compound according to claim 1, wherein $R^{1a}$, $R^{1b}$, $R^{1c}$, $R^{1d}$, mutually independently, in each case represent —H; —F; —Cl; —Br; —I; —$NO_2$; —CN; —$CF_3$; —$SF_5$; —$NH_2$; —S(=O)—$NH_2$, —$NHR^4$; —$NR^5R^6$; —C(=O)—$OR^{12}$; —$(CH^?)_m$—C(=O)—$OR^{13}$ with m=1, 2 or 3; —O—C(=O)—$R^{14}$; —$OR^{16}$; —$(CH^?)_o$—$R^{17}$ with o=1, 2 or 3; a linear or branched alkyl group selected from the group consisting of methyl, ethyl, n-propyl, iso-propyl, n-butyl, iso-butyl, sec-butyl and tert-butyl, or represent an aryl or heteroaryl group selected from the group consisting of phenyl, furanyl, thiophenyl and pyridinyl, which is in each case unsubstituted or substituted with 1, 2, 3, 4 or 5 substituents mutually independently selected from the group consisting of F, Cl, Br, —CN, methyl, ethyl, n-propyl, iso-propyl, n-butyl, sec-butyl, iso-butyl, tert-butyl, —OH, —O—$CH_3$, —O—$C_2H_5$ and is optionally attached via a —$(CH_2)$—, —$(CH_2)_2$— or —$(CH_2)_3$ group.

10. A compound according to claim 1, wherein $R^{1a}$, $R^{1b}$, $R^{1c}$, $R^{1d}$, mutually independently, in each case represent —H; —F; —Cl; —Br; —$CF_3$; —CN; —$SF_5$; —S(=O)—$NH_2$, —C(=O)—$OR^{12}$; —$(CH_2)_m$—C(=O)—$OR^{13}$ with m=1 or 2; —O—C(=O)—$R^{14}$; —$OR^{16}$; —$(CH_2)_o$—O—$R^{17}$ with o=1 or 2; a linear or branched alkyl group selected from the group consisting of methyl, ethyl, n-propyl, iso-propyl, n-butyl, iso-butyl, sec-butyl and tert-butyl, or represent a phenyl group, which is unsubstituted or substituted with 1, 2 or 3 substituents mutually independently selected from the group consisting of F, Cl, Br, methyl, ethyl, n-propyl, iso-propyl, n-butyl, sec-butyl, iso-butyl, tert-butyl, —O—$CH_3$, —O—$C_2H_5$ and is optionally attached via a —$(CH_2)$—, —$(CH_2)_2$— or —$(CH_2)_3$ group.

11. A compound according to claim 1, wherein $R^{1a}$, $R^{1b}$, $R^{1c}$, $R^{1d}$, mutually independently, in each case represent —H; —F; —Cl; —Br; —$CF_3$; —CN; —$SF_5$; —S(=O)—$NH_2$, —C(=O)—OR$^{12}$; —(CH$_2$)$_m$—C(=O)—OR$^{13}$ with m=1; —O—C(=O)—R$^{14}$; —OR$^{16}$; —(CH$_2$)$_o$—O—R$^{17}$ with o=1; a linear or branched alkyl group selected from the group consisting of methyl, ethyl, n-propyl, iso-propyl, n-butyl, iso-butyl, sec-butyl and tert-butyl; or represent an unsubstituted phenyl group, which is optionally attached via a —(CH$_2$)—, —(CH$_2$)$_2$— or —(CH$_2$)$_3$ group.

12. A compound according to claim 1, wherein R$^{1a}$ and R$^{1b}$ or R$^{1b}$ and R$^{1c}$ or R$^{1c}$ and R$^{1d}$, together with the C—C bridge joining them together, form an anellated phenyl group which may be substituted with 1, 2, 3 or 4 substituents mutually independently selected from the group consisting of F, Cl, Br, —CN, methyl, ethyl, n-propyl, iso-propyl, n-butyl, sec-butyl, iso-butyl, tert-butyl, —OH, —O—CH$_3$, —O—C$_2$H$_5$.

13. A compound according to claim 1, wherein R$^2$ and R$^3$, mutually independently, in each case represent a hydrogen; —C(=O)—R$^{20}$; —(CH$_2$)$_q$—C(=O)—R$^{21}$ with q=1, 2, 3, 4 or 5; —(CH$_2$)$_r$—C(=O)—O—R$^{23}$ with r=1, 2, 3, 4 or 5; —C(=O)—NHR$^{24}$; a linear or branched C$_{1-16}$ alkyl group; an unsubstituted or at least monosubstituted C$_{4-8}$ cycloalkyl group, which may be attached via a linear or branched C$_{1-3}$ alkylene group; or represent an unsubstituted or at least monosubstituted, 5- or 6-membered aryl or heteroaryl group, which may be attached via a linear or branched C$_{1-3}$ alkylene.

14. A compound according to claim 1, wherein R$^2$ and R$^3$, mutually independently, in each case represent a hydrogen; —C(=O)—R$^{20}$; —(CH$_2$)$_q$—C(=O)—R$^{21}$ with q=1, 2 or 3; —(CH$_2$)$_r$—C(=O)—O—R$^{23}$ with r=1, 2 or 3; a linear or branched C$_{1-10}$ alkyl group; a C$_{4-8}$ cycloalkyl group, which is in each case unsubstituted or substituted with 1, 2, 3, 4 or 5 substituents mutually independently selected from the group consisting of F, Cl, Br, —CN, —CF$_3$, methyl, ethyl, n-propyl, iso-propyl, n-butyl, sec-butyl, iso-butyl, tert-butyl, —OH, —O—CH$_3$ and —O—C$_2$H$_5$ and is optionally attached via a linear or branched C$_{1-3}$ alkylene group; or represent an aryl or heteroaryl group selected from the group consisting of phenyl, thiophenyl, furanyl and pyridinyl, which is in each case unsubstituted or substituted with 1, 2, 3, 4 or 5 substituents mutually independently selected from the group consisting of F, Cl, Br, —CN, —CF$_3$, methyl, ethyl, n-propyl, iso-propyl, n-butyl, sec-butyl, iso-butyl, tert-butyl, —OH, —O—CH$_3$ and —O—C$_2$H$_5$ and is optionally attached via a linear or branched C$_{1-3}$ alkylene group.

15. A compound according to claim 1, wherein R$^2$ and R$^3$, mutually independently, in each case represent a hydrogen; —C(=O)—R$^{20}$; —(CH$_2$)$_q$—C(=O)—R$^{21}$ with q=1 or 2; —(CH$^2$)$_r$—C(=O)—O—R$^{23}$ with r=1 or 2; an alkyl group selected from the group consisting of methyl; ethyl; propyl; iso-propyl; n-butyl; tert-butyl; sec-butyl; iso-butyl; n-pentyl; n-hexyl; n-heptyl; n-octyl; (1,1,3,3)-tetramethyl-butyl; (1,1)-dimethyl-pentyl and (1,1)-dimethyl-butyl; an unsubstituted cyclopentyl or cyclohexyl group, which may in each case be attached via a —(CH$_2$)—, —(CH$_2$)$_2$— or —(CH$_2$)$_3$ group; or represent a phenyl, 2-pyridinyl, 3-pyridinyl, 4-pyridinyl, 2-furanyl, 3-furanyl, 2-thiophenyl or 3-thiophenyl group, which is in each case unsubstituted or optionally substituted with 1, 2, 3, 4 or 5 substituents mutually independently selected from the group consisting of F, Cl, Br, —CN, —CF$_3$, methyl, ethyl, n-propyl, iso-propyl, n-butyl, sec-butyl, iso-butyl, tert-butyl, —O—CH$_3$ and —O—C$_2$H$_5$ and is optionally attached via a —(CH$_2$)—, —(CH$_2$)$_2$—, —C(H)(CH$_3$)— or —(CH$_2$)$_3$ group.

16. A compound according to claim 1, wherein R$^2$ and R$^3$, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl, which may in each case be unsubstituted or optionally substituted with 1, 2, 3, 4 or 5 substituents mutually independently selected from the group consisting of F, Cl, Br, I, —CN, methyl, ethyl, n-propyl, iso-propyl, n-butyl, sec-butyl, iso-butyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH—C$_2$H$_5$, —O—CF$_3$, —S—CF$_3$, —S(=O)—CH$_3$, —S(=O)—C$_2$H$_5$, —S(=O)$_2$—CH$_3$, —S(=O)$_2$—C$_2$H$_5$, —C(=O)—OH, —C(=O)—H, —C(=O)—CH$_3$, —C(=O)—C$_2$H$_5$, —C(=O)—N(CH$_3$)$_2$, —C(=O)—NH—CH$_3$, —C(=O)—NH$_2$, —C(=O)—O—CH$_3$, —C(=O)—O—C$_2$H$_5$ and —C(=O)—O—C(CH$_3$)$_3$.

17. A compound according to claim 1, wherein R$^2$ and R$^3$, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl.

18. A compound according to claim 1, wherein R$^4$, R$^5$, R$^6$, R$^7$, R$^9$, R$^{10}$, R$^{11}$, R$^{14}$ and R$^{15}$, in each case mutually independently represent a linear or branched C$_{1-4}$ alkyl group or an unsubstituted or at least monosubstituted 5- to 14-membered aryl or heteroaryl group, which may be attached via a linear or branched C$_{1-5}$ alkylene group.

19. A compound according to claim 1, wherein R$^4$, R$^5$, R$^6$, R$^7$, R$^9$, R$^{10}$, R$^{11}$, R$^{14}$ and R$^{15}$, in each case mutually independently, represent an alkyl group selected from the group consisting of methyl, ethyl, n-propyl, iso-propyl, n-butyl, iso-butyl, sec-butyl and tert-butyl, or represent an unsubstituted or at least monosubstituted 5- or 6-membered aryl or heteroaryl group, which may be attached via a linear or branched C$_{1-3}$ alkylene group.

20. A compound according to claim 1, wherein R$^4$, R$^5$, R$^6$, R$^7$, R$^9$, R$^{10}$, R$^{11}$, R$^{14}$ and R$^{15}$, in each case mutually independently, represent an alkyl group selected from the group consisting of methyl, ethyl, n-propyl and iso-propyl, or represent a phenyl group, which is in each case unsubstituted or substituted with 1, 2 or 3 substituents mutually independently selected from the group consisting of F, Cl, Br, —CN, —CF$_3$, —SF$_5$, methyl, ethyl, n-propyl, iso-propyl, tert-butyl, —O—CH$_3$ and —O—C$_2$H$_5$ and is optionally attached via a —(CH$_2$), —(CH$_2$)$_2$ or —(CH$_2$)$_3$ group.

21. A compound according to claim 1, wherein R$^8$, R$^{12}$, R$^{13}$, R$^{16}$, R$^{17}$, R$^{18}$, R$^{19}$, R$^{20}$ R$^{21}$, R$^{22}$ R$^{23}$, R$^{24}$, R$^{25}$, R$^{26}$, R$^{27}$, R$^{28}$ and R$^{29}$, in each case mutually independently represent a hydrogen; a linear or branched C$_{1-8}$ alkyl group, or represent an unsubstituted or at least monosubstituted 5- to 14-membered aryl or heteroaryl group, which may be attached via a linear or branched C$_{1-5}$ alkylene group.

22. A compound according to claim 1, wherein R$^8$, R$^{12}$, R$^{13}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$ and R$^{29}$, in each case mutually independently, represent a hydrogen; a linear or branched, saturated or unsaturated aliphatic C$_{1-4}$ group or an unsubstituted or at least monosubstituted 5- to 6-membered aryl or heteroaryl group, which may be attached via a linear or branched C$_{1-3}$ alkylene group.

23. A compound according to claim 1, wherein R$^8$, R$^{12}$, R$^{13}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{28}$ and R$^{29}$, in each case mutually independently, represent a hydrogen; an alkyl group selected from the group consisting of methyl, ethyl, n-propyl and iso-propyl and tert-butyl, or represent a phenyl group, which is in each case unsubstituted or substituted with 1, 2 or 3 substituents mutually independently selected from the group consisting of F, Cl, Br, —CN, —CF$_3$, —SF$_5$, methyl, ethyl, n-propyl, iso-propyl, tert-butyl, —O—CH$_3$ and —O—C$_2$H$_5$ and is optionally attached via a —(CH$_2$), —(CH$_2$)$_2$ or —(CH$_2$)$_3$ group.

24. A compound according to claim 1, wherein M¹ represents a 5- or 6-membered aryl or heteroaryl group, which may optionally be substituted with at least one further substituent, wherein the heteroaryl group optionally comprises 1, 2, 3, 4 or 5 heteroatom(s) as ring member(s), which are mutually independently selected from the group consisting of nitrogen, oxygen and sulfur.

25. A compound according to claim 1, wherein M¹ represents an aryl or heteroaryl group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, imidazolyl, oxadiazolyl, triazolyl, diazinyl, triazinyl, tetrazinyl and tetrazolyl, which may optionally be substituted with at least one further substituent.

26. A compound according to claim 1, wherein M¹ is selected from the group consisting of groups 1 to 38, 1
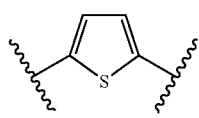

2
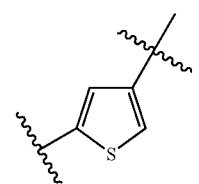

3
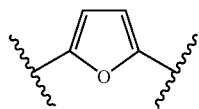

4
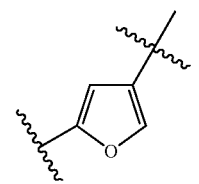

5
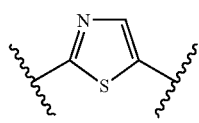

6
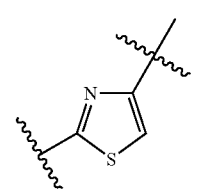

7
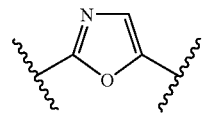

8
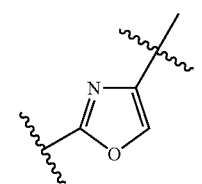

9
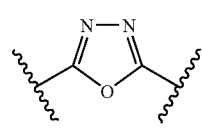

10
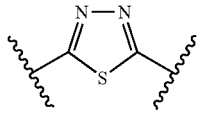

11
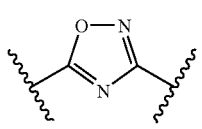

12
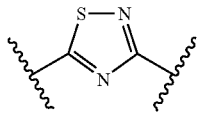

13
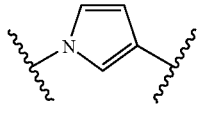

14
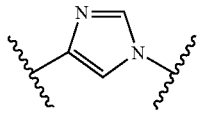

15
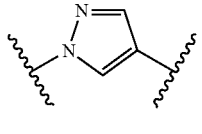

16
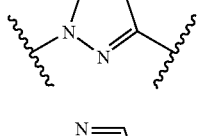

17
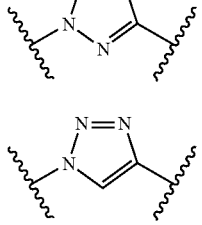

18
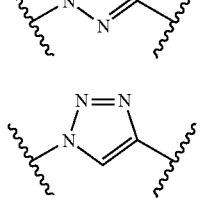

-continued
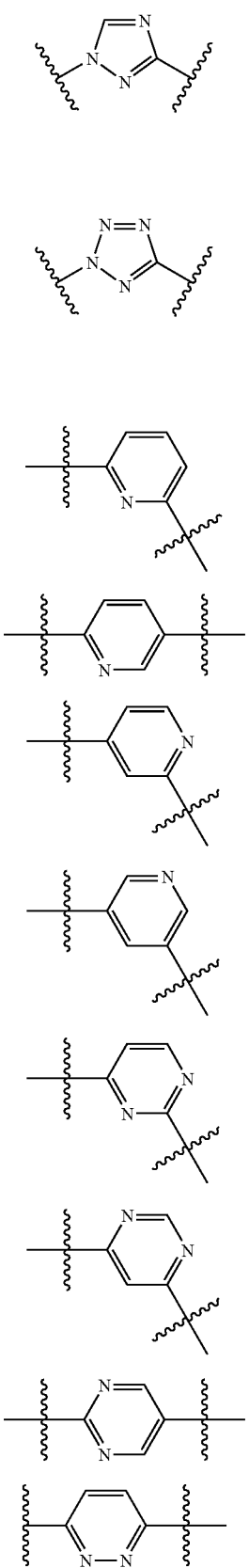
-continued
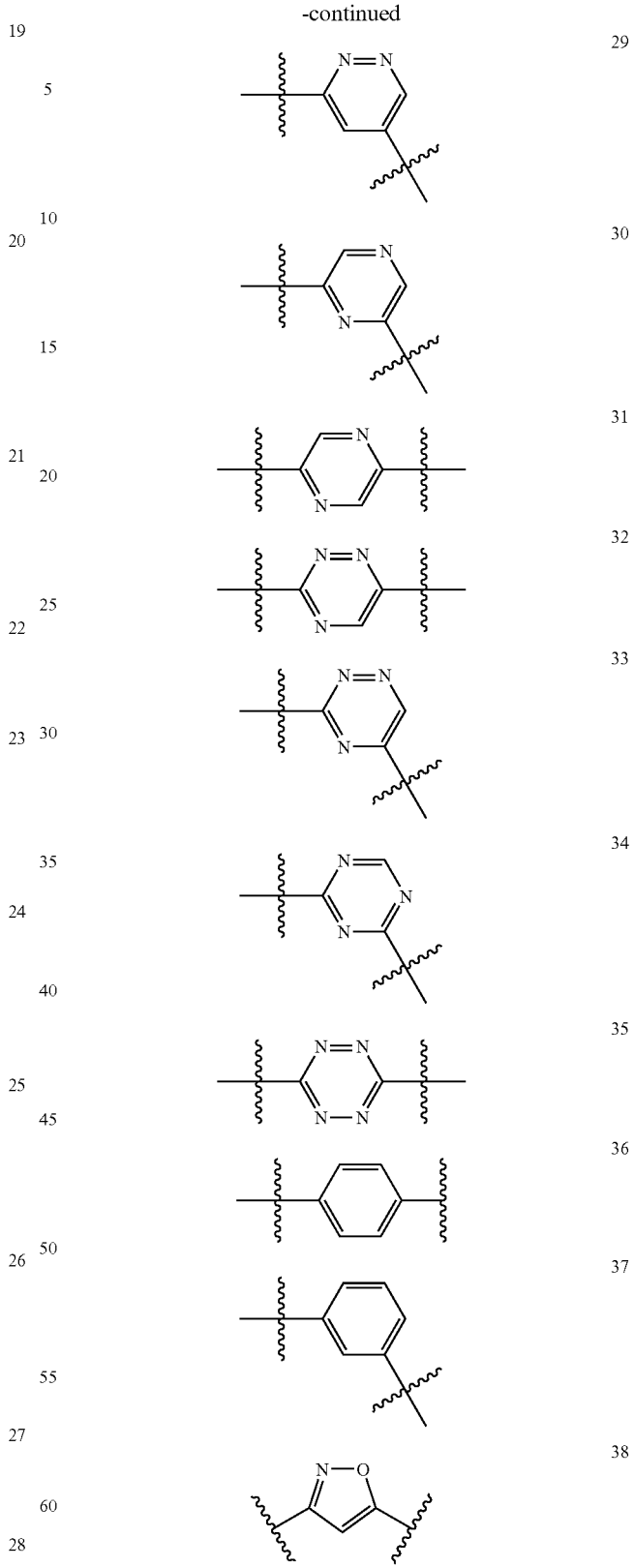
which may in each case be substituted with at least one further substituent and which may in each case be linked in any desired direction via the positions indicated with a wavy line to the bicyclic ring system and to the carbon atom of the triple bond.

27. A compound according to claim 1, wherein $M^1$ is selected from the group consisting of groups 1 to 9, 11, 21, 22 and 36 to 38,

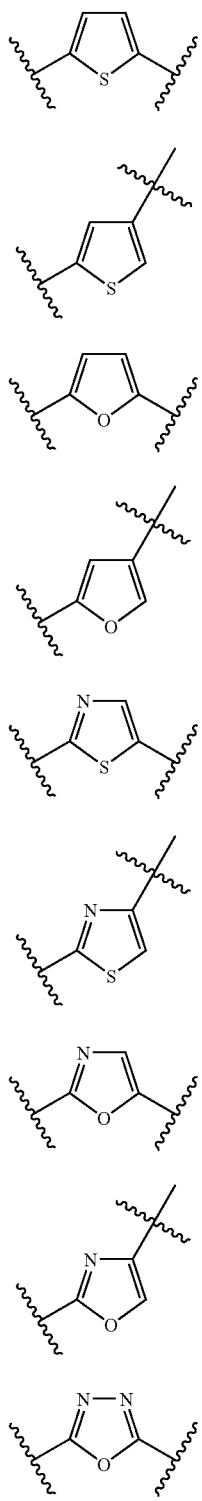

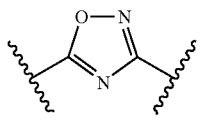

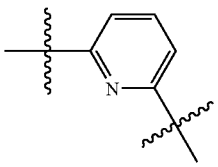

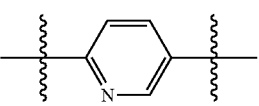

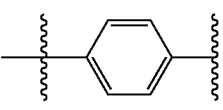

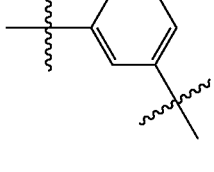

which may in each case be linked in any desired direction via the positions indicated with a wavy line to the bicyclic ring system and to the carbon aton of the triple bond and is optionally substituted with 1, 2, 3 or 4 further substituents, which are mutually independently selected from the group consisting of F, Cl, Br, —CN, —CH$_2$—CN, —CF$_3$, —SF$_5$, methyl, ethyl, n-propyl, iso-propyl, n-butyl, sec-butyl, iso-butyl, tert-butyl, —OH, —O—CH$_3$, —O—C$_2$H$_5$, —O—C$_3$H$_7$, —NH$_2$, —N(CH$_3$)$_2$, —N(C$_2$H$_5$)$_2$, —NO$_2$, —O—CF$_3$, —S—CF$_3$, —SH, —C(=O)—CH$_3$ and —C(=O)—C$_2$H$_5$.

28. A compound according to claim 1, wherein $M^1$ is selected from the group consisting of groups 1 to 9, 11, 21, 22 and 36 to 38,

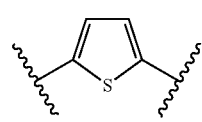

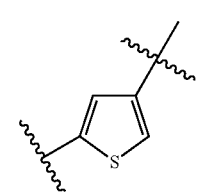

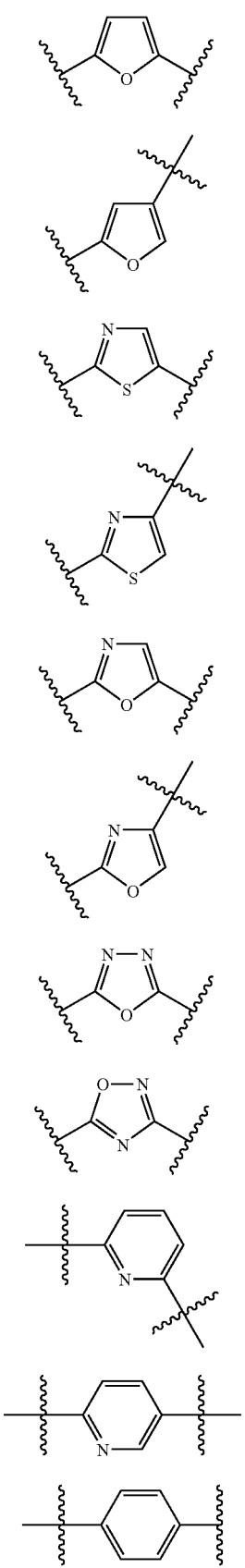
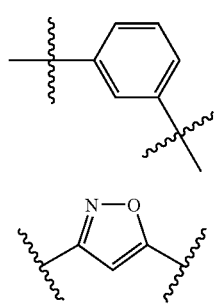

which may in each case be linked in any desired direction via the positions indicated with a wavy line to the bicyclic ring system and to the carbon atom of the triple bond and is optionally substituted with 1 or 2 further substituents, which are mutually independently selected from the group consisting of F, Cl, Br, —CN, —CH$_2$—CH, —CF$_3$, —SF$_5$, methyl, ethyl, n-propyl, iso-propyl, n-butyl, iso-butyl, sec-butyl, tert-butyl, —O—CH$_3$ and —O—CF$_3$.

29. A compound according to claim 1, wherein M$^2$ represents an unsubstituted or at least monosubstituted, 5- or 6-membered aryl or heteroaryl group, wherein the heteroaryl group comprises 1, 2, 3, 4 or 5 heteroatom(s) as ring member(s), which are mutually independently selected from the group consisting of nitrogen, oxygen and sulfur, and wherein the aryl or heteroaryl group may be fused with an unsubstituted or at least monosubstituted mono- or bicyclic ring system, wherein the rings of the ring system are in each case 5- or 6-membered and may in each case comprise 1, 2, 3 or 4 heteroatom(s) as ring member(s), which are mutually independently selected from the group consisting of nitrogen, oxygen and sulphur.

30. A compound according to claim 1, wherein M$^2$ represents a group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, wherein the group may in each case be unsubstituted or at least monosubstituted.

31. A compound according to claim 1, wherein M$^2$ represents a group selected from the group consisting of phenyl, furanyl, thiophenyl, pyrazolyl, pyrazinyl, pyridazinyl, pyrimidinyl, pyridinyl, pyrrolyl, oxazolyl, isoxazolyl, thiazolyl, thiadiazolyl, oxadiazolyl, triazolyl, diazinyl, triazinyl, tetrazinyl, tetrazolyl, pentazolyl, imidazolyl, quinolinyl, isoquinolinyl, naphthyl, indolyl, isoindolyl, benzofuranyl, isobenzofuranyl, benzothiophenyl and isobenzothiophenyl, wherein the particular group may be unsubstituted or optionally substituted with 1, 2, 3, 4 or 5 substituents, which are in each case mutually independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —C(=O)—H, —S—CF$_3$, —SH, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —C(=O)—CH$_3$, —C(=O)—C$_2$H$_5$, —NH—S(=O)$_2$—CH$_3$, —NH—S (=O)$_2$—C$_2$H$_5$, —S(=O)$_2$—NH$_2$, —S(=O)$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$; —NH—C(=NH)—NH$_2$, —NH—S(=O)$_2$—OH and —S(=O)$_2$—N(CH$_3$)$_2$.
32. A compound according to claim 1, wherein M$^2$ represents a group selected from the group consisting of groups 1 to 36,
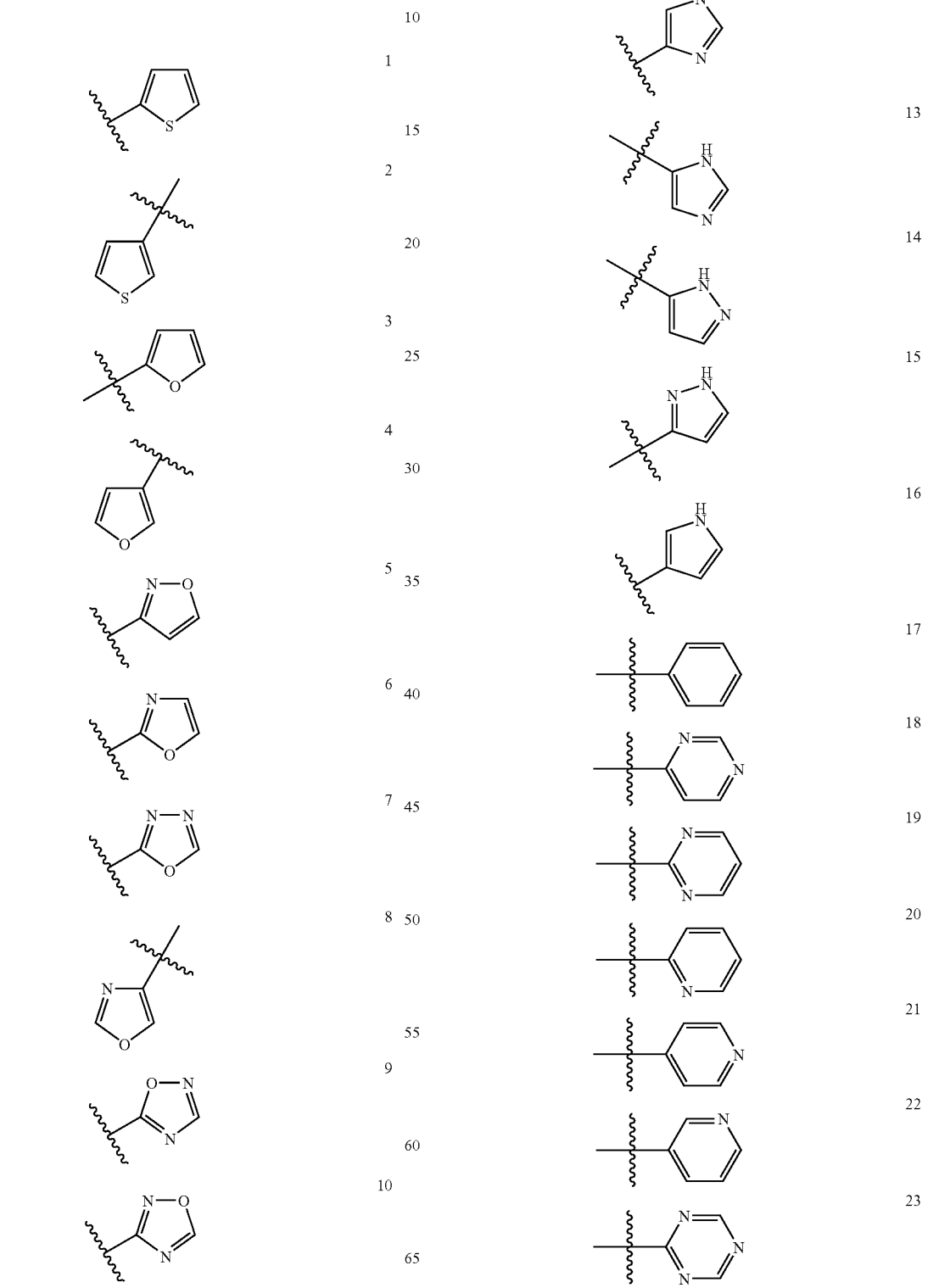

-continued

24 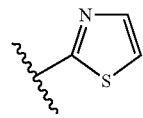

25 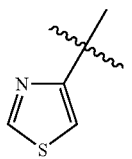

26 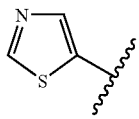

27 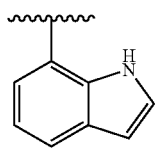

28 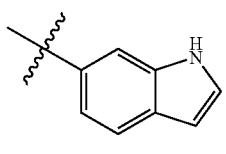

29 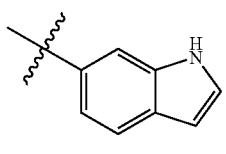

30 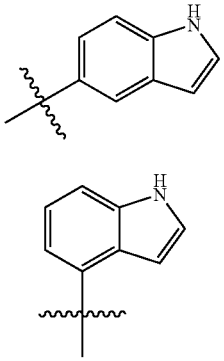

31 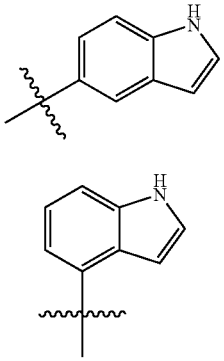

32 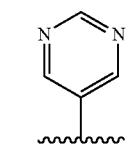

33 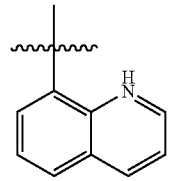

-continued

34 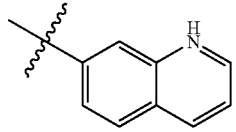

35 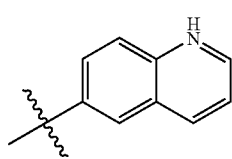

36 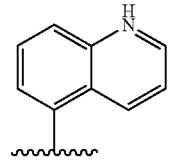

which is in each case linked via the position indicated with a wavy line to the carbon atom of the triple bond and is unsubstituted or substituted with 1, 2, 3, 4 or 5 substituents, which are mutually independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, sec-butyl, iso-butyl, tert-butyl, ethenyl, propenyl, —OH, —O—CH$_3$, —O—C$_2$H$_5$, —O—C$_3$H$_7$, —NH$_2$, —N(CH$_3$)$_2$, —NH—CH$_3$, —CH$_2$—NH$_2$, —N(C$_2$H$_5$)$_2$, —NO$_2$, —O—CF$_3$, —S—CF$_3$, —SH, —C(=O)—H, —C(=O)—O—CH$_3$, —C(=O)—O—C$_2$H$_5$, phenyl, pyrrolyl, (1,3)-dioxolanyl, Si(phenyl)$_2$[C(CH$_3$)$_3$], —C(=O)—CH$_3$, —C(=O)—C$_2$H$_5$, NH—S(=O)$_2$—CH$_3$, —NH—S(=O)$_2$—C$_2$H$_5$, —S(=O)$_2$—NH$_2$, —S(=O$_2$—NH—CH$_3$, —CH$_2$—OH, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$.

33. A compound according to claim 1, wherein M$^2$ is unsubstituted or substituted with 1, 2 or 3 substituents, which are mutually independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, tert-butyl, ethenyl, propenyl, —O—CH$_3$, —O—C$_2$H$_5$, —NH$_2$, —N(CH$_3$)$_2$, —NH—CH$_3$, —CH$_2$—NH$_2$, —O—CF$_3$, —C(=O)—H, —C(=O)—O—CH$_3$, —C(=O)—O—C$_2$H$_5$, phenyl, pyrrolyl, (1,3)-dioxolanyl, —Si(phenyl)2[C(CH$_3$)$_3$], —NO$_2$, NH—S(=O)$_2$—CH$_3$, —NH—S(=O)$_2$—C$_2$H$_5$, —S(=O)2-NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —S(=O)$_2$—N(CH$_3$)$_2$, —NH—S(=O)$_2$—OH and —NH—C(=NH)—NH$_2$.

34. A compound according to claim 1, wherein
A$^1$ represents a C—R$^{1a}$ group,
A$^2$ represents a C—R$^{1b}$ group,
A$^3$ represents a C—R$^{1c}$ group and
A$^4$ represents a C—R$^{1d}$ group;
or
A$^1$ represents a nitrogen atom,
A$^2$ represents a C—R$^{1b}$ group,
A$^3$ represents a C—R$^{1c}$ group and
A$^4$ represents a C—R$^{1d}$ group;

or

A$^1$ represents a C—R$^{1a}$ group,

A$^2$ represents a nitrogen atom,

A$^3$ represents a C—R$^{1c}$ group and

A$^4$ represents a C—R$^{1d}$ group, and

R$^{1a}$, R$^{1b}$, R$^{1c}$, R$^{1d}$, mutually independently, in each case represent —H; —F; —Cl; —Br; —I; —NO$_2$; —CN; —CF$_3$; —SF$_5$; —NH$_2$; —S(=O)—NH$_2$, —NHR$^4$; —NR$^5$R$^6$; —C(=O)—OR$^{12}$; —(CH$^2$)$_m$—C(=O)—OR$^{13}$ with m=1, 2 or 3; —O—C(=O)—R$^{14}$; —OR$^{16}$; —(CH$^2$)$_o$—O—R$^{17}$ with o=1, 2 or 3; a linear or branched alkyl group selected from the group consisting of methyl, ethyl, n-propyl, iso-propyl, n-butyl, iso-butyl, sec-butyl and tert-butyl, or represent an aryl or heteroaryl group selected from the group consisting of phenyl, furanyl, thiophenyl and pyridinyl, which is in each case unsubstituted or substituted with 1, 2, 3, 4 or 5 substituents mutually independently selected from the group consisting of F, Cl, Br, —CN, methyl, ethyl, n-propyl, iso-propyl, n-butyl, sec-butyl, iso-butyl, tert-butyl, —OH, —O—CH$_3$, —O—C$_2$H$_5$ and is optionally attached via a —(CH$_2$)—, —(CH$_2$)$_2$— or —(CH$_2$)$_3$ group;

or R$^{1a}$ and R$^{1b}$ or R$^{1b}$ and R$^{1c}$ or R$^{1c}$ and R$^{1d}$, together with the C—C bridge joining them together, form an anellated phenyl group, which may be substituted with 1, 2, 3 or 4 substituents mutually independently selected from the group consisting of F, Cl, Br, —CN, methyl, ethyl, n-propyl, iso-propyl, n-butyl, sec-butyl, iso-butyl, tert-butyl, —OH, —O—CH$_3$, —O—C$_2$H$_5$;

R$^2$ and R$^3$, mutually independently, in each case represent a hydrogen; —C(=O)—R$^{20}$; —(CH$^2$)$_q$—C(=O)—R$^{21}$ with q=1, 2 or 3; —(CH$_2$)$_r$—C(=O)—O—R$^{23}$ with r=1, 2 or 3; a linear or branched C$_{1-10}$ alkyl group; a C$_{4-8}$ cycloalkyl group, which is in each case unsubstituted or substituted with 1, 2, 3, 4 or 5 substituents mutually independently selected from the group consisting of F, Cl, Br, —CN, —CF$_3$, methyl, ethyl, n-propyl, iso-propyl, n-butyl, sec-butyl, iso-butyl, tert-butyl, —OH, —O—CH$_3$ and —O—C$_2$H$_5$ and is optionally attached via a linear or branched C$_{1-3}$ alkylene group; or represent an aryl or heteroaryl group selected from the group consisting of phenyl, thiophenyl, furanyl and pyridinyl, which is in each case unsubstituted or substituted with 1, 2, 3, 4 or 5 substituents mutually independently selected from the group consisting of F, Cl, Br, —CN, —CF$_3$, methyl, ethyl, n-propyl, iso-propyl, n-butyl, sec-butyl, iso-butyl, tert-butyl, —OH, —O—CH$_3$ and —O—C$_2$H$_5$ and is optionally attached via a linear or branched C$_{1-3}$ alkylene group;

or R$^2$ and R$^3$, together with the nitrogen atom joining them together as a ring member, form a group selected from the group consisting of imidazolidinyl, piperidinyl, piperazinyl, morpholinyl, pyrrolidinyl, thiomorpholinyl, azepanyl, diazepanyl and azocanyl, which may in each case be unsubstituted or optionally substituted with 1, 2, 3, 4 or 5 substituents mutually independently selected from the group consisting of F, Cl, Br, I, —CN, methyl, ethyl, n-propyl, iso-propyl, n-butyl, sec-butyl, iso-butyl, tert-butyl, —OH, oxo, thioxo, —O—CH$_3$, —O—C$_2$H$_5$, —O—C$_3$H$_7$, —NH$_2$, —N(CH$_3$)$_2$, —N(C$_2$H$_5$)$_2$, —NH—CH$_3$, —NH-C$_2$H$_5$, —O—CF$_3$, —S—CF$_3$, —S(=O)—CH$_3$, —S(=O)—C$_2$H$_5$, —S(=O)$_2$—CH$_3$, —S(=O)$_2$—C$_2$H$_5$, —C(=O)—OH, —C(=O)—H, —C(=O)—CH$_3$, —C(=O)—C$_2$H$_5$, —C(=O)—N(CH$_3$)$_2$, —C(=O)—NH—CH$_3$, —C(=O)—NH$_2$, —C(=O)—O—CH$_3$, —C(=O)—O—C$_2$H$_5$ and —C(=O)—O—C(CH$_3$)$_3$;

R$^4$, R$^5$, R$^6$ and R$^{14}$, in each case mutually independently, represent an alkyl group selected from the group consisting of methyl, ethyl, n-propyl and iso-propyl, or represent a phenyl group, which is in each case unsubstituted or substituted with 1, 2 or 3 substituents mutually independently selected from the group consisting of F, Cl, Br, —CN, —CF$_3$, —SF$_5$, methyl, ethyl, n-propyl, iso-propyl, tert-butyl, —O—CH$_3$ and —O—C$_2$H$_5$ and is optionally attached via a —(CH$_2$), —(CH$_2$)$_2$ or —(CH$_2$)$_3$ group;

R$^{12}$, R$^{13}$, R$^{16}$, R$^{17}$, R$^{20}$, R$^{21}$ and R$^{23}$, in each case mutually independently, represent a hydrogen; an alkyl group selected from the group consisting of methyl, ethyl, n-propyl, iso-propyl and tert-butyl, or a phenyl group, which is in each case unsubstituted or substituted with 1, 2 or 3 substituents mutually independently selected from the group consisting of F, Cl, Br, —CN, —CF$_3$, —SF$_5$, methyl, ethyl, n-propyl, iso-propyl, tert-butyl, —O—CH$_3$ and —O—C$_2$H$_5$ and is optionally attached via a —(CH$_2$), —(CH$_2$)$_2$ or —(CH$_2$)$_3$ group;

M1 represents a group selected from the group consisting of groups 1, 9, 11, 21, 22 and 36 to 38,

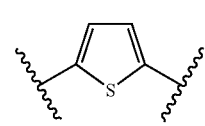

1

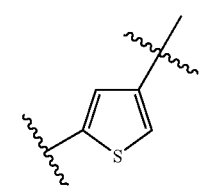

2

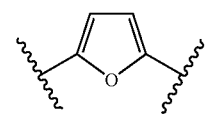

3

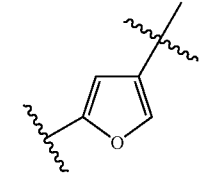

4

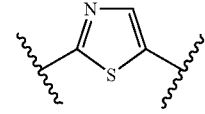

5

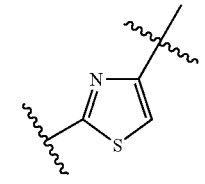

6

-continued

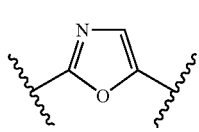
7

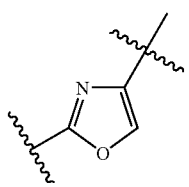
8

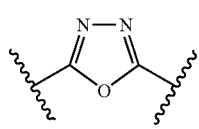
9

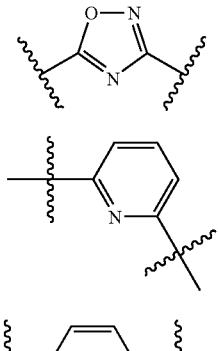
11
21

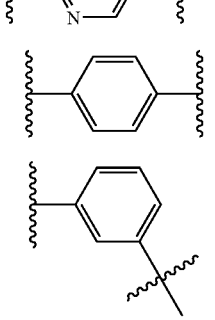
22
36

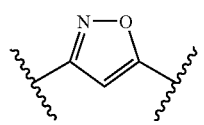
37

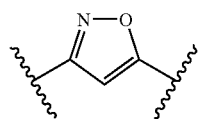

38 which may in each case be linked in any desired direction via the positions indicated with a wavy line to the bicyclic ring system and to the carbon atom of the triple bond and is optionally substituted with 1 or 2 further substituents, which are mutually independently selected from the group consisting of F, Cl, Br, —CN, —CH$_2$—CH, —CF$_3$, —SF$_5$, methyl, ethyl, n-propyl, iso-propyl, n-butyl, iso-butyl, sec-butyl, tert-butyl, —O—CH$_3$ and —O—CF$_3$; and M$^2$ represents a group selected from the group consisting of groups 1 to 36,

1

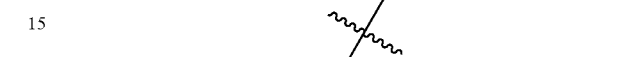
2

2

4

5

6

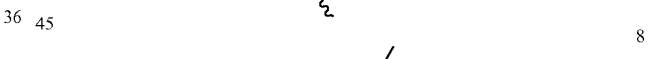
7

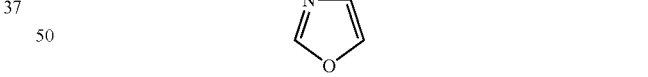
8

9

10

11

-continued
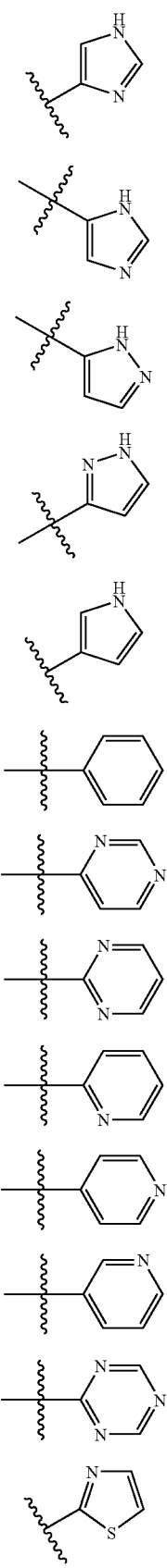
-continued
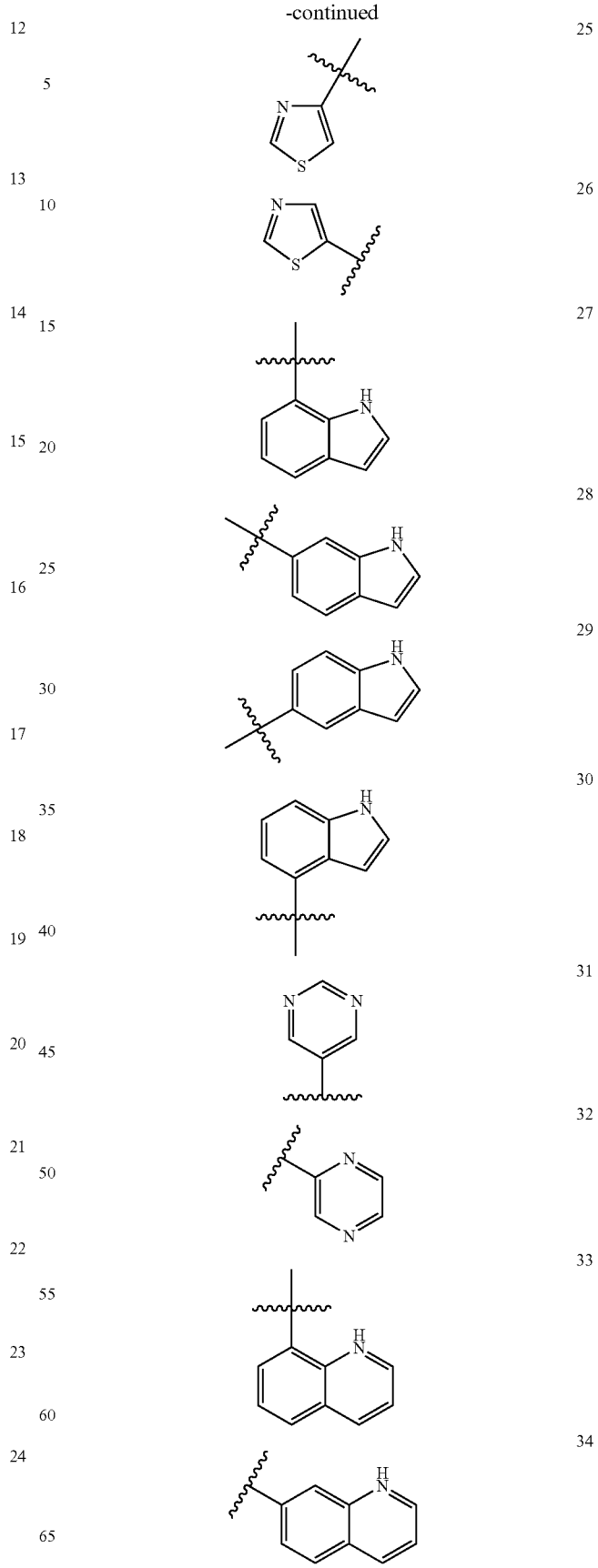

-continued

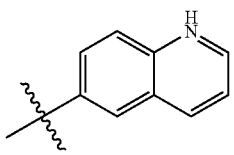
35

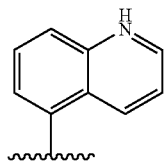
36 which is in each case linked via the position indicated with a wavy line with the carbon atom of triple bond and is unsubstituted or optionally substituted with 1, 2 or 3 substituents, which are mutually independently selected from the group consisting of F, Cl, Br, —CN, —CF$_3$, —SF$_5$, —S—CH$_3$, —S—C$_2$H$_5$, methyl, ethyl, n-propyl, iso-propyl, n-butyl, tert-butyl, ethenyl, propenyl, —O—CH$_3$, —O—C$_2$H$_5$, —NH$_2$, —N(CH$_3$)$_2$, —NH—CH$_3$, —CH$_2$—NH$_2$, —O—CF$_3$, —C(=O)—H, —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], —NO$_2$, NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —S(=O)$_2$—N(CH$_3$)$_2$, —NH—S(=O)$_2$—OH and —NH—C(=NH)—NH$_2$ or a salt thereof.

35. A compound according to claim 1, wherein
A$^1$ represents a C—R$^{1a}$ group,
A$^2$ represents a C—R$^{1b}$ group,
A$^3$ represents a C—R$^{1c}$ group and
A$^4$ represents a C—R$^{1d}$ group, or A$^1$ represents a nitrogen atom,
A$^2$ represents a C—R$^{1b}$ group,
A$^3$ represents a C—R$^{1c}$ group and
A$^4$ represents a C—R$^{1d}$ group, or A$^1$ represents a C—R$^{1a}$ group,
A$^2$ represents a nitrogen atom,
A$^3$ represents a C—R$^{1c}$ group and
A$^4$ represents a C—R$^{1d}$ group, and R$^{1a}$, R$^{1b}$, R$^{1c}$, R$^{1d}$, in each case mutually independently represent a hydrogen; —OR$^{16}$; —F; —Cl, —Br; —CN; —S(=O)$_2$—NH$_2$; —CF$_3$; —C(=O)—OR$^{12}$; an alkyl group selected from the group consisting of methyl, ethyl, n-propyl, iso-propyl, n-butyl, sec-butyl, iso-butyl and tert-butyl; a phenyl group; a benzyl group; a phenethyl group or represent a (3-phenyl)-prop-1-yl group, or R$^{1a}$ and R$^{1b}$, together with the C—C bridge joining them together, form an unsubstituted anellated phenyl group;
or R$^{1c}$ and R$^{1d}$, together with the C—C bridge joining them together, form an unsubstituted anellated phenyl group;

R$^2$ and R$^3$, mutually independently, in each case represent a hydrogen; —C(=O)—R$^{20}$; —(CH$^2$)$_q$—C(=O)—R$^{21}$ with q=1; —(CH$_2$)$_r$—C(=O)—O—R$^{23}$ with r=1; an alkyl group selected from the group consisting of methyl; ethyl; n-propyl; iso-propyl; n-butyl; tert-butyl; sec-butyl; iso-butyl; n-pentyl; n-hexyl; n-heptyl; n-octyl; (1,1,3,3)-tetramethyl-butyl; (1,1)-dimethyl-pentyl and (1,1)-dimethylbutyl; an unsubstituted cyclopentyl or cyclohexyl group, which may in each case be attached via a —(CH$_2$)—, —(CH$_2$)$_2$— or —(CH$_2$)$_3$ group; or represent a phenyl, pyridinyl, thiophenyl or furanyl group, which is in each case unsubstituted or optionally substituted with 1, 2, 3, 4 or 5 substituents mutually independently selected from the group consisting of F, Cl, Br, —CN, —CF$_3$, methyl, ethyl, n-propyl, iso-propyl, tert-butyl, —O—CH$_3$ and —O—C$_2$H$_5$ and is optionally attached via a —(CH$_2$)—, —(CH$_2$)$_2$—, —(CH(CH$_3$))— or —(CH$_2$)$_3$ group, or R$^2$ and R$^3$, together with the nitrogen atom joining them together as a ring member, form a heterocycloaliphatic group selected from the group consisting of pyrrolidinyl, piperidinyl, piperazinyl and morpholinyl, R$^{12}$ represents a hydrogen or an alkyl group selected from the group consisting of methyl, ethyl, n-propyl, iso-propyl and tert-butyl;

R$^{16}$, R$^{20}$, R$^{21}$ and R$^{23}$, in each case mutually independently represent an alkyl group selected from the group consisting of methyl, ethyl, n-propyl, iso-propyl and tert-butyl, or a phenyl group, which is in each case unsubstituted or substituted with 1 or 2 substituents mutually independently selected from the group consisting of F, Cl, Br, methyl, ethyl, —O—CH$_3$ and —O—C$_2$H$_5$ and is optionally attached via a —(CH$_2$) group, M$^1$ represents a group selected from the group consisting of groups 1 to 6, 21, 22, 36 and 37,

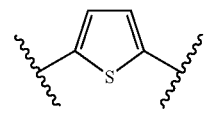
1

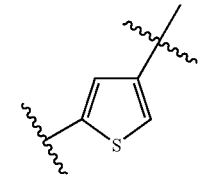
2

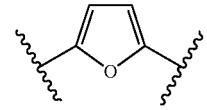
3

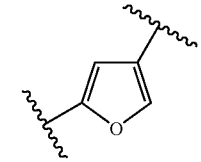
4

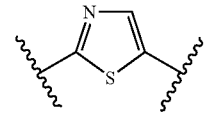
5

-continued

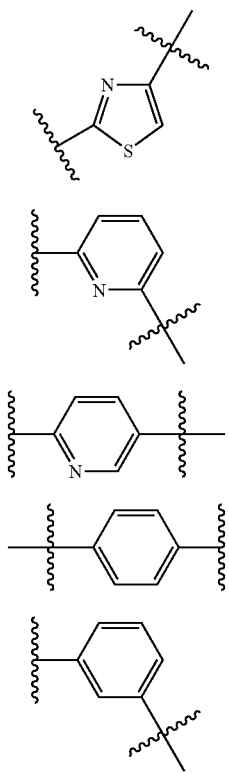

which may in each case be linked in any desired direction via the positions indicated with a wavy line to the bicyclic ring system and to the carbon atom of the triple bond and is optionally substituted with 1 or 2 further substituents, which are mutually independently selected from the group consisting of F, Cl, Br, —CN, —CH$_2$—CH, —CF$_3$, —SF$_5$, methyl, ethyl, n-propyl, iso-propyl, n-butyl, iso-butyl, sec-butyl, tert-butyl, —O—CH$_3$ and —O—CF$_3$, and M$^2$ represents a group selected from the group consisting of phenyl, 2-pyridinyl, 3-pyridinyl, 4-pyridinyl, 2-thiazolyl, 4-thiazolyl, 5-thiazolyl, 4-indolyl, 5-indolyl, 6-indolyl, 7-indolyl, 2-thiophenyl, 3-thiophenyl, 2-imidazolyl, 4-imidazolyl, 5-imidazolyl, 2-pyrimidinyl, 4-pyrimidinyl, 5-pyrimidinyl, 2-pyrazinyl, 5-quinolinyl, 6-quinolinyl, 7-quinolinyl and 8-quinolinyl, wherein the particular group is unsubstituted or optionally substituted with 1, 2, 3, 4 or 5 substituents, which are mutually independently selected from the group consisting of F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)3], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

or a salt thereof.

36. A compound according to claim 35, said compound corresponding to formula Id

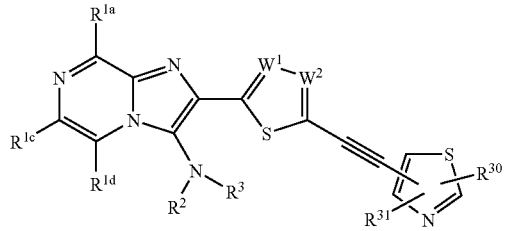

wherein
W$^1$ represents C and W$^2$ represents C
or W$^1$ represents C and W$^2$ represents N
or W$^1$ represents N and W$^2$ represents C;
and R$^{30}$ and R$^{31}$, mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

or a salt thereof.

37. A compound according to claim 35, said compound corresponding to formula Ie

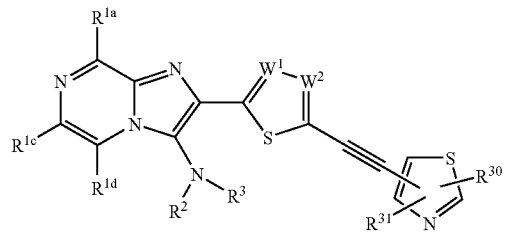

wherein
W$^1$ represents C and W$^2$ represents C,
or W$^1$ represents C and W$^2$ represents N,
or W$^1$ represents N and W$^2$ represents C; and R$^{30}$ and R$^{31}$, mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—

NH—CH$_3$, —NH—C(=O)—CH$_3$, —NH—C(=NH)—NH$_2$, —NH—S(=O)$_2$—OH and —S(=O)$_2$—N(CH$_3$)$_2$;
or a salt thereof.

38. A compound according to claim 35, said compound corresponding to formula If

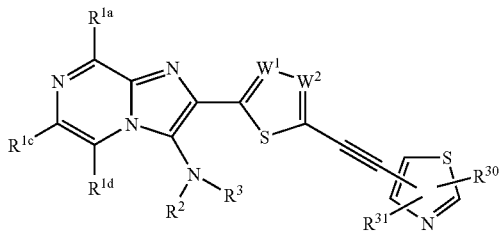

If wherein
W$^1$ represents C and W$^2$ represents C,
or W$^1$ represents C and W$^2$ represents N,
or W$^1$ represents N and W$^2$ represents C;
W$^3$ represents C—R$^{32}$; W$^4$ represents C—R$^{33}$ and W$^5$ represents C—R$^{34}$;
or one of the groups W$^3$, W$^4$ and W$^5$ represents N and the other two groups selected from the group consisting of W$^3$, W$^4$ and W$^5$ represent C—R$^{32}$ or C—R$^{33}$; and
R$^{32}$, R$^{33}$, R$^{34}$, R$^{35}$ and R$^{36}$, mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—O—CH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$ —NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;
or a salt thereof.

39. A compound according to claim 35, said compound corresponding to formula Ig

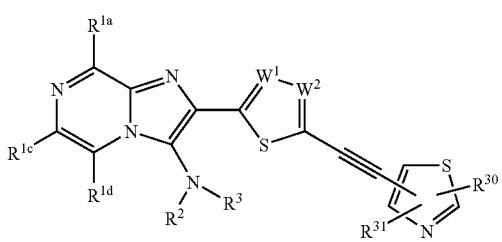

Ig wherein
W$^1$ represents C and W$^2$ represents C,
or W$^1$ represents C and W$^2$ represents N,
or W$^1$ represents N and W$^2$ represents C;
W$^3$ represents C—R$^{32}$; W$^4$ represents C—R$^{33}$ and W$^5$ represents C—R$^{34}$; or one of the groups W$^3$, W$^4$ and W$^5$ represent N and the other two groups selected from the group consisting of W$^3$, W$^4$ and W$^5$ represent C—R$^{32}$ or C—R$^{33}$; and
R$^{32}$, R$^{33}$, R$^{34}$, R$^{35}$ and R$^{36}$, mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)2[C(CH$_3$)3], NH—S(=O)$_2$—CH$_3$, —NH—S(=O)$_2$—C$_2$H$_5$, —S(=O)$_2$—NH$_2$, —S(=O)$_2$ —NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;
or a salt thereof.

40. A compound according to claim 35, said compound corresponding to formula Ih

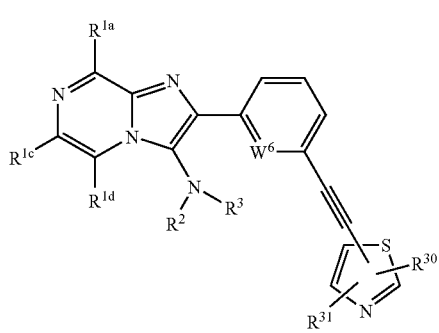

Ih wherein
W$^6$ represents C or N;
and
R$^{30}$ and R$^{31}$, mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;
or a salt thereof.

41. A compound according to claim 35, said compound corresponding to formula Ik

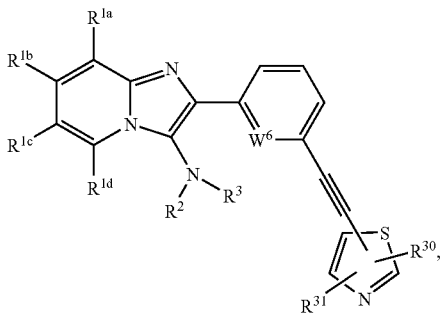

Ik wherein
W[6] represents C or N;
and
R[30] and R[31], mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S—(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

or a salt thereof.

42. A compound according to claim 35, said compound corresponding to formula Im

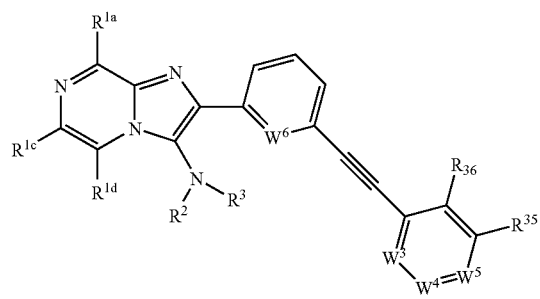

Im wherein
W[6] represents C or N;
W[3] represents C—R[32]; W[4] represents C—R[33] and W[5] represents C—R[34]; or one of the groups W[3], W[4] and W[5] represent N and the other two selected from the group consisting of W[3], W[4] and W[5] represent C—R[32] or C—R[33]; and
R[32], R[33], R[34], R[35] and R[36], mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

or a salt thereof.

43. A compound according to claim 35, said compound corresponding to formula In

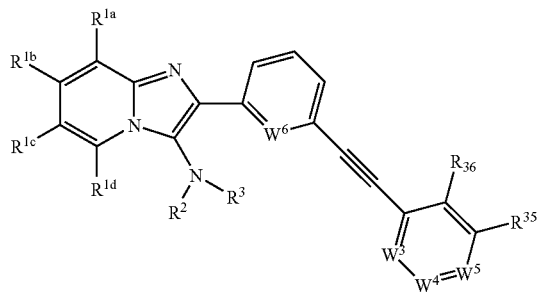

In wherein
W[6] represents C or N;
W[3] represents C—R[32]; W[4] represents C—R[33] and W[5] represents C—R[34];
or one of the groups W[3], W[4] and W[5] represent N and the other two groups selected from the group consisting of W[3], W[4] and W[5] represent C—R[32] or C—R[33]; and
R[32], R[33], R[34], R[35] and R[36], mutually independently, in each case represent a group selected from the group consisting of H, F, Cl, Br, —CN, —CF$_3$, —SF$_5$, —S—CH$_3$, —S—C$_2$H$_5$, methyl, ethyl, iso-propyl, tert-butyl, ethenyl, propenyl, —OH, —O—CH$_3$, —O—C$_2$H$_5$, —NH$_2$, —N(CH$_3$)$_2$, —NH—CH$_3$, —CH$_2$—NH$_2$, —NO$_2$, —O—CF$_3$, —C(=O)—H; —C(=O)—OCH$_3$, —C(=O)—O—C$_2$H$_5$, phenyl, pyrrolyl, (1,3)-dioxolanyl, —Si(phenyl)$_2$[C(CH$_3$)$_3$], NH—S(=O)$_2$—CH$_3$, —NH—S(=O)$_2$—C$_2$H$_5$, —S(=O)$_2$—NH$_2$, —S(=O)$_2$—NH—CH$_3$, —CH$_2$—OH, —C(=O)—CH$_3$, —C(=O)—OH, —CH$_2$—O—CH$_3$, —C(=O)—NH$_2$, —C(=O)—NH—CH$_3$, —NH—C(=O)—CH$_3$, —NH—C(=NH)—NH$_2$, —NH—S(=O)$_2$—OH and —S(=O)$_2$—N(CH$_3$)$_2$;

or a salt thereof.

44. A compound according to claim 1, wherein said compound is selected from the group consisting of:

[1] cyclopentyl-[2-(5-phenylethynyl-thiophen-2-yl)-imidazo[1,2-a]pyrazin-3-yl]-amine,

[2] cyclohexylmethyl-[5-methyl-2-(5-phenylethynyl-thiophen-2-yl)-imidazo[1,2-a]pyridin-3-yl]-amine,

[3] cyclohexylmethyl-[6-methyl-2-(5-phenylethynyl-thiophen-2-yl)-imidazo[1,2-a]pyridin-3-yl]-amine,

[4] cyclohexylmethyl-[7-methyl-2-(5-phenylethynyl-thiophen-2-yl)-imidazo[1,2-a]pyridin-3-yl]-amine,

[5] cyclohexylmethyl-[8-methyl-2-(5-phenylethynyl-thiophen-2-yl)-imidazo[1,2-a]pyridin-3-yl]-amine,

[6] cyclohexylmethyl-[5,7-dimethyl-2-(5-phenylethynyl-thiophen-2-yl)-imidazo[1,2-a]pyridin-3-yl]-amine,

[7] [8-benzyloxy-2-(5-phenylethynyl-thiophen-2-yl)-imidazo[1,2-a]pyridin-3-yl]-cyclohexylmethyl-amine,

[8] cyclohexylmethyl-[2-(5-phenylethynyl-thiophen-2-yl)-imidazo[1,2-a]pyrazin-3-yl]-amine,
[9] cyclohexylmethyl-[2-(5-phenylethynyl-thiophen-2-yl)-imidazo[1,2-a]pyrimidin-3-yl]-amine,
[10] (4-methoxy-benzyl)-[5-methyl-2-(5-phenylethynyl-thiophen-2-yl)-imidazo[1,2-a]pyridin-3-yl]-amine,
[11] (4-methoxy-benzyl)-[6-methyl-2-(5-phenylethynyl-thiophen-2-yl)-imidazo[1,2-a]pyridin-3-yl]-amine,
[12] (4-methoxy-benzyl)-[7-methyl-2-(5-phenylethynyl-thiophen-2-yl)-imidazo[1,2-a]pyridin-3-yl]-amine,
[13] (4-methoxy-benzyl)-[8-methyl-2-(5-phenylethynyl-thiophen-2-yl)-imidazo[1,2-a]pyridin-3-yl]-amine,
[14] [5,7-dimethyl-2-(5-phenylethynyl-thiophen-2-yl)-imidazo[1,2-a]pyridin-3-yl]-(4-methoxy-benzyl)-amine,
[15] [8-benzyloxy-2-(5-phenylethynyl-thiophen-2-yl)-imidazo[1,2-a]pyridin-3-yl]-(4-methoxy-benzyl)-amine,
[16] (4-methoxy-benzyl)-[2-(5-phenylethynyl-thiophen-2-yl)-imidazo[1,2-a]pyridin-3-yl]-amine,
[17] (4-methoxy-benzyl)-[2-(5-phenylethynyl-thiophen-2-yl)-imidazo[1,2-a]pyrazin-3-yl]-amine,
[18] tert-butyl-[2-(5-phenylethynyl-thiophen-2-yl)-imidazo[1,2-a]pyrazin-3-yl]-amine,
[19] tert-butyl-[6-methyl-2-(5-phenylethynyl-thiophen-2-yl)-imidazo[1,2-a]pyridin-3-yl]-amine,
[20] [8-benzyloxy-2-(5-phenylethynyl-thiophen-2-yl)-imidazo[1,2-a]pyridin-3-yl]-(3-methoxy-phenyl)-amine,
[21] (3-methoxy-benzyl)-[5-methyl-2-(5-phenylethynyl-thiophen-2-yl)-imidazo[1,2-a]pyridin-3-yl]-amine,
[22] (3-methoxy-benzyl)-[8-methyl-2-(5-phenylethynyl-thiophen-2-yl)-imidazo[1,2-a]pyridin-3-yl]-amine,
[23] [5,7-dimethyl-2-(5-phenylethynyl-thiophen-2-yl)-imidazo[1,2-a]pyridin-3-yl]-(3-methoxy-benzyl)-amine,
[24] [8-benzyloxy-2-(5-phenylethynyl-thiophen-2-yl)-imidazo[1,2-a]pyridin-3-yl]-(3-methoxy-benzyl)-amine,
[25] (3-methoxy-benzyl)-[2-(5-phenylethynyl-thiophen-2-yl)-imidazo[1,2-a]pyridin-3-yl]-amine,
[26] (3-methoxy-benzyl)-[2-(5-phenylethynyl-thiophen-2-yl)-imidazo[1,2-a]pyrazin-3-yl]-amine,
[27] [6-methyl-2-(5-phenylethynyl-thiophen-2-yl)-imidazo[1,2-a]pyridin-3-yl]-(1-phenyl-ethyl)-amine,
[28] [7-methyl-2-(5-phenylethynyl-thiophen-2-yl)-imidazo[1,2-a]pyridin-3-yl]-(1-phenyl-ethyl)-amine,
[29] [5,7-dimethyl-2-(5-phenylethynyl-thiophen-2-yl)-imidazo[1,2-a]pyridin-3-yl]-(1-phenyl-ethyl)-amine,
[30] [8-benzyloxy-2-(5-phenylethynyl-thiophen-2-yl)-imidazo[1,2-a]pyridin-3-yl]-(1-phenyl-ethyl)-amine,
[31] (1-phenyl-ethyl)-[2-(5-phenylethynyl-thiophen-2-yl)-imidazo[1,2-a]pyrazin-3-yl]-amine,
[32] (2-chloro-benzyl)-[5,7-dimethyl-2-(5-phenylethynyl-thiophen-2-yl)-imidazo[1,2-a]pyridin-3-yl]-amine,
[33] (3-chloro-4-fluoro-phenyl)-[7-phenyl-2-(5-phenylethynyl-thiophen-2-yl)-imidazo[1,2-a]pyridin-3-yl]-amine,
[34] (4-methoxy-benzyl)-[7-methyl-2-(5-phenylethynyl-thiophen-2-yl)-imidazo[1,2-a]pyrimidin-3-yl]- amine,
[35] [8-methyl-2-(5-phenylethynyl-thiophen-2-yl)-imidazo[1,2-a]pyridin-3-yl]-(1-phenyl-ethyl)-amine,
[36] [7-methyl-2-(5-phenylethynyl-thiophen-2-yl)-imidazo[1,2-a]pyrimidin-3-yl]-(1-phenyl-ethyl)-amine,
[37] (2-methoxy-benzyl)-[7-methyl-2-(5-phenylethynyl-thiophen-2-yl)-imidazo[1,2-a]pyridin-3-yl]-amine,
[38] (2-methoxy-benzyl)-[2-(5-phenylethynyl-thiophen-2-yl)-imidazo[1,2-a]pyridin-3-yl]- amine,
[39] (2-chloro-benzyl)-[2-(5-phenylethynyl-thiophen-2-yl)-imidazo[1,2-a]pyridin-3-yl]-amine,
[40] (2-methoxy-benzyl)-[7-methyl-2-(5-phenylethynyl-thiophen-2-yl)-imidazo[1,2-a]pyrimidin-3-yl]-amine,
[41] (3-methoxy-phenyl)-[6-methyl-2-(5-phenylethynyl-thiophen-2-yl)-imidazo[1,2-a]pyridin-3-yl]-amine,
[42] [5,7-dimethyl-2-(5-phenylethynyl-thiophen-2-yl)-imidazo[1,2-a]pyridin-3-yl]-(3-methoxy-phenyl)-amine,
[43] (3-methoxy-phenyl)-[2-(5-phenylethynyl-thiophen-2-yl)-imidazo[1,2-a]pyrazin-3-yl]-amine,
[44] [7-ethyl-2-(5-phenylethynyl-thiophen-2-yl)-imidazo[1,2-a]pyridin-3-yl]-(2-methoxy-benzyl)-amine,
[45] (2-chloro-benzyl)-[7-ethyl-2-(5-phenylethynyl-thiophen-2-yl)-imidazo[1,2-a]pyridin-3-yl]-amine,
[46] [7-tert-butyl-2-(5-phenylethynyl-thiophen-2-yl)-imidazo[1,2-a]pyridin-3-yl]-(3-chloro-4-fluoro-phenyl)-amine,
[47] (3-methoxy-benzyl)-[7-methyl-2-(5-phenylethynyl-thiophen-2-yl)-imidazo[1,2-a]pyrimidin-3-yl]-amine,
[48] [7-ethyl-2-(5-phenylethynyl-thiophen-2-yl)-imidazo[1,2-a]pyridin-3-yl]-(2-fluoro-phenyl)-amine,
[49] [7-tert-butyl-2-(5-phenylethynyl-thiophen-2-yl)-imidazo[1,2-a]pyridin-3-yl]-(2-fluoro-phenyl)-amine,
[50] (2,4-difluoro-phenyl)-[2-(5-phenylethynyl-thiophen-2-yl)-7-(3-phenyl-propyl)-imidazo[1,2-a]pyridin-3-yl]-amine,
[51] (4-fluoro-benzyl)-[7-methyl-2-(5-phenylethynyl-thiophen-2-yl)-imidazo[1,2-a]pyridin-3-yl]-amine,
[52] [5,7-dimethyl-2-(5-phenylethynyl-thiophen-2-yl)-imidazo[1,2-a]pyridin-3-yl]-(4-fluoro-benzyl)-amine,
[53] [7-ethyl-2-(5-phenylethynyl-thiophen-2-yl)-imidazo[1,2-a]pyridin-3-yl]-(3-trifluoromethyl-benzyl)-amine,
[54] [7-isopropyl-2-(5-phenylethynyl-thiophen-2-yl)-imidazo[1,2-a]pyridin-3-yl]-(3-trifluoromethyl-benzyl)-amine,
[55] tert-butyl-[2-(4-phenylethynyl-thiophen-2-yl)-imidazo[1,2-a]pyrazin-3-yl]-amine,
[56] [2-(5-phenylethynyl-thiophen-2-yl)-imidazo[1,2-a]pyrazin-3-yl]-(1,1,3,3-tetramethyl-butyl)-amine,
[57] butyl-[2-(4-phenylethynyl-thiophen-2-yl)-imidazo[1,2-a]pyrazin-3-yl]-amine,
[59] [2-(5-phenylethynyl-thiophen-2-yl)-imidazo[1,2-a]pyridin-3-yl]-(1,1,3,3-tetramethyl-butyl)-amine,
[60] [2-(5-pyridinyl-thiophen-2-yl)-imidazo[1,2-a]pyrazin-3-yl]-(1,1,3,3-tetramethyl-butyl)-amine,
[61] [2-(5-pyridin-4-ylethynyl-thiophen-2-yl)-imidazo[1,2-a]pyrazin-3-yl]-(1,1,3,3-tetramethyl-butyl)-amine,
[62] [6-chloro-2-(5-phenylethynyl-thiophen-2-yl)-imidazo[1,2-a]pyridin-3-yl]-(1,1,3,3-tetramethyl-butyl)-amine,
[63] [6,8-dichloro-2-(5-phenylethynyl-thiophen-2-yl)-imidazo[1,2-a]pyridin-3-yl]-(1,1,3,3-tetramethyl-butyl)-amine,
[64] [2-(5-pyridin-2-ylethynyl-thiophen-2-yl)-imidazo[1,2-a]pyrazin-3-yl]-(1,1,3,3-tetramethyl-butyl)-amine,
[65] dimethyl-[2-(5-phenylethynyl-thiophen-2-yl)-imidazo[1,2-a]pyrazin-3-yl]-amine,
[66] methyl-[2-(5-phenylethynyl-thiophen-2-yl)-imidazo[1,2-a]pyrazin-3-yl]-amine,
[67] N-[2-(5-phenylethynyl-thiophen-2-yl)-imidazo[1,2-a]pyrazin-3-yl]-acetamide,
[68] ethyl-[2-(5-phenylethynyl-thiophen-2-yl)-imidazo[1,2-a]pyrazin-3-yl]-amine,

[69] propyl-[2-(5-phenylethynyl-thiophen-2-yl)-imidazo[1,2-a]pyrazin-3-yl]-amine,
[70] butyl-[2-(5-phenylethynyl-thiophen-2-yl)-imidazo[1,2-a]pyrazin-3-yl]-amine,
[71] (2-methylpropyl)-[2-(5-phenylethynyl-thiophen-2-yl)-imidazo[1,2-a]pyrazin-3-yl]-amine,
[72] pentyl-[2-(5-phenylethynyl-thiophen-2-yl)-imidazo[1,2-a]pyrazin-3-yl]-amine,
[73] {(methoxycarbonylmethyl)-[2-(5-phenylethynyl-thiophen-2-yl)-imidazo[1,2-a]pyrazin-3-yl]-amino}-acetic acid methyl ester,
[74] benzyl-[2-(5-phenylethynyl-thiophen-2-yl)-imidazo[1,2-a]pyrazin-3-yl]-amine,
[75] [2-(5-phenylethynyl-thiophen-2-yl)-imidazo[1,2-a]pyrazin-3-ylamino]-acetic acid methyl ester,
[76] tert-butyl-[2-(5-pyridin-4-ylethynyl-thiophen-2-yl)-imidazo[1,2-a]pyrazin-3-yl]-amine,
[77] tert-butyl-[2-(5-pyridin-2-ylethynyl-thiophen-2-yl)-imidazo[1,2-a]pyrazin-3-yl]-amine,
[78] N-[2-(5-phenylethynyl-thiophen-2-yl)-imidazo[1,2-a]pyrazin-3-yl]-benzamide,
[79] [2-(5-phenylethynyl-thiophen-2-yl)-imidazo[1,2-a]pyrazin-3-yl]-bis-pyridin-3-ylmethyl-amine,
[80] 2,2-dimethyl-N-[2-(5-phenylethynyl-thiophen-2-yl)-imidazo[1,2-a]pyrazin-3-yl]-propionamide,
[81] 3-methoxy-N-[2-(5-phenylethynyl-thiophen-2-yl)-imidazo[1,2-a]pyrazin-3-yl]-benzamide,
[82] tert-butyl-[2-(5-pyridin-2-ylethynyl-thiophen-2-yl)-imidazo[1,2-a]pyrazin-3-yl]-amine
[83] 2-(5-phenylethynyl-thiophen-2-yl)-imidazo[1,2-a]pyrazin-3-ylamine
[84] methyl-2-(5-(phenylethynyl)thiophen-2-yl)-3-(2,4,4-trimethylpentan-2-ylamino)imidazo[1,2-a]pyrazine-8-carboxylate
[85] 2-(5-(phenylethynyl)thiophen-2-yl)-N-(2,4,4-trimethylpentan-2-yl)imidazo[1,2-a]pyrimidin-3-amine
[86] 2-(5-((6-methylpyridin-2-yl)ethynyl)thiophen-2-yl)-N-(2,4,4-trimethylpentan-2-yl)imidazo[1,2-a]pyrazin-3-amine
[87] N--cyclohexyl-2-(5-(phenylethynyl)thiophen-2-yl)imidazo[1,2-a]pyrazin-3-amine
[88] 2-(5-(phenylethynyl)thiophen-2-yl)-3-(piperidin-1-yl)imidazo[1,2-a]pyrazine
[89] N-tert-butyl-N-methyl-2-(5-(phenylethynyl)thiophen-2-yl)imidazo[1,2-a]pyrazin-3-amine
[90] methyl-2-(5-(phenylethynyl)thiophen-2-yl)-3-(2,4,4-trimethylpentan-2-ylamino)imidazo[1,2-a]pyridine-6-carboxylate
[91] N-tert-butyl-2-(5-(pyridin-2-ylethynyl)thiophen-2-yl)imidazo[1,2-a]pyrazin-3-amine hydrochloride
[92] 8-bromo-N-cyclopentyl-6-methyl-2-(5-(pyridin-2-ylethynyl)thiophen-2-yl)imidazo[1,2-a]pyridin-3-amine
[93] N,N-diethyl-2-(5-(phenylethynyl)thiophen-2-yl)imidazo[1,2-a]pyrazin-3-amine
[94] N-tert-butyl-2-(5-(pyridin-2-ylethynyl)thiophen-2-yl)imidazo[1,2-a]pyridin-3-amine
[95] N-tert-butyl-2-(5-(phenylethynyl)furan-2-yl)imidazo[1,2-a]pyrazin-3-amine
[96] 8-bromo-N-tert-butyl-6-methyl-2-(3-(pyridin-2-ylethynyl)phenyl)imidazo[1,2-a]pyridin-3-amine
[97] N-tert-butyl-8-methyl-2-(5-(phenylethynyl)thiophen-2-yl)imidazo[1,2-a]pyridin-3-amine
[98] N-methyl-2-(5-(phenylethynyl)thiophen-2-yl)-N-(2,4,4-trimethylpentan-2-yl)imidazo[1,2-a]pyrazin-3-amine hydrochloride
[99] 2-(5-(phenylethynyl)thiophen-2-yl)-3-(pyrrolidin-1-yl)imidazo[1,2-a]pyrazine hydrochloride
[100] N-tert-butyl-2-(5-((4-fluorophenyl)ethynyl)thiophen-2-yl)imidazo[1,2-a]pyrazin-3-amine hydrochloride
[101] N-tert-butyl-7-methyl-2-(5-(phenylethynyl)thiophen-2-yl)imidazo[1,2-a]pyridin-3-amine
[102] N-tert-butyl-5-methyl-2-(5-(phenylethynyl)thiophen-2-yl)imidazo[1,2-a]pyridin-3-amine
[103] 8-chloro-2-(3-(pyridin-2-ylethynyl)phenyl)-6-(trifluoromethyl)-N-(2,4,4-trimethylpentan-2-yl)imidazo[1,2-a]pyridin-3-amine
[104] N-tert-butyl-2-(5-((3-fluorophenyl)ethynyl)thiophen-2-yl)imidazo[1,2-a]pyrazin-3-amine hydrochloride
[105] N-tert-butyl-2-(5-((2-fluorophenyl)ethynyl)thiophen-2-yl)imidazo[1,2-a]pyrazin-3-amine hydrochloride
[106] methyl-3-(tert-butylamino)-2-(5-(phenylethynyl)thiophen-2-yl)imidazo[1,2-a]pyrazine-8-carboxylate
[107] N-tert-butyl-2-(5-(pyrazin-2-ylethynyl)thiophen-2-yl)imidazo[1,2-a]pyrazin-3-amine
[108] 2-(5-((4-aminophenyl)ethynyl)thiophen-2-yl)-N-tert-butylimidazo[1,2-a]pyrazin-3-amine
[109] N-isopropyl-2-(5-(phenylethynyl)thiophen-2-yl)imidazo[1,2-a]pyrazin-3-amine
[110] N-tert-butyl-2-(5-(thiophen-2-ylethynyl)thiophen-2-yl)imidazo[1,2-a]pyrazin-3-amine hydrochloride
[111] N-tert-butyl-2-(3-(pyridin-2-ylethynyl)phenyl)imidazo[1,2-a]pyrazin-3-amine
[112] N-tert-butyl-2-(5-((2-methoxyphenyl)ethynyl)thiophen-2-yl)imidazo[1,2-a]pyrazin-3-amine hydrochloride
[113] N-tert-butyl-2-(5-((3-methoxyphenyl)ethynyl)thiophen-2-yl)imidazo[1,2-a]pyrazin-3-amine hydrochloride
[114] N-tert-butyl-2-(5-((4-methoxyphenyl)ethynyl)thiophen-2-yl)imidazo[1,2-a]pyrazin-3-amine hydrochloride
[115] N-tert-butyl-2-(5-(phenylethynyl)thiophen-2-yl)imidazo[1,2-a]quinolin-1-amine
[116] N-tert-butyl-2-(4-(pyridin-2-ylethynyl)phenyl)imidazo[1,2-a]pyrazin-3-amine
[117] N-tert-butyl-2-(3-((6-methylpyridin-2-yl)ethynyl)phenyl)imidazo[1,2-a]pyrazin-3-amine
[118] N-tert-butyl-2-(2-methyl-6-(phenylethynyl)pyridin-3-yl)imidazo[1,2-a]pyrazin-3-amine
[119] N-tert-butyl-2-(5-(pyridin-2-ylethynyl)furan-2-yl)imidazo[1,2-a]pyrazin-3-amine
[120] 3-(tert-butylamino)-2-(5-(phenylethynyl)thiophen-2-yl)imidazo[1,2-a]pyrazine-8-carboxylic acid
[121] 4-((5-(3-(tert-butylamino)imidazo[1,2-a]pyrazin-2-yl)thiophen-2-yl)ethynyl)phenol hydrochloride
[122] 3-((5-(3-(tert-butylamino)imidazo[1,2-a]pyrazin-2-yl)thiophen-2-yl)ethynyl)phenol
[123] 2-(5-((3-aminophenyl)ethynyl)thiophen-2-yl)-N-tert-butylimidazo[1,2-a]pyrazin-3-amine hydrochloride
[124] 2-(5-((2-aminophenyl)ethynyl)thiophen-2-yl)-N-tert-butylimidazo[1,2-a]pyrazin-3-amine hydrochloride
[125] N-tert-butyl-2-(5-(phenylethynyl)thiophen-2-yl)imidazo[2,1-a]isoquinolin-3-amine
[126] N-tert-butyl-2-(6-(phenylethynyl)pyridin-3-yl)imidazo[1,2-a]pyrazin-3-amine
[127] N-tert-butyl-2-(5-(pyridin-4-ylethynyl)thiophen-2-yl)imidazo[1,2-a]pyrazin-3-amine hydrochloride

[128] 2-(5-((6-aminopyridin-3-yl)ethynyl)thiophen-2-yl)-N-tert-butylimidazo[1,2-a]pyrazin-3-amine hydrochloride
[129] N-tert-butyl-2-(5-(pyrimidin-2-ylethynyl)thiophen-2-yl)imidazo[1,2-a]pyrazin-3-amine hydrochloride
[130] N-tert-butyl-2-(5-((4-methylpyridin-2-yl)ethynyl)thiophen-2-yl)imidazo[1,2-a]pyrazin-3-amine hydrochloride
[131] N-tert-butyl-2-(5-((5-methylpyridin-2-yl)ethynyl)thiophen-2-yl)imidazo[1,2-a]pyrazin-3-amine hydrochloride
[132] N-tert-butyl-2-(5-(pyridin-4-ylethynyl)thiophen-2-yl)imidazo[1,2-a]pyridin-3-amine hydrochloride
[133] N-tert-butyl-2-(5-(thiazol-2-ylethynyl)thiophen-2-yl)imidazo[1,2-a]pyrazin-3-amine
[134] 2-(5-(pyridin-2-ylethynyl)thiophen-2-yl)imidazo[1,2-a]pyrazin-3-amine hydrochloride
[135] N-tert-butyl-2-(5-((5-methylthiophen-2-yl)ethynyl)thiophen-2-yl)imidazo[1,2-a]pyrazin-3-amine hydrochloride
[136] 2-(5-((6-aminopyridin-2-yl)ethynyl)thiophen-2-yl)-N-tert-butylimidazo[1,2-a]pyrazin-3-amine hydrochloride
[137] N-tert-butyl-2-(5-((3-methylthiophen-2-yl)ethynyl)thiophen-2-yl)imidazo[1,2-a]pyrazin-3-amine
[138] N-tert-butyl-2-(4-(phenylethynyl)thiazol-2-yl)imidazo[1,2-a]pyrazin-3-amine
[139] N-tert-butyl-2-(5-(m-tolylethynyl)thiophen-2-yl)imidazo[1,2-a]pyrazin-3-amine
[140] 3-((5-(3-(tert-butylamino)imidazo[1,2-a]pyrazin-2-yl)thiophen-2-yl)ethynyl)benzonitrile hydrochloride
[141] N-tert-butyl-2-(5-(pyridin-2-ylethynyl)thiophen-2-yl)imidazo[1,2-a]pyrimidin-3-amine
[142] N-tert-butyl-2-(6-(phenylethynyl)pyridin-2-yl)imidazo[1,2-a]pyrazin-3-amine hydrochloride
[143] N-tert-butyl-N-methyl-2-(5-(pyridin-2-ylethynyl)thiophen-2-yl)imidazo[1,2-a]pyrazin-3-amine
[144] 4-((5-(3-(tert-butylamino)imidazo[1,2-a]pyrazin-2-yl)thiophen-2-yl)ethynyl)benzonitrile hydrochloride
[145] 2-(5-((1H-indol-6-yl)ethynyl)thiophen-2-yl)-N-tert-butylimidazo[1,2-a]pyrazin-3-amine hydrochloride
[146] N-tert-butyl-2-(2-(phenylethynyl)thiazol-5-yl)imidazo[1,2-a]pyrazin-3-amine
[147] N-tert-butyl-2-(5-(quinolin-6-ylethynyl)thiophen-2-yl)imidazo[1,2-a]pyrazin-3-amine hydrochloride
[148] 2-(5-((3-(1H-pyrrol-1-yl)phenyl)ethynyl)thiophen-2-yl)-N-tert-butylimidazo[1,2-a]pyrazin-3-amine hydrochloride
[149] 2-(5-((1H-indol-4-yl)ethynyl)thiophen-2-yl)-N-tert-butylimidazo[1,2-a]pyrazin-3-amine hydrochloride
[150] N-tert-butyl-2-(5-((3-nitrophenyl)ethynyl)thiophen-2-yl)imidazo[1,2-a]pyrazin-3-amine hydrochloride
[151] N-tert-butyl-2-(5-((4-nitrophenyl)ethynyl)thiophen-2-yl)imidazo[1,2-a]pyrazin-3-amine hydrochloride
[152] N-tert-butyl-2-(5-(thiazol-4-ylethynyl)thiophen-2-yl)imidazo[1,2-a]pyrazin-3-amine hydrochloride
[153] 2-((5-(3-(tert-butylamino)imidazo[1,2-a]pyrazin-2-yl)thiophen-2-yl)ethynyl)phenol
[154] 2-(5-((3-(aminomethyl)phenyl)ethynyl)thiophen-2-yl)-N-tert-butylimidazo[1,2-a]pyrazin-3-amine
[155] 2-(5-(biphenyl-3-ylethynyl)thiophen-2-yl)-N-tert-butylimidazo[1,2-a]pyrazin-3-amine hydrochloride
[156] N-tert-butyl-2-(5-(thiophen-3-ylethynyl)thiophen-2-yl)imidazo[1,2-a]pyrazin-3-amine hydrochloride
[157] N-tert-butyl-2-(5-((3-(dimethylamino)phenyl)ethynyl)thiophen-2-yl)imidazo[1,2-a]pyrazin-3-amine hydrochloride
[158] N-tert-butyl-2-(5-((6-methylpyridin-2-yl)ethynyl)thiophen-2-yl)imidazo[1,2-a]pyrazin-3-amine hydrochloride
[159] N-tert-butyl-2-(5-((3-fluoropyridin-2-yl)ethynyl)thiophen-2-yl)imidazo[1,2-a]pyrazin-3-amine hydrochloride
[160] N-tert-butyl-2-(5-((3-(methylamino)phenyl)ethynyl)thiophen-2-yl)imidazo[1,2-a]pyrazin-3-amine hydrochloride
[161] N-tert-butyl-2-(5-(p-tolylethynyl)thiophen-2-yl)imidazo[1,2-a]pyrazin-3-amine
[162] N-tert-butyl-2-(5-(o-tolylethynyl)thiophen-2-yl)imidazo[1,2-a]pyrazin-3-amine hydrochloride
[163] N-tert-butyl-2-(4-methyl-5-(phenylethynyl)thiophen-2-yl)imidazo[1,2-a]pyrazin-3-amine hydrochloride
[164] N-tert-butyl-2-(4-methyl-5-(pyridin-2-ylethynyl)thiophen-2-yl)imidazo[1,2-a]pyrazin-3-amine hydrochloride
[165] N-tert-butyl-2-(5-((6-fluoropyridin-2-yl)ethynyl)thiophen-2-yl)imidazo[1,2-a]pyrazin-3-amine
[166] N-tert-butyl-2-(5-((2-nitrophenyl)ethynyl)thiophen-2-yl)imidazo[1,2-a]pyrazin-3-amine
[167] N-tert-butyl-8-chloro-2-(5-(pyridin-2-ylethynyl)thiophen-2-yl)imidazo[1,2-a]pyrazin-3-amine
[168] N-tert-butyl-2-(5-((6-methoxypyridin-2-yl)ethynyl)thiophen-2-yl)imidazo[1,2-a]pyrazin-3-amine
[169] N-tert-butyl-2-(5-((5-fluoropyridin-2-yl)ethynyl)thiophen-2-yl)imidazo[1,2-a]pyrazin-3-amine hydrochloride
[170] 2-(4-(3-(tert-butylamino)imidazo[1,2-a]pyrazin-2-yl)-2-(phenylethynyl)phenyl)acetonitrile
[171] N-tert-butyl-2-(5-((5-methoxypyridin-3-yl)ethynyl)thiophen-2-yl)imidazo[1,2-a]pyrazin-3-amine hydrochloride
[172] 5-((5-(3-(tert-butylamino)imidazo[1,2-a]pyrazin-2-yl)thiophen-2-yl)ethynyl)nicotinonitrile hydrochloride
[173] N-tert-butyl-2-(5-((3-(methylthio)phenyl)ethynyl)thiophen-2-yl)imidazo[1,2-a]pyrazin-3-amine
[174] methyl-3-((5-(3-(tert-butylamino)imidazo[1,2-a]pyrazin-2-yl)thiophen-2-yl)ethynyl)benzoate
[175] N-tert-butyl-2-(5-((3,5-difluoropyridin-2-yl)ethynyl)thiophen-2-yl)imidazo[1,2-a]pyrazin-3-amine
[176] N-tert-butyl-2-(5-(phenylethynyl)thiazol-2-yl)imidazo[1,2-a]pyrazin-3-amine
[177] N-tert-butyl-2-(2-(pyridin-4-ylethynyl)thiazol-5-yl)imidazo[1,2-a]pyrazin-3-amine
[178] 3-((5-(3-(tert-butylamino)imidazo[1,2-a]pyrazin-2-yl)thiophen-2-yl)ethynyl)benzaldehyde
[179] 3-((5-(3-(tert-butylamino)imidazo[1,2-a]pyrazin-2-yl)thiophen-2-yl)ethynyl)-4-fluorobenzonitrile
[180] N-tert-butyl-2-(5-((3-(trifluoromethyl)phenyl)ethynyl)thiophen-2-yl)imidazo[1,2-a]pyrazin-3-amine hydrochloride
[181] N-tert-butyl-2-(2-(pyridin-2-ylethynyl)thiazol-5-yl)imidazo[1,2-a]pyrazin-3-amine
[182] N-tert-butyl-2-(3-methyl-5-(phenylethynyl)thiophen-2-yl)imidazo[1,2-a]pyrazin-3-amine hydrochloride
[183] N-tert-butyl-2-(3-methyl-5-(pyridin-2-ylethynyl)thiophen-2-yl)imidazo[1,2-a]pyrazin-3-amine hydrochloride
[184] N-tert-butyl-2-(5-((3-vinylphenyl)ethynyl)thiophen-2-yl)imidazo[1,2-a]pyrazin-3-amine
[185] 2-(5-((1H-imidazol-4-yl)ethynyl)thiophen-2-yl)-N-tert-butylimidazo[1,2-a]pyrazin-3-amine hydrochloride

[186] N-tert-butyl-2-(5-((3-methylpyridin-2-yl)ethynyl)thiophen-2-yl)imidazo[1,2-a]pyrazin-3-amine

[187] N,N-dimethyl-2-(5-(pyridin-2-ylethynyl)thiophen-2-yl)imidazo[1,2-a]pyrazin-3-amine

[188] N-tert-butyl-2-(5-((2-(tert-butyldiphenylsilyl)thiazol-5-yl)ethynyl)thiophen-2-yl)imidazo[1,2-a]pyridin-3-amine

[189] 3-((5-(3-(tert-butylamino)imidazo[1,2-a]pyridin-2-yl)thiophen-2-yl)ethynyl)benzonitrile

[190] N-tert-butyl-2-(5-(phenylethynyl)thiazol-2-yl)imidazo[1,2-a]pyridin-3-amine

[191] N-tert-butyl-2-(5-(thiazol-5-ylethynyl)thiophen-2-yl)imidazo[1,2-a]pyridin-3-amine

[192] N-tert-butyl-2-(5-(pyridin-2-ylethynyl)thiophen-2-yl)imidazo[1,2-a]pyridin-3-amine hydrochloride

[193] 6-chloro-N-cyclohexyl-2-(3-((6-methylpyridin-2-yl)ethynyl)phenyl)imidazo[1,2-a]pyridin-3-amine

[194] 5,7-dimethyl-N-phenethyl-2-(5-(phenylethynyl)thiophen-2-yl)imidazo[1,2-a]pyrimidin-3-amine

[195] N-(3-methoxyphenethyl)-5,7-dimethyl-2-(5-(phenylethynyl)thiophen-2-yl)imidazo[1,2-a]pyrimidin-3-amine

[196] N-(3-methoxyphenethyl)-5,7-dimethyl-2-(4-(phenylethynyl)thiophen-2-yl)imidazo[1,2-a]pyrimidin-3-amine

[197] N-(3-methoxyphenethyl)-5,7-dimethyl-2-(5-(phenylethynyl)furan-2-yl)imidazo[1,2-a]pyrimidin-3-amine

[198] N-(4-chlorobenzyl)-8-methyl-2-(5-(phenylethynyl)thiophen-2-yl)imidazo[1,2-a]pyridin-3-amine

[199] N-(3-methoxyphenethyl)-5-methyl-2-(4-(phenylethynyl)thiophen-2-yl)imidazo[1,2-a]pyridin-3-amine

[200] N-(2-methylhexan-2-yl)-2-(4-(phenylethynyl)thiophen-2-yl)imidazo[1,2-a]pyrazin-3-amine

[201] N-phenethyl-2-(4-(phenylethynyl)thiophen-2-yl)imidazo[1,2-a]pyrazin-3-amine

[202] N-(3-methoxyphenethyl)-2-(4-(phenylethynyl)thiophen-2-yl)imidazo[1,2-a]pyrazin-3-amine

[203] 2-(4-(phenylethynyl)thiophen-2-yl)-N-(2-(thiophen-2-yl)ethyl)imidazo[1,2-a]pyrazin-3-amine

[204] N-(4-chlorobenzyl)-2-(5-(phenylethynyl)thiophen-2-yl)imidazo[1,2-a]pyridin-3-amine

[205] N-(2-methylpentan-2-yl)-2-(5-(phenylethynyl)thiophen-2-yl)imidazo[1,2-a]pyrazin-3-amine

[206] N-(cyclohexylmethyl)-2-(4-(phenylethynyl)thiophen-2-yl)imidazo[1,2-a]pyrazin-3-amine

[207] N-(2-methoxybenzyl)-2-(5-(phenylethynyl)furan-2-yl)imidazo[1,2-a]pyrazin-3-amine

[208] N-(cyclohexylmethyl)-2-(4-(phenylethynyl)thiophen-2-yl)imidazo[1,2-a]pyridin-3-amine

[209] N-(2-methylpentan-2-yl)-2-(4-(phenylethynyl)thiophen-2-yl)imidazo[1,2-a]pyridin-3-amine

[210] 8-bromo-6-methyl-2-(3-((6-methylpyridin-2-yl)ethynyl)phenyl)-N-(2,4,4-trimethylpentan-2-yl)imidazo[1,2-a]pyridin-3-amine

[211] 8-bromo-N-cyclopentyl-6-methyl-2-(3-(pyridin-2-ylethynyl)phenyl)imidazo[1,2-a]pyridin-3-amine

[212] N-cyclopentyl-2-(4-(phenylethynyl)thiophen-2-yl)imidazo[1,2-a]pyrazin-3-amine

[213] N-(1-phenylethyl)-2-(4-(henylethynyl)thiophen-2-yl)imidazo[1,2-a]pyrazin-3-amine

[214] N-(2-methylpentan-2-yl)-2-(4-(phenylethynyl)thiophen-2-yl)imidazo[1,2-a]pyrazin-3-amine

[215] 8-bromo-N-cyclopentyl-6-methyl-2-(5-(pyridin-2-ylethynyl)furan-2-yl)imidazo[1,2-a]pyridin-3-amine

[216] N-cyclopentyl-2-(5-(phenylethynyl)furan-2-yl)imidazo[1,2-a]pyrazin-3-amine

[217] N-(3-methoxyphenethyl)-7-methyl-2-(4-(phenylethynyl)thiophen-2-yl)imidazo[1,2-a]pyrimidin-3-amine

[218] 8-(benzyloxy)-2-(5-(phenylethynyl)thiophen-2-yl)-N-(2,4,4-trimethylpentan-2-yl)imidazo[1,2-a]pyridin-3-amine

[219] 8-(benzyloxy)-N-cyclopentyl-2-(4-(phenylethynyl)thiophen-2-yl)imidazo[1,2-a]pyridin-3-amine

[220] 8-(benzyloxy)-N-(2-methylpentan-2-yl)-2-(4-(phenylethynyl)thiophen-2-yl)imidazo[1,2-a]pyridin-3-amine

[221] 6-chloro-N-(4-fluorobenzyl)-2-(5-(phenylethynyl)furan-2-yl)imidazo[1,2-a]pyridin-3-amine

[222] 6-bromo-N-butyl-5-methyl-2-(4-(phenylethynyl)thiophen-2-yl)imidazo[1,2-a]pyridin-3-amine

[223] N-(furan-2-yl)-8-methyl-2-(5-(phenylethynyl)furan-2-yl)imidazo[1,2-a]pyridin-3-amine

[224] N-(furan-2-yl)-2-(5-(phenylethynyl)furan-2-yl)imidazo[1,2-a]pyridin-3-amine

[225] N-(furan-2-yl)-2-(5-(phenylethynyl)furan-2-yl)-7-propylimidazo[1,2-a]pyridin-3-amine

[226] 5,7-dimethyl-2-(4-(phenylethynyl)thiophen-2-yl)-N-(3-(trifluoromethyl)phenyl)imidazo[1,2-a]pyrimidin-3-amine

[227] 6-bromo-N-(4-chlorophenethyl)-8-methyl-2-(4-(phenylethynyl)thiophen-2-yl)imidazo[1,2-a]pyridin-3-amine

[228] N-(4-chlorophenethyl)-7-phenyl-2-(4-(phenylethynyl)thiophen-2-yl)imidazo[1,2-a]pyridin-3-amine

[229] N-phenethyl-7-phenyl-2-(4-(phenylethynyl)thiophen-2-yl)imidazo[1,2-a]pyridin-3-amine

[230] N-(4-chlorobenzyl)-5,7-dimethyl-2-(4-(phenylethynyl)thiophen-2-yl)imidazo[1,2-a]pyridin-3-amine

[231] 6-bromo-N-(4-chlorobenzyl)-5-methyl-2-(4-(phenylethynyl)thiophen-2-yl)imidazo[1,2-a]pyridin-3-amine

[232] 8-bromo-N-(4-chlorobenzyl)-6-methyl-2-(4-(phenylethynyl)thiophen-2-yl)imidazo[1,2-a]pyridin-3-amine

[233] N-(3-methoxyphenethyl)-2-(4-(phenylethynyl)thiophen-2-yl)-5-propylimidazo[1,2-a]pyridin-3-amine

[234] 6-bromo-8-methyl-2-(4-(phenylethynyl)thiophen-2-yl)-N-(2-(thiophen-2-yl)ethyl)imidazo[1,2-a]pyridin-3-amine

[235] 7-phenyl-2-(4-(phenylethynyl)thiophen-2-yl)-N-(2-(thiophen-2-yl)ethyl)imidazo[1,2-a]pyridin-3-amine

[236] 6,8-dibromo-N-(2-methylpentan-2-yl)-2-(5-(phenylethynyl)thiophen-2-yl)imidazo[1,2-a]pyridin-3-amine

[237] 6-bromo-N-(2,6-dimethylphenyl)-8-methyl-2-(4-(phenylethynyl)thiophen-2-yl)imidazo[1,2-a]pyridin-3-amine

[238] N-cyclohexyl-2-(3-(pyridin-2-ylethynyl)phenyl)imidazo[1,2-a]pyrazin-3-amine

[239] 2-(3-(pyridin-2-ylethynyl)phenyl)-N-(2,4,4-trimethylpentan-2-yl)imidazo[1,2-a]pyrazin-3-amine

[240] N-cyclopentyl-2-(4-(pyridin-2-ylethynyl)phenyl)imidazo[1,2-a]pyrazin-3-amine

[241] 8-chloro-2-(4-(pyridin-2-ylethynyl)phenyl)-6-(trifluoromethyl)-N-(2,4,4-trimethylpentan-2-yl)imidazo[1,2-a]pyridin-3-amine

[242] N-(4-fluorophenyl)-2-(4-(pyridin-2-ylethynyl)phenyl)imidazo[1,2-a]pyrazin-3-amine

[243] N-cyclopentyl-2-(2-methyl-6-(phenylethynyl)pyridin-3-yl)imidazo[1,2-a]pyrazin-3-amine

[244] N-cyclohexyl-2-(2-methyl-6-(phenylethynyl)pyridin-3-yl)imidazo[1,2-a]pyrazin-3-amine

[245] N-cyclopentyl-2-(5-(pyridin-2-ylethynyl)furan-2-yl)imidazo[1,2-a]pyrazin-3-amine
[246] 8-bromo-N-cyclopentyl-6-methyl-2-(5-(pyridin-2-ylethynyl)furan-2-yl)imidazo[1,2-a]pyridin-3-amine
[247] N-cyclohexyl-2-(5-(pyridin-2-ylethynyl)furan-2-yl)imidazo[1,2-a]pyrazin-3-amine
[248] 2-(5-(pyridin-2-ylethynyl)furan-2-yl)-N-(2,4,4-trimethylpentan-2-yl)imidazo[1,2-a]pyrazin-3-amine
[249] N-cyclopentyl-2-(3-((6-methylpyridin-2-yl)ethynyl)phenyl)imidazo[1,2-a]pyrazin-3-amine
[250] 8-bromo-N-cyclopentyl-6-methyl-2-(4-(pyridin-2-ylethynyl)phenyl)imidazo[1,2-a]pyridin-3-amine
[251] N-cyclohexyl-2-(3-((6-methylpyridin-2-yl)ethynyl)phenyl)imidazo[1,2-a]pyrazin-3-amine
[252] N-(4-fluorophenyl)-2-(3-((6-methylpyridin-2-yl)ethynyl)phenyl)imidazo[1,2-a]pyrazin-3-amine
[253] 2-(5-(pyridin-2-ylethynyl)thiophen-2-yl)-N-(2,4,4-trimethylpentan-2-yl)imidazo[1,2-a]pyrimidin-3-amine
[254] N-cyclohexyl-2-(3-(pyridin-2-ylethynyl)phenyl)imidazo[1,2-a]pyrimidin-3-amine
[255] 2-(3-(pyridin-2-ylethynyl)phenyl)-N-(2,4,4-trimethylpentan-2-yl)imidazo[1,2-a]pyrimidin-3-amine
[256] 2-(6-(phenylethynyl)pyridin-3-yl)-N-(2,4,4-trimethylpentan-2-yl)imidazo[1,2-a]pyrimidin-3-amine
[257] N-cyclopentyl-2-(5-(pyridin-2-ylethynyl)furan-2-yl)imidazo[1,2-a]pyrimidin-3-amine
[258] N-tert-butyl-2-(5-(pyridin-2-ylethynyl)furan-2-yl)imidazo[1,2-a]pyrimidin-3-amine
[259] N-cyclopentyl-2-(3-((6-methylpyridin-2-yl)ethynyl)phenyl)imidazo[1,2-a]pyrimidin-3-amine
[260] N-cyclopentyl-2-(3-(pyridin-2-ylethynyl)phenyl)imidazo[1,2-a]pyridin-3-amine
[261] N-tert-butyl-2-(3-(pyridin-2-ylethynyl)phenyl)imidazo[1,2-a]pyridin-3-amine
[262] 2-(3-(pyridin-2-ylethynyl)phenyl)-N-(2,4,4-trimethylpentan-2-yl)imidazo[1,2-a]pyridin-3-amine
[263] N-(4-fluorophenyl)-2-(3-(pyridin-2-ylethynyl)phenyl)imidazo[1,2-a]pyridin-3-amine
[264] N-tert-butyl-2-(4-(pyridin-2-ylethynyl)phenyl)imidazo[1,2-a]pyridin-3-amine
[265] N-cyclopentyl-2-(2-methyl-6-(phenylethynyl)pyridin-3-yl)imidazo[1,2-a]pyridin-3-amine
[266] N-(4-fluorophenyl)-2-(2-methyl-6-(phenylethynyl)pyridin-3-yl)imidazo[1,2-a]pyridin-3-amine
[267] N-cyclopentyl-6-methyl-2-(5-(pyridin-2-ylethynyl)thiophen-2-yl)imidazo[1,2-a]pyridin-3-amine
[268] N-tert-butyl-6-methyl-2-(5-(pyridin-2-ylethynyl)thiophen-2-yl)imidazo[1,2-a]pyridin-3-amine
[269] N-cyclohexyl-6-methyl-2-(5-(pyridin-2-ylethynyl)thiophen-2-yl)imidazo[1,2-a]pyridin-3-amine
[270] 6-methyl-2-(5-(pyridin-2-ylethynyl)thiophen-2-yl)-N-(2,4,4-trimethylpentan-2-yl)imidazo[1,2-a]pyridin-3-amine
[271] 6-methyl-2-(2-methyl-6-(phenylethynyl)pyridin-3-yl)-N-(2,4,4-trimethylpentan-2-yl)imidazo[1,2-a]pyridin-3-amine
[272] N-cyclopentyl-6-methyl-2-(5-(pyridin-2-ylethynyl)furan-2-yl)imidazo[1,2-a]pyridin-3-amine
[273] N-cyclohexyl-6-methyl-2-(3-((6-methylpyridin-2-yl)ethynyl)phenyl)imidazo[1,2-a]pyridin-3-amine
[274] N-cyclohexyl-7-methyl-2-(5-(pyridin-2-ylethynyl)thiophen-2-yl)imidazo[1,2-a]pyridin-3-amine
[275] 7-methyl-2-(5-(pyridin-2-ylethynyl)thiophen-2-yl)-N-(2,4,4-trimethylpentan-2-yl)imidazo[1,2-a]pyridin-3-amine
[276] N-tert-butyl-7-methyl-2-(3-(pyridin-2-ylethynyl)phenyl)imidazo[1,2-a]pyridin-3-amine
[277] N-(4-fluorophenyl)-7-methyl-2-(3-(pyridin-2-ylethynyl)phenyl)imidazo[1,2-a]pyridin-3-amine
[278] N-tert-butyl-7-methyl-2-(4-(pyridin-2-ylethynyl)phenyl)imidazo[1,2-a]pyridin-3-amine
[279] N-(4-fluorophenyl)-7-methyl-2-(5-(pyridin-2-ylethynyl)furan-2-yl)imidazo[1,2-a]pyridin-3-amine
[280] N-cyclohexyl-8-methyl-2-(6-(phenylethynyl)pyridin-3-yl)imidazo[1,2-a]pyridin-3-amine
[281] N-cyclopentyl-2-(6-(phenylethynyl)pyridin-3-yl)imidazo[1,2-a]pyridin-3-amine
[282] N-tert-butyl-2-(6-(phenylethynyl)pyridin-3-yl)imidazo[1,2-a]pyridin-3-amine
[283] N-cyclohexyl-2-(6-(phenylethynyl)pyridin-3-yl)imidazo[1,2-a]pyridin-3-amine
[284] 2-(6-(phenylethynyl)pyridin-3-yl)-N-(2,4,4-trimethylpentan-2-yl)imidazo[1,2-a]pyridin-3-amine
[285] N-tert-butyl-2-(5-(pyridin-2-ylethynyl)furan-2-yl)imidazo[1,2-a]pyridin-3-amine
[286] N-cyclohexyl-2-(5-(pyridin-2-ylethynyl)furan-2-yl)imidazo[1,2-a]pyridin-3-amine
[287] N-(4-fluorophenyl)-2-(5-(pyridin-2-ylethynyl)furan-2-yl)imidazo[1,2-a]pyridin-3-amine
[288] N-cyclohexyl-2-(3-((6-methylpyridin-2-yl)ethynyl)phenyl)imidazo[1,2-a]pyridin-3-amine
[289] 2-(3-((6-methylpyridin-2-yl)ethynyl)phenyl)-N-(2,4,4-trimethylpentan-2-yl)imidazo[1,2-a]pyridin-3-amine
[290] N-tert-butyl-5-methyl-2-(3-((6-methylpyridin-2-yl)ethynyl)phenyl)imidazo[1,2-a]pyridin-3-amine
[291] 5-methyl-2-(3-((6-methylpyridin-2-yl)ethynyl)phenyl)-N-(2,4,4-trimethylpentan-2-yl)imidazo[1,2-a]pyridin-3-amine
[292] N-cyclohexyl-5,7-dimethyl-2-(3-(pyridin-2-ylethynyl)phenyl)imidazo[1,2-a]pyrimidin-3-amine
[293] N-cyclohexyl-5,7-dimethyl-2-(2-methyl-6-(phenylethynyl)pyridin-3-yl)imidazo[1,2-a]pyrimidin-3-amine
[294] N-cyclopentyl-5,7-dimethyl-2-(5-(pyridin-2-ylethynyl)furan-2-yl)imidazo[1,2-a]pyrimidin-3-amine
[295] N-tert-butyl-5,7-dimethyl-2-(5-(pyridin-2-ylethynyl)furan-2-yl)imidazo[1,2-a]pyrimidin-3-amine
[296] N-(4-fluorophenyl)-8-methyl-2-(3-(pyridin-2-ylethynyl)phenyl)imidazo[1,2-a]pyridin-3-amine
[297] N-cyclohexyl-8-methyl-2-(4-(pyridin-2-ylethynyl)phenyl)imidazo[1,2-a]pyridin-3-amine
[298] N-cyclohexyl-7-ethyl-2-(5-(pyridin-2-ylethynyl)thiophen-2-yl)imidazo[1,2-a]pyridin-3-amine
[299] 7-ethyl-2-(5-(pyridin-2-ylethynyl)thiophen-2-yl)-N-(2,4,4-trimethylpentan-2-yl)imidazo[1,2-a]pyridin-3-amine
[300] N-cyclohexyl-7-ethyl-2-(3-(pyridin-2-ylethynyl)phenyl)imidazo[1,2-a]pyridin-3-amine
[301] N-cyclopentyl-7-ethyl-2-(4-(pyridin-2-ylethynyl)phenyl)imidazo[1,2-a]pyridin-3-amine
[302] N-cyclopentyl-7-ethyl-2-(6-(phenylethynyl)pyridin-3-yl)imidazo[1,2-a]pyridin-3-amine
[303] N-tert-butyl-7-ethyl-2-(6-(phenylethynyl)pyridin-3-yl)imidazo[1,2-a]pyridin-3-amine
[304] N-tert-butyl-7-ethyl-2-(5-(pyridin-2-ylethynyl)furan-2-yl)imidazo[1,2-a]pyridin-3-amine
[305] 7-isopropyl-2-(5-(pyridin-2-ylethynyl)thiophen-2-yl)-N-(2,4,4-trimethylpentan-2-yl)imidazo[1,2-a]pyridin-3-amine
[306] N-tert-butyl-7-isopropyl-2-(3-(pyridin-2-ylethynyl)phenyl)imidazo[1,2-a]pyridin-3-amine

[307] N-tert-butyl-7-isopropyl-2-(4-(pyridin-2-ylethynyl)phenyl)imidazo[1,2-a]pyridin-3-amine
[308] N-cyclohexyl-7-isopropyl-2-(5-(pyridin-2-ylethynyl)furan-2-yl)imidazo[1,2-a]pyridin-3-amine
[309] N-tert-butyl-7-isopropyl-2-(3-((6-methylpyridin-2-yl)ethynyl)phenyl)imidazo[1,2-a]pyridin-3-amine
[310] 6-chloro-N-cyclopentyl-2-(5-(pyridin-2-ylethynyl)thiophen-2-yl)imidazo[1,2-a]pyridin-3-amine
[311] N-tert-butyl-6-chloro-2-(5-(pyridin-2-ylethynyl)thiophen-2-yl)imidazo[1,2-a]pyridin-3-amine
[312] 6-chloro-N-cyclohexyl-2-(3-(pyridin-2-ylethynyl)phenyl)imidazo[1,2-a]pyridin-3-amine
[313] 6-chloro-2-(3-(pyridin-2-ylethynyl)phenyl)-N-(2,4,4-trimethylpentan-2-yl)imidazo[1,2-a]pyridin-3-amine
[314] N-tert-butyl-6-chloro-2-(4-(pyridin-2-ylethynyl)phenyl)imidazo[1,2-a]pyridin-3-amine
[315] 6-chloro-N-cyclohexyl-2-(4-(pyridin-2-ylethynyl)phenyl)imidazo[1,2-a]pyridin-3-amine
[316] N-tert-butyl-6-chloro-2-(5-(pyridin-2-ylethynyl)furan-2-yl)imidazo[1,2-a]pyridin-3-amine
[317] 6-chloro-N-cyclohexyl-2-(5-(pyridin-2-ylethynyl)furan-2-yl)imidazo[1,2-a]pyridin-3-amine
[318] 6-chloro-2-(5-(pyridin-2-ylethynyl)furan-2-yl)-N-(2,4,4-trimethylpentan-2-yl)imidazo[1,2-a]pyridin-3-amine
[319] 6-chloro-N-cyclopentyl-2-(3-((6-methylpyridin-2-yl)ethynyl)phenyl)imidazo[1,2-a]pyridin-3-amine
[320] N-tert-butyl-6-chloro-2-(3-((6-methylpyridin-2-yl)ethynyl)phenyl)imidazo[1,2-a]pyridin-3-amine
[321] N-tert-butyl-2-(5-(pyridin-2-ylethynyl)thiophen-2-yl)imidazo[1,2-a]pyridin-3-amine bis-hydrochloride
[322] N-methyl-2-(5-(pyridin-2-ylethynyl)thiophen-2-yl)imidazo[1,2-a]pyrazin-3-amine
[323] N-tert-butyl-2-(5-(pyridin-2-ylethynyl)thiophen-2-yl)imidazo[1,2-a]pyridin-3-amine bis-hydrochloride
[324] [2-(5-pyridin-2-ylethynyl-thiophen-2-yl)-imidazo[1,2-a]pyridin-3-yl]-(1,1,3,3-tetramethyl-butyl)-amine
[325] tert-butyl-[2-(5-pyrimidin-2-ylethynyl-thiophen-2-yl)-imidazo[1,2-a]pyridin-3-yl]-amine hydrochloride
[326] {2-[5-(3-amino-pyridin-2-ylethynyl)-thiophen-2-yl]-imidazo[1,2-a]pyridin-3-yl}-tert-butyl-amine
[327] tert-butyl-[2-(5-pyridin-2-ylethynyl-thiazol-2-yl)-imidazo[1,2-a]pyridin-3-yl]-amine
[328] tert-butyl-[2-(2-pyridin-2-ylethynyl-thiazol-5-yl)-imidazo[1,2-a]pyridin-3-yl]-amine
[329] tert-butyl-{2-[5-(6-fluoro-pyridin-2-ylethynyl)-thiophen-2-yl]-imidazo[1,2-a]pyridin-3-yl}-amine hydrochloride
[330] tert-butyl-{2-[5-(3-chloro-5-fluoro-phenylethynyl)-thiophen-2-yl]-imidazo[1,2-a]pyridin-3-yl}-amine hydrochloride
[331] tert-butyl-[2-(5-pyridin-2-ylethynyl-thiophen-2-yl)-imidazo[1,2-b]pyridazin-3-yl]-amine hydrochloride
[332] tert-butyl-[2-(5-thiazol-2-ylethynyl-thiophen-2-yl)-imidazo[1,2-a]pyridin-3-yl]-amine hydrochloride
[333] tert-butyl-{2-[5-(3-trifluoromethoxy-phenylethynyl)-thiophen-2-yl]-imidazo[1,2-a]pyrazin-3-yl}-amine
[334] tert-butyl-{2-[5-(3-[1,3]dioxolan-2-yl-phenylethynyl)-thiophen-2-yl]-imidazo[1,2-a]pyridin-3-yl}-amine
[335] tert-butyl-{2-[5-(3,5-dimethyl-phenylethynyl)-thiophen-2-yl]-imidazo[1,2-a]pyridin-3-yl}-amine hydrochloride
[336] tert-butyl-{2-[5-(3-fluoro-pyridin-2-ylethynyl)-thiophen-2-yl]-imidazo[1,2-a]pyridin-3-yl}-amine hydrochloride
[337] tert-butyl-{2-[5-(3-methyl-3H-imidazol-4-ylethynyl)-thiophen-2-yl]-imidazo[1,2-a]pyridin-3-yl}-amine hydrochloride and
[338] tert-butyl-{2-[5-(5-chloro-thiophen-2-ylethynyl)-thiophen-2-yl]-imidazo[1,2-a]pyridin-3-yl}-amine hydrochloride
[339] tert-butyl-{2-[5-(5-methyl-pyridin-2-ylethynyl)-thiophen-2-yl]-imidazo[1,2-a]pyridin-3-yl}-amine hydrochloride
[340] 1-{3-[5-(3-tert-butylamino-imidazo[1,2-a]pyridin-2-yl)-thiophen-2-ylethynyl]-phenyl}-ethanone hydrochloride
[341] {3-[5-(3-tert-butylamino-imidazo[1,2-a]pyridin-2-yl)-thiophen-2-ylethynyl]-phenyl}-methanol hydrochloride
[342] N-tert-butyl-2-(5-((3-methoxypyridin-2-yl)ethynyl)thiophen-2-yl)imidazo[1,2-a]pyridin-3-amine
[343] N-tert-butyl-2-(5-(thiophen-2-ylethynyl)thiophen-2-yl)imidazo[1,2-a]pyridin-3-amine hydrochloride
[344] 5-((5-(3-(tert-butylamino)imidazo[1,2-a]pyridin-2-yl)thiophen-2-yl)ethynyl)-2-fluorobenzonitrile hydrochloride
[345] N-tert-butyl-2-(5-((3,4-difluorophenyl)ethynyl)thiophen-2-yl)imidazo[1,2-a]pyridin-3-amine
[346] N-tert-butyl-2-(5-((3-(methoxymethyl)phenyl)ethynyl)thiophen-2-yl)imidazo[1,2-a]pyridin-3-amine
[347] 2-(5-((3-aminophenyl)ethynyl)thiophen-2-yl)-N-tert-butylimidazo[1,2-a]pyridin-3-amine hydrochloride
[348] N-tert-butyl-2-(5-((4-fluoro-3-methylphenyl)ethynyl)thiophen-2-yl)imidazo[1,2-a]pyridin-3-amine hydrochloride
[349] N-tert-butyl-2-(5-((3,5-difluorophenyl)ethynyl)thiophen-2-yl)imidazo[1,2-a]pyridin-3-amine
[350] N-tert-butyl-2-(5-(thiophen-3-ylethynyl)thiophen-2-yl)imidazo[1,2-a]pyridin-3-amine hydrochloride
[351] N-tert-butyl-2-(5-((3-methylpyridin-2-yl)ethynyl)thiophen-2-yl)imidazo[1,2-a]pyridin-3-amine hydrochloride
[352] 3-((5-(3-(tert-butylamino)imidazo[1,2-a]pyridin-2-yl)thiophen-2-yl)ethynyl)benzenesulfonamide hydrochloride
[353] 3-((5-(3-(tert-butylamino)imidazo[1,2-a]pyridin-2-yl)hiophen-2-yl)ethynyl)benzoic acid
[354] 3-((5-(3-(tert-butylamino)imidazo[1,2-a]pyridin-2-yl)thiophen-2-yl)ethynyl)benzamide hydrochloride
[355] N-(3-((5-(3-(tert-butylamino)imidazo[1,2-a]pyridin-2-yl)thiophen-2-yl)ethynyl)phenyl)acetamide
[356] N-tert-butyl-N-methyl-2-(5-(pyridin-2-ylethynyl)thiophen-2-yl)imidazo[1,2-a]pyridin-3-amine
[357] N,N-dimethyl-2-(5-(pyridin-2-ylethynyl)thiophen-2-yl)imidazo[1,2-a]pyridin-3-amine
[358] N-tert-butyl-N-methyl-2-(5-(pyridin-2-ylethynyl)thiazol-2-yl)imidazo[1,2-a]pyridin-3-amine
[359] (6-((5-(3-(tert-butylamino)imidazo[1,2-a]pyridin-2-yl)thiophen-2-yl)ethynyl)pyridin-2-yl)methanol
[360] N-(3-((5-(3-(tert-butylamino)imidazo[1,2-a]pyridin-2-yl)thiophen-2-yl)ethynyl)phenyl)methanesulfonamide
[361] N-tert-butyl-8-methyl-2-(5-(pyridin-2-ylethynyl)thiophen-2-yl)imidazo[1,2-a]pyrazin-3-amine hydrochloride
[362] 2-(5-(pyridin-2-ylethynyl)thiophen-2-yl)imidazo[1,2-a]pyridin-3-amine
[363] N-tert-butyl-2-(5-((3-chlorophenyl)ethynyl)thiophen-2-yl)imidazo[1,2-a]pyridin-3-amine
[364] N-tert-butyl-2-(5-((2,3-difluorophenyl)ethynyl)thiophen-2-yl)imidazo[1,2-a]pyridin-3-amine and

[365] N-tert-butyl-7-chloro-2-(5-(pyridin-2-ylethynyl)thiophen-2-yl)imidazo[1,2-a]pyridin-3-amine or a salt or solvate thereof.

45. A process for preparing a bicyclic imidazo-3-yl-amine compound corresponding to formula I of claim 1, comprising the steps reacting at least one compound of the formula II,

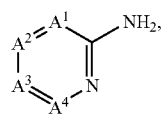

II in a reaction medium, optionally in the presence of at least one organic or inorganic acid or at least one transition metal salt with at least one isocyanide of formula III,

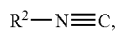

III and at least one aldehyde of formula IV,

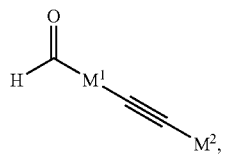

IV to obtain a compound of formula V,

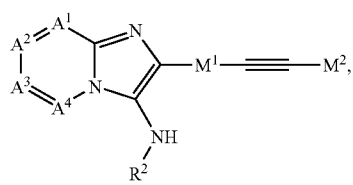

V in which $A^1$, $A^2$, $A^3$, $A^4$, $R^2$, $M^1$ and $M^2$ have the above-stated meaning, is optionally purified and/or isolated, and optionally converted into a corresponding salt and this is optionally purified or isolated, or reacting at least one compound of formula II,

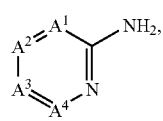

II in a reaction medium, which may include at least one organic or inorganic acid or at least one transition metal salt, with at least one isocyanide of the general formula III,

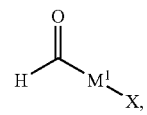

III and at least one aldehyde of the general formula VI,

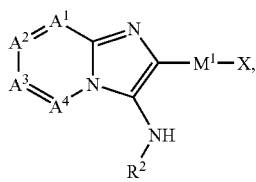

VI wherein X represents a leaving group, to obtain a compound of formula VII,

VII optionally purified or isolated, and optionally converted into a corresponding salt and this is optionally purified or isolated, and reacting said compound of formula VII with at least one acetylene of formula XI, $$H\text{——}\equiv\text{——}SiR_3,$$

XI in which R, mutually independently, in each case represents a linear or branched alkyl group or represents an unsubstituted phenyl group, in a reaction medium, which may include at least one suitable catalyst and may include at least one inorganic or organic base, to obtain a compound of formula XII, and is optionally purified and/or isolated, and optionally converted into a

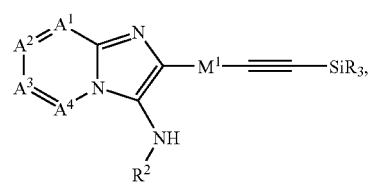

XII corresponding salt and this is optionally purified and/or isolated, and converting at least one compound of formula XII in a reaction medium, which may include at least one inorganic or organic base, and may include at least one inorganic salt, and may include at least one ammonium salt, into a compound of formula XIII,

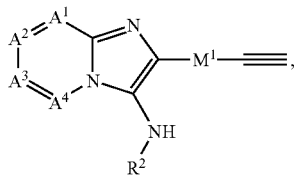

optionally purified and/or isolated, and optionally converted into a corresponding salt and this is optionally purified and/or isolated, and reacting at least one compound of formula XIII or at least one compound of formula XII with at least one compound of formula $M^2$-X, optionally in the presence of at least one suitable catalyst, and optionally in the presence of at least one inorganic or organic base, and optionally in the presence of at least one inorganic salt and optionally in the presence of at least one ammonium salt to obtain a compound of formula V,

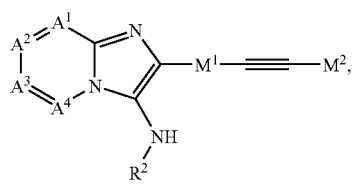

is optionally purified and/or isolated, and optionally converted into a corresponding salt and this is optionally purified and/or isolated, or reacting a compound of formula VII with at least one acetylene of the general formula VIII,

in a reaction medium, which may include at least one catalyst and which may include at least one inorganic or organic base, to obtain a compound of formula V,

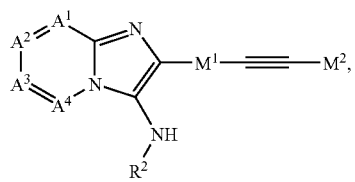

and is optionally purified and/or isolated, and optionally converted into a corresponding salt and this is optionally purified and/or isolated, and reacting the compound of formula V with at least one compound of formula $R^3$—X, in a reaction medium, in the presence of at least one organic or inorganic base, and optionally in the presence of at least one metal hydride salt, or reacting at least one compound of formula $R^{20}$—C(=O)—OH, in a reaction medium, which may include at least one organic or inorganic base and may include at least one coupling agent, or reacting at least one compound of formula $R^{20}$—C(=O)—X, in a reaction medium, which may include at least one organic or inorganic base, or reacting at least one compound of formula $R^{20}$—C(=O)—H, in a reaction medium, which may include at least one reducing agent, to obtain a compound of corresponding to formula I, or a salt thereof.

46. The process of claim 45, further comprising at least one of the steps of purifying or isolating at least one of the compounds according to formulas I, V, VII, XII, or XIII or converting one of these compounds into a salt which may then be purified or isolated.

47. The process of claim 45, wherein X represents a halogen or a sulfonic acid ester.

48. The process of claim 45, wherein X represents chlorine, bromine or trifluoromethanesulfonate.

49. A process for producing a bicyclic imidazo-3-yl-amine compound corresponding to formula I of claim 1, comprising the steps of reacting a compound of formula V,

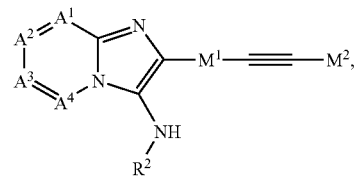

in a reaction medium in the presence of at least one organic or inorganic acid, to obtain a compound of formula IX,

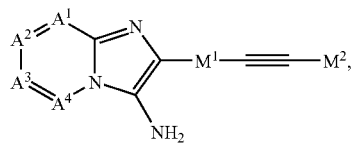

and reacting the compound of formula IX:

in a reaction medium, in the presence of at least one inorganic or organic base, and which may include at least one metal hydride salt, with at least one compound of formula $R^3$—X, or in a reaction medium, which may include at least one organic or inorganic base and may include at least one coupling agent, with at least one compound of formula $R^{20}$—C(=O)—OH, or in a reaction medium, which may include at least one organic or inorganic base, with at least one compound of formula $R^{20}$—C(=O)—X, or in a reaction medium, which may include at least one reducing agent, with at least one compound of formula $R^{20}$—C(=O)—H, to form a compound of formula X, or a salt thereof,

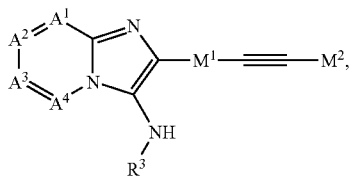

and reacting the compound of formula X with at least one compound of formula R²—X, in a reaction medium, in the presence of at least one organic or inorganic base, which may include at least one metal hydride salt,

- or reacting with at least one compound of formula R²⁰—C(=O)—OH, in a reaction medium, which may include at least one organic or inorganic base and may include at least one coupling agent,
- or reacting with at least one compound of formula R²⁰—C(=O)—X, in a reaction medium, which may include at least one organic or inorganic base,
- or reacting with at least one compound of formula R²⁰—C(=O)—H, in a reaction medium, which may include at least one reducing agent, to form a compound of formula I, or a salt thereof.

50. The process of claim 49, further comprising at least one of the steps of purifying or isolating at least one of the compounds according to formulas I, IX or X or converting one of these compounds into a salt which may then be purified or isolated.

51. The process of claim 49, wherein X represents a halogen or a sulfonic acid ester.

52. The process of claim 49, wherein X represents chlorine, bromine or trifluoromethanesulfonate.

53. A pharmaceutical composition containing at last one compound according to claim 1 and one or more physiologically acceptable auxiliary substances.

54. A method of inhibiting the mGluR5 receptor in a subject, said method comprising the step of administering to said subject an effective mGluR5 receptor inhibiting amount of a compound according to claim 1.

55. A method of treating pain comprising the step of administering to a patient a pharmaceutically effective amount of a compound according to claim 1.

56. The method of claim 55, wherein said pain selected from the group consisting of acute pain, chronic pain, neuropathic pain and visceral pain.

57. A method of producing a pharmaceutical formulation comprising the step of combining a compound according to claim 1 with one or more physiologically acceptable auxiliary substances.

* * * * *